(12) United States Patent
Klein et al.

(10) Patent No.: US 11,369,606 B2
(45) Date of Patent: Jun. 28, 2022

(54) COMBINATIONS COMPRISING POSITIVE ALLOSTERIC MODULATORS OR ORTHOSTERIC AGONISTS OF METABOTROPIC GLUTAMATERGIC RECEPTOR SUBTYPE 2 AND THEIR USE

(71) Applicant: Janssen Pharmaceutica NV, Beerse (BE)

(72) Inventors: Brian D. Klein, Potomac Maryland, MD (US); Hilde Lavreysen, Lommel (BE); Stefan Maria Christiaan Pype, Boechout (BE); Roy E. Twyman, Doylestown, PA (US); Nancy Eulalie Sylvain Van Osselaer, Lier (BE); H. Steven White, Seattle, WA (US); Marc André Ceusters, Diest (BE); José Maria Cid-Núñez, Toledo (ES); Andrés Avelino Trabanco-Suárez, Olias del Rey (ES); Roger Francis Bone, Bridgewater, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/720,750

(22) Filed: Dec. 19, 2019

(65) Prior Publication Data
US 2020/0138814 A1 May 7, 2020

Related U.S. Application Data

(63) Continuation of application No. 15/112,818, filed as application No. PCT/EP2015/051029 on Jan. 20, 2015, now Pat. No. 10,537,573.

(60) Provisional application No. 61/929,795, filed on Jan. 21, 2014, provisional application No. 62/091,668, filed on Dec. 15, 2014.

(30) Foreign Application Priority Data

| Feb. 4, 2014 | (EP) | 14153880 |
| Feb. 4, 2014 | (EP) | 14153887 |
| Sep. 3, 2014 | (EP) | 14183324 |
| Oct. 2, 2014 | (EP) | 14187429 |

(51) Int. Cl.

| A61K 31/506 | (2006.01) |
| A61K 31/496 | (2006.01) |
| A61K 31/4545 | (2006.01) |
| A61K 31/437 | (2006.01) |
| A61K 31/4015 | (2006.01) |
| A61P 25/02 | (2006.01) |
| A61K 9/48 | (2006.01) |
| A61P 25/06 | (2006.01) |
| A61K 45/06 | (2006.01) |
| A61P 25/18 | (2006.01) |
| A61P 25/08 | (2006.01) |
| A61K 31/381 | (2006.01) |

(52) U.S. Cl.
CPC .......... *A61K 31/506* (2013.01); *A61K 9/4858* (2013.01); *A61K 31/381* (2013.01); *A61K 31/4015* (2013.01); *A61K 31/437* (2013.01); *A61K 31/4545* (2013.01); *A61K 31/496* (2013.01); *A61K 45/06* (2013.01); *A61P 25/02* (2018.01); *A61P 25/06* (2018.01); *A61P 25/08* (2018.01); *A61P 25/18* (2018.01)

(58) Field of Classification Search
CPC ............ A61K 2300/00; A61K 31/4015; A61K 31/437; A61K 31/4545; A61K 31/496; A61K 31/381; A61K 31/506; A61K 45/06; A61K 9/4858; A61P 25/02; A61P 25/06; A61P 25/08; A61P 25/18
See application file for complete search history.

(56) References Cited

U.S. PATENT DOCUMENTS

| 2,976,146 A | 3/1961 | Salminen et al. |
| 4,051,244 A | 9/1977 | Matiioda et al. |
| 4,066,651 A | 1/1978 | Brittain et al. |
| 4,146,716 A | 3/1979 | Cox et al. |
| 4,196,207 A | 4/1980 | Webber et al. |
| 4,256,738 A | 3/1981 | Woitun et al. |
| 4,358,453 A | 11/1982 | Bristol et al. |
| 4,550,166 A | 10/1985 | Moran et al. |
| 4,696,943 A | 9/1987 | Gobert et al. |
| 4,837,224 A | 6/1989 | Gobert et al. |
| 4,866,074 A | 9/1989 | Spada et al. |

(Continued)

FOREIGN PATENT DOCUMENTS

| BE | 841390 | 11/1976 |
| CA | 1019323 | 10/1977 |

(Continued)

OTHER PUBLICATIONS

Keppra, FDA Document, 2010 (Year: 2010).*
Addex Partner Completes ADX71149 Phase I Program, Press release Aug. 25, 2010, http://www.addextherapeutics.com/investors/press-releases/news-deta-ils/?tx_ttnews%5Btt_newe/%5D%20=103&cHash=91fade38b1d3dc85979989357b1a9281-, retrieved on Aug. 22, 2013.
Addex Partner to Initiate Phase 2 Clinical Trial of ADX71149 for the Treatment of Major Depressive Disorder with Anxiety Symptoms, Press Release Jun. 5, 2012 http://www.addextherapeutics.com/investors/press-releases/news-details/?-x_ttnews%5Btt_news%5D%20=204&cHash=1865c3b31d0b9042f84c017bb2b5f32c, retrieved on Aug. 22, 2013.

(Continued)

*Primary Examiner* — Umamaheswari Ramachandran
(74) *Attorney, Agent, or Firm* — Fay Kaplun & Marcin, LLP

(57) ABSTRACT

The present invention relates to combinations comprising a positive allosteric modulator ("PAM") of metabotropic glutamatergic receptor subtype 2 ("mGluR2") or a pharmaceutically acceptable salt or a solvate thereof, or an orthosteric agonist of metabotropic glutamatergic receptor subtype 2 compound or a pharmaceutically acceptable salt or a solvate thereof, and a synaptic vesicle protein 2A ("SV2A") ligand.

20 Claims, 6 Drawing Sheets

(56) References Cited

U.S. PATENT DOCUMENTS

| | | |
|---|---|---|
| 4,898,654 A | 2/1990 | Toda et al. |
| 4,978,663 A | 12/1990 | Effland et al. |
| 5,032,602 A | 7/1991 | Fey et al. |
| 5,130,442 A | 7/1992 | Meisel et al. |
| 5,175,157 A | 12/1992 | Psiorz et al. |
| 5,204,198 A | 4/1993 | Bugner et al. |
| 5,236,917 A | 8/1993 | Dunlap et al. |
| 5,254,543 A | 10/1993 | Hanko et al. |
| 5,260,293 A | 11/1993 | Baker et al. |
| 5,280,026 A | 1/1994 | Brown et al. |
| 5,332,750 A | 7/1994 | Mederski et al. |
| 5,356,911 A | 10/1994 | Muller-Gillemann et al. |
| 5,366,981 A | 11/1994 | Vecchietti et al. |
| 5,371,074 A | 12/1994 | Dunlap et al. |
| 5,374,513 A | 12/1994 | Ohzeki et al. |
| 5,378,720 A | 1/1995 | Hlasta et al. |
| 5,407,948 A | 4/1995 | Fey et al. |
| 5,418,243 A | 5/1995 | Angerbauer et al. |
| 5,424,435 A | 6/1995 | Hani et al. |
| 5,473,077 A | 12/1995 | Monn et al. |
| 5,498,774 A | 3/1996 | Mitsudera et al. |
| 5,500,420 A | 3/1996 | Maiese |
| 5,512,576 A | 4/1996 | Desai et al. |
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hofgen et al. |
| 5,741,798 A | 4/1998 | Lazer et al. |
| 5,801,179 A | 9/1998 | Van Lommen et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van Lommen et al. |
| 6,103,475 A | 8/2000 | Burned, Jr. et al. |
| 6,107,342 A | 8/2000 | Adam et al. |
| 6,110,920 A | 8/2000 | Roches et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Tercero et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Bilodeau et al. |
| 6,472,392 B1 | 10/2002 | Starck et al. |
| 6,479,436 B1 | 11/2002 | Otten et al. |
| 6,498,180 B1 | 12/2002 | Collado Cane et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatierer et al. |
| 6,835,726 B2 | 12/2004 | Cushing et al. |
| 6,977,266 B2 | 12/2005 | Tada et al. |
| 7,393,549 B2 | 7/2008 | Ebinuma |
| 7,456,289 B2 | 11/2008 | Hsieh et al. |
| 7,572,807 B2 | 8/2009 | Li et al. |
| 7,579,360 B2 | 8/2009 | Li et al. |
| 7,700,593 B2 | 4/2010 | Chakrabarti et al. |
| 7,879,837 B2 | 2/2011 | Hayashi et al. |
| 7,960,563 B2 | 6/2011 | Johnson et al. |
| 7,977,325 B2 | 7/2011 | Schwede et al. |
| 8,252,937 B2 | 8/2012 | Cid-Nunez et al. |
| 8,299,101 B2 | 10/2012 | Cid-Nunez et al. |
| 8,318,184 B2 | 11/2012 | Monn et al. |
| 8,399,493 B2 | 3/2013 | Bolea et al. |
| 8,912,201 B2 | 12/2014 | Heine et al. |
| 8,937,060 B2 | 1/2015 | Cid-Nunez et al. |
| 9,012,448 B2 | 4/2015 | Cid-Nunez et al. |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | Defeo-Jones et al. |
| 2002/0137770 A1 | 9/2002 | Nara et al. |
| 2002/0147362 A1 | 10/2002 | Kozikowski et al. |
| 2002/0193367 A1 | 12/2002 | Adam et al. |
| 2002/0198197 A1 | 12/2002 | Adam et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazoto et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0058997 A1 | 3/2004 | Daniel |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado Cano et al. |
| 2004/0106791 A1 | 6/2004 | Yoakim et al. |
| 2004/0116489 A1 | 6/2004 | Massey |
| 2004/0127936 A1 | 7/2004 | Salahieh et al. |
| 2004/0132723 A1 | 7/2004 | Yoakim et al. |
| 2004/0138204 A1 | 7/2004 | James, Jr. |
| 2004/0138238 A1 | 7/2004 | Dhanoa et al. |
| 2004/0167123 A1 | 8/2004 | Prati et al. |
| 2004/0176385 A1 | 9/2004 | Nuss et al. |
| 2004/0204448 A1 | 10/2004 | Muller et al. |
| 2004/0220222 A1 | 11/2004 | Galley et al. |
| 2005/0004142 A1 | 1/2005 | Adams et al. |
| 2005/0026935 A1 | 2/2005 | Ford et al. |
| 2005/0054819 A1 | 3/2005 | Catalano et al. |
| 2005/0070538 A1 | 3/2005 | Cheng et al. |
| 2005/0113283 A1 | 5/2005 | Solow-Cordero et al. |
| 2005/0187227 A1 | 8/2005 | Himmelsbach et al. |
| 2005/0245530 A1 | 11/2005 | Borzilleri et al. |
| 2006/0083676 A1 | 4/2006 | Lesage et al. |
| 2006/0240501 A1 | 10/2006 | Ebinuma |
| 2007/0032469 A1 | 2/2007 | Isaac et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2008/0221179 A1 | 9/2008 | Gaul et al. |
| 2008/0286265 A1 | 11/2008 | Gaul et al. |
| 2008/0306077 A1 | 12/2008 | Clayton et al. |

(56) References Cited

U.S. PATENT DOCUMENTS

| | | |
|---|---|---|
| 2009/0031422 A1 | 1/2009 | Aaron et al. |
| 2009/0111855 A1 | 4/2009 | Gaul et al. |
| 2009/0124609 A1 | 5/2009 | Albrecht et al. |
| 2009/0124612 A1 | 5/2009 | Albrecht et al. |
| 2009/0203668 A1 | 8/2009 | Li et al. |
| 2009/0275751 A1 | 11/2009 | Nagato et al. |
| 2009/0318436 A1 | 12/2009 | Albrechet et al. |
| 2010/0063054 A1 | 3/2010 | Bressi et al. |
| 2010/0063092 A1 | 3/2010 | Cid-Nunez et al. |
| 2010/0087487 A1 | 4/2010 | Cid-Nunez et al. |
| 2010/0099715 A1 | 4/2010 | Cid-Nunez et al. |
| 2010/0166655 A1 | 7/2010 | Imogai et al. |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2010/0292241 A1 | 11/2010 | Brnardic et al. |
| 2011/0009441 A1 | 1/2011 | Trabanco-Suarez et al. |
| 2011/0237602 A1 | 9/2011 | Meltzer et al. |
| 2011/0245232 A1 | 10/2011 | Braje et al. |
| 2011/0245247 A1 | 10/2011 | Braje et al. |
| 2011/0275624 A1 | 11/2011 | Cid-Nunez et al. |
| 2011/0306642 A1 | 12/2011 | Cid-Nunez et al. |
| 2012/0035167 A1 | 2/2012 | Cid-Nunez et al. |
| 2012/0135977 A1 | 5/2012 | Beshore et al. |
| 2012/0184525 A1 | 7/2012 | Cid-Nunez et al. |
| 2012/0184527 A1 | 7/2012 | Cic-Nunez et al. |
| 2012/0184528 A1 | 7/2012 | Cic-Nunez et al. |
| 2012/0309793 A1 | 12/2012 | Duvey et al. |
| 2013/0109052 A1 | 5/2013 | Yan et al. |
| 2013/0150412 A1 | 6/2013 | Cid-Nunez et al. |
| 2013/0196992 A1 | 8/2013 | Cid-Nunez et al. |
| 2013/0197019 A1 | 8/2013 | Cid-Nunez et al. |
| 2015/0336930 A1 | 11/2015 | Cid-Nunez et al. |

FOREIGN PATENT DOCUMENTS

| | | |
|---|---|---|
| CA | 2035144 | 7/1991 |
| CA | 2390948 | 12/2000 |
| CN | 1842532 | 10/2006 |
| CN | 102002040 | 4/2011 |
| DE | 19507522 | 9/1996 |
| EP | 0082023 | 6/1983 |
| EP | 82023 | 6/1983 |
| EP | 0154190 | 9/1985 |
| EP | 154190 | 9/1985 |
| EP | 162036 | 11/1985 |
| EP | 0292840 | 11/1988 |
| EP | 292840 | 11/1988 |
| EP | 0308020 | 3/1989 |
| EP | 308020 | 3/1989 |
| EP | 0365486 | 4/1990 |
| EP | 365486 | 4/1990 |
| EP | 0373423 | 6/1990 |
| EP | 373423 | 6/1990 |
| EP | 0379806 | 8/1990 |
| EP | 379806 | 8/1990 |
| EP | 0430385 | 6/1991 |
| EP | 430385 | 6/1991 |
| EP | 0441718 | 8/1991 |
| EP | 441718 | 8/1991 |
| EP | 0447118 | 9/1991 |
| EP | 447118 | 9/1991 |
| EP | 0447891 | 9/1991 |
| EP | 447891 | 9/1991 |
| EP | 0478195 | 9/1991 |
| EP | 478195 | 9/1991 |
| EP | 0452002 | 10/1991 |
| EP | 452002 | 10/1991 |
| EP | 482939 | 4/1992 |
| EP | 0482939 | 4/1992 |
| EP | 530702 | 3/1993 |
| EP | 0530702 | 3/1993 |
| EP | 542059 | 5/1993 |
| EP | 0542059 | 5/1993 |
| EP | 0547708 | 6/1993 |
| EP | 547708 | 6/1993 |
| EP | 0548934 | 6/1993 |
| EP | 548934 | 6/1993 |
| EP | 0557016 | 8/1993 |
| EP | 557016 | 8/1993 |
| EP | 0612746 | 8/1994 |
| EP | 612746 | 8/1994 |
| EP | 626378 | 11/1994 |
| EP | 0626378 | 11/1994 |
| EP | 0728759 | 8/1996 |
| EP | 728759 | 8/1996 |
| EP | 0799826 | 10/1997 |
| EP | 799826 | 10/1997 |
| EP | 838458 | 4/1998 |
| EP | 0838458 | 4/1998 |
| EP | 0856255 | 8/1998 |
| EP | 856255 | 8/1998 |
| EP | 0903343 | 3/1999 |
| EP | 903343 | 3/1999 |
| EP | 0955301 | 11/1999 |
| EP | 955301 | 11/1999 |
| EP | 1006112 | 6/2000 |
| EP | 1203766 | 5/2002 |
| EP | 1277726 | 1/2003 |
| EP | 1459765 | 9/2004 |
| EP | 176436 7 | 3/2007 |
| EP | 1764099 | 3/2007 |
| EP | 1764367 | 3/2007 |
| EP | 1806339 | 7/2007 |
| EP | 1809339 | 7/2007 |
| EP | 2039687 | 3/2009 |
| EP | 2462990 | 6/2012 |
| EP | 2462990 A1 | 6/2012 |
| GB | 1039113 | 8/1966 |
| GB | 1309692 | 3/1973 |
| GB | 1392849 | 4/1975 |
| GB | 1502312 | 3/1978 |
| GB | 2225322 | 5/1990 |
| JP | 50106981 | 8/1975 |
| JP | 53082783 | 7/1978 |
| JP | 57052334 | 11/1982 |
| JP | 6110557 | 1/1986 |
| JP | 02503317 | 10/1990 |
| JP | 2503317 | 10/1990 |
| JP | 2277044 | 11/1990 |
| JP | 5204071 | 8/1993 |
| JP | 2124871 | 5/1994 |
| JP | 6211797 | 8/1994 |
| JP | 6211798 | 8/1994 |
| JP | 7070018 | 3/1995 |
| JP | 7101861 | 4/1995 |
| JP | 10029979 | 2/1998 |
| JP | 10045750 | 2/1998 |
| JP | 2000/072731 | 3/2000 |
| JP | 2000/072751 | 3/2000 |
| JP | 2001/089367 | 4/2001 |
| JP | 2002/003401 | 1/2002 |
| JP | 2002/105085 | 4/2002 |
| JP | 2002/308882 | 10/2002 |
| JP | 2003/012653 | 1/2003 |
| JP | 2004/525192 | 8/2004 |
| JP | 2004/339080 | 12/2004 |
| JP | 2005/531501 | 10/2005 |
| JP | 2008/509714 | 4/2008 |
| JP | 2008/513414 | 5/2008 |
| RU | 1796625 | 2/1993 |
| RU | 2143433 | 12/1999 |
| SU | 509578 | 4/1976 |
| SU | 1796625 | 2/1993 |
| WO | 84/00544 | 2/1984 |
| WO | WO 84/00544 | 2/1984 |
| WO | 84/00685 | 3/1984 |
| WO | WO 84/00685 | 3/1984 |
| WO | 91/09848 | 7/1991 |
| WO | WO 91/09848 | 7/1991 |
| WO | 92/18115 | 10/1992 |
| WO | WO 92/18115 | 10/1992 |
| WO | 93/01195 | 1/1993 |
| WO | WO 93/01195 | 1/1993 |

(56) References Cited

FOREIGN PATENT DOCUMENTS

| | | |
|---|---|---|
| WO | 93/15056 | 8/1993 |
| WO | WO 93/15056 | 8/1993 |
| WO | 94/19315 | 9/1994 |
| WO | WO 94/19315 | 9/1994 |
| WO | 95/04733 | 2/1995 |
| WO | WO 95/04733 | 2/1995 |
| WO | 95/06032 | 3/1995 |
| WO | WO 95/06032 | 3/1995 |
| WO | 95/11233 | 4/1995 |
| WO | WO 95/011233 | 4/1995 |
| WO | 95/17397 | 6/1995 |
| WO | WO 95/17397 | 6/1995 |
| WO | 95/24393 | 9/1995 |
| WO | WO 95/24393 | 9/1995 |
| WO | 95/35293 | 12/1995 |
| WO | WO 95/35293 | 12/1995 |
| WO | 96/05828 | 2/1996 |
| WO | 96/06167 | 2/1996 |
| WO | WO 96/05828 | 2/1996 |
| WO | WO 96/06167 | 2/1996 |
| WO | 96/15108 | 5/1996 |
| WO | WO 96/15108 | 5/1996 |
| WO | 96/22021 | 7/1996 |
| WO | WO 96/22021 | 7/1996 |
| WO | 96/33974 | 10/1996 |
| WO | WO 96/33974 | 10/1996 |
| WO | 96/37481 | 11/1996 |
| WO | WO 96/37481 | 11/1996 |
| WO | 96/41639 | 12/1996 |
| WO | WO 96/41639 | 12/1996 |
| WO | 97/10229 | 3/1997 |
| WO | 97/10238 | 3/1997 |
| WO | WO 97/10229 | 3/1997 |
| WO | WO 97/10238 | 3/1997 |
| WO | 97/18199 | 6/1997 |
| WO | 97/21701 | 6/1997 |
| WO | WO 97/21701 | 6/1997 |
| WO | 97/46532 | 12/1997 |
| WO | 97/48724 | 12/1997 |
| WO | WO 97/46532 | 12/1997 |
| WO | WO 97/48724 | 12/1997 |
| WO | 98/06724 | 2/1998 |
| WO | WO 98/06724 | 2/1998 |
| WO | 98/11075 | 3/1998 |
| WO | WO 98/11075 | 3/1998 |
| WO | 98/17668 | 4/1998 |
| WO | WO 98/17668 | 4/1998 |
| WO | 98/24780 | 6/1998 |
| WO | WO 98/24780 | 6/1998 |
| WO | 98/32762 | 7/1998 |
| WO | WO 98/32762 | 7/1998 |
| WO | 98/38168 | 9/1998 |
| WO | WO 98/38168 | 9/1998 |
| WO | 98/50384 | 11/1998 |
| WO | WO 98/50384 | 11/1998 |
| WO | 99/06041 | 2/1999 |
| WO | WO 99/06041 | 2/1999 |
| WO | 99/11622 | 3/1999 |
| WO | 99/11628 | 3/1999 |
| WO | 99/11649 | 3/1999 |
| WO | 99/12532 | 3/1999 |
| WO | WO 99/11622 | 3/1999 |
| WO | WO 99/11628 | 3/1999 |
| WO | WO 99/11649 | 3/1999 |
| WO | WO 99/12532 | 3/1999 |
| WO | 99/16755 | 4/1999 |
| WO | 99/18096 | 4/1999 |
| WO | WO 99/16755 | 4/1999 |
| WO | WO 99/18096 | 4/1999 |
| WO | 99/21992 | 5/1999 |
| WO | WO 99/21992 | 5/1999 |
| WO | 99/31062 | 6/1999 |
| WO | 99/31066 | 6/1999 |
| WO | WO 99/31062 | 6/1999 |
| WO | WO 99/31066 | 6/1999 |
| WO | 99/32448 | 7/1999 |
| WO | 99/33829 | 7/1999 |
| WO | 99/36072 | 7/1999 |
| WO | WO 99/32448 | 7/1999 |
| WO | WO 99/33829 | 7/1999 |
| WO | WO 99/36072 | 7/1999 |
| WO | 99/52893 | 10/1999 |
| WO | 99/53956 | 10/1999 |
| WO | WO 99/52893 | 10/1999 |
| WO | WO 99/53956 | 10/1999 |
| WO | 99/62908 | 12/1999 |
| WO | WO 99/62908 | 12/1999 |
| WO | 00/03990 | 1/2000 |
| WO | WO 00/03990 | 1/2000 |
| WO | 00/12089 | 3/2000 |
| WO | WO 00/12089 | 3/2000 |
| WO | 00/21934 | 4/2000 |
| WO | WO 00/21934 | 4/2000 |
| WO | 00/34244 | 6/2000 |
| WO | WO 00/34244 | 6/2000 |
| WO | 00/53605 | 9/2000 |
| WO | WO 00/53605 | 9/2000 |
| WO | 00/61126 | 10/2000 |
| WO | WO 00/61126 | 10/2000 |
| WO | 00/69816 | 11/2000 |
| WO | WO 00/69816 | 11/2000 |
| WO | 00/73283 | 12/2000 |
| WO | WO 00/73283 | 12/2000 |
| WO | 01/10846 | 2/2001 |
| WO | WO 01/10846 | 2/2001 |
| WO | 01/29025 | 4/2001 |
| WO | WO 01/29025 | 4/2001 |
| WO | 01/32632 | 5/2001 |
| WO | 01/32644 | 5/2001 |
| WO | WO 01/32632 | 5/2001 |
| WO | WO 01/32644 | 5/2001 |
| WO | 01/39779 | 6/2001 |
| WO | 01/46190 | 6/2001 |
| WO | WO 01/46190 | 6/2001 |
| WO | 01/53288 | 7/2001 |
| WO | WO 01/53288 | 7/2001 |
| WO | 01/55132 | 8/2001 |
| WO | 01/56990 | 8/2001 |
| WO | 01/62726 | 8/2001 |
| WO | WO 01/55132 | 8/2001 |
| WO | WO 01/56990 | 8/2001 |
| WO | 01/68097 | 9/2001 |
| WO | 01/70731 | 9/2001 |
| WO | WO 01/68097 | 9/2001 |
| WO | WO 01/70731 | 9/2001 |
| WO | 01/72712 | 10/2001 |
| WO | WO 01/72712 | 10/2001 |
| WO | 01/83421 | 11/2001 |
| WO | 01/83431 | 11/2001 |
| WO | 01/83481 | 11/2001 |
| WO | 01/85716 | 11/2001 |
| WO | WO 01/83421 | 11/2001 |
| WO | WO 01/83431 | 11/2001 |
| WO | WO 01/83481 | 11/2001 |
| WO | WO 01/85716 | 11/2001 |
| WO | 01/96308 | 12/2001 |
| WO | WO 01/96308 | 12/2001 |
| WO | 02/02568 | 1/2002 |
| WO | WO 02/02568 | 1/2002 |
| WO | 02/10807 | 2/2002 |
| WO | 02/12236 | 2/2002 |
| WO | 02/14282 | 2/2002 |
| WO | WO 02/10807 | 2/2002 |
| WO | WO 02/12236 | 2/2002 |
| WO | WO 02/14282 | 2/2002 |
| WO | 02/22598 | 3/2002 |
| WO | WO 02/22598 | 3/2002 |
| WO | 02/28837 | 4/2002 |
| WO | WO 02/28837 | 4/2002 |
| WO | 02/051849 | 7/2002 |
| WO | WO 02/51849 | 7/2002 |
| WO | 02/074025 | 9/2002 |
| WO | WO 02/074025 | 9/2002 |
| WO | 02/079498 | 10/2002 |

(56) References Cited

FOREIGN PATENT DOCUMENTS

| | | |
|---|---|---|
| WO | WO 02/079498 | 10/2002 |
| WO | 02/090333 | 11/2002 |
| WO | 02/094264 | 11/2002 |
| WO | WO 02/090333 | 11/2002 |
| WO | WO 02/094264 | 11/2002 |
| WO | 02/096318 | 12/2002 |
| WO | 02/096363 | 12/2002 |
| WO | 02/098869 | 12/2002 |
| WO | 02/102807 | 12/2002 |
| WO | WO 02/096318 | 12/2002 |
| WO | WO 02/096363 | 12/2002 |
| WO | WO 02/098869 | 12/2002 |
| WO | WO 02/102807 | 12/2002 |
| WO | 03/011293 | 2/2003 |
| WO | WO 03/011293 | 2/2003 |
| WO | 03/029209 | 4/2003 |
| WO | WO 03/029209 | 4/2003 |
| WO | 03/035639 | 5/2003 |
| WO | 03/042989 | 5/2003 |
| WO | 03/044021 | 5/2003 |
| WO | WO 03/035639 | 5/2003 |
| WO | WO 03/042989 | 5/2003 |
| WO | WO 03/044021 | 5/2003 |
| WO | 03/047577 | 6/2003 |
| WO | 03/051481 | 6/2003 |
| WO | 03/051842 | 6/2003 |
| WO | WO 03/04757 7 | 6/2003 |
| WO | WO 03/051481 | 6/2003 |
| WO | WO 03/051842 | 6/2003 |
| WO | 03/055878 | 7/2003 |
| WO | 03/059871 | 7/2003 |
| WO | 03/059884 | 7/2003 |
| WO | 03/062392 | 7/2003 |
| WO | WO 03/055878 | 7/2003 |
| WO | WO 03/059871 | 7/2003 |
| WO | WO 03/059884 | 7/2003 |
| WO | WO 03/062392 | 7/2003 |
| WO | 03/064428 | 8/2003 |
| WO | 03/065994 | 8/2003 |
| WO | 03/068230 | 8/2003 |
| WO | 03/068750 | 8/2003 |
| WO | 03/070712 | 8/2003 |
| WO | WO 03/064428 | 8/2003 |
| WO | WO 03/065994 | 8/2003 |
| WO | WO 03/068230 | 8/2003 |
| WO | WO 03/068750 | 8/2003 |
| WO | WO 03/070712 | 8/2003 |
| WO | 03/076405 | 9/2003 |
| WO | WO 03/076405 | 9/2003 |
| WO | 03/082191 | 10/2003 |
| WO | 03/084610 | 10/2003 |
| WO | WO 03/082191 | 10/2003 |
| WO | WO 03/084610 | 10/2003 |
| WO | 03/092595 | 11/2003 |
| WO | WO 03/092595 | 11/2003 |
| WO | 03/099808 | 12/2003 |
| WO | 03/104217 | 12/2003 |
| WO | 03/105846 | 12/2003 |
| WO | 2004/000846 | 12/2003 |
| WO | WO 03/099808 | 12/2003 |
| WO | WO 03/104217 | 12/2003 |
| WO | WO 03/105846 | 12/2003 |
| WO | WO 2004/000846 | 12/2003 |
| WO | 2004/004720 | 1/2004 |
| WO | WO 2004/004720 | 1/2004 |
| WO | 2004/011441 | 2/2004 |
| WO | 2004/014859 | 2/2004 |
| WO | 2004/014920 | 2/2004 |
| WO | WO 2004/011441 | 2/2004 |
| WO | WO 2004/014859 | 2/2004 |
| WO | WO 2004/014920 | 2/2004 |
| WO | 2004/017950 | 3/2004 |
| WO | 2004/018386 | 3/2004 |
| WO | 2004/019863 | 3/2004 |
| WO | 2004/021984 | 3/2004 |
| WO | 2004/024150 | 3/2004 |
| WO | WO 2004/017950 | 3/2004 |
| WO | WO 2004/018386 | 3/2004 |
| WO | WO 2004/019863 | 3/2004 |
| WO | WO 2004/021984 | 3/2004 |
| WO | WO 2004/024150 | 3/2004 |
| WO | 2004/029060 | 4/2004 |
| WO | 2004/031189 | 4/2004 |
| WO | WO 2004/029060 | 4/2004 |
| WO | WO 2004/031189 | 4/2004 |
| WO | 2004/041818 | 5/2004 |
| WO | 2004/043927 | 5/2004 |
| WO | WO 2004/041818 | 5/2004 |
| WO | WO 2004/043927 | 5/2004 |
| WO | 2004/054979 | 7/2004 |
| WO | WO 2004/054979 | 7/2004 |
| WO | 2004/065380 | 8/2004 |
| WO | 2004/067002 | 8/2004 |
| WO | 2004/072025 | 8/2004 |
| WO | WO 2004/065380 | 8/2004 |
| WO | WO 2004/067002 | 8/2004 |
| WO | WO 2004/072025 | 8/2004 |
| WO | 2004/076413 | 9/2004 |
| WO | 2004/078175 | 9/2004 |
| WO | 2004/078176 | 9/2004 |
| WO | 2004/080981 | 9/2004 |
| WO | WO 2004/076413 | 9/2004 |
| WO | WO 2004/078175 | 9/2004 |
| WO | WO 2004/078176 | 9/2004 |
| WO | WO 2004/080981 | 9/2004 |
| WO | 2004/024936 | 10/2004 |
| WO | 2004/087658 | 10/2004 |
| WO | 2004/092123 | 10/2004 |
| WO | 2004/092135 | 10/2004 |
| WO | WO 2004/024936 | 10/2004 |
| WO | WO 2004/092123 | 10/2004 |
| WO | WO 2004/092135 | 10/2004 |
| WO | 2005/002585 | 1/2005 |
| WO | 2005/007144 | 1/2005 |
| WO | WO 2005/002585 | 1/2005 |
| WO | WO 2005/007144 | 1/2005 |
| WO | 2005/021552 | 3/2005 |
| WO | 2005/028445 | 3/2005 |
| WO | WO 2005/021552 | 3/2005 |
| WO | WO 2005/028445 | 3/2005 |
| WO | 2005/040337 | 5/2005 |
| WO | WO 2005/040337 | 5/2005 |
| WO | 2005/054188 | 6/2005 |
| WO | 2005/080356 | 9/2005 |
| WO | WO 2005/080356 | 9/2005 |
| WO | 2005/097052 | 10/2005 |
| WO | 2005/100365 | 10/2005 |
| WO | WO 2005/097052 | 10/2005 |
| WO | WO 2005/100365 | 10/2005 |
| WO | 2005/121082 | 12/2005 |
| WO | 2005/123703 | 12/2005 |
| WO | WO 2005/123703 | 12/2005 |
| WO | 2006/012622 | 2/2006 |
| WO | 2006/014918 | 2/2006 |
| WO | 2006/015158 | 2/2006 |
| WO | 2006/015737 | 2/2006 |
| WO | 2006/018727 | 2/2006 |
| WO | 2006/020879 | 2/2006 |
| WO | WO 2006/012622 | 2/2006 |
| WO | WO 2006/014918 | 2/2006 |
| WO | WO 2006/015158 | 2/2006 |
| WO | WO 2006/015737 | 2/2006 |
| WO | WO 2006/018727 | 2/2006 |
| WO | WO 2006/020879 | 2/2006 |
| WO | 2006/029980 | 3/2006 |
| WO | 2006/030031 | 3/2006 |
| WO | 2006/030032 | 3/2006 |
| WO | WO 2006/029980 | 3/2006 |
| WO | WO 2006/030031 | 3/2006 |
| WO | WO 2006/030032 | 3/2006 |
| WO | 2006/047237 | 5/2006 |
| WO | WO 2006/047237 | 5/2006 |
| WO | 2006/057860 | 6/2006 |
| WO | 2006/057869 | 6/2006 |

(56) References Cited

FOREIGN PATENT DOCUMENTS

| | | |
|---|---|---|
| WO | WO 2006/057860 | 6/2006 |
| WO | WO 2006/057869 | 6/2006 |
| WO | 2006/071730 | 7/2006 |
| WO | 2006/074041 | 7/2006 |
| WO | WO 2006/071730 | 7/2006 |
| WO | WO 2006/074041 | 7/2006 |
| WO | 2006/091496 | 8/2006 |
| WO | WO 2006/091496 | 8/2006 |
| WO | 2006/099972 | 9/2006 |
| WO | WO 2006/099972 | 9/2006 |
| WO | 2006/109876 | 10/2006 |
| WO | WO 2006/109876 | 10/2006 |
| WO | 2006/128692 | 12/2006 |
| WO | 2006/128693 | 12/2006 |
| WO | 2006/137350 | 12/2006 |
| WO | WO 2006/137350 | 12/2006 |
| WO | 2007/021308 | 2/2007 |
| WO | 2007/021309 | 2/2007 |
| WO | WO 2007/021308 | 2/2007 |
| WO | WO 2007/021309 | 2/2007 |
| WO | 2007/027669 | 3/2007 |
| WO | 2007/031558 | 3/2007 |
| WO | WO 2007/027669 | 3/2007 |
| WO | WO 2007/031558 | 3/2007 |
| WO | 2007/039439 | 4/2007 |
| WO | WO 2007/039439 | 4/2007 |
| WO | 2007/059257 | 5/2007 |
| WO | WO 2007/059257 | 5/2007 |
| WO | 2007/065595 | 6/2007 |
| WO | 2007/078523 | 7/2007 |
| WO | WO 2007/078523 | 7/2007 |
| WO | 2007/095024 | 8/2007 |
| WO | WO 2007/095024 | 8/2007 |
| WO | 2007/103760 | 9/2007 |
| WO | 2007/104783 | 9/2007 |
| WO | WO 2007/103760 | 9/2007 |
| WO | WO 2007/104783 | 9/2007 |
| WO | 2007/113276 | 10/2007 |
| WO | WO 2007/113276 | 10/2007 |
| WO | 2007/122258 | 11/2007 |
| WO | 2007/135527 | 11/2007 |
| WO | 2007/135529 | 11/2007 |
| WO | WO 2007/122258 | 11/2007 |
| WO | WO 2007/135527 | 11/2007 |
| WO | WO 2007/135529 | 11/2007 |
| WO | 2008/006540 | 1/2008 |
| WO | 2008/008539 | 1/2008 |
| WO | 2008/012622 | 1/2008 |
| WO | 2008/012623 | 1/2008 |
| WO | WO 2008/006540 | 1/2008 |
| WO | WO 2008/008539 | 1/2008 |
| WO | WO 2008/012622 | 1/2008 |
| WO | WO 2008/012623 | 1/2008 |
| WO | 2008/032191 | 3/2008 |
| WO | WO 2008/032191 | 3/2008 |
| WO | 2008/045393 | 4/2008 |
| WO | WO 2008/045393 | 4/2008 |
| WO | 2008/051197 | 5/2008 |
| WO | 2008/057855 | 5/2008 |
| WO | WO 2008/051197 | 5/2008 |
| WO | WO 2008/057855 | 5/2008 |
| WO | 2008/076225 | 6/2008 |
| WO | WO 2008/076225 | 6/2008 |
| WO | 2008/078091 | 7/2008 |
| WO | 2008/078100 | 7/2008 |
| WO | WO 2008/078091 | 7/2008 |
| WO | WO 2008/078100 | 7/2008 |
| WO | 2008/100715 | 8/2008 |
| WO | WO 2008/100715 | 8/2008 |
| WO | 2008/107125 | 9/2008 |
| WO | 2008/107479 | 9/2008 |
| WO | 2008/107480 | 9/2008 |
| WO | 2008/107481 | 9/2008 |
| WO | 2008/112483 | 9/2008 |
| WO | WO 2008/107125 | 9/2008 |
| WO | WO 2008/107479 | 9/2008 |
| WO | WO 2008/107480 | 9/2008 |
| WO | WO 2008/107481 | 9/2008 |
| WO | WO 2008/112483 | 9/2008 |
| WO | 2008/124085 | 10/2008 |
| WO | 2008/130853 | 10/2008 |
| WO | WO 2008/124085 | 10/2008 |
| WO | WO 2008/130853 | 10/2008 |
| WO | 2008/132139 | 11/2008 |
| WO | 2008/132142 | 11/2008 |
| WO | 2008/145616 | 12/2008 |
| WO | 2008/150232 | 12/2008 |
| WO | 2008/150233 | 12/2008 |
| WO | WO 2008/145616 | 12/2008 |
| WO | WO 2008/150232 | 12/2008 |
| WO | WO 2008/150233 | 12/2008 |
| WO | 2009/004430 | 1/2009 |
| WO | WO 2009/004430 | 1/2009 |
| WO | 2009/033702 | 3/2009 |
| WO | 2009/033703 | 3/2009 |
| WO | 2009/033704 | 3/2009 |
| WO | WO 2009/033702 | 3/2009 |
| WO | WO 2009/033703 | 3/2009 |
| WO | WO 2009/033704 | 3/2009 |
| WO | 2009/041567 | 4/2009 |
| WO | 2009/045753 | 4/2009 |
| WO | WO 2009/041567 | 4/2009 |
| WO | WO 2009/045753 | 4/2009 |
| WO | 2009/062676 | 5/2009 |
| WO | WO 2009/062676 | 5/2009 |
| WO | 2009/091374 | 7/2009 |
| WO | 2009/094265 | 7/2009 |
| WO | WO 2009/091374 | 7/2009 |
| WO | WO 2009/094265 | 7/2009 |
| WO | 2009/110901 | 9/2009 |
| WO | WO 2009/110901 | 9/2009 |
| WO | 2009/124609 | 10/2009 |
| WO | WO 2009/124609 | 10/2009 |
| WO | 2009/140163 | 11/2009 |
| WO | 2009/140166 | 11/2009 |
| WO | WO 2009/140163 | 11/2009 |
| WO | WO 2009/140166 | 11/2009 |
| WO | 2009/148403 | 12/2009 |
| WO | WO 2009/148403 | 12/2009 |
| WO | 2010/009062 | 1/2010 |
| WO | WO 2010/009062 | 1/2010 |
| WO | 2010/022076 | 2/2010 |
| WO | 2010/022081 | 2/2010 |
| WO | WO 2 010/022 081 | 2/2010 |
| WO | WO 2010/022076 | 2/2010 |
| WO | 2010/025890 | 3/2010 |
| WO | WO 2010/025890 | 3/2010 |
| WO | 2010/043396 | 4/2010 |
| WO | WO 2010/043396 | 4/2010 |
| WO | 2010/060589 | 6/2010 |
| WO | 2010/063054 | 6/2010 |
| WO | WO 2010/060589 | 6/2010 |
| WO | WO 2010/063054 | 6/2010 |
| WO | 2010/089303 | 8/2010 |
| WO | 2010/089372 | 8/2010 |
| WO | WO 2010/089303 | 8/2010 |
| WO | 2010/114726 | 10/2010 |
| WO | 2010/117926 | 10/2010 |
| WO | WO 2010/114726 | 10/2010 |
| WO | WO 2010/117926 | 10/2010 |
| WO | 2010/130422 | 11/2010 |
| WO | 2010/130423 | 11/2010 |
| WO | 2010/130424 | 11/2010 |
| WO | WO 2010/130422 | 11/2010 |
| WO | WO 2010/130423 | 11/2010 |
| WO | WO 2010/130424 | 11/2010 |
| WO | WO-2010130424 A1 * 11/2010 ............. A61K 45/06 |
| WO | 2010/141360 | 12/2010 |
| WO | WO 2010/141360 | 12/2010 |
| WO | 2011/014462 | 2/2011 |
| WO | 2011/022312 | 2/2011 |
| WO | WO 2011/022312 | 2/2011 |
| WO | 2011/034741 | 3/2011 |
| WO | 2011/034828 | 3/2011 |

(56) References Cited

FOREIGN PATENT DOCUMENTS

| WO | 2011/034830 | 3/2011 |
|---|---|---|
| WO | 2011/034832 | 3/2011 |
| WO | WO 2011/034741 | 3/2011 |
| WO | WO 2011/034828 | 3/2011 |
| WO | WO 2011/034830 | 3/2011 |
| WO | WO 2011/034832 | 3/2011 |
| WO | 2011/047860 | 4/2011 |
| WO | 2011/051490 | 5/2011 |
| WO | WO 2011/051490 | 5/2011 |
| WO | 2011/073347 | 6/2011 |
| WO | 2011/109277 | 9/2011 |
| WO | 2011/116356 | 9/2011 |
| WO | WO 2011/109277 | 9/2011 |
| WO | WO 2011/116356 | 9/2011 |
| WO | 2011/136723 | 11/2011 |
| WO | 2011/137046 | 11/2011 |
| WO | WO 2011/136723 | 11/2011 |
| WO | WO 2011/137046 | 11/2011 |
| WO | 2011/156245 | 12/2011 |
| WO | WO 2011/156245 | 12/2011 |
| WO | 2012/021382 | 2/2012 |
| WO | WO 2012/021382 | 2/2012 |
| WO | 2012/062750 | 5/2012 |
| WO | 2012/062751 | 5/2012 |
| WO | 2012/062752 | 5/2012 |
| WO | 2012/062759 | 5/2012 |
| WO | WO 2012/062750 | 5/2012 |
| WO | WO 2012/062751 | 5/2012 |
| WO | WO 2012/062752 | 5/2012 |
| WO | WO 2012/062759 | 5/2012 |
| WO | 2012/109491 A1 | 8/2012 |
| WO | 2012/143116 | 10/2012 |
| WO | 2012/143117 | 10/2012 |
| WO | 2012/151136 | 11/2012 |
| WO | 2012/151139 | 11/2012 |
| WO | 2012/151140 | 11/2012 |
| WO | WO 2012/151136 | 11/2012 |
| WO | WO 2012/151139 | 11/2012 |
| WO | WO 2012/151140 | 11/2012 |
| WO | 2013/138687 | 9/2013 |
| WO | 2013/192306 | 12/2013 |
| WO | 2014/078377 A1 | 5/2014 |
| WO | 2014/078568 | 5/2014 |
| WO | 2014/144663 | 9/2014 |
| WO | 2014/176460 | 10/2014 |
| WO | 2014/195311 | 12/2014 |
| WO | 2015/032790 | 3/2015 |
| WO | 2016/016380 | 2/2016 |
| WO | 2016/092002 | 6/2016 |

OTHER PUBLICATIONS

Ago et al., "Activation of Metabotropic Glutamate 2/3 Receptors Attenuates Methamphetamine-Induced Hyperlocomotion and Increase in Prefrontal Serotonergic Neurotransmission", Psychopharmacology, 2011, 217, 443-452.
Allen et al., "Group II Metabotropic Glutamate Receptor Activation Attenuates Traumatic Neuronal Injury and Improves Neurological Recovery After Traumatic Brain Injury", J Pharmacol. Exp. Ther., 1999, 290(1), 112-120.
Altamura et al., "Plasma and Platelet Exctitatory Amino Acids in Psychiatric Disorders", Am J Psychiatry, 1993, 150(11), 1731-1733.
Anantha Shekhar et al, Panic disorder and agoraphobia: Novel glutamate mechanisms and therapeutic approaches from preclinical model, ACNP 52nd Annual Conference, 2013, S582-S583, article No. W220.
Aronica et al., "Status Epilepticus-Induced Alterations in Metabotropic Glutamate Receptor Expression in Young and Adult Rats", J. Neurosci., 1997, 17(21), 8588-8595.
Aronson et al., "Triiodothyronine Augmentation in the Treatment of Refractory Depression. A Meta-Analysis", Arch Gen Psychiatry, 1996, 53, 842-848.

Bakker et al., "Activation of the Metabotropic Glutamate Receptor 2 (Mglu2) by Orthosteric and Allosteric Ligands", Poster 642.6/E30 Presented at the 40.sup.th Annual Meeting of Society for Neuroscience 2010, 1 page.
Battaglia et al., "Selective Activation of Group-II Metabotropic Glutamate Receptors is Protective Against Excitotoxic Neuronal Death," European Journal of Pharmacology, 1998, 356(2-3), 271-274.
Bertha et al., "Measurement of Glutamate and Glutamine in the Medial Prefrontal Cortex of Never-Treated Schizophrenic Patients and Healthy Controls by Proton Magnetic Resonance Spectroscopy", Archives of General Psychiatry, 1997, 54(10), 959-965.
Bespalov et al., "Behavioral Characterization of the Mglu Group II/III Receptor Antagonist, Ly-341495, in Animal Models of Anxiety and Depression", European Journal of Pharmacology 2008, 592, 96-102.
Bilkei-Gorzo et al., "MCPP-Induced Anxiety in the Light-Dark Box in Rats—A New Method for Screening Anxiolytic Activity", Psychopharmacology (Berl), 1998, 136(3), 291-298.
Black et al., "Compound A, A Novel, Potent and Selective Mglur2 Positive Allosteric Modulator: II. Effects in Models Predictive of Therapeutic Activity Against Cognitive Impairment Associated with Schizophrenia", Poster 767.7 Presented at the 40.sup.th Annual Meeting of Society for Neuroscience, Nov. 2010, 1 page.
Bortolotto et al., "Roles of Metabotropic Glutamate Receptors in LTP and LTD in the Hippocampus", Current Opinion in Neurobiology, 1999, 9(3), 299-304.
Brauner-Osborne et al., "A New Highly Selective Metabotropic Excitatory Amino Acid Agonist: 2-Amino-4-(3-Hydroxy-5-Methylisoxazol-4-Yl)Butyric Acid", Journal of Medicinal Chemistry, 1996, 39(16), 3188-3194.
Brauner-Osborne et al., "Interaction of CPCCOET with a Chimeric Mglulb and Calcium Sensing Receptor", Neuroreport, 1999, 10(18), 3923-3925.
Bruno et al., "Activation of Metabotropic Glutamate Receptors Coupled to Inositol Phospholipid Hydrolysis Amplifies NMDA-Induced Neuronal Degeneration in Cultured Cortical Cells", Neuropharmacology, 1995, 34(8), 1089-1098.
Bruno et al., "Molecular Dynamics Simulation of the Heterodimeric Mglur2/5ht(2a) Complex. An Atomistic Resolution Study of a Potential New Target in Psychiatric Conditions", J. Chem. Inf. Model., 2009, 49(6), 1602-1616.
Bruno et al., "The Neuroprotective Activity of Group-II Metabotropic Glutamate Receptors Requires New Protein Synthesis and Involves a Glial-Neuronal Signaling", J. Neurosci., 1997, 17(6), 1891-1897.
Buisson et al., "The Inhibitory Mglur Agonist, S-4-Carboxy-3-Hydroxy-Phenylglycine Selectively Attenuates NMDA Neurotoxicity and Oxygen-Glucose Deprivation-Induced Neuronal Death", Neuropharmacology, 1995, 34(8), 1081-1087.
Byrnes et al., "Metabotropic Glutamate Receptors as Targets for Multipotential Treatment of Neurological Disorders", Neurotherapeutics, 2009, 6(1), 94-107.
Campbell et al., "An Update on Regional Brain Volume Differences Associated with Mood Disorders", Curr Opin Psychiatry, 2006, 19(1), 25-33.
Carl E. Stafstorm., Mechanisms of action of antiepileptic drugs: the search for synergy, Current Opinion in Neurology, 2010, pp. 157-163, vol. 23.
Cartmell et al., "Tolerance to the Motor Impairment, But Not the Reversal of PCP-Induced Motor Activities by Oral Administration of the Mglu2/3 Receptor Agonist, Ly379268", Naunyn Schmiedebergs Arch Pharmacol, 2000, 361, 39-46.
Cid, "Discovery of a Potent and Orally Bioavailable Positive Allosteric Modulator of Mglur2 for the Treatment of CNS Disorders", Presentation Slides, 16.sup.th SCI/RSC Medicinal Chemistry Symposium, Cambridge, Sep. 2011, 26 pages.
Cid, "JNJ-42153605: A Novel Positive Allosteric Modulator of Mglur2 for the Treatment of CNS Disorders" Presentation Slides, RICT 2012--48.sup.th International Conference on Medicinal Chemistry, Poitiers 2012, 28 pages.
Citrome, "Adjunctive Aripiprazole, Olanzapine, or Quetiapine for Major Depressive Disorder: An Analysis of Number Needed to

(56) References Cited

OTHER PUBLICATIONS

Treat, Number Needed to Harm, and Likelihood to Be Helped or Harmed", Postgraduate Medicine, 2010, 122(4), 39-48.
Cozzi et al., "Type 2 Metabotropic Glutamate (Mglu) Receptors Tonically Inhibit Transmitter Release in Rat Caudate Nucleus: in Vivo Studies with (2s,1's,2's,3'r)-2-(2'-Carboxy-3'-Phenylcyclopropyl)Glycine, A New Potent and Selective Antagonist", European Journal of Neuroscience, 1997, 9(7), 1350-1355.
Cube et al., "3-(2-Ethoxy-4-{4[3-Hydroxy-2-Methyl-4-(3-Methylbutanoyl)-Phenoxy]Butoxy}Phenyl)Propanoic Acid: A Brain Penetrant Allosteric Potentiator at the Metabotropic Glutamate Receptor 2 (Mglur2)", Bioorganic & Medicinal Chemistry Letters, 2005, 15, 2389-2393.
D'Onofrio et al., "Neuroprotection Mediated by Glial Group-II Metabotropic Glutamate Receptors Requires the Activation of the Map Kinase and the Phosphatidylinositol-3-Kinase Pathways", Journal of Neurochemistry, 2001, 78(3), 435-445.
De Boer et al., "Characterization of the Clinical Effect of a Positive Allosteric Modulator of the Metabotropic Glutamate Receptor-2", Society of Biological Psychiatry 67.sup.th Annual Scientific Convention, May 2012, 2 pages.
De Novellis et al., "Type 1 and II Metabotropic Glutamate Receptors Modulate Periaqueductal Grey Glycine Release: Interaction Between Mglu2/3 and A1 Adenosine Receptors", Neuropharmacology, 2002, 43(7), 1061-1069.
Del Rio et al., "Differential Coupling of G-Protein-Linked Receptors to Ca2+ Mobilization Through Inositol(1,4,5)Trisphosphate or Ryanodine Receptors in Cerebellar Granule Cells in Primary Culture", European Journal of Neuroscience, 1999, 11(9), 3015-3022.
Dhami et al., "Regulation of Metabotropic Glutamate Receptor Signaling, Desensitization and Endocytosis", Pharmacol. Ther., 2006, 111(1), 260-271.
Ermolinsky et al., "Differential Changes in Mglu2 and Mglu3 Gene Expression Following Pilocarpine-Induced Status Epilepticus: A Comparative Real-Time Pcr Analysis", Brain Research, 2008, 1226, 173-180.
Eurasian Patent Organization : Euraisian Notification "On the Necessity to Present Additional Matters", dated Dec. 17, 2008, 3 pages.
Feinberg et al., "The Metabotropic Glutamate (Mglu)2/3 Receptor Antagonist Ly341495 [2s-2-Amino-2-(1s,2s-2-Carboxycyclopropyl-1-Yl)-3-(Xanth-9-Yl)Pr-opanoic Acid] Stimulates Waking and Fast Electroencephalogram Power and Blocks the Effects of the Mglu2/3 Receptor Agonist Ly379268 [(−)-2-Oxa-4-Aminobicyclo[3.1.0]Hexane-4,6-Dicarboxylate] in Rats", Jpet, 2005, 312, 826-833.
Fell et al., "Activation of Metabotropic Glutamate (Mglu)2 Receptors Suppresses Histamine Release in Limbic Brain Regions Following Acute Ketamine Challenge", Neuropharmacology, 2010, 58, 632-639.
Fell et al., "N-(4-((2-(Trifluoromethyl)-3-Hydroxy-4-(Isobutyryl)Phenoxy)Methyl)Benzyl- )-1-Methyl-1h-Imidazole-4-Carboxamide (Thiic), A Novel Metabotropic Glutamate 2 Potentiator with Potential Anxiolytic/Antidepressant Properties: in Vivo Profiling Suggests a Link Between Behavioral and Central Nervous System Neurochemical Changes", Jpet, 2011, 336, 165-177.
Fenton et al., "The Role of a Prescription in Anxiety Medication Use, Abuse, and Dependence", Am J Psychiatry, 2010, 167, 1247-1253.
Ferraguti et al., "Metabotropic Glutamate 1 Receptor: Current Concepts and Perspectives", Pharmacol Rev, 2008, 60, 536-581.
Fujii et al., "Lecterns. IX. Generation of Latam Carbonyl Function in 1,3-Disubstituted Piperidines by Mercuric Acetate-Edta Oxidation: Effects of Hydrocarbon Substituents at the 3-Postion", Chem. Pharm. Bull., 1977, 25(9), 2336-2342.
Fujita et al., "Studies on 1-Alkyl-2(1h)-Pyridone Derivatives XXXII. The Friedel-Crafts Reaction of 1-Alkyl-2(1h)-Pyridone Derivatives with Acid Anhydride", Journal of the Pharmaceutical Society of Japan, 1990, 110, 449-452.
Galici et al., "Biphenyl-Indanone A, A Positive Allosteric Modulator of the Metabotropic Glutamate Receptor Subtype 2, Has Antipsychotic- and Anxiolytic-Like Effects in Mice", Journal of Phamacology and Experimental Therapeutics, 2006, 318(1), 173-185.
Garriock et al., "Genetic Studies of Drug Response and Side Effects in the Star*D Study, Part 1", J Clin Psychiatry, 2009, 70(8), 1186-1187.
Gewald. "Heterocyclen Aus Ch-Aciden Nitrilen, VII. 2-Amino-Thiophene Aus A-Oxo-Mercaptanen Und Methylenaktiven Nitrilen", Chemische Berichte, 1965, 98, 3571-3577.
Giovannelli et al., "Comet Assay as a Novel Approach for Studying Dna Damage in Focal Cerebral Ischemia: Differential Effects of NMDA Receptor Antagonists and Poly(Adp-Ribose)956 Polymerase Inhibitors", Journal of Cerebral Blood Flow and Metabolism, 2002, 22, 697-704.
Goodman et al., "The Pharmacological Basis of Therapeutics: Chapter 21—Pharmacotherapy of the Epilepsies", 12.sup.th Edition, 2011, 27 pages.
Gouzoulis-Mayfrank, "Inhibition of Return in the Human 5ht2a Agonist and Nmda Antagonist Model of Psychosis", Neuropsychopharmacology, 2006, 31, 431-441.
H. Steve White et al., General Principles: Experimental Selection, Quantification, and Evaluation of Antiepileptic Drugs, Antiepeleptic Drugs, Fourth Edition, 1995, pp. 99-110, chapter 7, Raven Press, Ltd, New York.
Hanfeld et al., "Synthese Von 3-Cyan-6-Methyl-4-Pyridyl-Und 3-Cyan-4-Methyl-6-Pyridyl-Pyrid-2(1h)-Onen Und—Thionen", Pharmazie, 1988, 43, 762-764.
Hartveit et al., "Expression of the Mrna of Seven Metabotropic Glutamate Receptors (Mglurl to 7) in the Rat Retina. An in Situ Hybridization Study on Tissue Sections and Isolated Cells", Eur. J Neurosci., 1995, 7(7), 1472-1483.
He et al., "Conformational Color Polymorsphism and Control of Crystallization of 5-Methyl-2[(4-Methyl-2-Mitrophenyl0amino}-3-Thiophenecarbonitrile", Journal of Pharmaceutical Sciences, 2001, 90(3), 371-388.
Helton et al., "Anxiolytic and Side-Effect Profile for Ly354740: A Potent, Highly Selective, Orally Active Agonist for Group II Metobotropic Glutamate Receptors", Journal of Phamacologyand Experimental Therapeutics, 1998, 284(2), 651-660.
Hermans et al., "Structural, Signalling and Regulatory Properties of the Group 1 Metabotropic Glutamate Receptors: Prototypic Family C G-Protein-Coupled Receptors", Biochem. J., 2001, 359, 465-484.
Hirao et al., "Preparation of Optically Active 8,8'-Disubstituted 1,1'-Biisoquinoline", Heterocycles, 1996, 42(1), 415-422.
Hoeben et al., "Prediction of Serotonin 2a Receptor (5-Ht.sub.2ar) Occupancy in Man From Nonclinical Pharmacology Data. Exposure Vs. 5-Ht.sub.2ar Occupancy Modeling Used to Help Design a Positron Emission Tomography (Pet) Study in Healthy Male Subjects", Abstract, 2013 Annual Meeting of the Population Approach Group in Europe, 2 pages.
Horiguchi et al., "Interactions Among the Atypical Antipsychotic Drug (APD), Lurasidone, 5-HT1A and Metabotropic Glutamate Receptor 2/3 (Mglur2/3) Agonism, and 5-HT2A Antagonism, to Attenuate Phencyclidine (PCP)-Induced Deficit in Rat Novel Object Recognition (NOR)" Poster 610.12 Presented At the 40.sup.th Annual Meeting of Society for Neuroscience, 2010, 1 page.
Huang et al., "Potentiation of the Novel Atypical Antipsychotic Drug Lurasidone-Induced Dopamine Efflux in Rat Medial Prefrontal Cortex and Hippocampus by DA D1 and Mglur2/3 Agonism but not D3 Receptor Antagonism" Poster 610.13 Presented at the 40.sup.th Annual Meeting of Society for Neuroscience, Nov. 2010, 1 page.
Iacovelli et al., "Regulation of Group II Metabotropic Glutamate Receptors by G Protein-Coupled Receptor Kinases: Mglu2 Receptors are Resistant to Homologous Desensitization", Mol Pharmacol., 2009, 75(4), 991-1003.
Inset, et al., "Research Domain Criteria (Rdoc): Toward a New Classification Framework for Research on Mental Disorders", Am. J. Psychiatry, Jul. 2010, 167(7), 748-751.
International Patent Application No. PCT/EP2008/52767: International Search Report dated Jul. 2, 2008, 13 pages.
Japanese Patent Application No. 2008-558820: Office Action dated Aug. 28, 2012, 14 pages.

(56) References Cited

OTHER PUBLICATIONS

Japanese Patent Application No. 2009-552215: Office Action dated Dec. 18, 2012, 3 pages.
Jin et al., "The Mglur2 Positive Allosteric Modulator Bina Decreases Cocaine Self-Administration and Cue-Induced Cocaine-Seeking and Counteracts Cocaine-Induced Enhancement of Brain Reward Function in Rats", Neuropsych., 2010, 35(10), 2021-2036.
Johansen et al., "Excitatory Amino Acid Receptor Ligands: Resolution, Absolute Stereochemistry, and Enantiopharmacology of 2-Amino-3-(4-Butyl-3-Hydroxyisoxazol-5-Yl)Propionic Acid", J of Medicinal Chem, 1998, 41(6), 930-939.
John et al., "Rapid Changes in Glutamate Levels in the Posterior Hypothalamus Across Sleep-Wake States in Freely Behaving Rats", American Journal of Physiology—Regulatory Integrative & Comparative Physiology, 2008, 205(6), R2041-2049.
Johnson et al., "Allosteric Modulators of Metabotropic Glutamate Receptors: Lessons Learnt From Mglu1, Mglu2 and Mglu5 Potentiators and Antagonists", Biochemical Society Transactions, 2004, 32(5) 881-887.
Jones et al., "A Rotarod Suitable for Quantitative Measurements of Motor Incoordination in Naive Mice" Naunyn Schmiedebers Arch. Exper. Pathol. Pharmacol., 1968, 259, 211.
Jones et al., "Discovery, Synthesis, and Structure-Activity Relationship Development of a Series of N-4-(2,5-Dioxopyrrolidin-1-Yl)Phenylpicolinamides (Vu0400195, MI182): Characterization of a Novel Positive Allosteric Modulator of the Metabotropic Glutamate Receptor 4 (Mglu4) with Oral Efficacy in an Antiparkinsonian Animal Model", J Med Chem, 2011 54, 7639-7647.
Kappe et al., "Aktive Malonester Als Synthons Fur Heterocyclen: Eine Methode Zur Herstellung Von 4-Hydroxy-2(1h)-Pyridonen", Journal of Heterocyclic Chemistry, 1988, 463-468.
Kehne et al., "Anxiolytic Effects of Buspirone and Gepirone in the Fear-Potentiated Startle Paradigm", Psychopharmacoloqy, 1988, 94, 8-13.
Kellner et al. "Effects of Metabotropic Glutamate2/3 Receptor Agonist (Ly544344/Ly354740) on Panic Anxiety Induced by Cholecystokinin Tetrapeptide in Health Humans: Preliminary Results", Psychopharmacology, 2005, 179, 310-315.
Kenny et al., "Group II Metabotropic and Alpha-Amino-3-Hydroxy-5-Methyl-4-Isoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.
Kenny et al., "The Ups and Downs of Addiction: Role of Metabotropic Glutamate Receptors", Trends in Pharmacological Sciences, 2004, 25(5), 265-272.
Kent et al. "Efficacy and Safety of a Novel mGlu2 Receptor Positive Allosteric Modulator as an Adjunctive Treatment to an SSRI/SNRI in the Treatment of Anxious Depression" Abstract to poster and oral presentation, American Society of Clinical Psychopharmacology (ASCP) 2014 Annual Meeting, Jun. 16-19, 2014 Westin Diplomat, Hollywood, Florida).
Kew et al., "Activity-Dependent Presynaptic Autoinhibition by Group II Metabotropic Glutamate Receptors at the Perforant Path Inputs to the Dentate Gyrus and Ca1", Neuropharmacology, 2001, 40, 20-27.
Khimia Geterotsiklicheskikh Soedinenii, 1985, 5, 646-649.
Khimia Geterotsiklicheskikh Soedinenii, 1986, 8, 1118-1123.
Kim et al., "Neurofilament-M Interacts with the DI Dopamine Receptor to Regulate Cell Surface Expression and Desensitization", Journal of Neuroscience, 2002, 22(14), 5920-5930.
Kiselyov et al., "A One Pot Synthesis of Polysubstituted Inidazo[1,2-A]Pyridines", Tetrahedron Letters, 2006, 47, 2941-2944.
Kitano et al., "Synthesis and Antifouling Activity of 3-Isocyanotheonellin and Its Analogues", Jour Chem Soc Perkin Trans. 2002, 2251-2255.
Klein "Mixed Anxiety Depression. For and Against", L'encephale, 1993, 493-495.
Klodzinska et al., "Selective Group II Glutamate Metabotropic Receptor Agonist Ly354740 Attenuates Pentetrazole- and Picrotoxin-Induced Seizures", Pol J Pharmacol, 1999, 51, 543-545.
Koh et al., "Non-NMDA Receptor-Mediated Neurotoxicity in Cortical Culture", J. Neurosci., 1990, 10(2), 693-705.
Konstantakopoulos et al., "Lamotrigine Associated Exacerbation of Positive Symptoms in Paranoid Schizophrenia", Schizophr Res., 2008, 98(1-3), 325-326.
Koolschijn et al., "Brain Volume Abnormalities in Major Depressive Disorder: A Meta-Analysis of Magenetic Resonance Imaging Studies", Hum Brain Mapp, 2009, 30(11), 3719-3735.
Kostrzewa et al., "Supersensitized DI Receptors Mediate Enhanced Oral Activity After Neonatal 6-Ohda. Pharmacology". Biochemistry & Behavior, 1991, 39(3), 677-682.
Krohnke et at., "Methylketon-Addukte Der Chinolinium-Und Isochinolinium-Reihe", Justus Liebigs Annalen Der Chemie, 1956, 211-228.
Krystal et al., "NMDA Receptor Antagonist Effects, Cortical Glutamatergic Function, and Schizophrenia: Toward a Paradigm Shift in Medication Development", Psychopharmacology, 2003, 169(3-4), 215-33.
Lamers et al., "Comorbidity Patterns of Anxiety and Depressive Disorders in a Large Cohort Study: the Netherlands Study of Depression and Anxiety (Nesda)", J Clin Psychiatry, 2011, 72(3), 341-348.
Lavreysen et al., "[.sup.3h]R214127: A Novel High-Affinity Radioligand for the Mglu1 Receptor Reveals a Common Binding Site Shared by Multiple Allosteric Antagonists", Mol Pharmacol, 2003, 63, 1082-1093.
Lavreysen et al., "JNJ16259685, A Highly Potent, Selective and Systemically Active Mglu1 Receptor Antagonist" Neuropharmacology 2004, 47, 961-972.
Lebois, "Neither Typical Nor Atypical: Ly404039 Provides Proof of Concept That Selective Targeting of Mglur2/3 Receptors is a Valid Mechanism for Obtaining Antipsychotic Efficacy", Curr. Top. Med. Chem., 2008, 8(16), 1480-1481.
Lee et el., "The Mglu2/3 Receptor Agonist Ly354740 Suppresses Immobilization Stress-Induced Increase in Rat Prefrontal Cortical Bdnf Mrna Expression", Neuroscience Letters, 2006, 398, 328-332.
Leever et al., "Identification of a Site in Glur1 and Glur2 That is Important for Modulation of Deactivation and Desensitization", Mol Pharmacol, 2003, 64(1), 5.
Levine et al., "Abstracts/Neurupharmacology", 2002, 43, 294-295.
Li et al., "Design and Synthesis of 4-Arylpiperidinyl Amide and N-Arylpiperdin-3-Yl-Cyclopropane Carboxamide Derivatives as Novel Melatonin Receptor Ligands", Bioorganic & Medicinal Chemistry Letters, 2011, 21, 1236-1242.
Liebowitz et al., "Biological Accompaniments of Lactate-Induced Panic", Psychopharmacology Bulletin, 1984, 20(1), 43-44.
Liechti et al., "Metabotropic Glutamate 2/3 Receptor Activation Induced Reward Deficits But Did Not Aggravate Brain Reward Deficits Associated with Spontaneous Nicotine Withdrawal in Rats", Biochemical Pharmacology, 2007, 74, 1299-1307.
Lopez-Rodriguez et al., "Changes in Extracellular Glutamate Levels in Rat Orbitofrontal Cortext During Sleep and Wakefulness", Arch Med Res, 2007, 38, 52-55.
M. Foster Olive., Metabotropic Glutamate Receptor Ligands as Potential Therapeutics for Addiction, Current Drug Abuse Reviews, 2009, pp. 83-98, vol. 2 Issue 1, Bentham Science Publishers Ltd.
Macdonald "The Design of Allosteric Modulators for the Treatment of CNS Disorders", 11.sup.th Advances and Progress in Drug Design, Feb. 2012, 36 pages.
Macdonald, "Positive Allosteric Modulation of Mglur2 Receptors in the Treatment of CNS Disorders", 3.sup.rd Symposium on GPCRS in Medicinal Chemistry, Oss, Sep. 2010, 29 pages.
Macdonald, "The Design of Mglur Modulators for the Treatment of CNS Disorders" Presentation Slides, 6.sup.th Anglo-Swedish Medicinal Chemistry Symposium, Stockholm, 19.sup.th Jun. 2013, 1 page.
Maione et al., "Characterisation of Mglurs Which Modulate Nociception in the Pag of the Mouse", Neuropharmacology, 1998, 37(12), 1475-1483.

(56) References Cited

OTHER PUBLICATIONS

Malames et al., "N-Substituted Spirosuccinimide, Spiropyridazine, Spiroazetidine, and Acetic Acid Aidose Reductase Inhibitiors Derived From Isoquinoline-1,3-Dinoes. 2", J Med Chem., 1994, 37(13), 2059-2070.
Malatynska et al., "Levels of Mrna for A-, B-, and 1-Synuclein in the Brains of Newborn, Juvenile, and Adult Rats", J Mol Neurosci., 2006, 29(3), 269-77.
Martella et al., "Enhanced Sensitivity to Group II Mglu Receptor Activation at Corticostriatal Synapses in Mice Lacking the Familial Parkinsonism-Linked Genes Pink1 or Parkin.", Exp. Neurol., 2009, 215(2), 388-396.
Matrisciano et al., "Activation of Group-II Metabotropic Glutamate Receptors Promotes DNA Demethylation in the Mouse Brain", Molecular Pharmacology, Apr. 2011, 52 pages.
Matrisciano et al., "Defective Group-II Metaboropic Glutamate Receptors in the Hippocampus of Spontaneously Depressed Rats", Neuropharmacology, 2008, 55(4), 525-531.
Matrisciano, "Metabotropic Glutamate Receptors and Neuroadaptation to Antidepressants: Imipramine-Induced Down-Regulation of B-Adrenergic Receptors in Mice Treated with Metabotropic Glutamate 2/3 Receptor Ligands", Journal of Neurochemistry, 2005, 93, 1345-1352.
McElroy, "A 52-Week, Open-Label Continuation Study of Lamotrigine in the Treatment of Bipolar Depression", J. Clin. Psychiatry, 2004, 204-210.
Metman, "Huntington's Disease a Randomized, Controlled Trial Using the NMDA-Antagonist Amantadine", Neurology, 2002, 59, 694-699.
Moldrich et al., "Glutamate metabotropic receptors as targes for drug therapy in epilepsy", Eur J Pharmacol. 2003, vol. 476, pp. 3-16.
Mudge et al., "Genomic Convergence Analysis of Schizophrenia: Mrna Sequencing Reveals Altered Synaptic Vesicular Transport in Post-Mortem Cerebellum", Plos One, 2008, 3(11) 1-24.
Mula et al., The role of anticonvulsant drugs in anxiety disorders: a critical review of the evidence, J Clin Pshycopharmacol 2007, vol. 27, pp. 263-27.
Muralidharan and Bhagwagar, Potential of levetiracetam in mood disorders: a preliminary review, CNS Drugs 2006, vol. 20, pp. 959-979.
Muto et al., "Structures of the Extracellular Regions of the Group II/III Metabotropic Glutamate Receptors", Proc. Natl. Acad. Sci. USA, 2007, 104(10), 3759-3764.
Myhrer et al.. Capacities of metabotropic glutamate modulators in counteracting soman-induced seizures in rates, European Journal of Pharmacology, Sep. 7, 2013, pp. 253-261, 718.
Naimoli et al., "Compound A, A Novel Potent and Selective Mglur2 Positive Allosteric Modulator: III. Effects in Clinically Relevant Translational Cognition Models That Could be Used as Biomarkers" Poster 767.1 Presented at the 40.sup.th Annual Meeting of Society for Neuroscience, Nov. 2010, 1 page.
Nakamura et al., "An Efficient Synthesis of Platelet-Activating Factor (Paf) J'ij L-Qalkyl-2-.about.-(3-Isoxazolyl)-Sn_Glycero-3-Phosphocholine, A New Paf Agonist. Utilization of the 3-Isoxazolyloxy Group as a Protected Hydroxyl", Tetrahedron Letters, 1990, 31, 699-702.
Neale, "The Neurotransmitter N-Acetylaspartylglutamate in Models of Pain, Als, Diabetic Neuropathy CNS Injury and Schizophrenia", Trends in Pharmacological Sciences 2005, 26(9), 477-484.
Ngomba et al., "The Preferential Mglu2/3 Receptor Antagonist, Ly341495, Reduces the Frequency of Spike-Wave Discharges in the Wag/Rij Rat Model of Absence Epilepsy", Neuropharmacology, 2006, 19, 80 103.
Nicoletti et al., "Metabotropic Glutamate Receptors: New Targets for the Control of Tumor Growth", Trends in Phermecological Sciences, 2007, 206-213.
Niemegeers et al., "Protection of Rats from Compound 48/80-Induced Lethality. A Simple Test for Inhibitors of Mast Cell-Mediated Shock", Arch. Int. Pharmacodyn., 1978, 234, 164-176.
Nofzinger et al., "Changes in Forebrain Function from Waking to Rem Sleep in Depression: Preliminary Analyses of [18]Fdg Pet Studies", Psychiatry Res, 1999, 91, 59-78.
Nowack et al., Levetiracetam reverses synaptic deficits produced by overexpression of SV2A, PLoS One 2011, vol. 6 (12), e29560).
Olszewski et al., "Naag Peptidase Inhibition Reduces Locomotor Activity and Some Stereotypes in the Pep Model of Schizophrenia Via Group II Mglur", J. Neurochem., 2004, 89(4), 876-885.
Orlowski et al., "D-and L-Stereoisomers of Allylglycine: Conulsive Action and Inhibition of Brain L-Glutamate Decarboxylase", J Neurochem, 1977, 28, 349-353.
Orrenius et al., "Calcium Ions and Oxidative Cell Injury", Annals of Neurology, 1992, 32 (Supp)-42), S33-S42.
Overstreet et al., "A 5-Htla Agonist and a 5-Ht2c Antagonist Reduce Social Interaction Deficit Induced by Multiple Ethanol Withdrawals in Rats", Psychopharmacology, 2003, 167, 344-352.
Palop et al., "Amyloid-B—Induced Neuronal Dysfunction in Alzheimer's Disease: From Synapses Toward Neural Networks", Nature Neuroscience, 2010, 13(7), 812-818.
Patani et al. (Chem Rev, 1996, 96, 3147-3176).
Patsalos, Pharmacokinetic profile of levetiracetam: toward ideal characteristics, Pharmacology & Therapeutics 2000, vol. 85, 77-85.
Peter de Boer et al., Characterization of the Clinical Effect of a Positive Allosteric Modulator of the Metabotropic Glutamate Receptor-2, Society of Biological Psychiatry 67th annual Scientific Convention & Program May 3-5, 2012, PA, US, Dec. 15, 2012, 2013-P-1060-SOBP, Poster Abstract.
Petroff et al., Glutamate-glutamine cycling in the epileptic human hippocampus, Epilepsia 2002, vol. 43(7), pp. 703-710.
Piazzini et al., Levetiracetam: An improvement of attention and of oral fluency in patients with partial epilepsy, Epilepsy Research 2006, vol. 68, pp. 181-188.
Pilc et al., "Mood Disorders: Regulation by Metabotropic Glutamate Receptors", Biochemical Pharmacology, 2000, 75, 997-1006.
Potts et al., "1,2,4-Trizoles. Xxv. he Effect of Pyridine Substitution on the Isomerization of S-Triazolo [4,3-A] Pyridines Into S-Triazolo [1,5-A] Pyridines (1)", J. Heterocycl. Chem., 1970, 7, 1019-1027.
Price et al., Levetiracetam in the Treatment of Neuropathic Pain: Three Case Studies, Clinical Journal of Pain. Jan. 1, 2004, 33-36, vol. 20 No. 1.
Racine, Modification of seizure activity by electrical stimulation II. motor seizure, Electroenceph Clin Neurophysiol 1972, 32, pp. 281-294.
Redondo et al., "Selective Heteronuclear Noe Enhancements in Benzoheterocycles. Effect of Ring Size on Indirect Three-Spin Effects"; Magnetic Resonance in Chemistry, 1988, 26, 511-517.
Reis et al., "Reactions of Tricarbonyl(Vinylketene)Iron(0) Complexes with Imines", Organometallics, 1995, 14, 1586-1591.
Renslo et al., "Synthesis of Aza-, Oxa-, and Thiabicyclo[3.1.0]Hexane Heterocycles From a Common Synthetic Intermediate", Organic Letters, 2005, 7(13), 2627-2630.
Ried et al., "Reactions with Cyclobutenediones, Ix. 3-Hydroxy-Pyridones-(2) From Phenylcyclobutenedione and Enamines", Liebigs Ann. Chem., 1969, 725, 230-233.
Rogawski et al., The neurobiology of antiepileptic drugs for the treatment of nonepileptic conditions, Nat Med 2004, vol. 10, 2004, pp. 685-692, 10.
Ross et al., "Expression of Functional Metabotropic and Ionotropic Glutamate Receptors in Baculovirus-Infected Insect Cells", Neuroscience Letters, 1994, 173(1-2), 139-142.
Roychowdhury et al., "G Protein Betalgamma2 Subunits Promote Microtubule Assembly", J. Biol. Chem., 1997, 272(50), 31576-31581.
Russell et al., "Amyloid-B Acts as a Regulator of Neurotransmitter Release Disrupting the Interaction Between Synaptophysin and Vamp2", Plos One, 2012, 7(8), E43201, 1-14.
Sahara et al., "Cellular Localization of Metabotropic Glutamate Receptors Mglur1, 2/3, 5 and 7 in the Main and Accessory Olfactory Bulb of the Rat", Neuroscience Letters, 2001, 312(2), 59-62.
Sahni et al., "Compound A, A Novel, Potent and Selective Metabotropic Glutamate Receptor 2 (Mglur2) Positive Allosteric Modulator: 1.

(56) References Cited

OTHER PUBLICATIONS

Pharmacological Characterization" Poster 767.6 Presented at the 40.sup.th Annual Meeting of Society for Neuroscience, Nov. 2010, 1 page.
Salih et al. "Pharmacokinetic and pharmacodynamics characterization of JNJ-40411813, a positive allosteric modulator of mGluR2, in two randomized, doubleblind phase-I studies" Journal of Psychopharmacology, 2015, vol. 29(4) 414-425.
Salinska et al., "Metabotropic Glutamate Receptors (Mglurs) are Involved in Early Phase of Memory Formation: Possible Role of Modulation of Glutamate Release", Neurochemistry Intl, 2003, 43, 469-474.
Samadi et al., "Basal Ganglia Group II Metabotropic Glutamate Receptors Specific Binding in Non-Human Primate Model of L-Dopa-Induced Dyskinesias", Neuropharmacology, 2008, 54(2), 258-268.
Satow et al., "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Dedailed Investigations with a Selective Allosteric Metabotropic Glutamate Receptor 1 Antagonist, Ftidc [4-[1-(2-Fluoropyridine-3-Yl)-5-Methyl-1h-1,2,3-Triazol-4-Yl]-Nisopropyl—N-Methyl-3,6-Dihydropyridine-1(2h)-Carboxamide]", J. Pharmacol. Exper. Therapeut., 2008, 326, 577-586.
Saugstad et al., "Cloning and Expression of a New Member of the L-2-Amino-4-Phosphonobutyric Acid-Serisitive Class of Metabotropic Glutamate Receptors", Mol Pharmacol, 1994, 45, 367-372.
Scaccianoce et al., "Endogenous Activation of Group-II Metabotropic Glutamate Receptors Inhibits the Hypothalamic-Pituitary-Adrenocortical Axis", Neuropharmacology, 2003, 44, 555-561.
Schaffhauser et al., "Multiple Pathways for Regulation of the Kcl-Induced [3h]-Gaba Release by Metabotropic Glutamate Receptors, in Primary Rat Cortical Cultures", Brain Res., 1998, 782(1-2), 91-104.
Scheer et al., "Constitutively Active G Protein-Coupled Receptors: Potential Mechanisms of Receptor Activation", Journal of Receptor & Signal Transduction Research, 1997, 17(1-3), 57-73.
Schiffer et al., "Optimizing Experimental Protocols for Quantitative Behavioral Imaging with 18f-Fdg in Rodents", J Nucl Med, 2007, 48, 277-287.
Seedat et al., "Measuring Anxiety in Patients with Schizophrenia", J Nery Ment Dis. Apr. 2007, 195(4), 320-324.
Seneca, "Recent Advances in Positron Emission Tomography Imaging of Brain", Drugs of the Future, 2011, 36, 601-613.
Seroquel XR.RTM. Highlights of Prescribing Information 2013.
Shekhar, "Gabe Receptors in the Region of the Dorsomedial Hypothalamus of Rats Regulate Anxiety in the Elevated Plus-Maze Test. I. Behavioral Measures", Brain Research, 1993, 627(1), 9-16.
Shetty, Prospects of levetiracelam as a neuroprotective drug against status epilepticus, traumatic brain injury and stroke, Front Neur. 2013, 4:172. Doi: 10.3389/Ineur.2013,00172.
Shin et al., "Metabotropic Glutamate Receptors (Mglus) and Cellular Transformation", Neuropharmacoloqy, 2008, 55(4), 396-402.
Shipe et al., "Recent Advances in Positive All.sigma.steric Modulators of Metabotropic Glutamate Receptors", Current Opinion in Drug Discovery & Development, 2005, 8(4), 449-457.
Simonyi et al., "Expression of Groups I and II Metabotropic Glutamate Receptors in the Rat Brain During Aging", Brain Res, 2005, 1043, 95-106.
Sodhi et al., "Role of Glutamate in Schizophrenia: Integrating Excitatory Avenues of Research", Expert Rev Neurother, 2008, 8(9), 1389-1406.
Spijker, "The Course of Anxiety and Depression in Nemesis and Nesda", Abstract AS36-04 of the 20.sup.th European Congress of Psychiatry, Mar. 2012, 1 page.
Steckler et al., "Chapter 7—Neuroimaging as a Translational Tool in Animal and Human Models of Schizophrenia", Translational Neuroimaging, 2013, 195-220.
Steckler et al., "Effects of Mglu1 Receptor Blockade on Anxiety-Related Behavior in the Rat Lick Suppression Test", Psychopharmacology, 2005, 179, 198-206.
Steckler et al., "Pharmacological Treatment of PTST—Established and New Approaches", Neuropharmacology, 2012, 62, 617-627.
Stewart et al., "Discovery of Inhibitors of Cell Adhesion Molecule Expression in Human Endothelial Cell. 1. Selective Inhibition of Icam-1 and E-Selectin Expression", J Med Chem, 2001, 44, 998-1002.
Stout et al., "High-Affinity Calcium Indicators Underestimate Increases in Intracellular Calcium Concentrations Associated with Excitotoxic Glutamate Stimulations", Neuroscience, 1999, 89(1), 91-100.
Stowell et al., "Axon/Dendrite Targeting of Metabotropic Glutamate Receptors by Their Cytoplasmic Carboxy-Terminal Domains", Neuron, 1999, 22(3), 525-536.
Striano et al., Dramatic response to levetiracatam in post-ischaemic Holmes' tremor, J Neurol Neurosurg Psychiatry 2007, vol. 78, pp. 438-439.
Stulz et al., "Distinguishing Anxiety and Depression in Self-Report: Purification of the Beck Anxiety Inventory and Beck Depression Inventory-II", J Clin Psycho!, 2010, 66, 927-940.
Sun et al., "Mechanism of Glutamate Receptor Desensitization", Nature, 2002, 417, 245-253.
Suzuki et al., "Synthesis of the Selective 5-Hydroxytryptamine 4 (5-Ht4) Receptor Agonist (+)-(S)-2-Chloro-5-Methoxy-4-[5-(2-Piperidylmethyl)-1,2,4-Oxadiazol-3-Yl]-Aniline", Chem. Pharm. Bull., 1999, 47(1), 120-122.
Svensson et al., "Ly2607540 (THLLC), A Novel Mglu2 Receptor Potentiator with Potential Anxiolytic/Antidepressant Properties: in Vivo Profiling Suggests a Link Between Behavioral and CNS Neurochemical Changes" Poster 642.4, 40.sup.th Annual Meeting of Society for Neuroscience, Nov. 2010, 1 page.
Szapiro et al., "Facilitation and Inhibition of Retrieval in Two Aversive Tasks in Rats by Intrahippocampal Infusion of Agonists of Specific Glutamate Metabotropic Receptor Subtypes", Psychopharmacology, 2001, 156(4), 397-401.
Taylor et al., "Stimulation of Microglial Metabotropic Glutamate Receptor Mglu2 Triggers Tumor Necrosis Factor?—Induced Neurotoxicity in Concert with Microglial-Derived Fas Ligand", Journal of Neuroscience, 2005, 25(11), 2952-2964.
Teitler et al., "4-[125i]Iodo-(2,5-Dimethoxy)Phenylisopropylamine and [3h]Ketanserin Labeling of 5-Hydroxytryptamine2 (5ht2) Receptors in Mammalian Cells Transfected with a Rat 5ht2 Cdna: Evidence for Multiple States and Not Multiple 5ht2 Receptor Subtypes", Molecular Pharmacology, 1990, 38, 594-598.
Toering et al., Expression patterns of synaptic vesicle protein 2A in focal cortical dysplasia and TSC-cortical tubers, Epilepsia 2009, 50, pp. 1409-1418.
Tokunaga et al., "Neuroimaging and Physiological Evidence for Involvement of Glutamatergic Transmission in Regulation of the Striatal Dopaminergic System", Journal of Neuroscience, 2009, 29(6), 1887-1896.
Trabanco et al., "Imidazo[1,2-A]Pyridines: Orally Active Positive Allosteric Modulators of the Metabotropic Glutamate 2 Receptor", J Med Chem, 2012, 55, 2688-2701.
Tresadern et al., "Scaffold Hopping From Pyridones to Imidazo[1,2-A]Pyridines. New Positive Allosteric Modulators of Metabotropic Glutamate 2 Receptor", Bioorganic & Medicinal Chemistry Letters, 2010, 20, 175-179.
Treutlein et al., "Dissection of Phenotype Reveals Possible Association Between Schizophrenia and Glutamate Receptor Delta 1 (Gridl) Gene Promoter", Schizophr. Res., 2009, 111(1-3), 123-130.
Tsai, "Central N-Acetyl Aspartylgiutamate Deficit: A Possible Pathogenesis of Schizophrenia", Med Sci. Monit., 2005, 11(9), Hy39-Hy45.
Tsiveriotis et al., "Nickel(II) and Cobalt(II) Complexes of 2,4-Diaminothieno[2,3-D]-Pyrimidines", Transition Metal Chemistry, 1994, 19, 335-339.
Turek et al., "Advances in the Directed Metallation of Azinesand Diazines (Pyridines, Pyrimidines, Pyrazines, Pyridazines, Quinolines, Benzodiazinesand Carbolines). Part 2: Metallation of Pyrimidines, Pyrazines, Pyridazines and Benzodiazines", Tetrahedron, 2001, 57(21), 4489-4505.

(56) References Cited

OTHER PUBLICATIONS

Valproate Information Available from Http://Www.Fda.Gov/Drugs/ Drugsafety/Postmarketdrugsafetyinformationforpat-ientsandproviders/ Ucml92645.Htm, 2011, 2 pages.

Van Der Linden et al., "In Vitro Chracterization of the Binding of the Mglu2 Receptor Positive Allosteric Modulator [3h]Jnj-40068782 to Native and Recombinant Mglu2 Receptors", 7.sup.th Int. Meeting on Metabotropic Glutamate Receptors 2011, 1 page.

Van Vliet et al., "Adaptive Changes in the Number of Gs- and Gi-Proteins Underlie Adenylyl Cyclase Sensitization in Morphine-Treated Rat Striatal Neurons", European Journal of Pharmacology, 1993, 245(1), 23-29.

Van Vliet et al., Decreased expression of synaptic vesicle protien 2A, the binding site for levetiracetam, during epileptogenesis and chronic epilepsy, Epilepsia 2009, 50, pp. 422-433.

Venallan et al., "Reactions of Some 4-Methylene-4h-Pyran Derivatives with Primary and Secondary Amines", Journal of Heterocyclic Chemistry, 1970, 7, 495-507.

Venkatesan et al., Altered balance between exicitatory and inhibitory inputs onto CA pyramidal neuros from SV2A-deficient but not Sv2B-deficient mice, J Neurosci Res 2012, 90, pp. 2317-2327.

Vilsmaier et al., "Diastereoselective Syntheses of N-Protected Derivatives of La,5a,6fi-6-Amino-3-Azabicyclo [3.101]Hexane: A Route to Trovafloxacin 6f1-Diastereomer", Synthesis, 1998, 739-744.

Vogel et al., "Evidence for REM Sleep Deprivation as the Mechanism of Action of Antidepressant Drugs", Prog Neuropsychopharmacol Biol Psychiatry, 1983, 7(2-3), 343-349.

Vollenweider et al., "Effect of Clozapine and Ketanserin on S-Ketamine-Induced Brain Activation and Psychotic Symptoms in Healthy Humans", Abstract, Symposia, 28th Cinp World Congress of Neuropsychopharmacology, 2012, 2 pages.

Wheless, Levetiracetam in the treatment of childhood epilepsy, Neuropsychiatric Disease and Treatment 2007, vol. 3(4), pp. 409-421.

Wieronska et al., "Opposing Efficacy of Group III Mglu Receptor Activators, Lsp1-2111 and Amn082, in Animal Models of Positive Symptoms of Schizophrenia", Psychopharmacology, Sep. 2011, 14 pages.

Williams et al., "Characterization of Polyamines Having Agonist, Antagonist, and Inverse Agonist Effects at the Polyamine Recognition Site of the NMDA Receptor", Neuron, 1990, 5(2), 199-208.

Winter et al., "Serotonergic/Glutamatergic Interactions: The Effects of Mglur2/3 Receptor Ligands in Rats Trained with LSD and PCP as Discriminative Stimuli.", Psychopharmacol. (Ben), 2004, 172, 233-240.

Wischhof et al., "Pre-Treatment with the Mglu2/3 Receptor Agonist Ly379268 Attenuates DOI-Induced Impulsive Responding and Regional C-Fos Protein Expression", Psychopharmacology, Aug. 2011, 14 pages.

Wittchen et al., "Disabilities and Quality of Live in Pure and Comorbid Generalized Anxiety Disorder and Major Depression in a National Survey", Intl Clinical Psychopharmacology, 2000, 15, 319-328.

Wojda, et al., Isobolographic characterization of interactions of levetiracetam with the various antiepileptic drugs in the mouse 6Hz psychomotor seizure model, Epilepsy Research, Jul. 10, 2009, pp. 163-174, vol. 86.

Woods et al., Effects of levetiracetam on tardive dyskinesia: a randomized, doubleblind, placebo-controlled study, J Clin Psychiatry 2008, vol. 69, pp. 546-554.

Yakovidis et al., "Copper(II) Complexes of Thieno[2,3-D] Pyrimidine Derivatives", Inorganica Chimica Acta, 1988, 151, 165-167.

Yanamala et al., "Preferential Binding of Allosteric Modulators to Active and Inactive Conformational States of Metabotropic Glutamate Receptors", BMC Bioinformatics, 2008, 9(Suppl 1), 516.

Young et al., "Evidence for a Role of Metabotropic Glutamate Receptors in Sustained Nociceptive Inputs to Rat Dorsal Horn Neurons," Neuropharmacology, 1994, 33(1), 141-144.

Yucel et al., "Anterior Cingulate Volumes in Never-Treated Patients with Major Depressive Disorder", Neuropsychopharmacology, 2008, 33, 3157-3163.

Yuzwa et al., "O-GlcNAc and neurodegeneration: biochemical mechanisms and potential roles in Alzheimer's disease and beyond", Chem. Soc. Rev., 2014, 43, 6839-6858.

Zhang et al., "1-[(1-Methyl-1h-Imidazol-2-Yl)Methyl]-4-Phenylpiperidines as Mglur2 Positive Allosteric Modulators for the Treatment of Psychosis", J Med Chem, 2011, 54, 1724-1739.

Zhang et al., "3-(Imidazolyl Methyl)-3-Aza-Bicyclo[3.1.0]Hexan-6-Yl)Methyl Ethers: a Novel Series of Mglur2 Positive Allosteric Modulators", Bioorg Med Chem Lett, 2008, 18, 5493-5496.

Zhang et al., Levetiracetam in social phobia: a placebo controlled pilot study, J Psychopharmacol 2005, vol. 19, pp. 551-553.

Zivkovic et al., Treatment of tardive dyskinesia with levetiracetam in a transplant patient, Acta Neurol Scand 2008, vol. 117, pp. 351-353.

Zuena et al., "Prenatal Restraint Stress Generates Two Distinct Behavioral and Neurochemical Profiles in Male and Female Rats", Plos. One, 2008, 3(5), E2170.

Zwart et al., "Sazetidine-A is a Potent and Selective Agonist at Native and Recombinant A4β2 Nicotinic Acetylcholine Receptors", Mol Pharmacol, 2008, 73, 1838-1843.

Bakker et al., Reduction of hippocampal hyperactivity improves cognition in amnestic mild cognitive impairment. Neuron, 2012, pp. 467-474, vol. 74, Elsevier Inc.

Barton et al., Barton et al. Pharmacological characterization of the 6 Hz psychomotor seizure model of partial epilepsy, 2001, pp. 217-222, vol. 47, Epilepsy Research.

Barton, et al., Comparison of the effect of glutamate receptor modulators in the 6 Hz and maximal electroshock seizure models, 2003, pp. 17-26, vol. 56, Epilepsy Research.

Barton, et al., Comparison of the effect of glutamate receptor modulators in the 6 Hz and maximal electroshock seizure models, Epilepsy Research, Aug. 4, 2003, pp. 17-26, vol. 56.

Barton, et al., Pharmacological characterization of the 6 Hz psychomotor seizure model of partial epilepsy, Epilepsy Research, Aug. 10, 2001, pp. 217-227, vol. 47.

Bushara et al., The effect of levetiracetam on essential tremor, Neurology, 2005, pp. 1078-1080, vol. 64.

Calabresi, et al., Antiepileptic drugs in migraine: from clinical aspects to cellular mechanisms, Trends in Pharmacologicai Sciences, 2007, pp. 188-195, vol. 28 issue 4.

Caulder, et al., Activation of Group 2 metabotropicglutamate receptors reduces behavioral andelectrographic correlates of pilocarpineinduced status epilepticus, Epilepsy Research, 2014, pp. 171-181, vol. 108.

Crowder et al, Abnormal neurotransmission in mice lacking synaptic vesicle protein 2A (SV2A), Proc Nat Acad Sci USA, 1999, p. 15268-15273, 96.

Daniels et al, Modulation of the conformational state of the SV2A protein by an allosteric mechanism as evidenced by ligand binding assays, British Journal of Pharmacology, 2013, pp. 1091-1101, vol. 169.

De Groot et al., Expression of synaptic vesicle protein 2A in epilepsy-associated brain tumors and in the peritumoral cortex. Neuro-Oncology, 2010, pp. 265-273, vol. 12.

De Groot et al., Levetiracetam improves verbal memory in high-grade glioma patients, Neuro-oncology, 2013, pp. 216-223, vol. 15(2).

Dedeurwaerdere, et al., In the grey zone between epilepsy and schizophrenia: alterations in group II metabotropicglutamate receptors, Acta Neurol Belg, Dec. 25, 2014, pp. 1-12, Page Number.

Dolder et al, "The efficacy and safety of newer anticonvulsants in patients with dementia", Drugs Aging, 2012, pp. 627-637, vol. 29(8).

Dunayevich et al., Efficacy and tolerability of an mGlu2/3 agonist in the treatment of generalized anxiety disorder, Neuropsychopharmacology, 2008. pp. 1603-1610, vol. 33(7).

Dunteman, Levetiracetam as an adjunctive analgesic in neoplastic plexopathies: case series and commentary, J Pain Palliative Care Pharmacother, 2005, pp. 35-43, vol. 19.

(56) References Cited

OTHER PUBLICATIONS

During, et al., Extracellular hippocampal glutamate and spontaneous seizure in the conscious human brain, Lancet, 1993, pp. 1607-1610, vol. 341 Issue 8861.
Dyaikin et al., Determination of the Absolute Configuration of a Key Tricyclic Component of a Novel Vasopressin Receptor Antagonist by Use of Vibrational Circular Dichroism, Chirality, 2002, pp. 215-219, vol. 14.
Eddy et al., The cognitive impact of antiepileptic drugs, Ther Adv Neurol Disord, 2011, pp. 385-407, vol. 4(6).
Enggaard et al., Specific effect of levetiracetam In experimental human pain models, Eur J Pain, 2006, pp. 193-198, vol. 10.
Feng et al., Down-regulation of synaptic vesicle protein 2A In the anterior temporal neocortex of patients with intractable epilepsy, J Mol Neurosci, 2009, pp. 354-359, 39.
Finney, Probit Analysis, 34d Ed 1971, London: Cambridge University Press.
Florek-Luszczki, et al., Interactionsoflevetiracetamwithcarbamazepine,phenytoin, topiramateandvigabatrininthemouse6Hzpsychomotorseizure model—A typellisobolographicanalysis, EuropeanJouralofPharmacology, 2014, pp. 410-418, vol. 723.
Hamann et al., Brivaracetam and seletracetam, two new SV2A ligands, improve paroxysmal dystonia in the dtsz mutant hamster, European Journal of Pharmacology, 2008, pp. 99-102, vol. 601.
Kaminski, et al., Benefit of combination therapy in epilepsy: A review of the preclinical evidence with levetiracetam, Epilepsia, 2009, pp. 387-397, vol. 50 Issue 3.
Kaminski, et al., Targeting SV2A for Discovery of Antiepileptic Drugs, Jasper's Basic Mechanisms of the Epilepsies, 2012, pp. 1-12, Fourth Edition.
Keppra, Epar summary for the public, An agency of the European Union, 2013, pp. 1-3, page number, European Medicines Agency.
Keppra, FDA Approved Labeling text dated Jul. 2013 Keppra®, Levetiracetam, 2009, pp. 1-34, page number.
Keppra, Highlights of Prescribing Information These highlights do not Include all the information needed to use, Keppra, 2017, pp. 1-32, page number.
Kinrys et al., Levetiracetam as adjunctive therapy for refractory anxiety disorders, J Ciin Psychiatry 2007,vol. 68, pp. 1010-1013.
Kinrys et al., Levetiracetam for treatment-refractory posttraumatic stress disorder, J Clin Psychiatry 2006, p. 211-214, vol. 67.
Klitgaard et al, Antiepileptic drug discovery: lessons from the past and future challenges, Acta Neurol Scand, Jan. 1, 2005, 68-72, vol. 112 No. 181.
Klitgaard et al., Levetiracetam: the preclinical profile of a new class of antiepileptic drugs, Epilepsia 2001, 42 (Supplement 4), pp. 13-18.
Landmark et al, Modifications of Antiepileptic Drugs for Improved Tolerability and Efficacy, Med. Chem., Apr. 10, 2008, 21-39, vol. 2.
Landmark., Antiepileptic drugs in non-epilepsy disorders: relations between mechanisms of action and clinical efficacy, CNS Drugs 2008, vol. 22(1), 2008, pp. 27-47, vol. 1.
Lee et al., Levetiracetam inhibits glutamate transmission through presynaptic P/Q-type calcium channels on the granule cells of the dentate gyrus, British Journal of Pharmacology 2009, vol. 158, 2009, pp. 1753-1762, vol. 158.
Lee, et al,, Rational Polytherapy with Antiepileptic Drugs, Pharmaceuticals, Jul. 26, 2010, pp. 2362-2379, vol. 3.
Lynch et al., The synaptic vesicle protein SV2A is the binding site for the antiepileptic drug levetiracetam, Proc. Natl. Acad. Sci. USA 2004, vol. 101, 2004, pp. 9861-9866, 101.
Löscher et al, Prevention or modification of epileptogenesis after brain insults: experimental approaches and translational research, Pharmacol Rev 2010, vol. 62, pp. 668-700.
M.Foster Olive, Metabotropic Glutamate Receptor Ligands as Potential Therapeutics for Addiction, Current Drug Abuse Reviews, 2009, pp. 83-98, vol. 2.
McGavin et al., Levetiracetam as a treatment for tardive dyskinesia: a case report, Neurology 2003, vol. 61,, pp. 41.

Mendoza-Torreblanca et al., Synaptic vesicle protein 2A: basic facts and role in synaptic function, European Journal of Neuroscience 2013, pp. 1-11.
Metcalf, et al., Efficacy of mGlu2-positive aiiosteric modulators alone and in combination with levetiracetam in the mouse 6 Hz model of psychomotor seizures, Epilepsia, Feb. 6, 2017, pp. 484-493, vol. 58 Issue 3.
Bennet et al., "Seletracetam (UCB 44212)", Neurotherapeutics: The Journal of the American Society for Experimental NeuroTherapeutics, vol. 4, Jan. 2007, pp. 117-122.
Farooq et al., "Levetiracetam for Managing Neurologic and Psychiatric Disorders", Am J Health Syst Pharm, vol. 66, No. 6, Mar. 2009, pp. 541-561.
FDA, https://www.accessdata.fda.gov/drugsatfda_docs/label/2009/021035s078s080,021505s021s024lbl.pdf, Apr. 2009, 40 sheets.
Rogawski, "Brivaracetam: a rational drug discovery success story", Brit J Pharmacology, vol. 154, Jun. 2008, pp. 1555-1557.
Rosenstiel, "Brivaracetam (UCB 34714)", Neurotherapeutics: The Journal of the American Society for Experimental NeuroTherapeutics, vol. 4, Jan. 2007, pp. 84-87.
Taer, "Essentials of Psychopharmacology: Guidelines for Prescription", Oct. 2009, p. 204. (Chinese language original and English translation).
Celanire S., et al., "mGluR2 Activators and mGluR5 Blockers Advancing in the Clinic for Major CNS Disorders", Annual Reports in Medicinal Chemistry, vol. 47, 2012, pp. 71-88.
Barton, et al., "Pharmacological characterization of the 6 Hz psychomotor seizure model of partial epilepsy", Epilepsy Research, 2001, pp. 217-227, v. 47.
Barton, et al., "comparison of the effect of glutamate receptor modulators in the 6 Hz and maximal electroshock seizure models", 2003, pp. 17-26, v. 56.
Metcalf, et al., "Efficacy of mGlu2-positive allosteric modulators alone and in combination with levetiracetam in the mouse 6 Hz model of psychomotor seizures", Epilepsia, 2017, pp. 484-493, v. 58(3).
Metcalf, et al., "Efficacy of mGlu2-positive allosteric modulators alone and in combination with levetriracetam in the mouse 6 Hz model of psychomotor seizures", Epilepsia, 2017, pp. 1-10.
Metcalf, et al., "Potent and selective pharmacodynamic synergy between the metabotropic glutamate receptor subtype 2-positive allosteric modulator JNJ-46356479 and Levetiracetam in the Mouse 6-hZ (44-Ma) model", Epilepsia, 2017, pp. 724-735, v. 59.
Rowley, et al., " Comparative anticonvulsant efficacy in the corneal kindled mouse model of partial epilepsy: Correlation with other seizure and epilepsy models", Epilepsy Research, 2010, pp. 163-169, v. 92.
Keppra Label—Keppra® (Ievetiracetam) Prescribing Information Oct. 2017.
Potschka, "Animal models of drug-resistant epilepsy", Epileptic Disord, 2012, pp. 226-234, v. 14(3).
Kent et al. "Efficacy and Safety of a Novel mGlu2 Receptor Positive Allosteric Modulator as an Adjunctive Treatment to an SSRI/SNRI in the Treatment of Anxious Depression" Abstract to poster and oral presentation, American Society of Clinical Psychopharmacology (ASCP) 2014 Annual Meeting, Jun. 16-19, 2014 Westin Diplomat, Hollywood, Florida).
Salih et al. "Pharmacokinetic and pharmacodynamics characterization of JNJ-40411813, a positive allosteric modulator of mGluR2, in two randomized, double-blind phase-1 studies" Journal of Psychopharmacology, 2015, vol. 29(4) 414-425.
Australian Patent Application No. 2005/284098: Office Action dated Oct. 11, 2010, 2 pages.
Australian Patent Application No. 2007/224431: Office Action dated Mar. 19, 2010, 6 pages.
Australian Patent Application No. 2008/223795: Office Action dated May 29, 2012, 2 pages.
Australian Patent Application No. 2008/223796: Examiner's Report dated Nov. 3, 2010, 2 pages.
Australian Patent Application No. 2008/297877: Examiner's Report dated Oct. 31, 2012, 3 pages.
Canadian Patent Application No. 2,581,144: Office Action dated Apr. 23, 2010, 2 pages.

(56) References Cited

OTHER PUBLICATIONS

Chilean Patent Application No. 2745-2008: Office Action dated Apr. 15, 2011, 2 pages.
Chilean Patent Application No. 671-2008: Office Action dated Oct. 29, 2010, 9 pages.
Chilean Patent Application No. 681-2007: Office Action dated Jan. 11, 2011, 6 pages.
Chinese Patent Application No. 200780009210.5: Office Action dated Jun. 19, 2012, 4 pages.
Chinese Patent Application No. 200880107135.0: Office Action dated Jul. 4, 2012, 4 pages.
Eurasian Patent Application No. 200801934/28: Office Action dated May 13, 2010, 4 pages.
Eurasian Patent Application No. 200901162/28: Office Action dated Apr. 18, 2011, 7 pages.
Eurasian Patent Organization : Euraisian Notification "On the Necessity to Present Additional Matters", dated Decemeber 17, 2008, 3 pages.
European Patent Application No. EP 08166832: Search Report dated May 8, 2009, 5 pages.
Fell et al., "Activation of Metabotropic Glutamate (Mglu)2 Receptors Suppresses Histamin Release in Limbic Brain Regions Following Acute Ketamine Challenge", Neuropharmacology, 2010, 58, 632-639.
Israeli Patent Application No. 192868: Office Action dated Dec. 21, 2011, 2 pages.
Itaya et al., "Purines. LXXV. Dimroth Rearrangement, Hydrolytic Deamination, and Pyrimidine-Ring Breakdown of 7-Alkylated 1-Alkoxyadenines: N(1)—C(2) Versus N(1)—C(6) Bond Fission", Chem, Pharm. Bull., 1997, 45 (5), 832-41.
Jaanese Patent Application No. 2008-558820: Office Action dated Aug. 28, 2012, 14 pages.
Japanese Patent Application No. 2009-552215: Office Action dated Dec. 18, 2012, 2 pages.
Japanese Patent Application No. 2010-524405: Office Action dated Jun. 5, 2012, 4 pages.
Kenakin, "Collateral Efficacy in Drug Discovery: Taking Advantage of the Good (Allosteric) Nature of 7tm Receptors", Trends Pharmacol. Sci., 2007, 28(8), 407-415.
Lourenco et al., "Differential Distribution of Metabotropic Glutamate Receptor Subtype MRNAS in the Thalamus of the Rat", Brain Research, 2000, 854(1 -2), 93-105.
Malatynska et al., "Submissive Behavior in Mice as a Test for Antidepressant Drug Activity", Pharmacol Biochem Behavior, 2005, 82, 306-313.
Marino et al., "Glutamate-Based Therapeutic Approaches: Allosteric Modulators of Metabotropic Glutamate Receptors", Current Opinion in Pharmacology, 2006, 6, 98-102.
McElroy, "A 52-Week, Open-Label Continuation Study of Lamotrigine in the Treatment of Bipolar Depression", J. Clin. Psychiatry, 2004, 204-210.
Mexican Patent Application No. MX/a/2009/009422: Office Action dated Jun. 28, 2011, 5 pages.
Redondo et al., "Selective Heteronuclear Noe Enhancements in Benzoheterocycles. Effect of Ring Size on Indirect Three-Spin Effects"; Magnetic Resonance in Chemistry, 1988, 26, 11-517.
Ribeiro et al., "Metabotropic Glutamate Receptor-Mediated Cell Signaling Pathways are Altered in a Mouse Model of Huntington's Disease", Journal of Neuroscience, 2010, 30(1), 316-324.
Rickels et al., "Long-Term Diazepam Therapy and Clinical Outcome", Jama, 1983, 250, 767-771.
Ried et al., "Reactions with Cyclobutenediones, lx. 3-Hydroxy-Pyridones-(2) From Phenylcyclobutenedione and Enamines", Liebigs Ann. Chem., 1969, 725, 230-233.
Riederer et al., "Pharmacotoxic Psychosis After Memantine in Parkinson's Disease", Lancet 1991, 338, 1022-1023.
Roberts et al., "Pharmacological Tools for the Investigation of Metabotropic Glutamate Receptors (Mglurs): Phenylglycine Derivatives and Other Selective Antagonists—An Update". Neuropharmacology, 1995, 34(8), 813-819.

Rudd et al., "Positive Allosteric Modulators of the Metabotropic Glutamate Receptor Subtype 2 (Mglur2)", Current Topics in Medicinal Chemistry, 2005, 5, 869-884.
Rush et al., "The Inventory for Depressive Symptomatology (Ids): Preliminary Findings", Psychiatry Res, May 1986, 18(1), 65-87.
Rush et al., "The inventory of Depressive Symptomatology (Ids)—Preliminary Findings", Psychopharmacology Bulletin, 1986, 22(3), 985-990.
Rush et al., "The Inventory of Depressive Symptomatology (Ids): Psychometric Properties", Psychol Med, May 1996, 26(3), 477-486.
Sahni et al., "Compound A, A Novel, Potent and Selective Metabotropic Glutamate Receptor 2 (Mglur2) Positive Allosteric Modulator: I. Pharmacological Characterization" Poster 767.6 Presented at the $40^{th}$ Annual Meeting of Society for Neuroscience, Nov. 2010, 1 page.
Sakamoto et al., "Condensed Heteroaromatic Ring Systems. VIII. Synthesis 3-Substituted Isocoumarins from O-Halobenzoic Acid Derivatives", Chem. Pharm. Bull., 1986, 34(7), 2754-2759.
Salinska et al., "Metabotropic Glutamate Receptors (Mglurs) are Involved in Early Phase Memory Formation: Possible Role of Modulation of Glutamate Release", Neurochemistry Intl, 2003, 43, 469-474.
Santi et al., "Temporal and Depolarization-Induced Changes in the Absolute Amounts of Mrnas Encoding Metabotropic Glutamate Receptors in Cerebellar Granule Neurons in Vitro". Journal of Neurochemistry, 1994, 63(4), 1207-1217.
Sareen et al., "Anxiety Disorders and Risk for Suicidal Ideation and Suicide Attempts", Arch Gen Psychiatry, 2005, 62, 1249-1257.
Sarter et al., "Cortical Cholinergic Transmission and Cortical information Processing in Schizophrenia", Schizophr. Bull, 2005, 31(1), 117-138.
Saugstad et al., "Cloning and Expression of a New Member of the L-2-Amino-4-Phosphonobutyric Acid-Sensitive Class of Metabotropic Glutamate Receptors", Mol Pharmacol, 1994, 45, 367-372.
Saugstad et al., "Metabotropic Glutamate Receptors Activate G-Protein-Coupled Inwardly Rectifying Potassium Channels in Xenopus Oocytes", J. Neurosci., 1996, 16(19), 5979-5985.
Schaffhauser et al., "Pharmacological Characterization of Metabotropic Glutamate Receptors Linked to the Inhibition of Adenylate Cyclase Activity in Rat Striatal Slices", Neuropharmacology, 1997, 36(7), 933-940.
Sheer et al., "Constitutively Active G Protein-Coupled Receptors: Potential Mechanisms of Receptor Activation", Journal of Receptor & Signal Transduction Research, 1997, 17(1-3), 57-73.
Schoepp et al., "Ly354740 is a Potent and Highly Selective Group II Metabotropic Glutamate Receptor Agonist in Cells Expressing Human Glutamate Receptors", Neuropharmacology, 1997, 36, 1-11.
Seeman et al., "Dopamine Partial Agonist Actions of the Glutamate Receptor Agonists Ly354740 and Ly379268", Synapse. 2008, 62, 154-158.
Seeman, "Glutamate and Dopamine Components in Schizophrenia", J Psychiatry Neurosci., 2009, 34(2), 143-149.
Seneca, "Recent Advances in Positron Emission Tomography Imaging of Brain", Drugs of of the Future, 2011, 36, 601-613.
Shear et al., "Multicenter Collaborative Panic Disorder Severity Scale", Am J Psychiatry, Nov. 1997, 154(11), 1571-1575.
Shekhar, "Gaba Receptors in the Region of the Dorsomedial Hypothalamus of Rats Regulate Anxiety in the Elevated Plus-Maze Test. I. Behavioral Measures", Brain Research, 1993, 627(1), 9-16.
Shih et al., "Protein Kinase C Deficiency Blocks Recovery From Agonist-Induced Desensitization", J. Biol. Chem., 1996, 271(35), 21478-21483.
Shipe et al., "Recent Advances in Positive Allosteric Modulators of Metabotropic Glutamat Receptors", Current Opinion in Drug Discovery & Development, 2005, 8(4), 449-457.
SIPO Office Action dated Jun. 30, 2010, 12 pages.
Skerry et al., "Glutamate Signalling in Non-Neuronal Tissues", Trends Pharmacol. Sci., 2001, 22(4), 174-181.
Sodhi et al., "Role of Glutamate in Schizophrenia: Integrating Excitatory Avenues of Rasearch", Expert Rev Neurother, 2008, 8(9), 1389-1406.

(56) References Cited

OTHER PUBLICATIONS

Sokoloff et al., "The [14c]Deoxyglucose Method for the Measurement of Local Cerebral Glucose Utilization: Theory, Procedure, and Normal Values in the Conscious and Anesthetized Albino Rat", J Neurochem, 1977, 28, 897-916.

Sortino et al., "Immortalized Hypothalamic Neurons Express Metabotropic Glutamate Receptors Positively Coupled to Cyclic Amp Formation", Eur. J Neurosci., 1996, 8(11), 2407-2415.

Souery et al., "Group for the Study of Resistant Depression. Clinical Factors Associated with Treatment Resistance in Major Depressive Disorder: Results From A EuropeanMulticenter Study", J. Clin. Psychiatry, Jul. 2007, 68(7), 1062-1070.

South Korean Patent Application No. 2010-053694958: Office Action dated Nov. 25 2010, 9 pages.

Star*D Research Methods Section (2001), Available from Http://Www.Edc.Gsph.Pitt.Edu/Stard/Public/Protocol/Star-D%20III%20research%20design%20methods.Pdf. 2001, 50 pages..

Stckler et al., "Chapter 7—Neuroimaging as a Translational Tool in Animal and Human Models of Schizophrenia", Translational Neuroimaging, 2013, 195-220.

Steru et al., "The Automated Tail Suspension Test: A Computerized Device Which Differentiates Psychotropic Drugs", Prog. Neuropsychopharmacol. Exp. Psychiatry, 1987, 11, 659-671.

Stone, "Imaging the Glutamate System in Humans: Relevance to Drug Discovery for Schizophrenia", Curr. Pharm. Des, 2009, 15(22), 2594-2602.

Stowell et al., "Axon/Dendrite Targeting of Metabotropic Glutamate Receptors by Their Cytoplasmic Carboxy-Temninal Domains", Neuron, 1999, 22(3), 525-536.

Structures, "Chemical Abstracts", May 2009. 23 pages.

Sun et al., "Mechanism of Glutamate Receptor Desensitization", Nature, 2002, 417, 245-2.

Suzuki et al., "Synthesis of the Selective 5-Hydroxytryptamine 4 (5-Ht4) Receptor Agonist (+)-(S)-2-Chloro-5-Methoxy-4-[5-(2-Piperidylmethyl)-1,2,4-Oxadiazol-3-YI]Aniline", Chem. Pharm. Bull., 1999, 47(1), 120-122.

Svensson et al., "Ly2607540 (THLLC), A Novel Mglu2 Receptor Potentiator with Potential Anxiolytic/Antidepressant Properties: in Vivo Profiling Suggests a Link Between Behaviors and CNS Neurochemical Changes" Poster 642.4, 40$^{th}$ Annual Meeting of Society for Neuroscience, Nov. 2010, 1 page.

Swerdlow et al., "Assessing the Validity of an Animal Model of Deficient Sensorimotor Gating in Schizophrenic Patients", Arch. Gen. Psychiatry, 1994, 51, 139-154.

Taiwanese Patent Application No. 094132375: Office Action dated Aug. 25, 2011, 10 pages.

Taiwanese Patent Application No. 096108666: Office Action, dated 2007, 3 pages.

Testa et al., "Immunohistochemical Localization of Metabotropic Glutamate Receptors Mglur1a and Mglur2/3 in the Rat Basal Ganglia", Journal of Comparative Neurology, 1998, 390(1), 5-19.

Thase et al., "Remission Rates Following Antidepressant Therapy with Bupropion or Selective Serotonin Reuptake Inhibitors: A Meta-Analysis of Original Data From 7 Randomized Controlled Trials", J Clin Psychiatry, 2005, 66(8), 974-981.

Trabanco et al., "Discovery of 5- and 6-Substituted Isoquinolones: A New Class of Positive Allosteric Modulators of the Metabotropic Glutamate 2 Receptor", XXI'ST International Symposium on Medicinal Chemistry, Sep. 2010, 1 page.

Van Der Linden et al., "In Vitro Chracterization of the Binding of the Mglu2 Receptor Positive Allosteric Modulator [3h]Jnj-40068782 To Native and Recombinant Mglu2 Receptors", 7$^{th}$ Int. Meeting on Metabotropic Glutamate Receptors 2011, 1 page.

Vogel et al., "Evidence for REM Sleep Deprivation as the Mechanism of Action of Aitidepressant Drugs", Prog Neuropsychopharmacol Biol Psychiatry, 1983, 7(2-3), 343-349.

West, "Solid State Chemistry and its Applications", Wiley, 1988, 2 pages.

Wittchen et al., "The Size and Burden of Mental Disorders and Other Disorders of the Brain in Europe 2010", European Neuropsychopharmacology, 2011, 21, 655-679.

Zarate, "A Randomized Trial of an N-Methyl-D-Aspartate Antagonist in Treatment-Resistant Major Depression," Arch. Gen. Psychiatry, Aug. 2006. 63(8), 856-864.

International Search Report re: PCT/EP2015/051029 dated Apr. 23, 2015.

Abi-Saab et al., "The NMDA Antagonist Model for Schizophrenia: Promise and Pitfalls". Pharmacopschiatry, 31, 1998, 104-109.

Abshire et al., "Injection of L-Allylglycine Into the Posterior Hypothalamus in Rats Causes Decreases in Local GABA Which Correlate with Increases in Heart Rate", Neuropharmacology, 1988, 27(11), 1171-1177.

Adam, "Symptomatic Treatment of Huntington Disease", Neurotherapeutics: the Journal of the American Society for Experimental Neurotherapeutics, Apr. 2008, 5, 181-197.

Adams et al., "Effect of Clozapine, Haloperidol, or M100907 on Phencyclidine-Activated Glutamate Efflux in the Prefrontal Cortex", Biol. Psychiatry 2001, 50(10), 750-757.

Adams, "A Long-Term, Phase 2, Multicenter, Randomized, Open-Label, Comparative Safety Study of Pomaglumetad Methionil (LY2140023 Monohydrate) Versus Atypical Antipsychotic Standard of Care in Patients with Schizophrenia", BMC Psychiatry 2013, 13(143), 1-9.

Addex Partner Completes ADX71149 Phase I Program, Press release Aug. 25, 2010, http://www.addextherapeutics.com/investors/press-releases/news-details/?tx_ttnews%5Btt_news%5D%20=103&cHash=91fade38b1d3dc85979989357b1a9281, retrieved on Aug. 22, 2013.

Addex Partner Doses First Patient in Phase 2 Clinical Study of ADX71149 for the Treatment of Major Depressive Disorder Patients with Anxiety Symptoms, Press Release Sep. 17, 2012, http://www.addextherapeutics.com/investors/press-releases/news-details/?tx_ttnews%5Btt_news%5D%20=214&cHash=12a9cc5ffefdb63c27d5b87a673f74eb, retrieved on Aug. 22, 2013.

Addex Partner to Initiate Phase 2 Clinical Trial of ADX71149 for the Treatment of Major Depressive Disorder with Anxiety Symptoms, Press Release Jun. 5, 2012 http://www.addextherapeutics.com/investors/press-releases/news-details/?tx_ttnews%5Btt_news%5D%20=204&cHash=1865c3b31d0b9042f84c017bb2b5f32c, retrieved on Aug. 22, 2013.

Addex Reports Top-line Data from a Successful Phase 2a Clinical Study with ADX71149 in Schizophrenia Patients, Press Release Nov. 5, 2012, http://www.addextherapeutics.com/investors/press-releases/news-details/?tx_ttnews%5Btt_news%5D%20=225&cHash=9e5e13cb042971e6135f8ac786ce7453 retrieved on Aug. 22, 2013.

Addington et al., "A depression rating scale for schizophrenics", Schizophr Res. 1990, 3(4), 247-251.

Ader et al., "Effects of Chlorpromazine on the Acquisition and Extinction of an Avoidance Response in the Rat", J. Pharmacol. Exp. Ther., 1957, 131, 144-148.

Agami et al., "An Efficient Synthesis of Polysubstituted 3-Halo-2(1H)-Pyridinones." Synthesis, 2002, 79-82.

Agari et al., "Intrapallidal Metabotropic Glutamate Receptor Activation in a Rat Model of Parkinson's Disease; Behavioral and Histological Analyses", Brain Res., 2008, 1203, 189-196.

Aghajanian etal, "Serotonin model of schizophrenia: Emerging role of glutamate Mechanisms", Brain Research Reviews, 2000, 31, 302-312.

Aghajanian, "Modeling 'Psychosis' in Vitro by Inducing Disordered Neuronal Network Activity in Cortical Brain Slices", Psychopharmacology 2009, 206(4), 575-585.

Agid et al., "How Can Drug Discovery for Psychiatric Disorders Be Improved?" Nature Reviews Drug Discovery, 2007, 6, 189-201.

Ago et al., "Activation of Metabotropic Glutamate 2/3 Receptors Attenuates Methamphetamine-Induced Hyperlocomotion and Increase in Prefrontal Serotonergic Neurotransmission", Psychopharmacoloqy, 2011, 217, 443-452.

Ahnaou et al., "Modulation of Group II Metabotropic Glutamate Receptor (Mglu2) Elicits Common Changes in Rat and Mice Sleep-Wake Architecture", European Journal of Pharmacology, 2009, 603, 62-72.

(56) References Cited

OTHER PUBLICATIONS

Ainslie et al., "Practical Drug Evaluation Method", Arch Gen Psychiat, 1965, 12, 368-373.
Alagarsamy et al., "Coordinate Regulation of Metabotropic Glutamate Receptors", Current Opinion in Neurobiology. 2001, 11(3), 357-362.
Albasanz et al., "Internalization of Metabotropic Glutamate Receptor in C6 Cells Through Clathrin-Coated Vesicles", Molecular Brain Research, 2002, 99, 54-66.
Alderson et al., "Purification and Characterization of a Soluble Cyclic Nucleotide-Independent Ca2+-Calmodulin-Sensitive Protein Kinase from Rat Brain", J. Neurochem., 1986, 46, 594-603.
Aleppo et al., "Metabotropic Glutamate Receptors and Neuronal Toxicity", Advances in Experimental Medicine & Biology, 1992, 318, 137-145.
Alexander et al., "Metabotropic Glutamate Receptors as a Strategic Target for the Treatment of Epilepsy", Epilepsy Res., 2006, 71(1), 1-22.
Allen et al., "Group II Metabotropic Glutamate Receptor Activation Attenuates Traumatic Neuronal Injury and Improves Neurologicai Recovery After Traumatic Brain Injury", J Pharmacol. Exp. Then, 1999, 290(1), 112-120.
Alley et al., "Memantine Lowers Amyloid-Beta Peptide Levels in Neuronal Cultures and in APP/PS1 Transgenic Mice", J Neurosci Res, 2010, 88, 143-154.
Al-Omran et al., "Studies with Polyfunctionally Substituted Heteroaromatics: New Routes for the Synthesis of Polyfunctionally Substituted Pyridines and 1,2,4-Triazolo[1,5-a]pyridines", Heteratom. Chemistry, 1995, 6(6), 545-551.
Alper, "Agonist-Stimulated [35s]Gtpys Binding", Current Protocols in Pharmacology, 1998, 1-10.
Al-Shamma et al., "Nelotanserin, a Novel Selective Human 5-Hydroxytryptamine2a Inverse Agonist for the Treatment of Insomnia", J Pharmacol Exp Ther, 2010, 332, 281-290.
Altamura et al., "Designing Outcome Studies to Determine Efficacy and Safety of Antipsychotics for 'Real World' Treatment of Schizophrenia", Int J Neuropsychopharmacol, 2010;13(7):971-973.
Altamura etai., "Plasma and Platelet Exctitatory Amino Acids in Psychiatric Disorders", Am J Psychiatry, 1993, 150(11), 1731-1733.
Altamura et al., "Plasma Concentrations of Excitatory Amino Acids Serine, Glycine, Taurine and Histidine in Major Depression", Eur Neuropsychopharmacol, 1995; 5(Suppl), 71-75.
Amiri et al., "A Role for Leu118 of Loop E in Agonist Binding to the α7 Nicotinic Acetylcholine Receptor" Mol Pharmacol, 2008, 73, 1659-1667.
Amitai et al., "Effects of Metabotropic Glutamate Receptor 2/3 Agonism and Antagonism on Schizophrenia-Like Cognitive Deficits Induced by Phencyclidine in Rats", European Journal of Pharmacology, 2010, 639, 67-80.
Andreescu et al., "Comorbid Anxiety and Depression: Bête Noire Or Quick Fix?", British Journal of Psychiatry 2012, 200:179-181.
Andreescu et al., "Effect of Comorbid Anxiety on Treatment Response and Relapse Risk in Late-Life Depression: Controlled Study", the British Journal of Psychiatry, 2007, 190, 344-349.
Andreescu et al., "The Default Mode Network in Late-Life Anxious Depression", Am J Geriatr Psychiatry, Nov. 2011, 19(11), 5 pages.
Andres et al., "2-(Dimethylaminomethyl)-Tetrahydroisoxazolopyridobenzazepine Derivatives. Synthesis of a New 5-HT2C Antagonist with Potential Anxiolytic Properties", Bioorganic & Medicinal Chemistry Letters, 2002, 12, 3573-3577.
Andres et al., "Synthesis, Evaluation, and Radiolabeling of New Potent Positive Allosteric Modulators of the Metabotropic Glutamate Receptor 2 As Potential Tracers for Positron Emission Tomography Imaging", J Med Chem, 2012, 55, 8685-8699.
Angenstein et al., "Activation of Metabotropic Glutamate Receptors Increases Endogenous Protein Kinase C Substrate Phosphorylation in Adult Hippocampal Slices", Brain Research, 1997, 745(1-2), 46-54.

Angers et al., "Dimerization: An Emerging Concept for G Protein-Coupled Receptor Ontogeny and Function", Annu. Rev. Pharmacol. Toxicol., 2002, 42, 409-435.
Antuono, "Decreased Glutamate 1 Glutamine in Alzheimer's Disease Detected in Vivo with 1H-MRS at 0.5 T", Neurology, 2001, 56:737-742.
Anwyl "Metabotropic Glutamate Receptor-Dependent Long-Term Potentiation", Neuropharmacology, 2009, 56, 735-740.
Anwyl "Metabotropic Glutamate Receptors: Electrophysiological Properties and Role in Plasticity", Brain Res. Brain Res., 1999, 29, 83-120.
Aparicio-Legarza et al., "Deficits of [3h]D-Aspartate Binding To Glutamate Uptake Sites in Striatal and Accumbens Tissue in Patients with Schizophrenia", Neuroscience Letters, 1997,232(1), 13-16.
Aparicio-Legarza et al., "Increased Density of Glutamate/N-Methyl-D-Aspartate Receptors in Putamen From Schizophrenic Patients" Neuroscience Letters,1998, 241(2-3), 143-146.
Armstrong et al., "Characterization of Competitive Inhibitors for the Transferase Activity of Pseudomonas Aeruginosa Exotoxin A", Journal of Enzyme Inhibition and Medicinal Chemistry, 2002, 1.7(4), 235-246.
Arnt, "Differential Effects of Classical and Newer Antipsychotics on the Hypermotility Induced by Two Dose Levels of D-Amphetamine", European Journal of Pharmacology, 1995, 283, 55-62.
Arnt, "Pharmacological Specificity of Conditioned Avoidance Response Inhibition in Rats: Inhibition By Neuroleptics and Correlation To Dopamine Receptor Blockade", Acta Pharmacol. Toxicol., 1982, 51, 321-329.
Aronica et al., "Metabotropic Glutamate Receptors in Cultured Cerebellar Granule Cells: Developmental Profile" Journal of Neurochemistry, 1993, 60(2), 559-565.
Aronica et al., "Pharmacological Characterization of Metabotropic Glutamate Receptors in Cultured Cerebellar Granule Cells", Neurochemical Research, 1993, 18(5), 605-612.
Arohica etai., "Status Epilepticus-lnduced Alterations in Metabotropic Glutamate Receptor Expression in Young and Adult Rats", J. Neurosci., 1997, 17(21), 8588-8595.
Aronson et al., "Triiodothyronine Augmentation in the Treatment of Refractory Depression. A Meta-Analysis", Arch Gen Psychiatry, 1996, 53, 842-848.
Arriza et al., "Functional Comparisons of Three Glutamate Transporter Subtypes Cloned From Human Motor Cortex", J. Neurosci., 1994, 14(9), 5559-5569.
Arundine, "Molecular Mechanisms of Glutamate-Dependent Neurodegeneration in Ischemia and Traumatic Brain Injury", Cellular and Molecular Life Sciences, 2004, 61, 657-668.
Atlante, "Glutamate Neurotoxicity, Oxidative Stress and Mitochondria", Febs Letters 497, 2001, 1-5.
Attwell et al. "Anticonvulsant and Glutamate Release-Inhibiting Properties of the Highly Potent Metabotropic Glutamate Receptor Agonist (2s, 2'r, 3'r)-2-(2',3'-Dicarboxycyclopropyl)Glycine (Dcg-Iv)", Brain Res., 1998, 805(1-2), 138-143.
Auer et al., "Reduced Glutamate in the Anterior Cingulate Cortex in Depression: An in Vivo Proton Magnetic Resonance Spectroscopy Study", Biol Psychiatry, 2000, 47(4), 305-313.
Auerbach et al., "Mutations Causing Syndromic Autism Define an Axis of Synaptic Pathophysiology", Nature, 2011, 480, 63-68.
Aultman et al., "Distinct Contributions of Glutamate and Dopamine Receptors to Temporal Aspects of Rodent Working Memory Using A Clinically Relevant Task", Psychopharmacology (Berl), 2001, 153(3), 353-364.
Austin et al., "Symptomatic and Neuroprotective Effects Following Activation of Nigral Group III Metabotropic Glutamate Receptors in Rodent Models of Parkinson's Disease", British Journal of Pharmacology, 2010, 160, 1741-1753.
Awouters et al., "Astemizole: Effects on General Behavior and Interactions with the Central Nervous System", Jap. Pharmacol. & Therapeutics, 1991, 19, 73-89.
Ayalew et al., "Convergent Functional Genomics of Schizophrenia: From Comprehensive Understanding to Genetic Risk Prediction", Molecular Psychiatry 2012, 1-19.

(56) References Cited

OTHER PUBLICATIONS

Ayan-Oshodi et al., "Adverse Events in Healthy Subjects Exposed to Single and Multiple Doses of Ly2140023 Monohydrate", J Clin Psychopharmacol, 2012, 32, 408-411.
Azimov et al., "Chemical Abstracts", Abstract No. 78798, 1986, 105(10), 1 page.
Azuma et al., "Synthesis and Reactions of 4-Chloro-1, 2-Dihydro-6-Methyl-2-Oxo-3-Pyridinecarbonitrile", Heterocycles, 2003, 60(6), 1461-1468.
Backstrom, "Suppression of Alcohol Self-Administration and Cue-Induced Reinstatement of Alcohol Seeking by the Mglu2/3 Receptor Agonist Ly379268 and the Mglu8 Receptor Agonist (S)-3,4-Dcpg", Eur. J. Pharmacol., 2005, 528, 110-118.
Badawy etaL, "Epilepsy: Ever-Changing States of Cortical Excitability" Neuroscience, 2012, 22, 89-99.
Baffa et al., "Norepinephrine and Serotonin Transporter Genes: Impact on Treatment Response in Depression", Neuropsychobiology, 2010, 62, 121-131.
Bagby et al., "Psychosocial and Clinical Predictors of Response to Pharmacotherapy for Depression"J Psychiatry Neurosci, 2002, 27(4), 250-7.
Bakker et al., "Activation of the Metabotropic Glutamate Receptor 2 (Mglu2) by Orthosteric and Allosteric Ligands", Poster 642.6/E30 Presented at the 40$^{th}$ Annual Meeting of Society for Neuroscience 2010, 1 page.
Bakker et al., "Reduction of Hippocampal Hyperactivity Improves Cognition in Amnestic Mild Cognitive Impairment", Neuron, 2012, 74(3), 467-474.
Balastrieri et al., "Assessing Mixed Anxiety-Depressive Disorder. A National Primary Care Survey", Psychiatry Research, 2010, 176, 197-201.
Balazs et al., "Metabotropic Glutamate Receptor Agonists Potentiate Cyclic Amp Formation Induced By Forskolin Or Beta-Adrenergic Receptor Activation in Cerebral Cortical Astrocytes in Culture", Journal of Neurochemistry, 1998, 70(6), 2446-2458.
Bandelow et al., "Adjunct Quetiapine XR in Patients with Major Depressive Disorder: A Pooled Analysis of Data From Patients with Anxious Depression", Abstracts of the 19th European Congress of Psychiatry, Mar. 2011, 1 page.
Barda et al., "Sar Study of A Subtype Selective Allosteric Potentiator of Metabotropic Glutamate 2 Receptor, N-(4-Phenoxyphenyl)-N-(3-Pyridinylmethyl)Ethanesulfonamide", Bioorganic & Medicinal Chemistry Letters, 2004, 14, 3099-3102.
Barker et al., "A Temporally Distinct Role for Group I and Group II Metabotropic Glutamate Receptors in Object Recognition Memory", Learn. Mem., 2006, 13(2), 178-186.
Barnes et al., "A Review of Central 5-Ht Receptors and their Function", Neuropharmacology, 1999, 38, 1083-1152.
Bar-Peled et al., "Distribution of Glutamate Transporter Subtypes During Human Brain Development", J Neurochem., 1997, 69(6), 2571-2580.
Barrett, "Mglur2-Positive Allosteric Modulators: Therapeutic Potential For Treating Cocaine Abuse?", Neuropsychopharmacology, 2010, 35, 2007-2008.
Bartha et al., "Measurement of Glutamate and Glutamine in the Medial Prefrontal Cortex of Never-Treated Schizophrenic Patients and Healthy Controls By Proton Magnetic Resonance Spectroscopy", Archives of General Psychiatry, 1997, 54(10), 959-965.
Barton et al., "Comparison of the Effect of Glutamate Receptor Modulators in the 6 Hz and Maximal Electroshock Seizure Models", Epilepsy Research, 2003, 56, 17-26.
Basan et al., "Valproate for Schizophrenia", Cochrane Collaboration, Cochrane Database Syst Rev., 2008, 2, 38 pages.
Batchelor et al., "Novel Synaptic Potentials in Cerebellar Purkinje Cells: Probable Mediation by Metabotropic Glutamate Receptors", Neuropharmacology, 1993, 32(1), 11-20.
Battaglia et al., "Selective Activation of Group-ll Metabotropic Glutamate Receptors Is Protective Against Excitotoxic Neuronal Death," European Journal of Pharmacology, 1998, 356(2-3), 271-274.

Bauer et al., "Extended Release Quetiapine as Adjunct to an Antidepressant in Patients with Major Depressive Disorder: Results of a Randomized, Placebo-Controlled, Double-Blind Study", J Clin Psychiatry 2009, 70(4), 540-549.
Bauzo et al., "Interactions Between the Mglur2/3 Agonist, Ly379268, and Cocaine on in Vivo Neurochemistry and Behavior in Squirrel Monkeys", Pharmacol. Biochem. Behav., 2009, 94(1), 204-210.
Bech et al., "Quantitative Rating of Depressive States", Acta Psychiatr Scand, 1975, 51(3), 161-170.
Bech, "Dose-Response Relationship of Pregabalin in Patients with Generalized Anxiety Disorder. A Pooled Analysis of Four Placebo-Controlled Trials", Pharmacopsychiatry, 2007, 40, 163-168.
Bech, "The Bech-Rafaelsen Melancholia Scale (Mes) in of Therapies in Depressive Disorders: A 20-Year Review of Its Use As Outcome Measure", Acta Psychiatr Scand, 2002, 106(4), 252-264.
Beesdo, "Incidence and Risk Patterns of Anxiety and Depressive Disorders and Categorization of Generalized Anxiety Disorder", Arch Gen Psychiatry, 2010, 67(1), 47-57.
Behrens et al., "Ketamine-Induced Loss of Phenotype of Fast-Spiking Interneurons is Mediated By Nadph-Oxidase", Science, 2007, 318, 1645-1647.
Belenikin et al., "Comparative Analysis of the Ligand-Binding Sites of the Metabotropic Glutamate Receptors Mglur1-Mglur8", Doklady Biochemistry & Biophysics., 2002, 386, 251-256.
Bell et al., "Altered Synaptic Function in Alzheimer's Disease", European Journal of Pharmacology, 2006, 545(1), 11-21.
Bellani et al., "Brain Anatomy of Major Depression II. Focus On Amygdala", Epidemiology and Psychiatric, Sciences. 2011, 20(1), 33-36.
Bellesi et al., "The Mglur2/3 Agonist Ly379268 Blocks the Effects of Glt-I Upregulation on Prepulse Inhibition of the Startle Reflex in Adult Rats", Neuropsychopharmacology, 2010, 1-8.
Bellesi et al., "The Mglur2/3 Agonist Ly379268 Blocks the Effects of Glt-1 Upregulation on Prepulse Inhibition of the Startle Reflex in Adult Rats", Neuropsychopharmacology, 2010, 35(6), 1253-1260.
Belousov et al., "Non-Cholinergic Excitation in Neurons After a Chronic Glutamate Receptor Blockade", Neuroreport, 2004, 15(1), 113-117.
Benarroch, "Metabotropic Glutamate Receptors: Synaptic Modulators and Therapeutic Targets For Neurologic Disease", Neurology, 2008, 70(12), 964-968.
Benca et al., "Sleep and Psychiatric Disorders. A Meta-Analysis", Arch Gen Psychiatry, 1992, 49, 651-670.
Beneyto et al., "Abnormal Glutamate Receptor Expression in the Medial Temporal Lobe in Schizophrenia and Mood Disorders", Neuropsychopharmacology, 2007, 32(9), 1888-1902.
Benilova et al., "The Toxic Aβ Oligomer and Alzheimer's Disease: An Emperor in Need of Clothes", Nature Neuroscience, 2012, 15(3), 349-357.
Benneyworth et al., "A Selective Positive Allosteric Modulator of Metabotropic Glutamate Receptor Subtype 2 Blocks a Hallucinogenic Drug Model of Psychosis", Mol. Pharmacol., 2007, 72, 477-484.
Benneyworth et al., "Chronic Phenethylamine Hallucinogen Treatment Alters Behavioral Sensitivity to a Metabotropic Glutamate 2/3 Receptor Agonist", Neuropsychopharmacology, 2008, 33(9), 2206-2216.
Benquet et al., "Two Distinct Signaling Pathways Upregulate Nmda Receptor Responses Via Two Distinct Metabotropic Glutamate Receptor Subtypes", Journal of Neuroscience, 2002, 22(22), 9679-9686.
Benson et al., "A Comparison of Observational Studies and Randomized, Controlled Studies", N Engl J Med., 2000, 342(25), 1878-1886.
Bergink et al., "Metabotropic Glutamate II Receptor Agonists in Panic Disorder: A Double Blind Clinical Trial with Ly354740", International Clinical Psychopharmacology, 2005, 20, 291-293.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, 68, 843-853.

(56) References Cited

OTHER PUBLICATIONS

Bermudo-Soriano, "New Perspectives in Glutamate and Anxiety", Pharmacol Biochem Behav, 2011, Epub. No Page Numbers, Doi:10.1016/J.Pbb.2011.04.010.
Berthele et al., "Distribution and Developmental Changes in Metabotropic Glutamate Receptor Messenger RNA Expression in the Rat Lumbar Spinal Cord", Developmental Brain Research, 1999, 112(1), 39-53.
Berthele et al., "Expression of Metabotropic Glutamate Receptor Subtype MRNA (Mglur1-8) in Human Cerebellum", Neuroreport, 1999, 10(18), 3861-3867.
Bertrand et al., "Common and Selective Molecular Determinants Involved in Metabotopic Glutamate Receptor Agonist Activity", J. Med. Chem., 2002, 45(15), 3171-3183.
Bespalov et al., "Behavioral Characterization of the Mglu Group ll/lll Receptor Antagonist, Ly-341495, in Animal Models of Anxiety and Depression", European Journal of Pharmacology 2008, 592, 96-102.
Bespalov et al., "Habituation Deficits Induced By Metabotropic Glutamate Receptors 2/3 Receptor Blockade in Mice: Reversal By Antipsychotic Drugs", Journal of Pharmacology & Experimental Therapeutics, 2007, 320(2), 944-950.
Bessho et al., "Glutamate and Quisqualate Regulate Expression of Metabotropic Glutamate Receptor MRNA in Cultured Cerebellar Granule Cells", Journal of Neurochemistry, 1993, 60(1), 253-259.
Bessis et al., "Metabotropic Glutamate Receptors: Exciting Possibilities in Excitatory Transmission", Celltransmissions, 2000, 17, 3-10.
Bick et al., "Photo-Oxidative Cleavage: An Alternative Method for Degrading Bisbenzylisoquinoline Alkaloids", Journal of Natural Products, 1986, 49(3), 373-385.
Bijl et al., "Current and Residual Functional Disability Associated with Psychopathology: Findings from the Netherlands Mental Health Survey and Incidence Study (Nemesis)", Psychological Medicine, May 2000, 657-668.
Bilkei-Gorzo et al., "MCPP-lnduced Anxiety in the Light-Dark Box in Rats-A New Method for Screening Anxiolytic Activity", Psychopharmacology (Berl), 1998, 136(3), 291-298.
Binder et al., "Association of Polymorphisms in Genes Regulating the Corticotropin-Releasing Factor System with Antidepressant Treatment Response", Arc Gen Psychiatry, 2010, 67(4), 369-370.
Black et al., "Compound A, A Novel, Potent and Selective Mglur2 Positive Allosteric Modulator: II. Effects in Models Predictive of Therapeutic Activity Against Cognitive Impairment Associated with Schizophrenia", Poster 767.7 Presented at the 40th Annual Meeting of Society for Neuroscience, Nov. 2010, 1 page.
Blaha et al., "Stimulation of the Ventral Subiculum of the Hippocampus Evokes Glutamate Receptor-Mediated Changes in Dopamine Efflux in the Rat Nucleus Accumbens", European Journal of Neuroscience, 1997, 9(5), 902-911.
Blanco et al., "Changes in the Prevalence of Non-Medical Prescription Drug Use and Drug Use Disorders in the United States: 1991-1992 and 2001-2002", Drug and Alcohol Dependence, 2007, 90, 252-260.
Boatman et al., "Alkylations at the Methyl or Alpha-Methylene Group of 6- Or 4-Alkyl-3-Cyano-2(1)-Pyridones Through Dianions", Journal of Organic Chemistry, 1965, 30(11), 3593-3597.
Bockaert et al., "Metabotropic Glutamate Receptors: An Original Family of G Protein-Coupled Receptors", Fundamental & Clinical Pharmacology, 1993, 7(9), 473-485.
Bockaert et al., "Molecular Tinkering of G Protein-Coupled Receptors: An Evolutionary Success", Embo Journal, 1999, 18(7), 1723-1729.
Bodick et al., "Protocols to Demonstrate Slowing of Alzheimer Disease Progression. Position Paper on the International Working Group on Harmonization of Dementia Drug Guidelines", Alzheimer Disease and Associated Disorders, 1997, 11 (Suppl 3), 50-53.
Bohm et al., "Thieno Compounds Part 5: Basically Substituted Thieno[2,3-D]Pyrimidines'", Pharmazie., 1986, 41, 23-25.
Bohme et al., "Darstellng Und Umsetzungen Von 3-Arylamino-2-Halogencrotononitilen", Chem. Ber., 1976, 109, 2908-2913.
Boldyrev et al., "Homocysteine and its Derivatives as Possible Modulators of Neuronal and Non-Neuronal Cell Glutamate Receptors in Alzheimer's Disease", J Alzheimers. Dis, 2007, 11(2), 219-228.
Bolton et al., "Exploring the Correlates of Suicide Attempts Among Individuals with Major Depressive Disorder: Findings from the National Epidemiologic Survey on Alcohol and Related Conditions", J Clin Psychiatry, 2008, 69, 1139-1149.
Bonanno et al., "Chronic Antidepressants Reduce Depolarization-Evoked Glutamate Release and Protein Interactions Favoring Formation of Snare Complex in Hippocampus", J Neurosci 2005, 25, 3270-3279.
Bond et al., "Neuroprotective Effects of Ly379268, A Selective Mglu2/3 Receptor Agonist: Investigations Into Possible Mechanism of Action in Vivo", J Pharmacol. Exp. Ther., 2000, 294(3), 800-809.
Bond et al., "Pharmacology of Metabotropic Glutamate Receptor-Mediated Enhancement of Responses To Excitatory and Inhibitory Amino Acids On Rat Spinal Neurones in Vivo", Neuropharmacology, 1995, 34(8), 1015-1023.
Bonnefous et al., "Biphenyl-Indanones: Allosteric Potentiators of Metabotropic Glutamate Subtype 2 Receptor", Bioorg Med Chem Lett, 2005, 15, 4354-4358.
Boris-Moller et al., "Changes in the Extracellular Levels of Glutamate and Aspartate During Ischemia and Hypoglycemia. Effects of Hypothermia", Experimental Brain Research, 1998, 121(3), 277-284.
Borowitz et al., "Organophosphorus Chemistry. III. The Reactions of Triphenylphosphine with Secondary A-Bromo Ketones and with 2-Bromodimedone", Journal of Organic Chemistry, Dec. 1966, 4031-4037.
Bortolotto et al., "Roles of Metabotropic Glutamate Receptors in LTP and LTD in the Hippocampus", Current Opinion in Neurobioloqy, 1999, 9(3), 299-304.
Boules et al., "Neurotensin Agonists: Potential in the Treatment of Schizophrenia", CNS Drugs, 2007, 21(1), 13-23.
Bouvrais-Veret et al., "Microtubule-Associated Stop Protein Deletion Triggers Restricted Changes in Dopaminergic Neurotransmission", J. Neurochem., 2008, 104, 745-756.
Boyette et al., "Factor Structure of the Yale-Brown Obsessive-Compulsive Scale (Y-Bocs) in a Large Sample of Patients with Schizophrenia or Related Disorders and Comorbid Obsessive-Compulsive Symptoms", Psychiatry Res., 2011, 409-413.
Brabet et al., "Comparative Effect of L-CCG-I, DCG-IV and Gamma-Carboxy-L-Glutamate on all Cloned Metabotropic Glutamate Receptor Subtypes", Neuropharmacology, 1998, 37, 1043-1051.
Bradley et al., "Activation of Group II Metabotropic Glutamate Receptors Inhibits Synaptic Excitation of the Subsantia Nigra Pars Reticulata", J. of Neuroscience, May 2000, 20(9), 3085-3094.
Braff et al., "Human Studies of Prepulse Inhibition of Startle: Normal Subjects, Patient Groups, and Pharmacological Studies", Psychopharmacology, 2001, 156, 234-258.
Braga et al., "Making Crystals from Crystals: A Green Route to Crystal Engineering and Polymorphism", Chem. Commun., 2005, 3635-3645.
Braish et al., "Construction of the (1x,5x,6x)-6-Amino-3-Azabicyclo[3.1.0]Hexane Ring System", Synlett, 1996, 1100-1102.
Brauner-Osborne et al., "A New Highly Selective Metabotropic Excitatory Amino Acid Agonist: 2-Amino-4-(3-Hydroxy-5-Methylisoxazol-4-YI)Butyric Acid", Journal of Medicinal Chemistry, 1996, 39(16), 3188-3194.
Brauner-Osborne et al., "Interaction of CPCCOET with a Chimeric Mglu1b and Calcium Sensing Receptor", Neuroreport, 1999, 10(18), 3923-3925.
Brauner-Osborne et al., "Molecular Pharmacology of 4-Substituted Glutamic Acid Analogues at Ionotropic and Metabotropic Excitatory Amino Acid Receptors", European Journal of Pharmacology, 1997, 335(2-3), R1-R3.
Brauner-Osborne et al., "Pharmacology of (S)-Homoquisqualic Acid and (S)-2-Amino-5-Phosphonopentanoic Acid [(S)-Ap5] at

(56) References Cited

OTHER PUBLICATIONS

Cloned Metabotropic Glutamate Receptors", British Journal of Pharmacology, 1998, 123(2), 269-274.
Brauner-Osborne, "Structure, Pharmacology and Therapeutic Prospects of Family C G-Protein Coupled Receptors", Current Drug Targets, 2007, 8, 169-184.
Breier et al., "Association of Ketamine-Induced Psychosis with Focal Activation of the Prefrontal Cortex in Healthy Volunteers", Am J Psychiatry, 1997, 154, 805-811.
Bremner et al., "Development and Preliminary Psychometric Properties of an Instrument for the Measurement of Childhood Trauma: The Early Trauma Inventory", Depress Anxiety, 2000, 12(1), 1-12.
Bremner et al., "Psychometric Properties of the Early Trauma Inventory-Self Report", J Nerv Ment Dis, 2007, 195(3), 211-218.
Brighty et al., "Synthesis of (1x,5x,6x)-6-Amino-3-Azabicyclo[3.1.0]Hexane: A Novel Achiral Diamine", Synlett, 1996, 1097-1099.
Brnardic et al., "3-Aryl-5-Phenoxymethyl-1,3-Oxazolidin-2-Ones As Positive Allosteric Modulators of Mglur2 for the Treatment of Schizophrenia: Hit-To-Lead Efforts", Bioorg Med Chem Lett, 2010, 20, 3129-3133.
Broekkamp et al., "Major Tranquillizers can be Distinguished From Minor Tranquillizers on the Basis of Effects on Marble Burying and Swim-Induced Grooming in Mice", Eur. J. Pharmacol., 1986, 126, 223-229.
Bruno et al., "Activation of Class II or III Metabotropic Glutamate Receptors Protects Cultured Cortical Neurons Against Excitotoxic Degeneration", European Journal of Neuroscience, 1995, 7(9), 1906-1913.
Bruno et al., "Activation of Metabotropic Glutamate Receptors Coupled To Inositol Phospholipid Hydrolysis Amplifies NMDA-Induced Neuronal Degeneration in Cultured Cortical Cells", Neuropharmacology, 1995, 34(8), 1089-1098.
Bruno et al., "Excitatory Amino Acids and Neurotoxicity", Functional Neurology 1993, 8(4), 279-292.
Bruno et al., "Metabotropic Glutamate Receptors and Neurodegeneration", Progress in Brain Research, 1998, 116, 209-221.
Bruno et al., "Metabotropic Glutamate Receptors and Neuronal Degeneration in Culture", Advances in Neurology, 1996, 71,47-52.
Bruno et al., "Molecular Dynamics Simulation of the Heterodimeric Mgtur2/5ht(2a) Complex. An Atomistic Resolution Study of a Potential New Target in Psychiatric Conditions", J. Chem. Inf. Model., 2009, 49(6), 1602-1616.
Bruno et al., "Neuroprotection by Glial Metabotropic Glutamate Receptors is Mediated By Transforming Growth Factor-Beta", J. Neurosci., 1998, 18(23), 9594-9600.
Bruno et al., "The Neuroprotective Activity of Group-ll Metabotropic Glutamate Receptors Requires New Protein Synthesis and Involves a Glial-Neuronal Signalling", J. Neurosci., 1997, 17(6), 1891-1897.
Bruno, "Metabotropic Glutamate Receptor Subtypes as Targets for Neuroprotective Drugs", Journal of Cerebral Blood Flow and Metabolism, 2001, 21, 1013-1033.
Buisson et al., "The Inhibitory Mglur Agonist, S-4-Carboxy-3-Hydroxy-Phenylglycine Selectively Attenuates NMDA Neurotoxicity and Oxygen-Glucose Deprivation-Induced Neuronal Death", Neuropharmacoloqy, 1995, 34(8), 1081-1087.
Bunch et al., "Excitatory Amino Acid Transporters as Potential Drug Targets", Expert Opin Ther Targets, 2009, 13(60), 719-731.
Bunney etaL, "Norepinephrine in Depression Reactions. A Review", Arch Gen Psychiatry, 1965, 13(6), 483-494.
Burford et al., "Strategies for the Identification of Allosteric Modulators of G-Protein-Coupled Receptors", Biochem Pharmacol, 2011, 1-12.
Bushell et al., "Pharmacological Antagonism of the Actions of Group II and III Mglur Agonists in the Lateral Perforant Path of Rat Hippocampal Slices", Br. J Pharmacol., 1996, 117(7), 1457-1462.
Bustillo et al., "1H-MRS At 4 Tesla in Minimally Treated Early Schizophrenia", Mol Psychiatry, 2010, 15(6), 629-636.
Butterfield et al., "The Glutamatergic System and Alzheimer's Disease: Therapeutic Implications" CNS Drugs, 2003, 17(9), 641-652.
Byrnes et ai., "Metabotropic Glutamate Receptors as Targets for Multipotential Treatment of Neurological Disorders". Neurotherapeutics, 2009, 6(1), 94-107.
Cacabelos et al., "The Glutamatergic System and Neurodegeneration in Dementia: Preventive Strategies in Alzheimer's Disease", International Journal of Geriatric Psychiatry, 1999, 14(1), 3-47.
Cai et al., "Local Potentiation of Excitatory Synapses by Serotonin and its Alteration in Rodent Models of Depression", Nature Neuroscience, 2013, 16(4), 464-472.
Calabresi, "Antiepileptic Drugs in Migraine: From Clinical Aspects To Cellular Mechanisms", Trends in Pharmacological Sci., 2007, 28(4), 188-195.
Campbell et al., "An Update On Regional Brain vol. Differences Associated with Mood Disorders", CurrOpin Psychiatry, 2006, 19(1), 25-33.
Canadian Patent Application No. 2,581,144: Office Action dated Dec. 4, 2012, 5 pages.
Canadian Patent Application No. 2,581,144: Office Action dated May 13, 2009, 5 pages.
Caraci et al., "Metabotropic Glutamate Receptors in Neurodegeneration/Neuroprotection: Still A Hot Topic?", Neurochemistry Intl, 2012, 61(4), 559-565.
Caraci et al., "Targeting Group II Metabotropic Glutamate (MGLU) Receptors for the Treatment of Psychosis Associated with Alzheimer's Disease: Selective Activation of Mglu2 Receptors Amplifies B-Amyloid Toxicity in Cultured Neurons, Whereas Dual Activation of Mglu2 and Mglu3 Receptors is Neuroprotective", Mol Pharmacol, 2011, 79, 618-626.
Carlsson et al., "Neurotransmitter Aberrations in Schizophrenia: New Perspectives and Therapeutic Implications", Life Sciences, 1997, 61(2), 75-94.
Carlsson, "The Neurochemical Circuitry of Schizophrenia", Pharmacopsychiatry, 2006, 39, S10-S14.
Carter, "Schizophrenia Susceptibility Genes Converge on Interlinked Pathways Related to Glutamatergic Transmission and Long-Term Potentiation, Oxidative Stress and Oligodendrocyte Viability", Schizophr. Res., 2006, 86(1-3), 1-14.
Cartmell et al., "Acute Increases in Monoamine Release in the Rat Prefrontal Cortex by the Mglu2/3 Agonist Ly379268 are Similar in Profile to Risperidone, Not Locally Mediated, and Can Be Elicited in the Presence of Uptake Blockade", Neuropharmacology, 2001, 40(7), 847-855.
Cartmell et al., "Attenuation of Specific Pcp-Evoked Behaviors By the Potent Mglu2/3 Receptor Agonist, Ly379268 and Comparison with the Atypical Antipsychotic, Clozapine", Psychopharmacology, 2000, 148, 423-429.
Cartmell et al., "Characterization of [3h]-(2s,2'r,3'r0-2-(2'3'-Dicarboxycyclopropyl)Glycine ([3h]-Dcg Iv) Binding to Metabotropic Mglu2 Receptor-Transfected Cell Membranes", British Journal of Pharmacology, 1998, 123, 497-504.
Cartmell et al., "Dopamine and 5-Ht Turnover are Increased by the Mglu2/3 Receptor Agonist Ly379268 in Rat Medial Prefrontal Cortex, Nucleus Accumbens and Striatum", Brain Res., 2000, 887(2), 378-384.
Cartmell et al., "Effect of Metabotropic Glutamate Receptor Activation on Receptor-Mediated Cyclic Amp Responses in Primary Cultures of Rat Striatal Neurones", Brain Res., 1998, 791(1-2), 191-199.
Cartmell et al., "Regulation of Neurotransmitter Release by Metabotropic Glutamate Receptors", J. Neurochem., 2000, 75(3), 889-907.
Cartmell et al., "the Metabotropic Glutamate 2/3 Receptor Agonists Ly354740 and Ly379268 Selectively Attenuate Phencyclidine Versus D-Amphetamine Motor Behavior in Rats", J Pharmacol ExpTher, 1999, 291, 161-170.
Cartmell et al., "The Mglu(2/3) Receptor Agonist Ly379268 Selectively Blocks Amphetamine Ambulations and Rearing", Eur. J Pharmacol., 2000, 400(2-3), 221-224.
Cartmell et al., "The Potent, Selective Mglu2/3 Receptor Agonist Ly379268 Increases Extracellular Levels of Dopamine, 3,4-Dihydroxyphenylacetic Acid, Homovanillic Acid, and 5-Hydroxyindole-3-Acetic Acid in the Medial Prefrontal Cortex of the Freely Moving Rat", J Neurochem., 2000, 75(3), 1147-1154.

(56) References Cited

OTHER PUBLICATIONS

Cartmell et al., "Tolerance To the Motor Impairment, But Not the Reversal of PCP-Induced Motor Activities By Oral Administration of the Mglu2/3 Receptor Agonist, Ly379268", Naunyn Schmiedebergs Arch Pharmacol, 2000, 361, 39-46.
Casado et al., "GPCR Homomers and Heteromers: A Better Choice as Targets for Drug Development Than GPCR Monomers?", Pharmacology & Therapeutics, 2009, 124, 248-257.
Castagne et al., "Preclinical Behavioral Models for Predicting Antipsychotic Activity", Adv. Pharmacol., 2009, 57, 381-418.
Catania et al., "Desensitization of Metabotropic Glutamate Receptors in Neuronal Cultures", Journal of Neurochemistry, 1991, 56(4), 1329-1335.
Catania et al., "Group I Metabotropic Glutamate Receptors: A Role in Neurodevelopmental Disorders?", Mol Neurobiol, 2007, 35, 298-307.
Catania et al., "Homologous Desensitization of Metabolotropic Glutamate Receptors in Neuronal Cultures", Pharmacological Research. 1990, 22(Suppl 1), 79-80.
Catania et al., "Metabotropic Glutamate Receptor Heterogeneity in Rat Brain", Molecular Pharmacology, 1994, 45(4), 626-636.
Catania et al., "Metabotropic Glutamate Receptors are Differentially Regulated During Development", Neuroscience. 1994, 61(3), 481-495.
Catterall, "Structure and Function of Neuronal Ca2+ Channels and Their Role in Neurotransmitter Release", Cell Calcium, 1998, 24(5-6), 307-323.
Cavalli et al., "Multi-Target-Directed Ligands To Combat Neurodegenerative Diseases", J. Med. Chem., 2007-2008, 26 pages.
Cavanni et al., "Pharmacological Analysis of Carboxyphenylglycines at Metabotropic Glutamate Receptors", European Journal of Pharmacology, 1994, 269(1), 9-15.
Celanire et al., "Recent Advances in the Drug Discovery of Metabotropic Glutamate Receptor 4 (mGluR4) Activators for the Treatment of CNS and Non-CNS Disorders", Expert Opin. Drug Discovery, 2012, 7(3). 261-280.
Chaki "Group II Metabotropic Glutamate Receptor Agonists as a Potential Drug For Schizophrenia", European Journal of Pharmacology, 2010, 639, 59-66.
Chaki et al., "Anxiolytic- and Antidepressant-Like Profile of a New Crf1 Receptor Antagonist, R278995/Cra0450", Eur J Pharmacol, 2004, 485, 145-158.
Chaki et al., "Mglu2/3 and Mglu5 Receptors: Potential Targets For Novel Antidepressants", Neuropharmacology, 2013, 66, 40-52.
Chaki et al., "Targeting of Metabotropic Glutamate Receptors for the Treatment of Schizophrenia", Current Pharmaceutical Design, 2011, 17, 94-102.
Chakos et al., "Baseline Use of Concomitant Psychotropic Medications to Treat Schizophrenia in the Catie Trial", PsychiatrServ., 2006, 57(8), 1094-1101.
Chakrabarty et al., "Glutamatergic Dysfunction in OCD", Neuropsychopharmacology, 2005, 30(9), 1735-1740.
Chakrasali et al., "Reaction of Acylketene S,N-Acetals with Malonyl Chloride: Synthesis of Novel 1,5-Substituted 4-Hydroxy-6-Methylthio-2 (1h)-Pyridones and 6,8-Substituted 4-Hydroxy-7-Methylthio-2,5-Dioxo-5,6-Dihydro-2h-Pyrano [3,2-C] Pyridines", Synthesis, Jan. 1988, 87-89.
Charney et al., "Increased Anxiogenic Effects of Caffeine in Panic Disorders", Arch Gen Psychiatry, 1985, 42, 233-243.
Charney et al., "Life Stress, Genes, and Depression: Multiple Pathways Lead to Increased Risk and New Opportunities for Intervention", Science's Stke, 2004, (225), Re5, 12 pages.
Charney et al., "Noradrenergic Function in Panic Anxiety. Effects of Yohimbine in Healthy Subjects and Patients with Agoraphobia and Panic Disorder", Arch. Gen. Psychiatry, 1984, 41, 751-763.
Chaudhari et al., "A Metabotropic Glutamate Receptor Variant Functions as a Taste Receptor", Nature Neuroscience, 2000, 3, 113-119.

Chavez-Noriega et al., "Metabotropic Glutamate Receptors: Potential Drug Targets for the Treatment of Schizophrenia", Current Drug Targets—CNS & Neurological Disorders, 2002, 1(3), 261-281.
Chavis et al., "Facilitatory Coupling Between a Glutamate Metabotropic Receptor and Dihydropyridine-Sensitive Calcium Channels in Cultured Cerebellar Granule Cells", J. Neurosci., 1995, 15(1), 135-143.
Chavis et al., "Modulation of Calcium Channels by Metabotropic Glutamate Receptors in Cerebellar Granule Cells", Neuropharmacology, 1995, 34(8), 929-937.
Chen et al., "Second-Generation Antipsychotics in Major Depressive Disorder: Update and Clinical Perspective", CurrOpin Psychiatry, 2011, 24, 19-17.
Chen, "The Chemical Biology of Clinically Tolerated NMDA Receptor Antagonists", Journal of Neurochemistry, 2006, 97, 1611-1626.
Chiarugi et al., "Novel Isoquinolinone-Derived Inhibitors of Poly(Adp-Ribose) Polymerase-1: Pharmacological Characterization and Neuroprotective Effects in an in Vitro Model of Cerebral Ischemia", Journal of Pharmacology and Experimental Therapeutics, 2003, 305(3), 943-949.
Chiechio et al., "Epigenetic Modulation of Mglu2 Receptors by Histone Deacetylase Inhibitors in the Treatment of Inflammatory Pain", Mol. Pharmacol., 2009, 75(5), 1014-1020.
Chiechio et al., "Metabotropic Glutamate Receptors and the Control of Chronic Pain", Curr Opin Pharmacol, 2012, 12, 28-34.
Chiechio et al., "Transcriptional Regulation of Type-2 Metabotropic Glutamate Receptors: An Epigenetic Path to Novel Treatments for Chronic Pain", Trends in Pharmacological Sciences, 2010, 31(4), 153-160.
Chin et al., "Amyloid Beta Protein Modulates Glutamate-Mediated Neurotransmission in the Rat Basal Forebrain: Involvement of Presynaptic Neuronal Nicotinic Acetylcholine and Metabotropic Glutamate Receptors", J. Neurosci., 2007, 27(35), 9262-9269.
Chin et al., "Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals", Jpet, 2011, 336, 709-715.
Chin et al., "Awake Rat Pharmacological MRI as a Translational Pharmacodynamic Biomarker: Mglur2/3 Agonist Modulation of Ketamine-Induced Bold Signals", Jpet, 2010, 22 pages.
Choi, "Methods for Antagonizing Glutamate Neurotoxicity", Cerebrovascular & Brain Metabolism Reviews. 1990, 2(2), 105-147.
Chojnacka-Wojcik et al., "Glutamate Receptor Ligands as Anxiolytics", Current Opinion in Investigational Drugs, 2001, 2(8), 1112-1119.
Christopolous et al., "G Protein-Coupled Receptor Allosterism and Complexing", Pharmacol Rev, 2002, 54, 323-374.
Chrostopoulos., "Allosteric Binding Sites on Cell-Sturcture Receptors: Novel Targets for Drug Discovery", Nature Rev., Mar. 2002, 1, 198-210.
Cid et al., "Discovery of 1,4-Disubstituted 3-Cyano-2-Pyridones: A New Class of Positive Allosteric Modulators of the Metabotropic Glutamate 2 Receptor", J Med Chem, 2012, 55, 2388-2405.
Cid et al., "Discovery of 1,5-Disubstituted Pyridones: A New Class of Positive Allosteric Modulators of the Metabotropic Glutamate 2 Receptor", ACS Chem Neurosci, 2010, 1, 788-795.
Cid et al., "Discovery of 3Cyclopropylmethyl-7-(4-Phenylpiperidin-1-Yl)-8-Trifluoromethyl[1,2,4]Triazolo[4,3 A]Pyridine (Jnj-42153605): A Positive Allosteric Modulator of the Metabotropic Glutamate 2 Receptor", J Med Chem, 2012, 55, 8770-8789.
Cid, "Discovery of a Potent and Orally Bioavailable Positive Allosteric Modulator of Mglur2 for the Treatment of CNS Disorders", Presentation Slides, 16th SCI/RSC Medicinal Chemistry Symposium, Cambridge, Sep. 2011, 26 pages.
Cid, "JNJ-421 53605: A Novel Positive Allosteric Modulator of Mglur2 For the Treatment of CNS Disorders" Presentation Slides, RICT 2012—48th International Conference On Medicinal Chemistry, Poitiers 2012, 28 pages.
Citrome, "Adjunctive Aripiprazole, Olanzapine, or Quetiapine for Major Depressive Disorder: An Analysis of Number Needed to Treat, No. Needed to Harm, and Likelihood to Be Helped or Harmed", Postgraduate Medicine, 2010, 122(4), 39-48.

(56) References Cited

OTHER PUBLICATIONS

Clark et al., "Effects of the Mglu2/3 Receptor Agonist Ly379268 on Motor Activity in Phencyclidine-Sensitized Rats", Pharmacol. Biochem. Behav., 2002, 73(2), 339-346.
Clark et al., "Synthesis of Thieno[2,3-Djpyrimidines from 4,6-Dichloropyrimidine-5-Carbaldehydes", Journal Heterocyclic Chem, 1993, 30, 1065-1072.
Clark, "Tripartite Model of Anxiety and Depression: Psychometric Evidence and Taxonomic Implications", J. Abnormal Psych., 1991, 100(3), 316-336.
Clayton et al., "Follow-Up and Family Study of Anxious Depression" Am J Psychiatry, 1991, 148, 1512-1517.
Cleary et al., "Factor Analysis of the Hamilton Depression Scale" Drugs Exptl Clin Res, 1977, 1(1-2), 115-120.
Clements et al., "The Time Course of Glutamate in the Synaptic Cleft", Science, 1992, 258(5087), 1498-1501.
Cleva et al., "Positive Allosteric Modulators of Type 5 Metabotropic Glutamate Receptors (mGluR5) and their Therapeutic Potential for the Treatment of CNS Disorders", Molecules, 2011, 16, 2097-2106.
Clinical Trials, "A Dose-Ranging Study of JNJ-40411813 in Healthy Male Volunteers", Available from http://clinicaltrials.gov/show/NCT01358006, retrieved on Aug. 1, 2013.
Clinical Trials, "A Study of [11C]JNJ-42491293, a Possible PET Ligand for the mGlu2 Receptor, in Healthy Adult Volunteers", Available from http://clinicaltrials.gov/show/NCT01359852, retrieved on Aug. 1, 2013.
Clinical Trials, "A Study of JNJ-40411813 as Supplementary Treatment to an Antidepressant in Adults with Depression and Anxiety Symptoms", Available from: http://clinicaltrials.gov/show/NCT01582815, retrieved on Aug. 1, 2013.
Clinical Trials, "AZD8529 Single Ascending Dose Study (Sad)", Clinicaltrials.Gov. No. NCT00755378, Available From: Http://Clinicaltrials.Gov/Show/Nct00755378, retrieved on Aug. 22, 2013.
Clinical Trials, "First-In-Patient Study to Assess the Safety and Tolerability and to Explore the Potential Therapeutic Efficacy of a Novel Glutamate Modulator as Monotherapy and as Add-On Therapy in Patients with Schizophrenia", Available From: Https://Www.Clinicaltrialsregister.Eu—Eudract No. 2010-023369-23, retrieved on Aug. 1, 2013.
Clinical Trials, "Investigation of the Safety, Tolerability and Potential Therapeutic Effects of JNJ-40411813 in Patients with Schizophrenia", Clinicaltrials Gov. No. NCT01323205, Available From: Http://Clinicaltrials.Gov/Show/NCT01323205, Retrieved Aug. 1, 2013.
Clinical Trials, "Ketamine Challenge Study with JNJ-40411813", Clinical Trials. Gov No. NCT01101659, Available From: Http://Clinicaltrials.Gov/Ct2/Show/Nct01101659, 2010, 3 pages.
Clinical Trials, "Study To Assess the Efficacy, Safety, and Tolerability of AZD8529 in Adult Schizophrenia Patients", Clinicaltrials.Gov. No. NCT00921804, Available From: Http://Clinicaltrials.Gov/Show/Nct00921804, retrieved on Aug. 23, 2013, 3 pages.
Clinical Trials, "The Effects Azd8529 On Cognition and Negative Symptoms in Schizophrenics", Clinicaltrials.Gov. No. NCT00986531, Available From: Http://Clinicaltrials.Gov/Show/Nct00986531, retrieved on Aug. 23, 2013, 2 pages.
Cloninger et al., "The Empirical Structure of Psychiatric Comorbidity and its Theoretical Significance", Comorbidity of Mood and Anxiety Disorders, 1990, 439-462.
Cohen et al., "A Global Measure of Perceived Stress", J Health Soc Behav, 1983 24(4), 385-396.
Colangelo et al., "Differential Effects of Acute Administration of Clozapine or Haloperidol on Local Cerebral Glucose Utilization in the Rat", Brain Research, 1997, 768, 273-278.
Collingridge et al., "Excitatory Amino Acid Receptors and Synaptic Plasticity", Trends in Pharmacological Sciences, 1990, 11(7), 290-296.
Collins et al., "Arachidonic Acid Metabolites and the Synaptic Potentiation Evoked By Activation of Metabotropic Glutamate Receptors", European Journal of Pharmacology, 1998, 342(2-3), 213-216.
Collins et al., "From Ligand Binding to Gene Expression: New Insights into the Regulation of G-Protein-Coupled Receptors", Trends in Biochemical Sciences, 1992, 17(1), 37-39.
Colpaert et al., "A Critical Study on Ro-4-1284 Antagonism in Mice", Arch. Int. Pharmacodyn., 1975, 215, 40-90.
Colzi et al., "Monoamine Oxidase-A Inhibitors and Dopamine Metabolism in Rat Caudatus: Evidence that an Increased Cytosolic Level of Dopamine Displaces Reversible Monoamine Oxidase-A Inhibitors in Vivo", J. Pharmacol. Exper. Therapeutics, 1993, 265, 103-111.
Comins et al., "N- Vs. O-Alkylation in the Mitsunobu Reaction of 2-Pyridone", Tetrahedron Letters, 1994, 35(18), 2819-2822.
Committee for Proprietary Medicinal Products (CPMP), European Agency For the Evaluation of Medicinal Products; Meeting Feb. 26, 1998, London (UK): Note For Guidance On the Clinical Investigation of Medicinal Products in the Treatment of Schizophrenia, 10.
Conigrave et al., "Allosteric Activation of Plasma Membrane Receptors-Physiological Implications and Structural Origins", Progress in Biophysics & Molecular Biology, 2003, 81(3), 219-40.
Conn et al., "Activation of Metabotropic Glutamate Receptors as a Novel Approach for the Treatment of Schizophrenia", Trends Pharmacol Sci, 2008, 30(1), 25-31.
Conn et al., "Allosteric Modulators of Gpcrs: A Novel Approach for the Treatment of CNS Disorders", Nature Reviews Drug Discovery, 2009, 8, 41-54.
Conn et al., "Metabotropic Glutamate Receptors in the Basal Ganglia Motor Circuit", Nature Reviews Neuroscience, 2005, 6, 787-798.
Conn et al., "Pharmacology and Functions of Metabotropic Glutamate Receptors", Annu Rev Pharmacol Toxicol, 1997, 37, 205-237.
Conn, "Physiological Roles and Therapeutic Potential of Metabotropic Glutamate Receptors" Annals of the New York Academy of Sciences, 2003, 1003, 12-21.
Connolly et al., "If At First You Don't Succeed: A Review of the Evidence for Antidepressant Augmentation, Combination and Switching Strategies", Drugs, 2011, 71(1), 43-64.
Cook et al., "Behavioral Effects of Some Psychopharmacological Agent", Ann. Ny Acad. Sci., 1957, 66, 740-752.
Cook et al., "Diethylaminoalkyl Ester Hydrochlorides of N-Alkyl-4-Carbostyrilcarboxylic Acids", J Am. Chem. Soc., 1952, 74, 543-554.
Cook et al., "Effects of Drugs On Avoidance and Escape Behavior", Fed. Proc. 23, 1964, 818-835.
Copani, "Activation of Metabotropic Glutamate Receptors Protects Cultured Neurons Against Apoptosis Induced By-Amyioid Peptide", Molecular Pharmacology, 1995, 47:890-897.
Copeland et al., "Positive Allosteric Modulation Reveals a Specific Role for Mglu2 Receptors in Sensory Processing in the Thalamus", J Physiol, 2012, 590.4, 937-951.
Corlett et al., "Glutamatergic Model Psychoses: Prediction Error, Learning, and Inference", Neuropsychopharmacology, 2011, 36(1), 294-315.
Corti, "The Use of Knock-Out Mice Unravels Distinct Roles For Mglu2 and Mglu3 Metabotropic Glutamate Receptors in Mechanisms of Neurodegeneration/Neuroprotection", J. Neurosci., 2007, 27(31), 8297-8308.
Coryell et al., "Effects of Anxiety on the Long-Term Course of Depressive Disorders", The British Journal of Psychiatry, 2012, 200, 210-215.
Costantino et al., "Modeling of Poly (Adp-Ribose) Polymerase (Parp) Inhibitors. Docking of Ligands and Quantitative Structure-Activity Relationship Analysis", Journal of Medicinal Chemistry. 2001, 440, 3786-3794.
Coyle, "The Gaba-Glutamate Connection in Schizophrenia: Which is the Proximate Cause?", Biochem. Pharmacol., 2004, 68(8), 1507-1514.
Cozzi et al., "Type 2 Metabotropic Glutamate (Mglu) Receptors Tonically Inhibit Transmitter Release in Rat Caudate Nucleus: in Vivo Studies with (2s,Ts,2's,3'r)-2-(2'-Carboxy-3'-Phenylcyclopropyl)Glycine, A New Potent and Selective Antagonist", European Journal of Neuroscience, 1997, 9(7), 1350-1355.
Craddock et al., "The Genetics of Schizophrenia and Bipolar Disorder: Dissecting Psychosis", J Med Genet, 2005, 42, 193-204.

(56) References Cited

OTHER PUBLICATIONS

Cropley et al., "Molecular Imaging of the Dopaminergic System and its Association with Human Cognitive Function", Biol.Psychiatry, 2006, 59, 898-907.
Cube et al., "3-(2-Ethoxy-4-{4-[3-Hydroxy-2-Methyl-4-(3-Methylbutanoyl)-Phenoxy]Butoxy}Phenyl)Propanoic Acid: A Brain Penetrant Allosteric Potentiator at the Metabotropic Glutamate Receptor 2 (Mglur2)", Bioorganic & Medicinal Chemistry Letters, 2005, 15, 2389-2393.
Cummings, "Behavioral Effects of Memantine in Alzheimer Disease Patients Receiving Donepezil Treatment" Neurology 2006, 67, 57-63.
Cymbalta, "Highlights of Prescribing Information", 2004, 1 page.
Czapski et al., "Effect of Poly (Adp-Ribose) Polymerase Inhibitors on Oxidative Stress Evoked Hydroxyl Radical Level and Macromolecules Oxidation in Cell Free System of Rat Brain Cortex", Neuroscience Letters, 2004, 356, 45-48.
D'Alessandro et al., "The Identification of Structurally Novel, Selective, Orally Bioavailable Positive Allosteric Modulators of Mglur2", Bioorg Med Chem Lett, 2010, 20, 759-762.
D'Antoni et al., "Metabotropic Glutamate Receptors in Glial Cells", Neurochem. Res., 2008, 33(12), 2436-2443.
Dale et al., "Mechanisms of Metabotropic Glutamate Receptor Desensitization: Role in the Patterning of Effector Enzyme Activation", Neurochemistry Intl, 2002, 41, 319-326.
Dale et al., "Spatial-Temporal Patterning of Metabotropic Glutamate Receptor-Mediated Inositol 1,4,5-Triphosphate, Calcium, and Protein Kinase C Oscillations: Protein Kinase C-Dependent Receptor Phosphorylation Is Not Required", J. Biol. Chem., 2001, 276(38), 35900-35908.
Danner et al., "Integrating Patients' Views Into Health Technology Assessment: Analytic Hierarchy Process (Ahp) as a Method to Elicit Patient Preferences", Intl Journal of Technology Assessment in Health Care, 2011, 27(4), 369-375.
D'Ascenzo et al., "Mglur5 Stimulates Gliotransmission in the Nucleus Accumbens", Proc. Natl. Acad. Sci., 2007, 104(6), 1995-2000.
Dash et al., "Long-Term Homeostasis of Extracellular Glutamate in the Rat Cerebral Cortex Across Sleep and Waking States", J Neurosci, 2009, 29, 620-629.
Datta et al., "Microinjection of Glutamate into the Pedunculopontine Tegmentum Induces Rem Sleep and Wakefulness in the Rat", Am J Physiol., Regul Integr Comp Physiol, 2001, 280, R752-R759.
Davidson et al., "Achieving Remission with Venlafaxine and Fluoxetine in Major Depression: Its Relationship to Anxiety Symptoms", Depression and Anxiety, 2002, 16, 4-13.
Davidson et al., "Differential Effects of Neuroleptic and Other Psychotropic Agents on Acquisition of Avoidance in Rats", Life Sci., 1976, 18, 1279-1284.
Davis et al., "2,1-Benzisothiazoles. Xii. [1], the Use of N-Substituted-2,1-Benzisothiazolium Salts as Synthetic Equivalents of O-Aminobenz-Aldehydes. A Simple Synthesis of Some 2-Quinolones", Journal of Heterocyclic Chemistry, 1983, 20, 1707-1708.
Davis, "Diazepam and Flurazepam: Effects on Conditioned Fear as Measured with the Potentiated Startle Paradigm", Psychopharmacology, 1979, 62, 1-7.
Davis, "Pharmacological and Anatomical Analysis of Fear Conditioning Using the Fear-Potentiated Startle Paradigm", Behavioral Neuroscience, 1986, 100, 814-824.
Dawson et al., "Novel Analysis for Improved Validity in Semi-Quantitative 2-Deoxyglucose Autoradiographic Imaging", Journal of Neuroscience Methods, 2008, 175, 25-35.
De Blasi et al., "Molecular Determinants of Metabotropic Glutamate Receptor Signaling", Trends in Pharmacological Sciences, 2001, 22 (3), 114-120.
De Boer et al., "Characterization of the Clinical Effect of A Positive Allosteric Modulator of the Metabotropic Glutamate Receptor-2", Society of Biological Psychiatry 67th Annual Scientific Convention, May 2012, 2 pages.
De Montis et al., "Selective Adenylate Cyclase Increase in the Limbic Area of Long-Term Imipramine-Treated Rats", European Journal of Pharmacology, 1990, 180(1), 169-174.
De Novellis et al., "Type I and II Metabotropic Glutamate Receptors Modulate Periaqueductal Grey Glycine Release: Interaction Between Mglu2/3 and A1 Adenosine Receptors", Neuropharmacoloqy, 2002, 43(7), 1061-1069.
Dean, "The Cortical Serotonin2a Receptor and the Pathology of Schizophrenia: A Likely Accomplice", J. Neurochem., 2003, 85, 1-13.
Dedeurwaerdere et al., "Memantine-Induced Brain Activation as a Model for the Rapid Screening of Potential Novel Antipsychotic Compounds: Exemplified by Activity of an Mglu2/3 Receptor Agonist", Psychopharmacology, 2011, 214, 505-514.
Del Rio et al., "Differential Coupling of G-Protein-Linked Receptors to Ca2+ Mobilization Through Inositol(1,4,5)Trisphosphateor Ryanodine Receptors in Cerebellar Granule Cells in Primary Culture", European Journal of Neuroscience, 1999, 11(9), 3015-3022.
Del'guidice et al., "Messing Up with Traffic: Different Effects of Antipsychotic Agents on Glutamate Receptor Complexes in Vivo" Mol. Pharmacol., 2008, 73(5), 1339-1342.
Delille et al., "Heterocomplex Formation of 5-HT2A-Mglu2 and its Relevance for Cellular Signaling Cascades", Neuropharmacology, 2012, 1-8.
Delille et al., "The Two Faces of the Pharmacological Interaction of Mglu2 and 5-Ht2a—Relevance of Receptor Heterocomplexes and Interaction Through Functional Brain Pathways", Neuropharmacology. 2013, 70, 296-305.
Derks et al., "Kreapelin Was Right: A Latent Class Analysis of Symptom Dimensions in Patients and Controls", Schizophrenia Bull., 2012, 38(3), 495-505.
Desseilles et al., "Assessing the Adequacy of Past Antidepressant Trials: A Clinician's Guide To the Antidepressant Treatment Response Questionnaire", J Clin Psychiatry, 2011, 72(8), 1152-1154.
Dhami et al., "G Protein-Coupled Receptor Kinase 2 Regulator of G Protein Signaling Homology Domain Binds to Both Metabotropic Glutamate Receptor 1a and Galphaq to Attenuate Signaling", Journal of Biological Chemistry, 2004, 279(16),16614-16620.
Dhami et al., "Regulation of Metabotropic Glutamate Receptor Signaling, Desensitization and Endocytosis", Pharmacol. Then, 2006, 111(1), 260-271.
Dhanya et al., "Design and Synthesis of an Orally Active Metabotropic Glutamate Receptor Subtype-2 (Mglur2) Positive Allosteric Modulator (Pam) That Decreases Cocaine SelfAdministration in Rats", J Med Chem, 2011, 54, 342-353.
Dhonnchadha et al., "Anxiolytic-Like Effects of 5-Ht2 Ligands on Three Mouse Models of Anxiety", Behavioural Brain Research, 2003, 140, 203-214.
Di Liberto et al., "Group II Metabotropic Glutamate Receptor Activation by Agonist Ly379268 Treatment Increases the Expression of Brain Derived Neurotrophic Factor in the Mouse Brain", Neuroscience, 2010, 165, 863-873.
Dimichelle et al., "The Natural Course of Schizophrenia and Psychopathological Predictors of Outcome", 2004, 37(2), 98-104.
Dingledine et al., "Excitatory Amino Acid Receptors in Epilepsy", Trends in Pharmacological Sciences, 1990, 11(8), 334-338.
Dingledine et al., "Peripheral Glutamate Receptors: Molecular Biology and Role in Taste Sensation", J Nutr, 2000, 130(4s Suppl): 1039s-1042s.
Doherty et al., "Functional Interactions Between Cannabinoid and Metabotropic Glutamate Receptors in the Central Nervous System", Current Opinion in Pharmacology, 2003, 3(1), 46-53.
Doherty et al., "Rapid Internalization and Surface Expression of a Functional, Fluorescently Tagged G-Protein-Coupled Glutamate Receptor", Biochemical Journal, 1999, 341(Pt2), 415-422.
Domschke et al., "Anxious Versus Non-Anxious Depression: Difference in Treatment Outcome", J Psychopharmacol, 2010, 24, 621-622.
D'Onofrio et al., "Neuroprotection Mediated By Glial Group-ll Metabotropic Glutamate Receptors Requires the Activation of the Map Kinase and the Phosphatidylinositol-3-Kinase Pathways", Journal of Neurochemistry, 2001,78(3), 435-445.

(56) References Cited

OTHER PUBLICATIONS

D'Onofrio et al., "Advances in the identification of g-secretase inhibitors for the treatment of Alzheimer's disease", Expert Opinion on Investigational Drugs, 2012, 7, 20-37.
Doreulee et al., "The Role of the Mglur Allosteric Modulation in the Nmda-Hypofunction Model of Schizophrenia", Georgian Medical News, 2009, 177, 59-65.
Doumazene et al., "A New Approach To Analyze Cell Surface Protein Complexes Reveals Specific Heterodimeric Metabotropic Glutamate Receptors", Faseb, 2011, 25, 66-77.
Doumazene, "Illuminating the Activation Mechanisms and Allosteric Properties of Metabotropic Glutamate Receptors", PNAS, 2013, 1-10.
Downey et al., "Ecdysone-Based System for Controlled Inducible Expression of Metabotropic Glutamate Receptor Subtypes 2,5, and 8", Journal of Biomolecular Screening, 2005, 10(8), 841-848.
Doyle et al., "Quantifying the Attenuation of the Ketamine Phmri Response in Humans: a Validation Using Antipsychotic and Glutamatergic Agents", Jpet Fast Forward, Jan. 31, 2013, 42 pages.
Drevets et al., "Functional Anatomical Correlates of Antidepressant Drug Treatment Assessed Using Pet Measures of Regional Glucose Metabolism", European Neuropsychopharmacology, 2002, 12, 527-544.
Drew et al., "Multiple Metabotropic Glutamate Receptor Subtypes Modulate Gabaergic Neurotransmission in Rat Periaqueductal Grey Neurons in Vitro", Neuropharmacology, 2004, 46(7), 927-934.
Dunayevich, "Efficacy and Tolerability of an Mglu2/3 Agonist in the Treatment of Generalized Anxiety Disorder", Neuropsychopharmacol., 2008, 33, 1603-1610.
Duncan et al., "Comparison of the Effects of Clozapine, Risperidone, and Olanzapine on Ketamine-Induced Alterations in Regional Brain Metabolism", Jpet, 2000, 293, 8-14.
Duncan et al., "Differential Effects of Clozapine and Haloperidol on Ketamine-Induced Brain Metabolic Activation", Brain Res, 1998, 812, 65-75.
Duncan et al., "Metabolic Mapping of the Rat Brain After Subanesthetic Doses of Ketamine: Potential Relevance to Schizophrenia", Brain Research, 1998, 787, 181-190.
Duncan et al., "Topographic Patterns of Brain Activity in Response to Swim Stress: Assessment By 2-Deoxyglucose Uptake and Expression- of Fos-Like Immunoreactivity", J Neurosci, 1993, 13, 3932-3943.
Dunlop, "Glutamate-Based Therapeutic Approaches: Targeting the Glutamate Transport System", Current Opinion in Pharmacology, 2006, 6 (1), 103-107.
Duong et al., "A Biogenetic Like Synthesis of Perloline, 6-(3,4-Dimethoxyphenyl)-5-Hydroxy-5,6-Dihydrobenzo[C][2,7]Naphthyridin-4(3h)-One", Aust. J. Chem., 1983, 36. 1431-1440.
Duplantier et al., "3-Benzyl-1,3-Oxazolidin-2-Ones as Mglur2 Positive Allosteric Modulators: Hit to Lead and Lead Optimization", Bioorg Med Chem Lett, 2009, 19, 2524-2529.
Durand et al., "Role of Metabotropic Glutamate Receptors in the Control of Neuroendocrine Function", Neuropharmacology, 2008, 55(4), 577-583.
During, "Extracellular Hippocampal Glutamate and Spontaneous Seizure in the Conscious Human Brain", Lancet, 1993, 341, 1607-1610.
Dutar et al., "Pharmacological Characterization of an Unusual Mglur-Evoked Neuronal Hyperpolarization Mediated by Activation of Girk Channels", Neuropharmacology, 1999, 38(4), 467-475.
Egan et al., "Neurobiology of Schizophrenia", Current Opinion in Neurobiology, 1997, 7(5), 701-707.
Egashira et al., "Impaired Social Interaction and Reduced Anxiety-Related Behavior in Vasopressin V1a Receptor Knockout Mice", Behav Brain Res, 2007, 5 pages.
Ehlert, "Analysis of Allosterism in Functional Assays", J Pharmacol. Exp. Ther., 2005, 315(2), 740-754.
Eintrei et al., "Effects of Diazepam and Ketamine Administered Individually or in Combination on Regional Rates of Glucose Utilization in Rat Brain", Br J Anaesth, 1999, 82, 596-602.

Eisa et al., "Synthesis of Some Novel Tetrazole Derivatives as Potential Antimicrobial Agents," Pakistan J. of Scientific and Industrial Res, 1990, 33, 417-420.
Elia et al., "Genome-Wide Copy Number Variation Study Associates Metabotropic Glutamate Receptor Gene Networks with Attention Deficit Hyperactivity Disorder", Nature Genetics, 2011, 9 pages.
Ellenbroek et al., "Animal Models with Construct Validity for Schizophrenia", Behavioural Pharmacology, 1990, 1, 469-490.
Emmitte, "Recent Advances in the Design and Development of Novel Negative Allosteric Modulators of Mglu5", Chem. Neurosci., 2011, 2, 411-432.
Engin et al., "The Effects of Intra-Cerebral Drug Infusions on Animals' Unconditioned Fear Reactions: A Systematic Review", Prog Neuropsychopharmacol Biol Psychiatry, 2008, 32, 1399-1419.
Enomoto et al., "Phencyclidine and Genetic Animal Models of Schizophrenia Developed in Relation to the Glutamate Hypothesis", Methods Find. Exp. Clin Pharmacol, 2007, 29(4), 291-301.
Erlenmeyer et al., "Uber Einige Derivate Des 2-Aminothiazols", Helvetica Chim Acta, 1949, 32, 35-38.
Ermolinsky et al., "Differential Changes in Mglu2 and Mglu3 Gene Expression Following Pilocarpine-Induced Status Epilepticus: A Comparative Real-Time Per Analysis", Brain Research, 2008, 1226, 173-180.
Ershov et al., "Chemical Abstracts", 1985, 103, 1 page.
Esposito et al., "Patterns of Benzodiazepine Use in a Canadian Population Sample", Epidemiol Psichiatr Soc., 2009, 18(3), 248-254.
Etkin et al., "Common Abnormalities and Disorder-Specific Compensation During Implicit Regulation of Emotional Processing in Generalized Anxiety and Major Depressive Disorders", Am J Psychiatry, 2011, 168, 968-978.
Etkin, "Neurobiology of Anxiety: From Neural Circuits To Novel Solutions?", Depression and Anxiety, 2012, 29, 355-358.
European Patent Application No. 05787278.0: Office Action dated May 11, 2012, 4 pages.
European Patent Application No. 07726932.2: Office Action dated Sep. 8, 2009, 10 pages.
European Patent Application No. 08717514.7: Office Action dated Jun. 28, 2010, 6 pages.
European Patent Application No. 08717515.4: Official Communication dated May 3, 2010, 5 pages.
European Patent Application No. 11181481.1: Office Action dated Dec. 6, 2012, 6 pages.
Ezquerra et al., "Efficient Reagents for the Synthesis of 5-, 7-, and 5,7-Substituted Indoles Starting from Aromatic Amines: Scopes and Limitations", J Org Chem, 1996, 61, 5804-5812.
Fagni et al., "Identification and Functional Roles of Metabotropic Glutamate Receptor-Interacting Proteins", Seminars in Cell & Developmental Biology, 2004, 15(3), 289-298.
Farabaugh et al., "Anxious Depression and Early Changes in the Hamd-17 Anxietysomatization Factor Items and Antidepressant Treatment Outcome", IntClin Psychopharmacol., Jul. 2010, 25(4), 214-217.
Faries et al., "The Double-Blind Variable Placebo Lead-in Period: Results from Two Antidepressant Clinical Trials", Journal of Clinical Psychopharmacology, 2001, 21, 561-568.
Fava et al., "Anxiety Disorders in Major Depression" Comprehensive Psychiatry 2000, 41(2), 97-102.
Fava et al., "Clinical Correlates and Symptom Patterns of Anxious Depression Among Patients with Major Depressive Disorder in Star*D", Psychological Medicine, 2004, 34, 1299-1308.
Fava et al., "Difference in Treatment Outcome in Outpatients with Anxious Versus Nonanxious Depression: A Star*D Report", Am J Psychiatry, 2008, 165, 342-351.
Fava et al., "Major Depressive Subtypes and Treatment Response", Biol. Psychiatry, 1997, 42, 568-576.
Fava et al., "Reliability and Validity of the Massachusetts General Hospital Cognitive and Physical Functioning Questionnaire", Psychother Psychosom, 2009, 78(2), 91-97.
Fava et al., "The Efficacy and Tolerability of Duloxetine in the Treatment of Anxious Versus Non-Anxious Depression: A Post-Hoc

(56) References Cited

OTHER PUBLICATIONS

Analysis of an Open-Label Outpatient Study", Annals of Clinical Psychiatry, 2007, 19(3), 187-195.
Fava et al., "The Problem of the Placebo Response in Clinical Trials for Psychiatric Disorders: Culprits, Possible Remedies, and a Novel Study Design Approach", Psychother Psychosom, 2003, 72, 115-127.
Fava et al., "What Clinical and Symptom Features and Comorbid Disorders Characterize Outpatients with Anxious Major Depressive Disorder: A Replication and Extension", Can J Psychiatry, Nov. 2006, 51(13), 823-835.
Fawcett et al., "Anxiety Syndromes and Their Relationship to Depressive Illness", J Clin Psychiatry, Aug. 1983, 44(8 Pt 2), 8-11.
Fawcett et al., "The Detection and Consequences of Anxiety in Clinical Depression", J Clin Psychiatry, 1997, 58(Suppl 8), 35-40.
Fawcett, "Treating Impulsivity and Anxiety in the Suicidal Patient", Ann NY Acad Sci., Apr. 2001, 932, 94-102.
FDA Center For Drug Evaluation and Research, "Introduction and Drug History", Pharmacology Reviews, 2003, NDA 21-487.
Feeley et al., "Mglurs: A Target for Pharmacotherapy in Parkinson Disease", Experimental Neurology, 2003, 184(Suppl-6), S30-S36.
Feenstra et al., "Local Activation of Metabotropic Glutamate Receptors Inhibits the Handling-Induced Increased Release of Dopamine in the Nucleus Accumbens but Not That of Dopamine or Noradrenaline in the Prefrontal Cortex: Comparison with Inhibition of Ionotropic Receptors", Journal of Neurochemistry, 1998, 70(3), 1104-1113.
Feinberg et al., "The Metabotropic Glutamate (Mglu)2/3 Receptor Antagonist Ly341495 [2s-2-Amino-2-(1s,2s-2-Carboxycyclopropyl-1-YI)-3-(Xanth-9-YI)PropanoicAcid] Stimulates Waking and Fast Electroencephalogram Power and Blocks the Effects of the Mglu2/3 Receptor Agonist Ly379268 [(-)-2-Oxa-4-Aminobicyclo[3.1.0]Hexane-4,6-Dicarboxylate] in Rats", Jpet, 2005, 312, 826-833.
Feinberg et al., "The Selective Group Mglu2/3 Receptor Agonist Ly379268 Suppresses Rem Sleep and Fast Eeg in the Rat", Pharmacology, Biochemistry and Behavior, 2002, 73, 467-474.
Fell et al., "Evidence for the Role of Mglu2 Not Mglu3 Receptors in the Preclinical Antipsychotic Pharmacology of the Mglu2/3 Receptor Agonist Ly404039", Journal of Pharmacology & Experimental Therapeutics, 2008, 326, 209-217.
Fell et al., "Group II Metabotropic Glutamate Receptor Agonists and Positive Allosteric Modulators as Novel Treatments for Schizophrenia", Neuropharmacology 2012, 62, 1473-1483.
Fell et al., "In Vitro and in Vivo Evidence for a Lack of Interaction with Dopamine D2 Receptors by the Metabotropic Glutamate 2/3 Receptor Agonists 1s,2s,5r,6s-2-Aminobicyclo[3.1.0] Hexane-2,6-Bicaroxylate Monohydrate (Ly354740) and (-)-2-Oxa-4-Aminobicyclo[3.1.0] Hexane-4,6-Dicarboxylic Acid (Ly379268)", Jpet, 2009, 331, 1126-1136.
Fell et al., "N-(4-((2-(Trifluoromethyl)-3-Hydroxy-4-(lsobutyryl)Phenoxy)Methyl)Benzyl)-1-Methyl-1h-Imidazole-4-Carboxamide (Thiic), A Novel Metabotropic Glutamate 2 Potentiator with Potential Anxiolytic/Antidepressant Properties: in Vivo Profiling Suggests a Link Between Behavioral and Central Nervous System Neurochemical Changes", Jpet, 2011, 336, 165-177.
Fendt et al., "Metabotropic Glutamate Receptors are Involved in Amygdaloid Plasticity", European Journal of Neuroscience, 2002, 15(9), 153 5-1541.
Fenton et al., "Role of a Prescription in Anxiety Medication Use, Abuse, and Dependence", Am J Psychiatry, 2010, 167, 1247-1253.
Ferraguti et al., "Activation of the Extracellular Signal-Regulated Kinase 2 By Metabotropic Glutamate Receptors", European Journal of Neuroscience, 1999, 11(6), 2073-2082.
Feraguti et al., "Metabotropic Glutamate 1 Receptor: Current Concepts and Perspectives", Pharmacol Rev, 2008, 60, 536-581.
Ferraguti et al., "Metabotropic Glutamate Receptors", Cell Tissue Res, 2006, 326, 483-504.
Ferris et al., "Interactions Between Ly354740, A Group II Metabotropic Agonist and the Gabaa-Benzodiazepine Receptor Complex in the Rat Elevated Plus-Maze", J Psychopharmacol, 2001, 15, 76-82.
Feyissa et al., "Elevated Level of Metabotropic Glutamate Receptor 2/3 in the Prefrontal Cortex in Major Depression", Prog. Neuropsychopharmacol. Biol. Psychiatry, 2010, 34(2), 279-283.
File, "The Use of Social Interaction as a Method for Detecting Anxiolytic Activity of Chlordiazepoxide-Like Drugs", Journal of Neuroscience Methods, 1980, 2(3), 219-38.
Filinger, "Effect of a Reserpine-Like Agent on the Release and Metabolism of [3h]Na in Cell Bodies and Terminals", Gen. Pharmac., 1994, 25, 1039-1043.
Fiorella et al., "The Role of the 5-Ht2a and 5-Ht2c Receptors in the Stimulus Effects of Hallucinogenic Drugs I: Antagonist Correlation Analysis", Psychopharmacology, 1995, 121, 347-356.
Fisher et al., "Antinociceptive Effects Following Intrathecal Pretreatment with Selective Metabotropic Glutamate Receptor Compounds in a Rat Model of Neuropathic Pain", Pharmacology, Biochemistry and Behavior, 2002, 73, 411-418.
Fisher et al., "Intrathecal Administration of the Mglur Compound, (S)-4cpg, Attenuates Hyperalgesia and Allodynia Associated with Sciatic Nerve Constriction Injury in Rats", Pain, 1998, 77(1), 59-66.
Fisher et al., "Non-Peptide Rgd Surrogates Which Mimic A Gly-Asp B-Turn: Potent Antagonists of Platelet Glycoprotein IIb-IIIa", J. Med. Chem., 1997, 40, 2085-2101.
Fisher et al., "The Contribution of Metabotropic Glutamate Receptors (Mglurs) to Formalin-Induced Nociception", Pain, 1996, 68(2-3), 255-263.
Flint et al., "Anxious Depression in Elderly Patients: Response to Antidepressant Treatment", Am J Geriatr Psychiatry, 1997, 5(2), 107-115.
Flohr et al., "Poly(Adp-Ribosyl)Ation Accelerates DNA Repair in A Pathway Dependent On Cockayne Syndrome B Protein", Nucleic Acids Research, 2003, 31(18), 5332-5337.
Flor et al., "Molecular Cloning, Functional Expression and Pharmacological Characterization of the Human Metabotropic Glutamate Receptor Type 2", Eur J Neurosci, 1995, 7, 622-629.
Fonnum et al., "Role of Glutamate and Glutamate Receptors in Memory Function and Alzheimer's Disease", Annals of the New York Academy of Sciences, 1995, 757, 475-486.
Forstl, "Clinical Features of Alzheimer's Disease", Eur Arch Psychiatry Clin Neurosci, 1999, 249, 288-290.
Fraley, "Positive Allosteric Modulators of the Metabotropic Glutamate Receptor 2 for the Treatment of Schizophrenia". Expert Opin. Ther. Patents, 2009, 19(9), 1259-1275.
Franco et al., "Novel Pharmacological Targets Based on Receptor Heteromers", Brain Research Reviews, 2008, 58, 475-482.
Franco et al., "The Two-State Dimer Receptor Model: A General Model for Receptor Dimers", Molecular Pharmacology, 2006, 69, 1906-1912.
Frank et al., "Depression and Health-Related Quality of Life for Low-Income African-American Women in the U.S.", Quality of Life Research, 2005, 14, 2293-2301.
Frauli et al., "Among the Twenty Classical L-Amino Acids, Only Glutamate Directly Activates Metabotropic Glutamate Receptors", Neuropharmacology, 2006, 50(2), 245-253.
Freedman et al., "Desensitization of G Protein-Coupled Receptors", Recent Progress in Hormone Research, 1996, 51, 319-351.
Freedman, "Schizophrenia", N. Engl. J. Med., 2003, 349, 1738-1749.
French et al., Subfield-Specific Immediate Early Gene Expression Associated with Hippocampal Long-Term Potentiation in Vivo. European Journal of Neuroscience 2001, 13 (5), 968-976.
Fribourg et al., "Decoding the Signaling of A Gpcr Heteromeric Complex Reveals a Unifying Mechanism of Action of Antipsychotic Drugs", Cell, 2011, 147, 1011-1023.
Fricker et al., "Effects of N-Acetylaspartylglutamate (Naag) At Group II Mglurs and Nmdar", Neuropharmacology, 2009, 56(6-7), 1060-1067.
Fuentes et al., "Synthesis of Heterocyclic Compounds; XI. Regioselective. Synthesis of 4-Subtituted 2-Amino-5-Cyano-6-Methoxy-3-Benzenesulfonylpyridines", Synthesis, 1984, 768-770.
Fujii et al., "A Chemical LTP Induced By Co-Activation of Metabotropic and N-Methyl-D-Aspartate Glutamate Receptors in Hippocampal Ca1 Neurons", Brain Research, 2004, 999(1), 20-28.

(56) References Cited

OTHER PUBLICATIONS

Fujii et al., "Lactams. IX. Generation of Latam Carbonyl Function in 1,3-Disubstituted Piperidines by Mercuric Acetate-Edta Oxidation: Effects of Hydrocarbon Substituents at the 3-Postion", Chem. Pharm. Bull., 1977, 25(9), 2336-2342.
Fujimoto et al., "Motor and Cognitive Function Evaluation Following Experimental Traumatic Brain Injury", Neurosci. and Biobehav. Rev., 2004, 28, 365-378.
Fujita et al., "Studies On 1-Alkyl-2(1h)-Pyridone Derivatives XXXII. The Friedel-Crafts Reaction of 1-Alkyl-2(1h)-Pyridone Derivatives with Acid Anhydride", Journal of the Pharmaceutical Society of Japan, 1990, 110, 449-452.
Furukawa et al., "Antidepressants Plus Benzodiazepines For Major Depression", The Cochrane Collaboration, 2009, 31 pages.
Fuxe et al., "Integrated Signaling in Heterodimers and Receptor Mosaics of Different Types of GPCRS of the Forebrain: Relevance for Schizophrenia", J Neural Transm, 2009, 116(8), 923-939.
Galici et al., "A Selective Allosteric Potentiator of Metabotropic Glutamate (Mglu) 2 Receptors Has Effects Similar to an Orthosteric Mglu2/3 Receptor Agonist in Mouse Models Predictive of Antipsychotic Activity", J of Pharmacology and Experimental Therapeutics, 2005, 315(3), 1181-1187.
Galici et al., "Biphenyl-lndanone A, A Positive Allosteric Modulator of the Metabotropic Glutamate Receptor Subtype 2, Has Antipsychotic- and Anxiolytic-Like Effects in Mice", Journal of Phamacology and Experimental Therapeutics, 2006, 318(1), 173-185.
Galimberti et al., "Long-Term Rearrangements of Hippocampal Mossy Fiber Terminal Connectivity in the AdultRegulated by Experience" Neuron 2006, 50, 749-763.
Gama et al., "Heterodimerization of Calcium Sensing Receptors with Metabotropic Glutamate Receptors in Neurons", J. Biol. Chem., 2001, 276(42), 39053-39059.
Garbaccio et al., "Discovery of Oxazolobenzimidazoles as Positive Allosteric Modulators for the Mglur2 Receptor" Acs Med Chem Lett, 2010, 1, 406-410.
Garrido-Sanabria et al., "Impaired Expression and Function of Group II Metabotropic Glutamate Receptors in Pilocarpine-Treated Chronically Epileptic Rats", Brain Res., 2008, 1240, 165-176.
Garriock et al., "Genetic Studies of Drug Response and Side Effects in the Sta*D Study, Part 1", J Clin Psychiatry, 2009, 70(8), 1186-1187.
Gasparini et al., "Allosteric Modulators for Mglu Receptors", Curr Neuropharmacol, 2007, 5, 187-194.
Gavezzotti, "Are Crystal Structures Predictable?", Accounts of Chemical Research, 1994, 27, 309-314.
Gerber et al., "Metabotropic Glutamate Receptors: Intracellular Signaling Pathways", Current Opinion in Pharmacology, 2007, 7(1), 56-61.
Gerwitz et al., "Behavioral Evidence for Interactions Between a Hallucinogenic Drug and Group II Metabotropic Glutamate Receptors", Neuropsychopharmacology, 2000, 23, 569-576.
Gewald et al., "Heterocyclen Aus Ch-Aciden Nitrilen, VIII. 2-Amino-Thiophene Aus Methylenaktiven Nitrilen Carbonylverbindungen Und Schwefel", Chemische Berichte, 1966, 99, 94-100.
Gewald. "Heterocyclen Aus Ch-Aciden Nitrilen, VIL 2-Amino-Thiophene Aus A-Oxo-Mercaptanen Und Methylenaktiven Nitrilen", Chemische Berichte, 1965, 98, 3571-3577.
Geyer, "Are Cross-Species Measures of Sensorimotor Gating Useful for the Discovery of Procognitive Cotreatments for Schizophrenia?", Dialogues Clin Neurosci., 2006, 8(1), 9-16.
Ghammamy et al., "Cetyltrimethylammonium Bromochromate: A New and Efficient Oxidant for Organic Substrates", Synthetic Communications, 2007, 37, 599-605.
Ghose et al., "Differential Expression of Metabotropic Glutamate Receptors 2 and 3 in Schizophrenia: A Mechanism for Antipsychotic Drug Action?", Am J Psychiatry, 2009, 166, 812-820.
Gill et al., "Immunochemical Localization of the Metabotropic Glutamate Receptors in the Rat Heart", Brain Research Bulletin, 1999, 48(2), 143-146.
Gilling et al., "Potency, Voltage-Dependency, Agonist Concentration-Dependency, Blocking Kinetics and Partial Untrapping of the Uncompetitive N-Methyl-D-Aspartate (NMDA) Channel Blocker Memantine at Human Nmda (Glun1/Glun2a) Receptors", Neuropharmacology 2009, 56, 866-875.
Gilmour et al., "Diverse and Often Opposite Behavioural Effects of NMDA Receptor Antagonists in Rats: Implications for NMDA Antagonist Modelling of Schizophrenia", Psychopharmacology, 2009, 205, 203-216.
Giovannelli et al., "Comet Assay as a Novel Approach for Studying Dna Damage in Focal Cerebral Ischemia: Differential Effects of NMDA Receptor Antagonists and Poly(Adp-Ribose) Polymerase Inhibitors'", Journal of Cerebral Blood Flow and Metabolism, 2002, 22, 697-704.
Girardi et al., "Differential Expression of Cerebellar Metabotropic Glutamate Receptors Mglur2/3 and Mglur4a After the Administration of a Convulsant Drug and the Adenosine Analogue Cyclopentyladenosine". Neurochem. Res., 2007, 32(7), 1120-1128.
Gjoni et al., "Receptor Activation Involving Positive Allosteric Modulation, Unlike Full Agonism, Does Not Result in Gabab Receptor Desensitization", Neuropharmacology, 2008, 55, 1293-1299.
Gleason et al., "Blockade of Phencyclidine-Induced Hyperlocomotion by Olanzapine, Clozapine, and Serotonin Receptor Subtype Selective Antagonists in Mice", Psychopharmacology, 1997, 129, 79-84.
Gleeson, "Generation of a Set of Simple, Interpretable Admet Rules of Thumb", J Med Chem, 2008, 51, 817-834.
Glick et al., "A Double-Blind Randomized Trial of Mood Stabilizer Augmentation Using Lamotrigine and Valproate for Patients with Schizophrenia Who Are Stabilized and Partially Responsive", J Clin Psychopharmacol, 2009, 29(3), 267-271.
Glick et al., "Concomitant Medications May Not improve Outcome of Antipsychotic Monotherapy for Stabilized Patients with Non-Acute Schizophrenia", J Clin Psychiatry, 2006, 67(8), 1261-1265.
Glin et al., "The Intermediate Stage of Sleep in Mice", Physiology & Behavior, 1991, 50, 951-953.
Gnecco et al., "Oxidation of Chiral Non-Racemic Pyridinium Salts to Enantiopure 2-Pyridine and 3-Alkyl-2-Pyridones", Tetrahedron: Asymmetry, 1998, 9, 2027-2029.
Goff et al., "Lamotrigine As Add-On Therapy in Schizophrenia: Results of 2 Placebo-Controlled Trials", J Clin Psychopharmacol., 2007, 27(6), 582-589.
Goldberg et al., "Novel Non-Benzodiazepine Anxiolytics", Neuropharmacology, 1983, 22, 1499-1504.
Gonzalez-Maeso et al., "Identification of a Serotonin/Glutamate Receptor Complex Implicated in Psychosis", Nature, 2008, 452, 93-97.
Gonzalez-Maeso et al., "Psychedelics and Schizophrenia", Trends Neurosci., 2009, 32(4), 225-232.
Gonzalez-Maeso, "Hallucinogens Recruit Specific Cortical 5-Ht2a Receptor-Mediated Signaling Pathways to Affect Behavior". Neuron, 2007, 53, 439-452.
Gonzalez-Maeso, "Transcriptome Fingerprints Distinguish Hallucinogenic and Nonhallucinogenic5-Hydroxytryptamine 2a Receptor Agonist Effects in Mouse Somatosensory Cortex", J. Neurosci., 2003, 23, 8836-8843.
Goodman et al., "The Pharmacological Basis of Therapeutics: Chapter 21 -Pharmacotherapy of the Epilepsies", 12th Edition, 2011, 27 pages.
Goodman et al., "The Yale-Brown Obsessive Compulsive Scale: I. Development, Use, and Reliability", Arch Gen Psychiatry, 1989, 46(11), 1006-1011.
Goodwin et al., "Advantages and Disadvantages of Combination Treatment with Antipsychotics", Nice. Eur Neuropsychoparmacol., 2009, 19(7), 520-532.
Gores et al., "Immunohistochemical Visualization of a Metabotropic Glutamate Receptor", Neuroreport, 1993, 4(3), 283-286.
Gorman et al., "A Hypothesized Role for Dendritic Remodeling in the Etiology of Mood and Anxiety Disorders", J Neuropsychiatry Clin Neurosci, 2010, 22(3), 256-264.
Gorman et al., "Anxiogenic Effects of Co2 and Hyperventilation in Patients with Panic Disorder", Am J Psychiatry, 1994, 151,547-553.

(56) References Cited

OTHER PUBLICATIONS

Gorman, "Comorbid Depression and Anxiety Spectrum Disorders", Depression and Anxiety, 1996/1997,4, 160-168.
Goudet et al., "Asymmetric Functioning of Dimeric Metabotropic Glutamate Receptors Disclosed by Positive Allosteric Modulators", J. Biol. Chem., 2005, 280(26), 24380-24385.
Goudet et al., "Metabotropic Receptors for Glutamate and Gaba in Pain", Brain Res. Rev., 2009,60(1), 43-56.
Gouzoulis-Mayfrank, "Inhibition of Return in the Human 5ht2a Agonist and Nmda Antagonist Model of Psychosis", Neuropsychopharmacoloqy, 2006, 31, 431-441.
Gouzoulis-Mayfrank, "Psychological Effects of (S)-Ketamine and N,N-Dimethyltryptamine (Dmt): A Double-Blind, Cross-Over Study in Healthy Volunteers", Pharmacopsychiatry, 2005, 38, 301-311.
Govek et al., "Benzazoles as Allosteric Potentiators of Metabotropic Glutamate Receptor 2 (Mglur2): Efficacy in an Animal Model for Schizophrenia", Bioorg. Med. Chem Lett., 2005, 15, 4068-4072.
Gozzi et al., "Differential Effects of Antipsychotic and Glutamatergic Agents on the Phmri Response to Phencyclidine", Neuropsychopharmacology, 2008, 33. 1690-1703.
Gray et al., "Functionalisation of 2-Methoxy-6-Methylpyridine", Synthetic Communications, 1994, 24(10), 1367-1379.
Gregory et al., "Allosteric Modulation of Metabotropic Glutamate Receptors: Structural Insights and Therapeutic Potential", Neuropharmacology, 2011, 60, 66-81.
Gregory et al., "Overview of Receptor Allosterism", Current Protocols in Pharmacology, 2010, 1.21.1-1.21.34.
Gregory et al., "Prefrontal Group II Metabotropic Glutamate Receptor Activation Decreases Performance on a Working Memory Task", Ann N Y. Acad. Sci., 2003, 1003. 405-409.
Grillon, et al., "Anxiolytic Effects of a Novel Group II Metabotropic Glutamate Receptor Agonist (Ly354740) in the Fear-Potentiated Startle Paradigm in Humans", Psychopharmacology, 2003, 168, 446-454.
Groebe, "Screening for Positive Allosteric Modulators of Biological Targets", Drug Discov. Today, 2006, 11(13-14), 632-639.
Grueter et al., "Group II and III Metabotropic Glutamate Receptors Suppress Excitatory Synaptic Transmission in the Dorsolateral Bed Nucleus of the Stria Terminalis", Neuropsychopharmacology, 2005, 30(7), 1302-1311.
Gu et al., "Distribution of Metabotropic Glutamate 2 and 3 Receptors in the Rat Forebrain: Implications in Emotional Responsesand Central Disinhibition", Brain Res, 2008, 1197, 47-62.
Gu et al., "Expression of Functional Metabotropic Glutamate Receptors in Primary Cultured Rat Osteoblasts. Cross-Talk with N-Methyl-D-Aspartate Receptors", J. Biol. Chem., 2000, 275(44), 34252-34259.
Gueremy et al., "2-Amino-6-Chloro-4-(N-Methylpiperazino)Pyrimidines, Inhibitors of Spiroperidol Binding", Journal of Medicinal Chemistry, 1982, 25, 1459-1465.
Guerineau et al., "G-Protein-Mediated Desensitization of Metabotropic Glutamatergic and Muscarinic Responses in Ca3 Cells in Rat Hippocampus", Journal of Physiology, 1997, 500(Pt 2), 487-496.
Guerineau et al., Activation of A Nonselective Cationic Conductance By Metabotropic Glutamatergic and Muscarinic Agonists in Ca3 Pyramidal Neurons of the Rat Hippocampus, J. Neurosci., 1995, 15(6), 4395-4407.
Guimaraes et al., "Ritanserin Facilitates Anxiety in a Simulated Public-Speaking Paradigm", Journal of Psychopharmacology, 1997, 11(3), 225-231.
Gunduz-Bruce, "The Acute Effects of Nmda Antagonism: from the Rodent to the Human Brain", Brain Res Rev, 2009, 60, 279-286.
Gupta et al., "Metabotropic Glutamate Receptor Protein Expression in the Prefrontal Cortex and Striatum in Schizophrenia", Synapse, 2005, 57(3), 123-131.
Gurevich et al., "Alterations in the Cortical Serotonergic System in Schizophrenia: A Postmortem Study", Biol. Psychiatry, 1997, 42, 529-545.

Haak et al., "Metabotropic Glutamate Receptor Activation Modulates Kainate and Serotonin Calcium Response in Astrocytes", J. Neurosci., 1997, 17(5), 1825-1837.
Hackler et al., "Selective Potentiation of the Metabotropic Glutamate Receptor Subtype 2 Blocks Phencyclidine-Induced Hyperlocomotion and Brain Activation", Neuroscience, 2010, 168(1), 209-218.
Hamaguchi et al., "Effects of Hetero Atom Substituents in the Decomposition of Pyrazolines: Abnormal Behavior of Methoxy Group Compared with Arylthio of Arylseleno Group.", Heterocycles, 1986, 24, 2111-2115.
Hamilton, "A Rating Scale For Depression", J Neurol Neurosurg Psychiatry, 1960, 23, 56-62.
Hamilton, "Diagnosis and Rating of Anxiety, in Studies of Anxiety", MM Lader, Ed., Meedley Bros., Kent, 1969, 76-79.
Hamilton, "Standardised Assessment and Recording of Depressive Symptoms", Psychiatr Neurol Neurochir, 1969, 72(2), 201-205.
Hamilton, "The Assessment of Anxiety States By Rating", Br J Med Psychol, 1959, 32(1), 50-55.
Hampson et al., "Characterization of Two Alternatively Spliced Forms of a Metabotropic Glutamate Receptor in the Central Nervous System of the Rat", Neuroscience, 1994, 60(2), 325-336.
Handley et al., "Effects of Alpha-Adrenoceptor Agonists and Antagonists in a Maze-Exploration Model of Fear-Motivated Behavior", Naunyn-Schmied. Arch. Pharmacol., 327, 1-5, 1984.
Hanfeld et al., "Synthese Von 3-Cyan-6-Methyl-4-Pyridyl-Und 3-Cyan-4-Methyl-6-Pyridyl-Pyrid-2(1h)-Onen Und -Thionen", Pharmazie, 1988, 43, 762-764.
Hanna et al., "Differentiating the Roles of Mglu2 and Mglu3 Receptors Using Ly541850, an Mglu2 Agonist/Mglu3 Antagonist", Neuropharmacology, 2012,1-8.
Hannah et al., "Heterocomplex Formation of 5-Ht2a-Mglu2 and Its Relevance for Cellular Signaling Cascades", Neuropharmacology, 2012, 62, 2184-2191.
Hansen et al., "Glutamate Joins the Ranks of Immunomodulators", Nature Medicine, 2010, 16(8), 856-858.
Happe et al., "Agonist-Stimulated [35s]Gtpgammas Autoradiograph: Optimization for High Sensitivity", Eur J Pharmacol, 2001, 422, 1-13.
Harald et al., "Meta-Review of Depressive Subtyping Models", Journal of Affective Disorders, 2012, 139, 126-140.
Harich, "Stimulation of the Metabotropic Glutamate 2/3 Receptor Attenuates Social Novelty Discrimination Deficits Induced by Neonatal Phencyclidine Treatment", Psychopharmacology, 2007, 192, 511-519.
Haro et al., "The Clinical Global Impression-Schizophrenia Scale: A Simple Instrument to Measure the Diversity of Symptoms Present in Schizophrenia", Acta Psychiatr Scand Suppl., 2003, 416, 16-23.
Harriman et al., "Synthesis of 4-Substituted 4-Arylpiperidines", Tetrahedron Letters, 2000, 41, 8853-8856.
Harrison et al., "The Group II Metabotropic Glutamate Receptor 3 (Mglur3, Mglu3, Grm3): . Expression, Function and Involvement in Schizophrenia", J. Psychopharmacol., 2008, 22(3), 308-322.
Harrison, "Metabotropic Glutamate Receptor Agonists for Schizophrenia", The British Journal of Psychiatry, 2008, 192, 86-87.
Hartveit et al., "Expression of the Mrna of Seven Metabotropic Glutamate Receptors (Mglur1 To 7) in the Rat Retina. An in Situ Hybridization Study On Tissue Sections and Isolated Cells", Eur. J Neurosci., 1995, 7(7), 1472-1483.
Hascup et al., "An Allosteric Modulator of Metabotropic Glutamate Receptors (Mglur2), (+)-Tfmpip, Inhibits Retraint Stress-Induced Phasic Glutamate Release in Rat Prefrontal Cortex", Journal of Neurochemistry, 2012, 122, 619-627.
Hashimoto et al., "Increased Levels of Glutamate in Brains from Patients with Mood Disorders", Biol Psychiatry, 2007, 62(11), 1310-1316.
Hashimoto, "Emerging Role of Glutamate in the Pathophysiology of Major Depressive Disorder", Brain Research Reviews, 2009, 61, 105-123.
Hasin et al., "Epidemiology of Major Depressive Disorder. Results from the National Epidemiologic Survey On Alcoholism and Related Conditions", Arch Gen Psychiatry, 2005, 62, 1097-1106.

(56) References Cited

OTHER PUBLICATIONS

Hasler et al., "Reduced Prefrontal Glutamate/Glutamine and Gamma-Aminobutyric Acid Levels in Major Depression Determined Using Proton Magnetic Resonance Spectroscopy", Arch Gen Psychiatry, 2007, 64(2), 193-200.
Hawgood et al., "Anxiety Disorders and Suicidal Behavior: An Update", Current Opinion in Psychiatry, 2008, 21, 51-64.
He et al., "Conformational Color Polymorsphism and Control of Crystallization of 5-Methyl-2-[(4-Methyl-2-MitrophenylOamino}-3-Thiophenecarbonitrile", Journal of Pharmaceutical Sciences, 2001, 90(3), 371-388.
Helton et al., "Anxiolytic and Side-Effect Profile for Ly354740: A Potent, Highly Selective, Orally Active Agonist for Group II Metabotropic Glutamate Receptors", Journal of Phamacology and Experimental Therapeutics, 1998, 284(2), 651-660.
Helton et al., "Ly354740: A Metabotropic Glutamate Receptor Agonist Which Ameliorates Symptoms of Nicotine Withdrawal in Rats", Neuropharmacology, 1997, 36(11/12), 1511-1516.
Hemstapat et al., "A Novel Family of Potent Negative Allosteric Modulators of Group II Metabotropic Glutamate Receptors", Jpet, 2007, 322, 254-264.
Henley et al., "Characterization of the Allosteric Modulatory Protein Associated with Non-Nmda Receptors", Biochemical Society Transactions, 1993, 21(1), 89-93.
Henry et al., "The Mglur5 Antagonist Mpep, But Not the Mglur2/3 Agonist Ly314582, Augments Pep Effects on Prepulse Inhibition and Locomotor Activity", Neuropharmacology, 2002, 43(8), 1199-209.
Herdeis et al., "[4+2] Cycloadducts of 5-Benzyloxy-2-Pyrindone with Electron Deficient Dienophiles. Regio- and Stereochemistry". Heterocycles, 1989, 29(2), 287-296.
Herdeis et al., "A Facile Entry to the 2-Azabicyclo[2.2.2]Octane-6-One Skeleton Via [4+2]-Cycloaddition", Synthesis, Jan. 1988, 76-78.
Herdeis et al., "A Three-Step Synthesis of B-Aminolaevulinic Acid", Arch. Pharm., 1984, 317, 304-306.
Herdeis et al., "Stereochemistry and Reactivity of Phenylsulfonyl-Substituted 2-Azabicyclo[2.2.2]Octan-6-Ones", Arch. Pharm., 1990, 323, 937-942.
Heresco-Levy, "Glutamatergic Neurotransmission Modulators as Emerging New Drugs for Schizophrenia", Expert Opin Emerging Drugs, 2005, 10(4), 827-844.
Hermann et al., "Human Eeg Gamma Oscillations in Neuropsychiatric Disorders", Clinical Neurophysiology. 2005, 116, 2719-2733.
Hermans et al., "Structural, Signalling and Regulatory Properties of the Group I Metabotropic Glutamate Receptors: Prototypic Family C G-Protein-Coupled Receptors", Biochem. J. 2001, 359, 465-484.
Herminghaus, "Brain Metabolism in Alzheimer Disease and Vascular Dementia Assessed By In Vivo Proton Magnetic Resonance Spectroscopy", Psychiatry Research Neuroimaging, 2003, 123, 183-190.
Herrero et al., "Functional Switch from Facilitation to Inhibition in the Control of Glutamate Release By Metabotropic Glutamate Receptors", J. Biol. Chem., 1998, 273(4), 1951-1958.
Herrero et al., "Positive Feedback of Glutamate Exocytosis By Metabotropic Presynaptic Receptor Stimulation", Nature, 1992, 360(6400), 163-166.
Herrero et al., "Rapid Desensitization of the Metabotropic Glutamate Receptor that Facilitates Glutamate Release in Rat Cerebrocortical Nerve Terminals", European Journal of Neuroscience, 1994, 6(1), 115-120.
Hettema "The Nosologic Relationship Between Generalized Anxiety Disorder and Major Depression", Depression and Anxiety, 2008, 25, 300-316.
Hetzenauer et al., "Individual Contribution of Metabotropic Glutamate Receptor (Mglu) 2 and 3 To C Expression Pattern Evoked By Mglu2/3 Antagonism", Psychopharmacology, 2008, 201, 1-13.
Hickinbottom, "Reactions of Organic Compounds", Gonti: Moscow, 1939, 360-2 (Russian with English Translation).

Higashida et al., "Subtype-Specific Coupling with Adp-Ribosyl Cyclase of Metabotropic Glutamate Receptors in Retina, Cervical Superior Ganglion and Ng108-15 Cells", Journal of Neurochemistry, 2003, 85, 1148-1158.
Higgins, "Pharmacological Manipulation of Mglu2 Receptors Influences Cognitive Performance in the Rodent", Neuropharmacology, 2004, 46, 907-917.
Hijzen et al., "Predictive Validity of the Potentiated Startle Response As A Behavioral Model for Anxiolytic Drugs", Psychopharmacology, 1995, 118, 150-154.
Hirao et al., "Preparation of Optically Active 8,8'-Disubstituted 1,1'-Btisoquinoline", Heterocycles, 1996, 42(1), 415-422.
Hlavackova et al., "Evidence For A Single Heptahelical Domain Being Turned On Upon Activation of A Dimeric GPCR", Embo, 2005, 24, 499-509.
Hoang et al., "Expression of Metabotropic Glutamate Receptors in Nodose Ganglia and the Nucleus of the Solitary Tract", Am J Physiol Heart Circ Physiol, 2001, 281, 457-462.
Hoeben et al., "Prediction of Serotonin 2a Receptor (5-$Ht_{2a}$ r) Occupancy in Man From Nonclinical Pharmacology Data. Exposure Vs. 5-$Ht_{2a}$ r Occupancy Modeling Used to Help Design a Positron Emission Tomography (Pet) Study in Healthy Male Subjects", Abstract, 2013 Annual Meeting of the Population Approach Group in Europe, 2 pages.
Hoffman et al., "Human and Economic Burden of Generalized Anxiety Disorder", Depression and Anxiety, 2008, 25. 72-90.
Hofmeijer-Sevink et al., "Clinical Relevance of Comorbidity in Anxiety Disorders: A Report From the Netherlands Study of Depression and Anxiety (NESDA)", Journal of Affective Disorders, 2012, 137, 106-112.
Hohnadel et al., "Effect of Repeated Nicotine Exposure on High-Affinity Nicotinic Acetylcholine Receptor Density in Spontaneously Hypertensive Rats", Neuroscience Letters, 2005, 382, 158-163.
Holcomb et al., "Effects of Noncompetitive Nmda Receptor Blockade On Anterior Cingulate Cerebral Blood Flow in Volunteers with Schizophrenia", Neuropsychopharmacology, 2005, 30, 2275-2282.
Holden, "Excited By Glutamate", Science, Jun. 2003, 300, 1866-1868.
Holloway et al., "Prenatal Stress Induces Schizophrenia-Like Alterations of Serotonin 2a and Metabotropic Glutamate 2 Receptors in the Adult Offspring: Role of Maternal Immune System", J. Neurosci., 2013, 33(3), 1088-1098.
Holscher et al., "Metabotropic Glutamate Receptor Activation and Blockade: Their Role in Long-Term Potentiation, Learning and Neurotoxicity", Neuroscience & Biobehavioral Reviews, 1999, 23(3), 399-410.
Homayoun et al., "Activation of Metabotropic Glutamate 2/3 Receptors Reverses the Effects of Nmda Receptor Hypofunction On Prefrontal Cortex Unit Activity in Awake Rats", J. Neurophysiol., 2005, 93(4), 1989-2001.
Homayoun et al., "Group 5 Metabotropic Glutamate Receptors: Role in Modulating Cortical Activity and Relevance to Cognition", European Journal of Pharmacology, 2010, 639, 33-39.
Homayoun et al., "Orbitofrontal Cortex Neurons as a Common Target for Classic and Glutamatergic Antipsychotic Drugs", Proc. Natl. Acad. Sci. USA, 2008, 105(46), 18041-18046.
Honer et al., "Clozapine Alone Versus Clozapine and Risperidone with Refractory Schizophrenia", N Engl J Med., 2006, 354(5), 472-482.
Hook, "Neuroproteases in Peptide Neurotramission and Neurodegenerative Diseases Applications to Drug Discovery Research", Biodrugs, 2006, 20, 105-119.
Hopkins "Is There a Path Forward for Mglu2 Positive Allosteric Modulators for the Treatment of Schizophrenia?", ACS Chem. Neurosci., 2013, 4, 211-213.
Horiguchi et al., "Interaction of Mglu2/3 Agonism with Clozapine and Lurasidone to Restore Novel Object Recognition in Subchronic Phencyclidine-Treated Rats", Psychopharmacology, 2011, 217, 13-24.
Horiguchi et al., "Interactions Among the Atypical Antipsychotic Drug (APD), Lurasidone, 5-HT1A and Metabotropic Glutamate Receptor 2/3 (Mglur2/3) Agonism, and 5-HT2A Antagonism, to Attenuate Phencyclidine (PCP)-lnduced Deficit in Rat Novel Object

(56) References Cited

OTHER PUBLICATIONS

Recognition (NOR)" Poster 610.12 Presented At the 40<sup>th</sup> Annual Meeting of Society for Neuroscience, 2010, 1 page.
Hostetler, "PET Tracer Discovery for Subtype-Specific Mglur Allosteric Modulators: Challenges and Insights" Presentation Slides 7th International Meeting On Metabotropic Glutamate Receptors, Merck, Oct. 2011, 8 pages.
Houamed et al., "Cloning, Expression, and Gene Structure of a G Protein-Coupled Glutamate Receptor from Rat Brain", Science, 1991, 252(5010), 1318-1321.
Hovelso, "Therapeutic Potential of Metabotropic Glutamate Receptor Modulators", Current Neuropharmacology, 2012, 10,12-48.
Hsia et al., "Evidence Against a Role for Metabotropic Glutamate Receptors in Mossy Fiber Ltp: the Use of Mutant Mice and Pharmacological Antagonists", Neuropharmacology, 1995, 34,1567-1572.
Hu et al., "Altered Profile of Gene Expression in Rat Hearts Induced by Chronic Nicotine Consumption", Biochemical and Biophysical Research Communications, 2002, 297, 729-736.
Hu et al., "Emotion Enhances Learning Via Norepinephrine Regulation of Ampa-Receptor Trafficking". Cells, 2007, 131, 160-173.
Hu et al., "Glutamate Receptors in Preclinical Research on Alzheimer's Disease: Update On Recent Advances", Pharmacology, Biochemistry and Behavior, 2012, 100, 855-862.
Hu et al., "Identification of Glutamate Receptors and Transporters in Mouse and Human Sperm", Journal of Andrology, 2004, 25(1), 140-6.
Hu et al., "Pyrimidine Methyl Anilines: Selective Potentiators for the Metabotropic Glutamate 2 Receptor", Bioorganic & Medicinal Chemistry Letters, 2004, 14, 5071-5074.
Hu et al., "The Regulation of Dopamine Transmission by Metabotropic Glutamate Receptors", J. Pharmacol. Exp. Ther., 1999, 289(1), 412-416.
Huang et al., "Alzheimer Mechanisms and Therapeutic Strategies", Cell, 2012, 148, 1204-1222.
Huang et al., "Inhibition of Microtubule Formation by Metabotropic Glutamate Receptors", Journal of Neurochemistry, 2000, 74(1), 104-113.
Huang et al., "Interdomain Movements in Metabotropic Glutamate Receptor Activation", Proc Natl Acad Sci USA, 2011, 108, 15480-15485.
Huang et al., "Potentiation of the Novel Atypical Antipsychotic Drug Lurasidone-Induced Dopamine Efflux in Rat Medial Prefrontal Cortex and Hippocampus by DA D1 and Mglur2/3 Agonism but not D3 Receptor Antagonism" Poster 610.13 Presented at the 40<sup>th</sup> Annual Meeting of Society For Neuroscience, Nov. 2010, 1 page.
Huang et al., "Prevalence, Correlates, and Comorbidity of Nonmedical Prescription Drug Use and Drug Use Disorders in the United States: Results of the National Epidemiologic Survey On Alcohol and Related Conditions", J Clin Psychiatry, 2006, 67, 1062-1073.
Hucho et al., "Epac Mediates a Camp-To-Pkc Signaling in Inflammatory Pain: An Isolectin B4(+) Neuron-Specific Mechanism", Journal of Neuroscience, 2005, 25(26), 6119-6126.
Hucho et al., "Estrogen Controls Pkce-Dependent Mechanical Hyperalgesia Through Direct Action On Nociceptive Neurons", European Journal of Neuroscience, 2006, 24, 527-534.
Huey et al., "Development of Subtle Psychotic Symptoms with Memantine: A Case Report", J Clin Psychiatry, 2005, 66, 658-659.
Hughes, "Progress in the Mitsunobu Reaction. A Review", Organic Preparations and Procedures International, 1996, 127-164.
Hughes, "The Mitsunobu Reaction", Organinc Reactions, 1992, 42, 335-656.
Huntington Study Group, "Dosage Effects of Riluzole in Huntington's Disease: A Multicenter Placebo-Controlled Study", Neurology, 2003, 61, 1551-1556.
Lacovelli et al., "Regulation of Group II Metabotropic Glutamate Receptors by G Protein-Coupled Receptor Kinases: Mglu2 Receptors are Resistant to Homologous Desensitization", Mol Pharmacol., 2009, 75(4), 991-1003.
Iglesias et al., "Metabotropic Glutamate Receptor/Phospholipase C System in Female Rat Heart", Brain Res., 2007, 1153, 1-11.
Imogai et al., "Cis-Disubstituted Cyclopropanes Via Asymmetric Catalytic Cyclopropenation: Synthesis of Cyclopropyl-Dehydroamino Acids and of Dictyopterene C.", Helvetica Chimica Acta, 1998, 81, 1754-1764.
Imre et al., "Dose-Response Characteristics of Ketamine Effect on Locomotion, Cognitive Function and Central Neuronal Activity", Brain Res. Bull, 2006, 69(3), 338-345.
Imre et al., "Effects of the Mglur2/3 Agonist Ly379268 On Ketamine-Evoked Behaviours and Neurochemical Changes in the Dentate Gyrus of the Rat", Pharmacology, Biochemistry and Behavior, 2006, 84, 392-399.
Imre et al., "Subchronic Administration of Ly354740 Does Not Modify Ketamine-Evoked Behavior and Neuronal Activity in Rats", Eur. J Pharmacol., 2006, 544(1-3), 77-81.
Imre, "The Preclinical Properties of a Novel Group II Metabotropic Glutamate Receptor Agonist Ly379268", CNS Drug Reviews, 2007, 13(4), 444-464.
Insel, et al., "Research Domain Criteria (Rdoc): Toward a New Classification Framework for Research on Mental Disorders", Am. J. Psychiatry, Jul. 2010, 167(7), 748-751.
Inta et al., "Mice with Genetically Altered Glutamate Receptors as Models of Schizophrenia: A Comprehensive Review", Neuroscience & Biobehavioral Reviews, 2010, 34(3), 285-94.
International Patent Application No. PCT/EP2007/52442: International Search Report dated Sep. 7, 2007, 6 pages.
International Patent Application No. PCT/EP2008/52766: International Search Report dated Jun. 10, 2008, 3 pages.
International Patent Application No. PCT/EP2008/52767: International Search Report dated July 2. 2008, 13 pages.
International Patent Application No. PCT/EP2008/52768: International Search Report dated Jun. 10, 2008, 3 pages.
International Patent Application No. PCT/EP2009/06326: International Search Report dated Oct. 26, 2009, 15 pages.
International Patent Application No. PCT/EP2011/69640: International Search Report dated Dec. 23, 2011, 3 pages.
International Patent Application No. PCT/EP2011/69641: International Search Report dated Dec. 23, 2011, 3 pages.
International Patent Application No. PCT/EP2011/69643: International Search Report dated Dec. 27, 2011, 4 pages.
International Patent Application No. PCT/EP2011/69654: International Search Report dated Dec. 23, 2011, 3 pages.
Ionescu et al., "Defining Anxious Depression: A Review of the Literature", CNS Spectrums, 2013, 1-9.
Iovieno et al., "Does the Presence of an Open-Label Antidepressant Treatment Period Influence Study Outcome in Clinical Trials Examining Augmentation/Combination Strategies in Treatment Partial Responders/Nonresponders with Major Depressive Disorder?", J Clin Psychiatry, 2012, 8 pages.
Irifune et al., "Riluzole, A Glutamate Release Inhibitor, Induces Loss of Righting Reflex, Antinociception, and Immobility in Response to Noxious Stimulation in Mice", Anesthesia & Analgesia, 2007, 104(6), 1415-1421.
Jablensky et al., "Polymorphisms Associated with Normal Memory Variation Also Affect Memory Impairment in Schizophrenia", Genes, Brain and Behavior, 2011, 10, 410-417.
Jain, et al., "A One-Step Preparation of Functionalized 3-Cyano-2-Pyridones", Tetrahedron Letters, 1995, 36 (19), 3307-3310.
Jane et al., "Potent Antagonists at the L-AP4- and (1s,3s)-ACPD-Sensitive Presynaptic Metabotropic Glutamate Receptors in the Neonatal Rat Spinal Cord", Neuropharmacology, 1996, 35(8), 1029-1035.
Janssens et al., "Glutamate Receptor Subunit Expression in Primary Neuronal and Secondary Glial Cultures", J Neurochem, 2001, 77, 1457-1474.
Japanese Patent Application No. 2007-531759: Office Action dated Jun. 27, 2011, 12 pages.
Japanese Patent Application No. 2010-553485: Office Action dated Jul. 11, 2013, 3 pages.
Javitt, "Glutamatergic Theories of Schizophrenia", ISR J Psychiatry Relat Sci, 2010. 47(1), 4-16.

(56) References Cited

OTHER PUBLICATIONS

Javitt et al., "Recent Advances in the Phenylcyclidine Model of Schizophrenia", Am J Psychiatry, 1991, 148, 1301-1308.
Jenkins et al., "Disturbances in Social Interaction Occur Along with Pathophysiological Deficits Following Sub-Chronic Phencyclidine Administration in the Rat", Behavioural Brain Research, 2008, 194, 230-235.
Jensen et al., "Allosteric Modulation of the Calcium-Sensing Receptor", Current Neuropharmacology, 2007, 5, 180-186.
Jhee et al., "B-amyloid therapies in Alzheimer's disease", Expert Opinion on Investigational Drugs. 2001, 10, 593-60 5.
Jin et al., "The Mglur2 Positive Allosteric Modulator Bina Decreases Cocaine Self-Administration and Cue-Induced Cocalne-Seeking and Counteracts Cocaine-Induced Enhancement of Brain Reward Function in Rats", Neuropsych., 2010, 35(10), 2021-2036.
Jingami et al., "Structure of the Metabotropic Glutamate Receptor", Current Opinion in Neurobiology, 2003, 13(3), 271-278.
Joffe et al., "Anxious and Nonanxious Depression", Am J Psychiatry, 1993, 150, 1257-1258.
Joffe et al., "Lifetime History of Depression and Anxiety Disorders as a Predictor of Quality of Life in Midlife Women in the Absence of Current Illness Episodes", Arch Gen Psychiatry, 2012,69(5), 484-492.
Johansen et al., "Excitatory Amino Acid Receptor Ligands: Resolution, Absolute Stereochemistry, and Enantiopharmacology of 2-Amino-3-(4-Butyl-3-Hydroxyisoxazol-5-YI)Propionic Acid", J of Medicinal Chem, 1998, 41(6), 930-939.
John et al., "Rapid Changes in Glutamate Levels in the Posterior Hypothalamus Across Sleep-Wake States in Freely Behaving Rats", American Journal of Physiology—Regulatory Integrative & Comparative Physiology, 2008, 295(6), R2041-2049.
Johnson et al., "Activation of Group II Metabotropic Glutamate Receptors Induces Long-Term Depression of Excitatory Synaptic Transmission in the Substantia Nigra Pars Reticulata", Neuroscience Letters, 2011,504, 102-106.
Johnson et al., "Allosteric Modulators of Metabotropic Glutamate Receptors: Lessons Learnt From Mglul, Mglu2 and Mglu5 Potentiators and Antagonists", Biochemical Society Transactions, 2004, 32(5) 881-887.
Johnson et al., "Discovery of Allosteric Potentiators for the Metabotropic Glutamate 2 Receptor: Synthesis and Subtype Selectivity of N-(4-(2-Methoxyphenoxy)Phenyl)-N-(2,2,2-Trifluorethylsulfonyl)Pyrid-3-Ylmethyl-Amine", J. Med. Chem., 2003, 46, 3189-3192.
Johnson et al., "Disruption of Gabaergic Tone in the Dorsomedial Hypothalamus Attenuates Responses in A Subset of Serotonergic Neurons in the Dorsal Raphe Nucleus Following Lactate-Induced Panic", J Psychopharmacol, 2008, 22, 642-652.
Johnson et al., "Glutamate Receptors as Therapeutic Targets for Parkinson's Disease", CNS Neurol Disord Drug Targets, 2009, 8, 475-491.
Johnson et al., "Group II Metabotropic Glutamate Receptor Type 2 Allosteric Potentiators Prevent Sodium Lactate-Induced Panic Like Response in Panic-Vulnerable Rats", J Psychopharmacol, 2013, 27, 152-161.
Johnson et al., "Metabotropic Glutamate 2 Receptor Potentiators: Receptor Modulation, Frequency-Dependent Synaptic Activity, and Efficacy in Preclinical Anxiety and Psychosis Model(S)", Psychopharmacology, 2005, 179, 271-283.
Johnson et al., "Selective, Non-Amino Acid Allosteric Mglu2 Receptor Potentiators Inhibit Dural Plasma Protein Extravasation; A Potential Role in the Treatment of Migraine", Abstracts/ Neuropharmacology, 2002, 43, 291.
Johnson et al., "Species Variations in Transmembrane Region V of the 5-Hydroxytryptamine Type 2a Receptor Alter the Structure-Activity Relationship of Certain Ergolines and Tryptamines" Molecular Pharmacology, 1994, 45, 277-286.
Jones et al., "A Rotarod Suitable For Quantitative Measurements of Motor Incoordination in Naive Mice", Naunyn Schmiedebergs Arch. Exper. Pathol. Pharmacol., 1968, 259, 211.
Jones et al., "Analgesic Effects of the Selective Group II (Mglu2/3) Metabotropic Glutamate Receptor Agonists Ly379268 and Ly389795 in Persistent and Inflammatory Pain Models After Acute and Repeated Dosing", Neuropharmacology, 2005, 49, 206-218.
Jones et al., "Discovery, Synthesis, and Structure-Activity Relationship Development of a Series of N-4-(2,5-Dioxopyrrolidin-1-YI)Phenylpicolinamides (Vu0400195, MI182): Characterization of a Novel Positive Allosteric Modulator of the Metabotropic Glutamate Receptor 4 (Mglu4) with Oral Efficacy in an Antiparkinsonian Animal Model", J Med Chem, 2011, 54, 7639-7647.
Jones et al., "The Mglur2/3 Agonist Ly379268 Reverses Post-Weaning Social Isolation-Induced Recognition Memory Deficits in the Rat", Psychopharmacology, 2011, 214, 269-283.
Julio-Pieper et al., "Exciting Times Beyond the Brain: Metabotropic Glutamate Receptors in Peripheral and Non-Neural Tissues", Pharmacological Review, 2011, 63, 35-58.
Kagaya et al., "Heterologous Supersensitization Between Serotonin2 and Alpha 2-Adrenergic Receptor-Mediated Intracellular Calcium Mobilization in Human Platelets", Journal of Neural Transmission, 1992, 88(1), 25-36.
Kahn et al., "Group2 Metabotropic Glutamate Receptors Induced Long Term Depression in Mouse Striatal Slices", Neurosci. Lett., 2001, 316(3), 178-182.
Kalivas et al., "Repeated Cocaine Administration Alters Extracellular Glutamate in the Ventral Tegmental Area", Journal of Neurochemistry, 1998, 70(4), 1497-1502.
Kambe et al., "A Convenient Method for the Preparation of 2-Pyridone Derivatives", Synthesis, 1977, 12, 841-842.
Kappe et al., "Aktive Malonester Ais Synthons Fur Heterocyclen: Eine Methode Zur Herstellung Von 4-Hydroxy-2(1h)-Pyridonen", Journal of Heterocyclic Chemistry, 1988, 463-468.
Kapur et al., "From Dopamine to Salience to Psychosis-Linking Biology, Pharmacology and Phenomenology of Psychosis", Schizophr. Res., 2005, 79, 59-68.
Karlsson et al., "Loss of Glial Glutamate and Aspartate Transporter (Excitatory Amino Acid Transporter 1) Causes Locomotor Hyperactivity and Exaggerated Responses to Psychotomimetics: Rescue by Haloperidol and Metabotropic Glutamate 2/3 Agonist", Biol. Psychiatry, 2000, 64(9), 810-814.
Kato "Molecular Genetics of Bipolar Disorder and Depression" Psychiatry and Clinical Neurosciences 2007, 61, 3-19.
Katon et al., "Major Depression: The Importance of Clinical Characteristics and Treatment Response to Prognosis", Depression and Anxiety, 2010, 27, 19-26.
Kaupmann et al., "Expression Cloning of Gaba(B) Receptors Uncovers Similarity to Metabotropic Glutamate Receptors", Nature, 1997, 386(6622), 239-246.
Kawabata et al., "Diversity of Calcium Signaling by Metabotropic Glutamate Receptors", J. Biol. Chem., 1998, 273(28), 17381-17385.
Kearney et al., "Intrasubthalamic Nucleus Metabotropic Glutamate Receptor Activation: A Behavioral, FOS Immunohistochemical and [14c]2-Deoxyglucose Autoradiographic Study", Neuroscience, 2000, 95(2), 409-416.
Kearney et al., "Metabotropic Glutamate Agonist-Induced Rotation: A Pharmacological, FOS Immunohistochemical, and [14c]-2-Deoxyglucose Autoradiographic Study", J Neurosci., 1997, 17(11), 4415-4425.
Kehne et al., "Anxiolytic Effects of Buspirone and Gepirone in the Fear-Potentiated Startle Paradigm", Psychopharmacology, 1988, 94, 8-13.
Keller et al., "Anxiety Symptom Relief in Depression Treatment Outcomes", J Clin Psychiatry, 1995, 56(Suppl 6), 22-29.
Kellner et al.,, "Effects of Metabotropic Glutamate2/3 Receptor Agonist (Ly544344/Ly354740) on Panic Anxiety Induced by Cholecystokinin Tetrapeptide in Health Humans: Preliminary Results", Psvchopharmacology, 2005, 179, 310-315.
Kenakin et al., "Seven Transmembrane Receptors as Shapeshifting Proteins: The Impact of Allosteric Modulation and Functional Selectivity on New Drug Discovery", Pharmacological Reviews, 2010, 62(2), 265-304.

(56) References Cited

OTHER PUBLICATIONS

Kenakin et al., "Signalling Bias in New Drug Discovery: Detection, Quantification and Therapeutic Impact", Nature Reviews Drug Discovery, 2013, 12, 205-216.
Kenakin, "A Holistic View of GPCR Signaling", Nature Biotechnology, 2010, 28, 928-929.
Kenakin, "Allosteric Agonist Modulators", Journal of Receptors and Signal Transduction, 2007, 27(4), 247 -259.
Kenakin, "Allosteric Modulators: The New Generation of Receptor Antagonist", Molecular Interventions, Aug. 2004, 4(4), 222-229.
Kenakin, "Seven Transmembrane Receptors As Nature's Prototype Allosteric Protein: DeEmphasizing the Geography of Binding" Molecular Pharmacology 2008, 74, 541-543.
Kendler et al., "Major Depression and Generalized Anxiety Disorder: Same Genes, (Partly) Different Environments?", Arch Gen Psychiatry, 1992, 49, 716-722.
Kendler, "The Nosologic Validity of Paranoia (Simple Delusional Disorder)", Arch Gen Psychiatry, 1980, 37, 699-706.
Kennett et al., "Evidence That 5-Ht2c Receptor Antagonists are Anxiolytic in the Rat Geller-Seifter Model of Anxiety", Psychopharmacology, 1994, 114, 90-96.
Kenny et al., "Group II Metabotropic and Alpha-Amino-3-Hydroxy-5-Methyl-4-lsoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.
Kenny et at., "The Ups and Downs of Addiction: Role of Metabotropic Glutamate Receptors", Trends in Pharmacological Sciences, 2004, 25(5), 265-272.
Kent, "Safety, Tolerability and Potential Therapeutic Efficacy of a Novel Glutamate Modulator as Adjunctive Treatment in Patients with Schizophrenia", Abstract No. 3160, American Psychiatric Association Annual Meeting, 2013, 1 page.
Kessler et al., "Comorbid Major Depression and Generalized Anxiety Disorders in the National Comorbidity Survey Follow-Up", Psychol Med., Mar. 2008, 38(3), 365-374.
Kessler et al., "Epidemiology of Anxiety Disorders", Current Topics in Behavioral Neurosciences, 2010, 2, 21-35.
Kessler et al., "Impairment in Pure and Comorbid Generalized Anxiety Disorder and Major Depression at 12 Months in Two National Surveys", American Journal of Psychiatry, 1999, 156(12), 1915-1923.
Kessler et al., "Lifetime and 12-Month Prevalence of DSM-III-R Psychiatric Disorders in the United States: Results From the National Comorbidity Survey", Arch Gen Psych, 1994, 51, 8 10.
Kessler et al., "Rethinking the Duration Requirement for Generalized Anxiety Disorder: Evidence from the National Comorbidity Survey Replication", Psychological Medicine, 2005, 7, 1073-1082.
Kessler et al., "The Epidemiology of Co-Ocurring Addictive and Mental Disorders: Implications for Prevention and Service Utilization", American Journal of Orthopsychiatry, 1996,66(1), 17-31.
Kessler et al., "The Epidemiology of Major Depressive Disorder: Results from the National Comorbidity Survey Replication (NCS-R)", JAMA, 2003, 289(23), 3095-3105.
Kew et al., "Activity-Dependent Presynaptic Autoinhibition by Group II Metabotropic Glutamate Receptors at the Perforant Path Inputs to the Dentate Gyrus and Cal", Neuropharmacology, 2001, 40, 20-27.
Kew et al., "Differential Regulation of Synaptic Transmission by Mglu2 and Mglu3 at the Perforant Path Inputs to the Dentate Gyrus and Ca1 Revealed in Mglu2 −/− Mice", Neuropharmacology, 2002, 43,215-221.
Kew et al., "Ionotropic and Metabotropic Glutamate Receptor Structure and Pharmacology", Psychopharmacology, 2005, 179, 4-29.
Kew, "Positive and Negative Allosteric Modulation of Metabotropic Glutamate Receptors: Emerging Therapeutic Potential", Pharmacology & Therapeutics, 2004, 104, 233-244.
Khimia Geterotsiklichesklkh Soedinenii, 1985, 5, 646-649.
Khimia Geterotsiklichesklkh Soedinenii, 1986, 8, 1118-1123.
Kilama et al., "A New Synthstic Approach to the C-D Ring Portion of Streptonigrin Analogues", Journal of Heterocyclic Chemistry, 1990, 27, 1437-1440.
Kilbride et al., "Presynaptic Group II Mglur Inhibition of Short-Term Depression in the Medial Perforant Path of the Dentate Gyrus In Vitro", Neurophysiol, 2001, 85, 2509-2515.
Kilbride et al., "Presynaptic Inhibitory Action of the Group II Metabotropic Glutamate Receptor Agonists, Ly354740 and DCG-IV", European Journal of Pharmacology, 1998, 356, 149-157.
Kim et al., "Activation of Metabotropic Glutamate Receptors in the Rat Nucleus Accumbens Increases Locomotor Activity in A Dopamine-Dependent Manner", Journal of Pharmacology & Experimental Therapeutics, 1997, 283(2), 962-968.
Kim et al., "Group II Metabotropic Glutamate Receptor Stimulation Triggers Production and Release of Alzheimer's Amyloid B42 From Isolated Intact Nerve Terminals", Journal of Neuroscience, 2010, 30(11), 3870-3875.
Kim et al., "Metabotropic Glutamate Receptors in the Rat Nucleus Accumbens Contribute to Amphetamine-Induced Locomotion", Journal of Pharmacology & Experimental Therapeutics, 1998, 284(1), 317-322.
Kim et al., "Metabotropic Glutamate Receptors, Phosphorylation and Receptor Signaling", Journal of Neuroscience Research, 2008, 86, 1-10.
Kim et al., "Neurofilament-M Interacts with the D1 Dopamine Receptor to Regulate Cell Surface Expression and Desensitization", Journal of Neuroscience, 2002, 22(14), 5920-5930.
Kim et al., "Predictors of 12-Week Remission in a Nationwide Cohort of People with Depressive Disorders: The Crescend Study", Hum. Psychopharmacol Clin Exp, 2011, 26, 41-50.
Kingston et al., "Ly341495 is a Nanomolar Potent and Selective Antagonist of Group II Metabotropic Glutamate Receptors", Neuropharmacology, 1998, 37, 1-12.
Kingston et al., "Neuroprotection by Metabotropic Glutamate Receptor Agonists: Ly354740, Ly379268 and Ly389795", European Journal of Pharmacology, 1999, 377, 155-165.
Kingston et al., "Neuroprotective Actions of Novel and Potent Ligands of Group 1 and Group II Metabotropic Glutamate Receptors", Annals New York Academy of Sciences, 1999, 890, 438-449.
Kinon, "A Multicenter, Inpatient, Phase 2, Double-Blind, Placebo-Controlled Dose-Ranging Study of Ly2140023 Monohydrate in Patients with DSM-IV Schizophrenia", J. Clin. Psychopharmacology, 2011, 31(3), 349-355.
Kiselyov et al., "A One Pot Synthesis of Polysubstituted lnidazo[1,2-A]Pyridines", Tetrahedron Letters, 2006, 47, 2941-2944.
Kitano et al., "Synthesis and Antifouling Activity of 3-lsocyanotheonellin and Its Analogues", Jour Chem Soc Perkin Trans, 2002. 2251-2255.
Kilts, "The Changing Roles and Targets For Animal Models of Schizophrenia", Biol. Psychiatr., 2001, 50, 845-855.
Klein "Mixed Anxiety Depression. For and Against", L'enéphale, 1993, 493-495.
Klein et al.,, "Glutamatergic Activation of Hippocampal Phospholipase D: Postnatal Fading and Receptor Desensitization", Journal of Neurochemistry, 1998, 70(4), 1679-1685.
Klemm et al., "Chemistry of Thienopyridines. VIII. Substitution Products Derived From Thieno[2,3-B] Pyridine 7-Oxide (1)", Journal of Heterocyclic Chemistry, 1970, 7(1), 81-89.
Klodzinska et al., "Group II Mglu Receptor Agonists Inhibit Behavioural and Electrophysiological Effects of Doi in Mice", Pharmacology, Biochemistry and Behavior, 2002, 73(2), 327-332.
Klodzinska et al., "Roles of Group II Metabotropic Glutamate Receptors in Modulation of Seizure Activity", Naunyn Schmiedebergs Arch Pharmacol, 2000, 361, 283-288.
Klodzinska et al., "Selective Group 11 Glutamate Metabotropic Receptor Agonist Ly354740 Attenuates Pentetrazole- and Picrotoxin-Induced Seizures", Pol J Pharmacol, 1999, 51, 543-545.
Knesevich, "Validity of Hamilton Rating-Scale for Depression", Br J Psychiatry, 1977, 131, 49-52.
Kniazeff et al., "Closed State of Both Binding Domains of Homodimeric Mglu Receptors is Required for Full Activity", Nat Struct Mol Biol, 2004, 11, 706-713.

(56) References Cited

OTHER PUBLICATIONS

Knight et al., "Pharmacological Characterization of the Agonist Radioligand Binding Site of 5-Ht2a, 5-Ht2b and 5-Ht2c Receptors", Naunyn-Schmiedeberg's Arch Pharmacol, 2004, 370, 114-123.
Knoflach et al., "R1315, A Potent Orally Active Non-Competitive Group II Metabotropic Glutamate Receptor Antagonist with Cognitive Enhancing Properties", 5th International Meeting on Metabotropic Glutamate Receptors, Taormina Sicily-Italy, Sep. 2005, 1 page.
Kodama et al., "Enhanced Glutamate Release During Rem Sleep in the Rostromedial Medulla As Measured by in Vivo Microdialysis", Brain Res, 1998, 780, 178-181.
Koh et al., "Deficits in Social Behavior and Sensorimotor Gating in Mice Lacking Phospholipase Cb1", Genes, Brain and Behavior, 2008, 7, 120-128.
Koh et al., "Non-NMDA Receptor-Mediated Neurotoxicity in Cortical Culture", J. Neurosci., 1990, 10(2), 693-705.
Koh et al., "Treatment Strategies Targeting Excess Hippocampal Activity Benefit Aged Rats with Cognitive Impairment", Neuropsychopharmacology, 2010, 35, 1016-1025.
Komossa et al., "Second-Generation Antipsychotics for Major Depressive Disorder and Dysthymia (Review)", The Cochrane Collaboration, 2012, 222 pages.
Konarski et al., "Volumetric Neuroimaging Investigations in Mood Disorders: Bipolar Disorder Versus Major Depressive Disorder", Bipolar Disord, 2008, 10(1), 1-37.
Konieczny et al., "Ly354740, A Group II Metabotropic Glutamate Receptor Agonist with Potential Antiparkinsonian Properties in Rats", Naunyn Schmiedebergs Arch. Pharmacol., 1998, 358(4), 500-502.
Konstantakopoulos et al., "Lamotrigine Associated Exacerbation of Positive Symptoms in Paranold Schizophrenia", Schizophr Res., 2008, 98(1-3), 325-326.
Koolschijn et al., "Brain vol. Abnormalities in Major Depressive Disorder: A MetaAnalysis of Magenetic Resonance Imaging Studies", Hum Brain Mapp, 2009, 30(11), 3719-3735.
Koroshetz et al., "Emerging Treatments for Stroke in Humans", Trends in Pharmacological Sciences, 1996, 17(6), 227-233.
Kostrzewa et al., "Supersensitized D1 Receptors Mediate Enhanced Oral Activity After Neonatal 6-Ohda. Pharmacology". Biochemistry & Behavior, 1991, 39(3), 677-682.
Kotlinska et al., "The Role of Group I Mglu Receptors in the Expression of Ethanol-Induced Conditioned Place Preference and Ethanol Withdrawal Seizures in Rats", European Journal of Pharmacology, 2011,670, 154-161.
Koulen et al., "Group II and Group III Metabotropic Glutamate Receptors in the Rat Retina: Distributions and Developmental Expression Patterns", European Journal of Neuroscience, 1996, 8(10), 2177-2187.
Kowal et al., "A [35s]Gtpgammas Binding Assessment of Metabotropic Glutamate Receptor Standards in Chinese Hamster Ovary Cell Lines Expressing the Human Metabotropic Receptor Subtypes 2 and 4", Neuropharmacology, 1998, 37(2), 179-187.
Kowal et al., "Functional Calcium Coupling with the Human Metabotropic Glutamate Receptor Subtypes 2 and 4 By Stable Co-Expression with a Calcium Pathway Facilitating G-Protein Chimera in Chinese Hamster Ovary Cells", Biochemical Pharmacology, 2003, 00(5), 785-790.
Krieger, "The Plasma Level of Cortisol as a Predictor of Suicide", Diseases of the Nervous System, 1974, 35(5), 237-240.
Krishnan et al., "The Molecular Neurobiology of Depression", Nature, 2008, 455, 894-902.
Krivoy et al., "The Possible Involvement of Metabotropic Glutamate Receptors in Schizophrenia", European Neuropsychopharmacology, 2008, 18, 395-405.
Krohnke et al., "Methylketon-Addukte Der Chinolinium-Und Isochinolinium-Reihe", Justus Liebigs Annalen Der Chemie, 1956, 211-228.
Krystal et al., "Comparative and Interactive Human Psychopharmacologic Effects of Ketamine and Amphetamine: Implications for Glutamatergic and Dopaminergic Model Psychoses and Cognitive Function", Archives of General Psychiatry, 2005, 62(9), 985-994.
Krystal et al., "Neuroplasticity as a Target for the Pharmacotherapy of Anxiety Disorders, Mood Disorders, and Schizophrenia", Drug Discov. Today, 2009, 14(13-14), 690-697.
Krystal et al., "NMDA Receptor Antagonist Effects, Cortical Glutamatergic Function, and Schizophrenia: Toward a Paradigm Shift in Medication Development", Psychopharmacoloqy, 2003, 169(3-4), 215-33.
Krystal et al., "Potential Psychiatric Applications of Metabotropic Glutamate Receptor Agonists and Antagonists". CNS Drugs, 2010, 24(8), 669-693.
Krystal et al., "Preliminary Evidence of Attenuation of the Disruptive Effects of the Nmda Glutamate Receptor Antagonist, Ketamine, on Working Memory by Pretreatment with the Group II Metabotropic Glutamate Receptor Agonist, Ly354740, in Healthy Human Subjects", Psychopharmacology (Berl)., 2005, 179(1), 303-309.
Krystal et al., "Subanesthetic Effects of the Noncompetitive NMDA Antagonist, Ketamine, in Humans. Psychotomimetic, Perceptual, Cognitive, and Neuroendocrine Responses", Arch Gen Psychiatry, 1994, 51(3), 199-214.
Krystal, "N-Methyl-D-Aspartate Glutamate Receptors and Alcoholism: Reward, Dependence, Treatment, and Vulnerability", Pharmacol. & Therapeutics, 2003, 99, 79-94.
Kubo et al., "Structural Basis for a Ca2+—Sensing Function of the Metabotropic Glutamate Receptors", Science, 1998, 279(5357), 1722-1725.
Kubokawa et al., "Cloning and Characterization of a Bifunctional Metabotropic Receptor Activated By Both Extracellular Calcium and Glutamate", Febs Letters, 1996, 392(1), 71-76.
Kucukibrahimoglu et al., "The Change in Plasma Gaba, Glutamine and Glutamate Levels in Fluoxetine- or S-Citalopram-Treated Female Patients with Major Depression", Eur J Clin Pharmacol, 2009, 65(6), 571 -577.
Kufahl et al., "Enhanced Sensitivity to Attenuation of Conditioned Reinstatement by the Mglur2/3 Agonist Ly379268 and Increased Functional Activity of Mglur2/3 in Rats with a History of Ethanol Dependence", Neuropsychopharmacology, 2011,1-12.
Kugaya et al., "Beyond Monoamines: Glutamatergic Function in Mood Disorders", CNS Spectr, 2005, 10, 808-819.
Kullmann et al., "Extrasynaptic Glutamate Spillover in the Hippocampus: Evidence and Implications", Trends Neurosci., 1998, 21(1), 8-14.
Kunishima et al., "Structural Basis of Glutamate Recognition by a Dimeric Metabotropic Glutamate Receptor", Nature, 2000, 407, 971-977.
Kuo, "Allosteric Cofactor-Mediated Enzyme Cooperativity: A Theoretical Treatment", Proc. Natl. Acad. Sci. USA, Sep. 1983, 80, 5243-5247.
Kurita et al., "Hdac2 Regulates Atypical Antipsychotic Responses through the Modulation of Mglu2 Promoter Activity", Nature Neuroscience, 2012, 15(9), 1245-1254.
Kurumaji et al., "Effects of Mk-801 Upon Local Cerebral Glucose Utilization in Conscious Rats and in Rats Anaesthetized with Halothane", J Cereb Blood Flow Metab, 1989, 9, 786-794.
Lahti et al., "Ketamine Activates Psychosis and Alters Limbic Blood Flow in Schizophrenia", Neuroreport, 1995, 6(6), 869-872.
Lam et al., "Effects of the Selective Metabotropic Glutamate Agonist Ly354740 in a Rat Model of Permanent Ischaemia", Neuroscience Letters, 1998, 254(2), 121-123.
Lambeng et al., "Selective Mglur2 Negative Allosteric Modulators Reverse the Scopolamine-Induced Memory Deficit in the Novel Object Recognition Test", Society for Neuroscience 40th Annual Meeting, Nov. 2010, 1 page.
Lambert et al., "Current Issues in Schizophrenia: Overview of Patient Acceptability, Functioning Capacity and Quality of Life", CNS Drugs, 2004, 18(Suppl 2), 5-17.
Larners et al., "Comorbidity Patterns of Anxiety and Depressive Disorders in a Large Cohort Study: the Netherlands Study of Depression and Anxiety (Nesda)", J Clin Psychiatry, 2011, 72(3), 341-348.
Lamotrigine, "Highlights of Prescribing Information", 2012, 1-64.

(56) References Cited

OTHER PUBLICATIONS

Lan et al., "Activation of Metabotropic Glutamate Receptor-1 Accelerates NMDA Receptor Trafficking", Neuropharmacology, 2002, 43, 294.
Landen et al., "A Randomized, Double-Blind, Placebo-Controlled Trial of Buspirone in Combination with an Ssri in Patients with Treatment-Refractory Depression", J Clin Psychiatry, 1998, 59, 664-668.
Landin et al., "The Impact of Restrictive Entry Criterion During the Placebo Lead-in Period", Biometrics, 2000, 56, 271-278.
Landmark, "Antiepileptic Drugs in Non-Epilepsy Disorders", CNS Drugs, 2008, 22(1), 27-47.
Landwehrmeyer, "Riluzole in Huntington's Disease: A 3-Year, Randomized Controlled Study", Ann Neurol, 2007, 62, 262-272.
Lane et al., "Bridging the Gap: Bitopic Ligands of G-Protein-Coupled Receptors", Trends in Pharmacological Sciences, Jan. 2013, 34(1), 59-66.
Lang et al., "Molecular Mechanisms of Depression Perspective on New Treatment Strategies", Cell Physiol Biochem, 2013, 31, 761-777.
Lang et al., "Molecular Mechanisms of Schizophrenia", Cell Physiol Biochem., 2007, 20(6), 687-702.
Langmead, "Ligand Properties and Behaviours in an Allosteric Age", Trends Pharmacol Sci, 2012, 33, 621-622.
Langmead, "Screening for Positive Allosteric Modulators: Assessment of Modulator Concentration-Response Curves as a Screening Paradigm", Journal of Biomolecular Screening, 2007, 668-676.
Large, "Do NMDA Receptor Antagonist Models of Schizophrenia Predict the Clinical Efficacy of Antipsychotic Drugs?". J Psychopharmacol, 2007, 21, 283-301.
Large, "The Potential Role of Lamotrigine in Schizophrenia", Psychopharmacol., 2005, 181, 415-436.
Larock, "Comprehensive Organic Transformations", VCH Publishers, 1989, 595-596.
Larsson et al., "Neurochemical and Behavioral Studies on Ethanol and Nicotine Interactions", Neuroscience and Biobehavioral Reviews, 2004, 27, 713-720.
Laruelle et al., "Glutamate, Dopamine, and Schizophrenia: From Pathophysiology To Treatment", Ann Ny Acad Sci, 2003, 1003, 138-158.
Laruelle et al., "Relationships Between Radiotracer Properties and Image Quality in Molecular Imaging of the Brain with Positron Emission Tomography", Mol Imaging Biol, 2003, 5, 363-375.
Larzabal et al., "Distribution of the Grlup II Metabotropic Glutamate Receptors (Mglur2/3) in the Enteric Nervous System of the Rat", Neuroscience Letters, 1999, 276, 91-94.
Laughren et al., "Food and Drug Administration Perspective on Negative Symptoms in Schizophrenia as a Target for a Drug Treatment Claim", Schizophr Bull., 2006, 32(2), 220-222.
Laughren, "The Scientific and Ethical Basis For Placebo-Controlled Trials in Depression and Schizophrenia: An Fda Perspective", Eur Psychiatry, 2001, 16, 418-423.
Laurie et al., "Cloning, Distribution and Functional Expression of the Human Mglu6 Metabotropic Glutamate Receptor", Neuropharmacology, 1997, 36(2), 145-52.
Lavreysen et al., "[$^3$h]R214127: A Novel High-Affinity Radioligand for the Mglu1 Receptor Reveals a Common Binding Site Shared by Multiple Allosteric Antagonists", Mol Pharmacol, 2003, 63, 1082-1093.
Lavreysen et al., "A Study on the Molecular Interaction Between Mglu2 Receptor Agonists and Positive Allosteric Modulators", International Meeting on Metabotropic Glutamate Receptors, Poster, Sep. 2008, 1 page.
Lavreysen et al., "A Study On the Molecular Interaction Between Mglu2 Receptor Agonists and Positive Allosteric Modulators" Poster, Society For Neuroscience Annual Meeting, 2009, 1 page.
Lavreysen et al., "JNJ16259685, A Highly Potent, Selective and Systemically Active Mglu1 Receptor Antagrist" Neuropliarmacology 2004, 47, 96I-972.
Lavreysen et al., "JNJ-40068782: A Novel Potent, Selective and Systemically Active Positive Allosteric Modulator of the Mglu2 Receptor" Abstract, Society For Neuroscience Annual Meeting, 2010, 1 page.
Lavreysen et al., "Pharmacological Characterization of JNJ-40068782, A New Potent, Selective, and Systemically Active Positive Allosteric Modulator of the Mglu2 Receptor and Its Radioligand [3h]Jnj-40068782", J Pharmacol Exp Ther, Sep. 2013, 346, 514-527.
Lavreysen et al., "Therapeutic Potential of Group III Metabotropic Glutamate Receptors", Current Medicinal Chemistry, 2008, 15, 671-684.
Lavreysen, "The Development of Mglu2 Pams: Identification of JNJ-40068782 as a Novel Tool Compound", Allosteric Modulator Drug Discovery Congress, Nov. 2010, 34 pages.
Leach et al., "Allosteric Gpcr Modulators: Taking Advantage of Permissive Receptor Pharmacology", Trends in Pharmacological Sciences, 2007, 28(8), 382-389.
Leach et al., "Quantification of Allosteric Interactions Unit 1.22 at G Protein-Coupled Receptors Using Radioligand Binding Assays", Current Protocols in Pharmacology, Mar. 2011, 1.22.1-1.22.41.
Leber, "Observations and Suggestions on Antidementia Drug Development", Alzheimer Disease and Associated Disorders, 1996, 10 (Suppl 1), 31-35.
Lebois, "Neither Typical Nor Atypical: Ly404039 Provides Proof of Concept That Selective Targeting of Mglur2/3 Receptors is a Valid Mechanism for Obtaining Antipsychotic Efficacy", Curr. Top. Med. Chern., 2008, 8(16), 1480-1481.
Lecci et al., "Pharmacological Validation of a Novel Animal Model of Anticipatory Anxiety in Mice", Psychopharmacology, 1990, 101, 255-261.
Lee et al., "Amyloid Precursor Protein Processing is Stimulated by Metabotropic Glutamate Receptors", National Academy of Sciences USA, 1995, 92(17), 8083-8087.
Lee et al., "Benzylic Bromination of Alkylbenzenes with Sodium Bromate-Bromotrimethylsilane", Bull. Korean Chem. Soc, 1995, 16, 371-374.
Lee et al., "Characterization of the Inward Current Induced by Metabotropic Glutamate Receptor Stimulation in Rat Ventromedial Hypothalamic Neurones", Journal of Physiology, 1997, 504(Pt 3), 649-663.
Lee et al., "Glutamategic Afferent Projections to the Dorsal Raphe Nucleus of the Rat", Brain Res, 2003, 963, 57-71.
Lee et al., "Low Doses of Cannabinoids Enhance the Antinociceptive Effects of Intracisternally Administered Mglurs Groups II and III Agonists in Formalin-Induced Tmj Nociception in Rats", Pain, 2008, 139(2), 367-375.
Lee et al., "The Effect of Mglur2 Activation on Signal Transduction Pathways and Neuronal Cell Survival". Brain Res., 2009, 1249, 244-250.
Lee et al., "The Mglu2/3 Receptur Agonist Ly354740 Suppresses Immobilization Stress-Induced Increase in Rat Prefrontal Cortical Bdnf Mrna Expression", Neuroscience Letters, 2006, 398, 328-332.
Lee, "The Role of Metabotropic Glutamate Receptors in Alzheimer's Disease", Acta Neurobiol Exp, 2004, 64, 89-98.
Leeson et al., "The Influence of Drug-Like Concepts on Decision-Making in Medicinal Chemistry", Nat Rev Drug Discovery, 2007, 6, 881-890.
Leever et al., "Identification of a Site in Glurl and Glur2 That is Important for Modulation of Deactivation and Desensitization", Mol Pharmacol, 2003, 64(1), 5.
Lennon et al., "Metabotropic Glutamate Receptor Mglu2 is Resistant to Homologous Agonist-Induced Desensitilization But Undergoes Protein Kinase C-Mediated Heterologous Desensitization", Eur J Phamacol, 2010, 649, 29-37.
Lenox et al., "Mechanism of Action of Antidepressants and Mood Stabilizers" Neuropsychopharmacology: Tthe Fifth Generation of Progress, American College of Neuropsychopharmacology, 2002, 1139-1163.
Leo et al., "The Application of Nuclear Magnetic Resonance-Based Metabonomics to the Dominant-Submissive Rat Behavioral Model", Analytical Biochemistry, 2005, 339, 174-178.

(56) References Cited

OTHER PUBLICATIONS

Lerner et al., "The Work Limitations Questionnaire", Med Care, 2001, 39(1), 72-85.
Leucht et al., "Second-Generation Versus First-Generation Antipsychotic Drugs for Schizophrenia: A Meta-Analysis", Lancet, 2009, 373(9657), 31-41.
Levine et al., "Abstracts/Neuropharmacology", 2002, 43, 294-295.
Levitz et al., "Optical Control of Metabotropic Glutamate Receptors", Nature Neuroscience, 2013, 16(4), 507-516.
Lewis et al., "Cognitive Dysfunction in Schizophrenia: Convergence of Gamma-Aminobutyric Acid and Glutamate Alterations", Arch. Neurol., 2006, 63(10), 1372-1376.
Lewis, "The Molecular Choreography of a Store-Operated Calcium Channel", Nature, 2007, 446, 284-287.
Leysen et al., "[3h]Ketanserin (R 41 468), A Selective 3h-Ligand For Serotonin2 Receptor Binding Sites. Binding Properties, Brain Distribution, and Functional Role", Molecular Pharmacology, 1982, 21(2), 301-314.
Leysen et al., "Receptor Interactions of New Antipsychotics; Relation to Pharmacodynamics and Clinical Effects", Intl Journal of Psychiatry in Clinical Practice, 1998, 2, S3-S17.
Li et al., "Design and Synthesis of 4-Arylpiperidinyl Amide and N-Arylpiperdin-3-YI-Cyclopropane Carboxamide Derivatives As Novel Melatonin Receptor Ligands", Bioorganic & Medicinal Chemistry Letters, 2011, 21, 1236-1242.
Li et al., "Evaluation of the Motor Initiation Hypothesis of Apd-Induced Conditioned Avoidance Decreases", Pharmacol. Biochem. Behav., 2004, 78, 811-819.
Lieberman et al., "A Randomized, Placebo-Controlled Study of Memantine as Adjunctive Treatment in Patients with Schizophrenia", Neuropsychopharmacology, 2009, 34, 1322-1329.
Lieberman et al., "Antipsychotic Drugs: Comparison in Animal Models of Efficacy, Neurotransmitter Regulation, and Neuroprotection", Pharmacol. Rev, 2008, 60(3), 358-403.
Lieberman et al., "Effectiveness of Antipsychotic Drugs in Patients with Chronic Schizophrenia", N Engl J Med., 2005, 353(12), 1209-1223.
Lieberman, "Serotonergic Basis of Antipsychotic Drug Effects in Schizophrenia", Biol. Psychiatry, 1998, 44, 1099-1117.
Liebowitz et al., "Biological Accompaniments of Lactate-Induced Panic", Psychopharmacoloqy Bulletin, 1984, 20(1), 43-44.
Liebowitz et al., "Lactate Provocation of Panic Attacks. I. Clinical and Behavioral Findings", Archives of General Psychiatry, 1984, 41(8), 764-70.
Liechti et al., "Interactive Effects of the Mglu5 Receptor Angatonist Mpep and the Mglu2/3 Receptor Antagonist Ly341495 on Nicotine Self-Administration and Reward Deficits Associated with Nicotine Withdrawal in Rats", European Journal of Pharmacology, 2007, 554, 164-174.
Liechti et al., "Metabotropic Glutamate 2/3 Receptor Activation Induced Reward Deficits But Did Not Aggravate Brain Reward Deficits Associated with Spontaneous Nicotine Withdrawal In Rate". Biochemical Pharmacology. 2007, 74, 1299-1307.
Liechti et al., "Metabotropic Glutamate 2/3 Receptors in the Ventral Tegmental Area and the Nucleus Accumbens Shell are Involved in Behaviors Relating To Nicotine Dependence", Journal of Neuroscience, 2007, 27(34), 9077-9085.
Liechti et al., "Role of the Glutamatergic System in Nicotine Dependence Implications for the Discovery and Development of New Pharmacological Smoking Cessation Therapies", CNS Drugs, 2008, 22(9), 705-724.
Lilly, "Stops Phase III Development of Pomaglumetad Methionil For the Treatment of Schizophrenia Based On Efficacy Results", Press Release, Aug. 29, 2012, 1 page.
Lin et al., "A Meta-Analytic Review of Double-Blind, Placebo-Controlled Trials of Antidepressant Efficacy of Omega-3 Fatty Acids", J Clin Psychiatry, 2007, 68(7), 1056-1061.
Lindemann et al., "Ctep: A Novel, Potent, Long-Acting, and Orally Bioavailable Metabotropic Glutamate Receptor 5 Inhibitor", Jpet, 2011, 339, 474-486.
Linden et al., "Anxiolytic Activity of the Mglu2/3 Receptor Agonist Ly354740 on the Elevated Plus Maze is Associated with the Suppression of Stress-Induced C-Fos in the Hippocampus and Increases in C-Fos Induction in Several Other Stress-Sensitive Brain Regions", Neuropsychopharmacology, 2004, 29, 502-513.
Linden et al., "Comparison of C-Fos Induction in the Brain By the Mglu2/3 Receptor Antagonist Ly341495 and Agonist Ly354740: Evidence for Widespread Endogenous Tone at Brain Mglu2/3 Receptors In Vivo", Neuropharmacology, 2005, 49(Suppl 1), 120-134.
Linden et al., "Effects of Mglu2 or Mglu3 Receptor Deletions on Mglu2/3 Receptor Agonist (Ly354740)-lnduced Brain C-Fos Expression: Specific Roles for Mglu2 in the Amygdala and Subcortical Nuclei, and Mglu3 in the Hippocampus", Neuropharmacology, 2006, 51, 213-228.
Linden et al., "Use of Mglur2 and Mglur3 Knockout Mice to Explore In Vivo Receptor Specificity of the Mglur2/3 Selective Agonist Ly341495", Neuropharmacology, 2009, 57, 172-182.
Linden, "Anxiolytic-Like Activity of the Mglu2/3 Receptor Agonist Ly354740 in the Elevated Plus Maze Test is Disrupted in Metabotropic Glutamate Receptor 2 and 3 Knock-Out Mice", Psychopharmacol., 2005, 179, 284-291.
Lindsley et al., "Progress Towards Validating the NMDA Receptor Hypofunction Hypothesis of Schizophrenia", Current Topics in Medicinal Chemistry, 2006, 6, 771-785.
Linn et al., "Activation of Metabotropic Glutamate Receptors Modulates the Voltage-Gated Sustained Calcium Current in a Teleost Horizontal Cell", Journal of Neurophysiology, 1999, 81(2), 425-434.
Lipton, "Excitatory Amino Acids as a Final Common Pathway for Neurologic Disorders", Mechanisms of Disease, New England Journal of Medicine, 1994, 330(9), 613-622.
Lissin et al., "An Immunocytochemical Assay for Activity-Dependent Redistribution of Glutamate Receptors from the Postsynaptic Plasma Membrane", Annals of the New York Academy of Sciences, 1999, 868, 550-553.
Litman, "AZD8529, A Positive Allosteric Modulator at the Mglur2 Receptor, Does Not Improve Symptoms in Schizophrenia: A Proof of Principle Study", NCDEU: An Annual Meeting Sponsored By Am Soc. of Clin. Psychopharmacology, Poster and Abstract, 2013, 3 pages.
Liu et al., "A Unified Theory of Two-Stage Adaptive Designs", Theory and Methods, 2002, 97, 1034-1041.
Liu et al., "Doubly Randomized Delayed-Start Design for Enrichment Studies with Responders or Nonresponders", Journal of Biopharmaceutical Statistics, 2012, 22(4), 737-757.
Liu et al., "Ischemic Insults Direct Glutamate Receptor Subunit 2-Lacking AMPA Receptors to Synaptic Sites", Journal of Neuroscience, May 17, 2006, 26(20), 5309-5319.
Liu et al., "Pharmacogenetic Analysis of the Mglu2/3 Agonist Ly2140023 Monohydrate in the Treatment of Schizophrenia", Pharmacogenomics Journal, 2010, 1-9.
Lopez-Rodriguez et al., "Changes in Extracellular Glutamate Levels in Rat Orbitofrontal Context During Sleep and Wakefulness", Arch Med Res, 2007, 38, 52-55.
Lorenzetti et al., "Structural Brain Abnormalities in Major Depressive Disorder: A Selective Review of Recent MRI Studies", J Affect Disord, 2009, 117(1-2), 1-17.
Lorrain et al., "Group II Mglu Receptor Activation Suppresses Norepinephrine Release in the Ventral Hippocampus and Locomotor Responses to Acute Ketamine Challenge", Neuropsychopharmacology, 2003, 28, 1622-1632.
Lou et al., "Allosteric Modulation of the Presynaptic Ca2+ Sensor for Vesicle Fusion", Nature. 2005, 435, 497-501.
Lowe et al., "Effects of a Novel Mglu2/3 Receptor Agonist Prodrug, Ly2140023 Monohydrate, on Central Monoamine Turnover as Determined in Human and Rat Cerebrospinal Fluid", Psychopharmacology, 2011,1-12.
Lowry et al., "Serotonergic Systems, Anxiety, and Affective Disorder: Focus on the Dorsomedial Part of the Dorsal Raphe Nucleus", Annals of the New York Academy of Sciences, 2008, 1148, 86-94.
Lujan et al., "Glutamate and Gaba Receptor Signalling in the Developing Brain", Neuroscience, 2005, 130, 567-580.

(56) References Cited

OTHER PUBLICATIONS

Luscher et al., "Group I Mglur-Dependent Synaptic Long-Term Depression: Mechanisms and Implications For Circuitry and Disease", Neuron, 2010, 65, 445-459.

Lyon et al., "Altered Hippocampal Expression of Glutamate Receptors and Transporters in Grm2 and Grm3 Knockout Mice", Synapse, 2008, 62, 842-850.

Lyon et al., "Fractionation of Spatial Memory in Grm2/3 (Mglu2/Mglu3) Double Knockout Mice Reveals a Role for Group II Metabotropic Glutamate Receptors at the Interface Between Arousal and Cognition", Neuropsychopharmacology, 2011, 1-13.

Macchiarulo et al., "The Role of Electrostatic Interaction in the Molecular Recognition of Selective Agonists to Metabotropic Glutamate Receptors", Proteins, 2003, 50(4), 609-619.

Macdonald "The Design of Allosteric Modulators for the Treatment of CNS Disorders", 11$^{th}$Advances and Progress in Drug Design, Feb. 2012, 36 pages.

Macdonald, "The Design of Mglur Modulators for the Treatment of CNS Disorders" Presentation Slides, 6$^{th}$Anglo-Swedish Medicinal Chemistry Symposium, Stockholm, Jun. 19, 2013, 1 page.

Macdonald, "Positive Allosteric Modulation of Mglur2 Receptors in the Treatment of CNS Disorders", 3$^{rd}$Symposium on GPCRS in Medicinal Chemistry, Oss, Sep. 2010, 29 pages.

Macek et al., "Differential Involvement of Group II and Group III Mglurs as Autoreceptors at Lateral and Medial Perforant Path Synapses", J Neurophysiol, 1996, 76(6), 3798-3806.

Macek et al., "Protein Kinase C and A3 Adenosine Receptor Activation Inhibit Presynaptic Metabotropic Glutamate Receptor (Mglur) Function and Uncouple Mglurs from Gtp-Binding Proteins", J. Neurosci., 1998, 18(16), 6138-6146.

Mackrill, "Protein-Protein Interactions in Intracellular Ca2+-Release Channel Function", Biochemical Journal, 1999, 337 (Pt 3), 345-361.

Maeda et al., "Different Roles of Group I and Group II Metabotropic Glutamate Receptors on Phencyclidine-Induced Dopamine Release in the Rat Prefrontal Cortex", Neuroscience Letters, 2003, 336 (3), 171-174.

Maeng, "Cellular Mechanisms Underlying the Antidepressant Effects of Ketamine: Role of Alpha-Amino-3-Hydroxy-5-Methylisoxazole-4-Propionic Acid Receptors," Biol. Psychiatry, 2008, 63, 349-352.

Maione et al., "Characterisation of Mglurs Which Modulate Nociception in the Pag of the Mouse", NeuropharmacologyJ998, 37(12), 1475-1483.

Makoff et al., "Molecular Characterization and Localization of Human Metabotropic Glutamate Receptor Type 3", Molecular Brain Research, 1996, 40(1), 55-63.

Malames et al., "N-Substituted Spirosuccinimide, Spiropyridazine, Spiroazetidine, and Acetic Acid Aidose Reductase Inhibitiors Derived From lsoquinoline-1,3-Dinoes. 2", J Med Chem., 1994, 37(13), 2059-2070.

Malatynska et al., "Assessing Activity Onset Time and Efficacy for Clinically Effective Antidepressant and Antimanic Drugs in Animal Models Based on Dominant-Submissive Relationships", Neuroscience and Biobehavioral Reviews, 2007, 31, 904-919.

Malatynska et al., "Dominant-Submissive Behavior As Models of Mania and Depression", Neuroscience and Biobehavioral Reviews, 2005, 29(4-5), 715-37.

Malatynska et al., "Levels of Mrna for A-, B-, and [-Synuclein in the Brains of Newborn, Juvenile, and Adult Rats", J Mol Neurosci., 2006, 29(3), 269-77.

Malatynska et al., "Reduction of Dominant or Submissive Behaviors as Models for Antimanicor Antidepressant Drug Testing: Technical Considerations", J Neurosci Methods, 2007, 165(2), 175-182.

Malenka et al., "Ltp and Ltd: An Embarrassment of Riches", Neuron, 2004, 44, 5-21.

Malherbe et al., "Identification of Essential Residues Involved in the Glutamate Binding Pocket of the Group II Metabotropic Glutamate Receptor", Molecular Pharmacology., 2001, 60 (5), 944-954.

Malherbe et al., "Opposite Effects of Zn on the in Vitro Binding of [3h]Ly354740 to Recombinant and Native Metabotropic Glutamate 2 and 3 Receptors", J Neurochem., 2005, 94(1), 150-160.

Malhi et al., "Recognizing the Anxious Face of Depression", Journal of Nervous and Mental Disease, 2002, 190(6), 366-73.

Malhotra et al., "NMDA Receptor Function and Human Cognition: The Effects of Ketamine in Healthy Volunteers", Neuropsychopharmacology, May 1996, 14(5), 301-307.

Mansbach et al., "Blockade of Potentiated Startle Responding in Rats by 5-Hydroxytryptamine1 a Receptor Ligands", Eur. J. Pharmacology, 1988, 156, 375-383.

Marcotte, "Animal Models of Schizophrenia: A Critical Review", Psychiatry Neurosci., 2001, 26(5), 395-410.

Marcus et al., "The Efficacy and Safety of Aripiprazole as Adjunctive Therapy in Major Depressive Disorder; A Second Multicenter, Randomized, Double-Blind, Placebo-Controlled Study", Journal of Clinical Psychopharmacology, 2008, 28(2), 156-165.

Marek, "Metabotropic Glutamate2/3 (Mglu2/3) Receptors, Schizophrenia and Cognition", European Journal of Pharmacology, 2010, 639, 81-90.

Marek et al., "5-Hydroxytryptamine2a (5-Ht2a) Receptor Regulation in Rat Prefrontal Cortex: Interaction of a Phenethylamine Hallucinogen and the Metabotropic Glutamate2/3 Receptor Agonist Ly354740", Neuroscience Letters, 2006, 403(3), 256-260.

Marek et al., "Glutamatergic (N-Methyl-D-Aspartate Receptor) Hypofrontality in Schizophrenia: Too Little Juice or A Miswired Brain?", Molecular Pharmacology, 2010, 77(3), 317-326.

Marek et al., "Physiological Antagonism Between 5-Hydroxytryptamine2a and Group II Metabotropic Glutamate Receptors in Prefrontal Cortex", J. Pharm. Exper. Therapeut., 2000, 292, 76-87.

Marek et al., "The Electrophysiology of Prefrontal Serotonin Systems: Therapeutic Implications for Mood and Psychosis", Biol Psychiatry, 1998, 44, 1118-1127.

Marek, "Metabotropic Glutamate 2/3 Receptors as Drug Targets", Curr. Opin. Pharmacol., 2004, 4, 18-22.

Markou, "The Role of Metabotropic Glutamate Receptors in Drug Reward, Motivation and Dependence", Drug News Perspect, 2007, 20(2), 103-108.

Marquet et al., "VIII. Nouvelle Methode De Synthese Des Furo[2,3-D]Pyrimidines Sustituees En Position 4 Et De Certains Thieno[2,3-D]Pyrimidines", Bulletin De La Societe Chimique De France, 1969, 12, 4344-4348.

Martella et al., "Enhanced Sensitivity to Group II Mglu Receptor Activation at Corticostriatal Synapses in Mice Lacking the Familial Parkinsonism-Linked Genes Pinkl or Parkin.", Exp. Neurol., 2009, 215(2), 388-396.

Martin et al., "Cellular Localization of A Metabotropic Glutamate Receptor in Rat Brain", Neuron, 1992, 9(2), 259-270.

Martin et al., "Cross-Talk Between Beta-Adrenergic and Metabotropic Glutamate Receptors in Rat C6 Glioma Cells", Biochimica Et Biophysica Acta, 1998, 1393(1), 186-192.

Mason, "Acamprosate in the Treatment of Alcohol Dependence", Expert Opin. Pharmacother., 2005, 6(12), 2103-2115.

Masu et al., "Sequence and Expression of a Metabotropic Glutamate Receptor", Nature, 1991, 349(6312), 760-765.

Matrisciano et al., "Activation of Group-ll Metabotropic Glutamate Receptors Promotes DNA Demethylation in the Mouse Brain", Molecular Pharmacology, Apr. 2011, 52 pages.

Matrisciano et al., "Defective Group-ll Metaboropic Glutamate Receptors in the Hippocampus of Spontaneously Depressed Rats", Neuropharmacology, 2008, 55(4), 525-531.

Matrisciano et al., "Group-II Metabotropic Glutamate Receptor Ligands as Adjunctive Drugs in the Treatment of Depression: A New Strategy To Shorten the Latency of Antidepressant Medication?", Molecular Psychiatry, 2007, 12, 704-706.

Matrisciano et al., "Imipramine Treatment Up-Regulates the Expression and Function of Mglu2/3 Metabotropic Glutamate Receptors in the Rat Hippocampus", Neuropharmacology, 2002, 42(8), 1008-1015.

Matrisciano, "Metabotropic Glutamate Receptors and Neuroadaptation to Antidepressants: Imipramine-lnduced Down-Regulation of

(56) References Cited

OTHER PUBLICATIONS

B-Adrenergic Receptors in Mice Treated with Metabotropic Glutamate 2/3 Receptor Ligands", Journal of Neurochemistry, 2005, 93, 1345-1352.
Matrisciano, "Synergism Between Fluoxetine and the Mglu2/3 Receptor Agonist, Ly379268, in an In Vitro Model for Antidepressant Drug-Induced Neurogenesis", Neuropharmacology, 2008, 54,428-437.
Maurel et al., "Cell-Surface Protein-Protein Interaction Analysis with Time-Resolved Fret and Snap-Tag Technologies: Application to Gpcr Oligomerization", Nat Methods, 2008, 5(6), 561-567.
Maxwell et al., "Ketamine Produces Lasting Disruptions in Encoding of Sensory Stimuli", J Pharmacol Exp Ther, 2006, 316, 315-324.
May et al., "Allosteric Modulation of G Protein-Coupled Receptors", Annu Rev Pharmacol Toxicol, 2007, 47, 14.1-14.51.
May et al., "Regional Serotonin Receptor Studies: Chronic Methysergide Treatment Induces A Selective and Dose-Dependent Decrease in Serotonin-2 Receptors in Mouse Cerebral Cortex", Life Sciences, 1986, 38(19), 1741-1747.
Mayers et al., "Antidepressants and Their Effect On Sleep", Hum Psychopharmacol., 2005, 20, 5333-559.
Mayo Clinic, "Mental Illness", 2012, 1-13.
Mcclintock et al., "Assessing Anxious Features in Depressed Outpatients" I nt. J. Methods Psychiatr. Res., 2011, 20(4), E69-E82.
McDermott et al., "Design and Analysis of Two-Period Studies of Potentially Disease-Mod ifying Treatments", Controlled Clinical Trials, 2002, 23, 635-649.
McElvain etaL, "Piperidine Derivatives. XXX. 1,4-Dialkyl-4-Arylpiperidines", J. Am. Chem. Soc, 1958, 80, 3915-3923.
McEvoy et al., "Effectiveness of Clozapine Versus Olanzapine, Quetiapine, and Risperidone in Patients with Chronic Schizophrenia Who Did Not Respond to Prior Atypical Antipsychotic Treatment", Am J Psychiatry, 2006. 163(4), 600-610.
McIntyre et al., "Quetiapine Adjunct to Selective Serotonin Reuptake Inhibitors or Venlafaxine in Patients with Major Depression, Comorbid Anxiety, and Residual Depressive Symptoms: A Randomized, Placebo-Controlled Pilot Study", Depression and Anxiety, 2007, 24, 487-494.
Meador-Woodruff et al., "Glutamate Receptor Expression in Schizophrenic Brain", Brain Res., 2000, 31(2-3), 288-294.
Melancon et al., "Allosteric Modulation of 7 Transmembrane Spanning Receptors: Theory, Practice and Opportunities for CNS Drug Discovery", J Med Chem, 2012, 55(4), 1445-1464.
Melartin et al., "Current Comorbidity of Psychiatric Disorders Among DSM-IV Major Depressive Disorder Patients in Psychiatric Care in the Vantaa Depression Study", J Clin Psychiatry, 2002, 63, 126-134.
Meldrum et al., "Excitatory Amino Acid Neurotoxicity and Neurodegenerative Disease", Trends in Pharmacological Sciences, 1990, 11(9), 379-387.
Meldrum et al., "Glutamate Receptors and Trasnporters in Genetic and Acquired Models of Epilepsy", Epilepsy Res, 1999, 36, 189-204.
Meltzer et al., "Serotonin Receptors: Their Key Role in Drugs to Treat Schizophrenia", Prog. Neuropsychopharmacol. Biol. Psychiatry, 2003, 27(7), 1159-1172.
Meltzer, "Illuminating the Molecular Basis for Some Antipsychotic Drug-Induced Metabolic Burden", Proc. Natl. Acad. Sci. USA, 2007, 104(9), 3019-3020.
Merikangas et al., "Longitudinal Trajectories of Depression and Anxiety in a Prospective Community Study", Arch Gen Psychiatry, 2003, 60, 993-1000.
Metman, "Huntington's Disease A Randomized, Controlled Trial Using the NMDA-Antaqonist Amantadine", Neurology, 2002, 59, 694-699.
Mezler et al., "Ly2140023, A Prodrug of the Group II Metabotropic Glutamate Receptor Agonist Ly-404039 for the Potential Treatment of Schizophrenia", Current Opinion in Investigational Drugs, 2010, 11(7), 833-845.
Michael et al., "Metabolic Changes Within the Left Dorsolateral Prefrontal Cortex Occurring with Electroconvulsive Therapy in Patients with Treatment Resistant Unipolar Depression", Psychol Med, 2003, 33(7), 1277-1284.
Michael et al., "Neurotrophic Effects of Eletroconvulsive Therapy: A Proton Magnetic Resonance Study of the Left Amygdalar Region in Patients with Treatment-Resistant Depression", Neuro- psychopharmacology, 2003, 28(4), 720-725.
Michelson, "Clinical Studies with Mglur2/3 Agonists: Ly3 54740 Compared with Placebo in Patients with Generalized Anxiety Disorder", Neuropharmacol., 2005, 49, 257.
Miller, "Mechanisms of Action of Antipsychotic Drugs of Different Classes, Refractoriness to Therapeutic Effects of Classical Neuroleptics, and Individual Variation in Sensitivity to Their Actions: Part I",Current Neuropharmacology, 2009, 7, 302-314.
Miller et al., "Roles of Metabotropic Glutamate Receptors in Brain Plasticity and Pathology", Annals of the New York Academy of Sciences, 1995, 757, 460-474.
Mills et al., "Epidemiology and Reporting of Randomized Trials Employing ReRandomization of Patient Groups: A Systematic Survey", Contemporary Clinical Trials, 2007, 28, 268-275.
Mitchell et al., "An Update on the Role of Glutamate in the Pathophysiology of Depression", Acta Psychiatrica Scandinavica, 2010, 122(3), 192-210.
Mitri et al., "Divergent Evolution in Metabotropic Glutamate Receptors. A New Receptor Activated by an Endogenous Ligand Different from Glutamate in Insects", Journal of Biological Chemistry, 2004, 279(10), 9313-9320.
Mittal et al., "Impact of Comorbid Anxiety Disorders on Health-Related Quality of Live Among Patients with Major Depressive Disorder", Psychiatric Services, 2006, 57(12), 1731-1737.
Miuller et al., "The Immunological Basis of Glutamatergic Disturbance in Schizophrenia: Towards an Integrated View", J Neural Transm, 2007, 72, 269-280.
Miyamoto et al., "Effects of Ketamine, Mk-801, and Amphetamine on Regional Brain 2-Deoxyglucose Uptake in Freely Moving Mice", Neuropsychopharmacology, 2000, 22, 400-412.
Miyamoto et al., "Treatments for Schizophrenia: A Critical Review of Pharmacology and Mechanisms of Action of Antipsychotic Drugs", Mol. Psychiatry, 2005, 10, 79-104.
Modafferi "Morphine Withdrawal Increases Metabotropic Glutamate 2/3 Receptors Expression in Nucleus Accumbens", Neurochemistry, 2008, 19(9), 911-914.
Moffitt et al., "Depression and Generalized Anxiety Disorder", Arch. Gen. Psychiatry, 2007, 64, 651-660.
Moghaddam et al., "Activation of Glutamatergic Neurotransmission By Ketamine: A Novel Step in the Pathway from NMDA Receptor Blockade to Dopaminergic and Cognitive Disruptions Associated with the Prefrontal Cortex", J Neurosci. 1997, 17(8), 2921-2927.
Moghaddam et al., "From Revolution to Evolution: the Glutamate Hypothesis of Schizophrenia and Its Implication for Treatment", Neuropsychopharmacology, 2012, 37,4-15.
Moghaddam et al., "Reversal of Phencyclidine Effects by a Group II Metabotropic Glutamate Receptor Agonist in Rats", Science, 1998, 281, 1349-1352.
Moghaddam, "Targeting Metabotropic Glutamate Receptors for Treatment of the Cognitive Symptoms of Schizophrenia", Psychopharmacology, 2004, 174(1), 39-44.
Moldrich et al., "Anti-Epileptic Activity of Group II Metabotropic Glutamate Receptor Agonists (++)-2-Oxa-4-Aminobicyclo[3.1.0]Hexane-4,6-Dicarboxylate (Ly379268) and (++)-2-Thia-4-Aminobicyclo[3.1,0]Hexane-4,6-Dicarboxylate (Ly389795)", Neuropharmacology, 2001, 41, 8-18.
Moldrich et al., "Astrocyte Mglu(2/3)-Mediated Camp Potentiation is Calcium Sensitive: Studies in Murine Neuronal and Astrocyte Cultures", Neuropharmacology, 2002, 43(2), 189-203.
Moldrich et al., "Emerging Signalling and Protein Interactions Mediated Via Metabotropic Glutamate Receptors", Curr. Drug Targets. CNS Neurol. Disord., 2003, 2(2), 109-122.
Moldrich et al., "Glutamate Metabotropic Receptors as Targets for Drug Therapy in Epilepsy", European Journal of Pharmacology, 2003, 476, 3-16.

(56) References Cited

OTHER PUBLICATIONS

Molina et al., "Polymorphic Variation at the Serotonin 1-A Receptor Gene is Associated with Comorbid Depression and Generalized Anxiety", Psychiatry Genetics, 2011, 21, 195-201.
Molinaro et al., "Activation of Mglu2/3 Metabotropic Glutamate Receptors Negatively Regulates the Stimulation of Inositol Phospholipid Hydrolysis Mediated By 5-Hydroxytryptamine2a Serotonin Receptors in the Frontal Cortex of Living Mice", Mol. Pharmacol., 2009, 76(2), 379-387.
Mondon et al., "Synthesis of Narciprimine and Related Compounds", Chem. Ber., 1972, 105, 3726-3747.
Mongin et al., "Advances in the Directed Metallation of Azines and Diazines (Pyridines, Pyrimidines, Pyrazines, Pyridazines, Quinolines, Benzodiazines and Carbolines). Part 1: Metallation of Pyridines, Quinolines and Carbolines", Tetrahedron, 2001, 57(19), 4059-4090.
Monn et al., "Design, Synthesis, and Pharmacological Characterization of (+)-2-Aminobicyclo[3.1.0]Hexane-2,6-Dicarboxylic Acid (Ly354740): A Potent, Selective, and Orally Active Group 2 Metabotropic Glutamate Receptor Agonist Possessing Anticonvulsant and Anxiolytic Properties", J Med Chem, 1997, 40, 528-537.
Monn et al., "Synthesis and Metabotropic Glutamate Receptor Activity of S-Oxidized Variants of (-)-4-Amino-2-Thiabicyclo-[3.1,0]Hexane-4,6-Dicarboxylate: Identification of Potent, Selective, and Orally Bioavailable Agonists ForMglu2/3 Receptors", J. Med. Chem., 2007, 50, 233-240.
Monn et al., "Synthesis, Pharmacological Characterization, and Molecular Modeling of Heterobicyclic Amino Acids Related To (+)-2-Aminobicyclo[3.1.0] Hexane-2,6-Dicarboxylic Acid (Ly354740): Identification of Two New Potent, Selective, and Systemically Active Agonists For Group II Metabotropic Glutamate Receptors", Journal of Medicinal Chemistry, 1999, 42(6), 1027-1040.
Monti et al., "Conventional and Power Spectrum Analysis of the Effects of Zolpidem on Sleep Eeg in Patients with Chronic Primary Insomnia", Sleep, 2000, 23, 1075-1084.
Moore et al., "Cycloadditions of Cyanoketenes to Cinnamylideneamines and Benzylideneamines. Synthetic Scope, Stereochemistry, and Mechanism", Journal Org. Chem., 1985, 50, 4231-4238.
Mora et al., "Role of 5-Ht2a and 5-Ht2c Receptor Subtypes in the Two Types of Fear Generated By the Elevated T-Maze", Pharmacology Biochemistry and Behavior, 1997, 58, 1051-1057.
Moreno et al., "Group II Metabotropic Glutamate Receptorsand Schizophrenia", Cell Mol. Life Sci., 2009, 66(23), 3777-3785.
Moreno et al., "Maternal Influenza Viral Infection Causes Schizophrenia-Like Alterations of 5-Ht2a and Mglu2 Receptors in the Adult Offspring", Journal of Neuroscience, 2011, 31(5), 1863-1872.
Moreno et al., "Metabotropic Glutamate Mglu2 Receptor is Necessary for the Pharmacological and Behavioral Effects Induced by Hallucinogenic 5-Ht2a Receptor Agonists", Neurosci. Lett., 2011, 493, 76-79.
Moreno et al., "Pindolol Augmentation of Treatment-Resistant Depressed Patients" J Clin Psychiatry 1997, 58, 437-439.
Morgan et al., "Is Persistent Ketamine Use A Valid Model of the Cognitive and Oculomotor Deficits in Schizophrenia?", Biol. Psychiatry, 2009, 65(12), 1099-1102.
Morikawa et al., "Two Intracellular Pathways Mediate Metabotropic Glutamate Receptor-Induced Ca2+ Mobilization in Dopamine Neurons", Journal of Neuroscience, 2003, 23(1), 149-157.
Morishima et al., "Enhanced Cocaine Responsiveness and Impaired Motor Coordination in Metabotropic Glutamate Receptor Subtype 2 Knockout Mice", Proc. Natl. Acad. Sci., 2005, 102(11), 4170-4175.
Morishita, "Clonazepam as a Therapeutic Adjunct to Improve the Management of Depression: A Brief Review", Hum Psychopharmacol Clin Exp, 2009, 24, 191-198.
Moroni et al., "Poly(Adp-Ribose) Polymerase Inhibitors Attenuate Necrotic But Not Apoptotic Neuronal Death in Experimental Models of Cerebral Ischemia", Cell Death and Differentiation, 2001, 8, 921-932.
Morpurgo et al., "Drug-Induced Modifications of Discriminated Avoidance Behavior in Rats", Psychopharmacol., 1965, 8, 91-99.
Morrill et al., "Synthesis of 4-Arylpiperidines from 1-Benzyl-4piperidone: Application of the Sharpiro Reaction and Alkenylsilane Cross-Coupling", Organic Letters, 2007, 9, 1505-1508.
Morrison et al., "Schizophrenia: More Evidence for Less Glutamate", Expert Rev Neurother., 2007, 7(1), 29-31.
Moussawi et al., "Group II Metabotropic Glutamate Receptors (Mglu2/3) in Drug Addiction", European Journal of Pharmacology, 2010, 639, 115-122.
Mudge et al., "Genomic Convergence Analysis of Schizophrenia: Mrna Sequencing Reveals Altered Synaptic Vesicular Transport in Post-Mortem Cerebellum", Pios One, 2008, 3(11) 1-24.
Mukhin et al., "Mglur Modulation of Post-Traumatic Neuronal Death: Role of NMDA Receptors", Neuroreport, 1997, 8(11), 2561-2566.
Muller, "Inflammation and the Glutamate System in Schizophrenia: Implications for Therapeutic Targets and Drug Development", Expert Opin. Ther. Targets, 2008, 12(12), 1497-1507.
Muly et al., "Group II Metabotropic Glutamate Receptors in Anxiety Circuitry: Correspondence of Physiological Response and Subcellular Distribution", J Comp Neurol., 2007, 505(6), 682-700.
Muntasir et al., "Inverse Agonist Activity of Sarpogrelate, A Selective 5-Ht2a-Receptor Antagonist, at the Constitutively Active Human 5-Ht2a Receptor", Journal of Pharmacological Sciences, 2006, 102(2), 189-195.
Murck et al., "State Markers of Depression in Sleep Eeg: Dependency On Drug and Gender in Patients Treated with Tianepine or Paroxetine", Neuropsychopharmacol. 2003, 28, 348-358.
Mutel et al., "Characterization of (2s,2'r,3'r)-2-(2',3'-[3h]-Dicarboxycyclopropyl)Glycine Binding in Rat Brain", J Neurochemistry, 71(6), 1998, 2558-2564.
Mutel, "Therapeutic Potential of Non-Competitive, Subtype-Selective Metabotropic Glutamate Receptor Ligands", Expert Opin. Ther. Patents, 2002, 12(12), 1845-1852.
Muto et al., "Structures of the Extracellular Regions of the Group ll/lll Metabotropic Glutamate Receptors", Proc. Natl. Acad. Sci. USA, 2007, 104(10), 3759-3764.
Nabeshima et al., "Animal Model of Schizophrenia. Dysfunction of Nmda Receptor-Signaling in Mice Following Withdrawal from Repeated Administration of Phencyclidine", Ann. N.Y. Acad. Sci., 2006, 1086, 160-168.
Nadin et al., "Synthesis of Tricyclic Pyridones by Radical Cyclization", Tetrahedron Letters, 1999, 40, 4073-4076.
Naimoli et al., "Compound A, A Novel Potent and Selective Mglur2 Positive Allosteric Modulator: III. Effects in Clinically Relevant Translational Cognition Models That Could be Used as Biomarkers" Poster 767.1 Presented at the 40[th]Annual Meeting of Society for Neuroscience, Nov. 2010, 1 page.
Nakamura et al., "An Efficient Synthesis of Platelet-Activating Factor (Paf) J'ij L-Qalkyl-2-~-(3-lsoxazolyl)-Sn_Glycero-3-Phosphocholine, A New Paf Agonist. Utilization of the 3-Isoxazolyloxy Group as a Protected Hydroxyl", Tetrahedron Letters. 1990. 31, 699-702.
Nakanishi, et al., "Glutamate Receptors: Brain Function and Signal Transduction", Brain Research Reviews, 1998, 26, 230-235.
Nakano et al., "1-Alkyl-3-Phenylpyridinium 1-Alkyl-2(1h)-Pyridone 3-Phenyl 5-Phenyl", Annual Report of Tohoku College of Pharmacy, 1998, 45, 145-148.
Nasca et al., "L-Acetylcarnitine Causes Rapid Antidepressant Effects Through the Epigenetic Induction of Mglu2 Receptors", Proceedings of the Nat. Acad, of Sci. of US, 2013, 110(12), 4804-4809.
Neale, "The Neurotransmitter N-Acetylaspartylglutamate in Models of Pain, Ais, Diabetic Neuropathy CNS Injury and Schizophrenia", Trends in Pharmacological Sciences 2005, 26(9), 477-484.
Neki et al., "Metabotropic Glutamate Receptors Mglur2 and Mglur5 are Expressed in Two Non-Overlapping Populations of Golgi Cells in the Rat Cerebellum", Neuroscience, 1996, 75(3), 815-826.
Neki et al., "Pre- and Postsynaptic Localization of a Metabotropic Glutamate Receptor, Mglur2, in the Rat Brain: An Immunohistochemical Study with a Monoclonal Antibody", Neurosci. Lett., 1996, 202(3), 197-200.
Nell et al., "Preparation of 4-Amino-3,5-Dicyano-2-Thiopyridines as Cardiovascular Agents", Caplus, 2008, 1 page.

(56) References Cited

OTHER PUBLICATIONS

Nelson, "Anxiety Does Not Predict Response to Duloxetine in Major Depression: Results of a Pooled Analysis of Individual Patient Data From 11 Placebo-Controlled Trials", Depression and Anxiety, 2010, 27, 12-18.
Nelson et al., "Anxiety Does Not Predict Response to Antidepressant Treatment in Late Life Depression: Results of A Meta-Analysis", Int J Geriatr Psychiatry, 2009, 24, 539-544.
Nelson et al., "Species Differences in the Pharmacology of the 5-Hydroxytrayptamine2 Receptor: Structurally Specific Differentiation by Ergolines and Tryptamines", Jpet, 1993, 265, 1272-1279.
Nelson, "Anxious Depression and Response to Treatment", Am J Psychiatry, 2008, 165(3), 297-299.
Nestler, "Common Molecular and Cellular Substrates of Addiction and Memory", Neurobiol. of Learning and Memory, 2002, 78, 637-647.
Neubig et al., "Specificity of Receptor-G Protein Coupling: Protein Structure and Cellular Determinants", Seminars in Neuroscience, 1998, 9, 189-197.
Neugebauer et al., "Groups II and III Metabotropic Glutamate Receptors Differentially Modulate Brief and Prolonged Nociception in Primate Stt Cells", J Neurophysiol, 2000, 84, 2998-3009.
Neugebauer et al., "Peripheral Metabotropic Glutamate Receptors as Drug Targets for Pain Relief", Expert Opinion on Therapeutic Targets, 2002, 6(3), 349-361.
Neugebauer et al., "Requirement of Metabotropic Glutamate Receptors For the Generation of Inflammation-Evoked Hyperexcitability in Rat Spinal Cord Neurons", European Journal of Neuroscience, 1994, 6(7), 1179-1186.
Neugebauer, "Metabotropic Glutamate Receptors—Important Modulators of Nociception and Pain Behavior", Pain, 2002, 98, 1-8.
"Neuroprotection As Initial Therapy in Acute Stroke", Third Report of An Ad Hoc Consensus Group Meeting, European Ad Hoc Consensus Group, Cerebrovascular Diseases 1998, 8(1), 59-72.
Ngomba et al., "Metabotropic Glutamate Receptors in the Thalamocortical Network: Strategic Targets For the Treatment of Absence Epilepsy", Epilepsia, 2011, 52(7), 1211-1222.
Ngomba et al., "The Preferential Mglu2/3 Receptor Antagonist, Ly341495, Reduces the Frequency of Spike-Wave Discharges in the Wag/Rij Rat Model of Absence Epilepsy", Neuropharmacology, 2006, 40, 80 103.
Nguyen et al., "An in Vivo Biosensor For Neurotransmitter Release and In Situ Receptor Activity", Nature Neuroscience, 2010, 13(1), 127-32.
Nicholls et al., "Mglur2 Acts Through Inhibitory G? Subunits to Regulate Transmission and Long-Term Plasticity at Hippocampal Mossy Fiber-Ca3 Synapses", Proc. Natl. Acad. Sci. USA, 2006, 103(16), 6380-6385.
Nicholls et al., "The Release and Uptake of Excitatory Amino Acids", Trends in Pharmacological Sciences, 1990, 11(11), 462-468.
Nicolas et al., "A Combined Marble Buyring-Locomotor Activity Test in Mice: A Practical Screening Test with Sensitivity to Different Classes of Anxiolytics and Antidepressants", Eur J Pharmacol., 2006, 547(1-3), 106-115.
Nicoletti et al., "Lesions of Putative Glutamatergic Pathways Potentiate the Increase of Inositol Phospholipid Hydrolysis Elicited by Excitatory Amino Acids", Brain Research, 1987, 436(1), 103-112.
Nicoletti et al., "Metabotropic Glutamate Receptors: Beyond the Regulation of Synaptic Transmission", Psychoneuroendocrinology, 2007, 32(Suppl 1), S40-S45.
Nicoletti et al., "Metabotropic Glutamate Receptors: from the Workbench to the Bedside", Neuropharmacology, 2011, 60, 1017-1041.
Nicoletti et al., "Metabotropic Glutamate Receptors: New Targets for the Control of Tumor Growth", Trends in Pharmacological Sciences, 2007, 206-213.
Nicoletti et al., "Pertussis Toxin Inhibits Signal Transduction at a Specific Metabolotropic Glutamate Receptor in Primary Cultures of Cerebellar Granule Cells", Neuropharmacology, 1988, 27(6), 551-556.
Nielson et al., "Phosphoramides XIV. Phosphorus Pentozide and Amine Hydrochlorides as Reagents in the Synthesis of Thieno{2,3-D]Pyrimidin-4(3h)-Ones", Chemica Scripta, 1981, 18, 135-138.
Niemegeers et al., "Direct Measurement of the Ph in the Stomach of the Conscious Rat, Using a Special Electrode", Experentia, 1979, 35, 1538-1539.
Niemegeers et al., "Interaction of Drugs with Apomorphine, Tryptamine, and Norepinephrine. A New 'in Vivo' Approach: the Atn-Test in Rats", Arch. Int. Pharmacodyn., 1977, 227, 238-253.
Niemegeers et al., "Protection of Rats from Compound 48/80-lnduced Lethality. A Simple Test for Inhibitors of Mast Cell-Mediated Shock", Arch. Int. Pharmacodyn., 1978, 234, 164-176.
Nierenberg et al., "Lithium Augmentation of Nortriptyline for Subject Resistant to Multiple Antidepressants", J Clin Psychopharmacol, 2003, 23, 92-95.
Nijholt et al., "Neuronal Akap150 Coordinates Pka and Epac-Mediated Pkb/Akt Phosphorylation", Cellular Signaling, 2008, 20, 1715-1724.
Nikiforuk et al., "Effects of A Positive Allosteric Modulator of Group II Metabotropic Glutamate Receptors, Ly487379, On Cognitive Flexibility and Impulsive-Like Responding in Rats", Jpet, 2010, 335, 665-673.
Ninomiya et al., "Photocyclisation of Enamides. Part 14. Substituent Effects in the Photocyclisation of N-A,B-Unsaturated Acylanilides", J. Chem. Soc. Perkin Transactions, 1980, 1, 197-202.
Nishi et al., "Pharmacological Characterization of Metabotropic Glutamate Receptor-Mediated High-Affinity Gtpase Activity in Rat Cerebral Cortical Membranes", British Journal of Pharmacology, 2000, 130, 1664-1670.
Niswender et al., "Metabotropic Glutamate Receptors: Physiology, Pharmacology, and Disease", Annu Rev Pharmacol Toxicol, 2010, 50, 295-322.
Nofzinger et al., "Changes in Forebrain Function from Waking to Rem Sleep in Depression: Preliminary Analyses of [18f]Fdg Pet Studies", Psychiatry Res, 1999, 91, 59-78.
Noguchi et al., "Quantum Chemical Study on Conformational Properties of Bipyridine Cardiotonics", Chem. Pharm. Bull.; 1993, 41(8), 1331-1336.
Nordquist, "Metabotropic Glutamate Receptor Modulation, Translational Methods, and Biomarkers: Relationships with Anxiety", Psychopharmacology, 2008, 199, 389-402.
Norman et al., "Structure-Activity Relationships of a Series of Pyrrolo[3,2-D]Pyrimidine Derivatives and Related Compounds as Neuropeptide Y5 Receptor Antagonists", J. Med. Chem., 2000, 43, 4288-4312.
O'Brien et al., "Molecular Mechanisms of Glutamate Receptor Clustering at Excitatory Synapses", Current Opinion in Neurobiology, 1998, 8(3), 364-369.
O'Connor et al., "Metabotropic Glutamate Receptor 7: At the Interface of Cognition and Emotion", European Journal of Pharmacology, 2010, 639, 123-131.
O'Neill et al.. "Effects of Ischaemic Conditions on Uptake of Glutamate, Aspartate, and Noradrenaline by Cell Lines Derived from the Human Nervous System", Journal of Neurochemistry, 1994, 63(2), 603-611.
O'Neill et al., "Recent Developments in Metabotropic Glutamate Receptors as Novel Drug Targets", Drugs of the Future, 2010, 35, 307-324.
Odagaki et al., "Functional Coupling Between Metabotropic Glutamate Receptors and G-Proteins in Rat Cerebral Cortex Assessed By Guanosine-5'-O-(3-[35s]Thio)Triphosphate ([35s]Gtpys) Binding Assay", Basic & Clinical Pharmacology & Toxicology, 2011, 44 pages.
Odagaki et al., "Group II Metabotropic Glutamate Receptor-Mediated Activation of G-Proteins in Rat Hippocampal and Striatal Membranes", Neuroscience Letters, 2013, 24 pages.
Oehlrich, "Positive Allosteric Modulation of Mglur2 Receptors in the Treatment of CNS Disorders", Neuroscience Med Chem, 2012, 31 pages.

(56) References Cited

OTHER PUBLICATIONS

Ohishi et al., "Distribution of a Metabotropic Glutamate Receptor, Mglur2, in the Central Nervous System of the Rat and Mouse: An Immunohistochemical Study with a Monoclonal Antibody", Neuroscience Research, 1998, 30, 65-82.
Ohishi et al., "Distribution of the Messenger Rna for Metabotropic Glutamate Receptor, Mglu2, in the Central Nervous System of the Rat", Neuroscience, 1993, 53, 1009-1018.
Ojima et al., "Hydroformation of Fluoro Olefins, Rfch=Ch2, Catalyzed by Group VIII Transition-Metal Catalysts. Crucial Factors for Extremly High Regioselectivity", Journal of American Chemical Society, 1987, 109, 7714-7720.
Olbrich et al., "Frontolimbic Glutamate Alterations in First Episode Schizophrenia: Evidence From A Magnetic Resonance Spectroscopy Study", World J Biol Psychiatry, 2008, 9(1), 59-63.
Oldenziel et al., "In Vivo Monitoring of Extracellular Glutamate in the Brain with a Microsensor", Brain Res., 2006, 1118(1), 34-42.
Olive, "Cognitive Effects of Group I Metabotropic Glutamate Receptor Ligands in the Context of Drug Addiction", European Journal of Pharmacology, 2010, 639, 47-58.
Olive, Metabotropic Glutamate Receptor Ligands as Potential Therapeutics for Addiction. Curr. Drug Abuse Rev 2009, 2 (1), 83-98.
Olivier et al., "Stress-Induced Hyperthermia and Anxiety: Pharmacological Validation", Eur J Pharmacol, 2003, 463, 117-132.
Olney et al., "NMDA Receptor Hypofunction Model of Schizophrenia", Journal of Psychiatric Research. 1999, 33, 523-533.
Olszewski et al., "Naag Peptidase Inhibition Reduces Locomotor Activity and Some Stereotypes in the Pcp Model of Schizophrenia Via Group II Mglur", J. Neurochem., 2004, 89(4), 876-885.
Olszewski et al., "Phencyclidine and Dizocilpine Induced Behaviors Reduced by N-Acetylaspartylglutamate Peptidase Inhibition Via Metabotropic Glutamate Receptors", Biol. Psychiatry, 2008, 63(1), 86-91.
Ong et al., "Localisation of Glutamate Receptors in the Substantia Nigra Pars Compacta of the Monkey", Journal Fur Hirnforschung. 1997, 38(3), 291-298.
Oquendo et al., "A Computer Algorithm for Calculating the Adequacy of Antidepressant Treatment in Unipolar and Bipolar Depression", J Clin Psychiatry, 2003, 64(7), 825-833.
Orlando, "The Role of Group I and Group II Metabotropic Glutamate Receptors in Modulation of Striatal Nmda and Quinolinic Acid Toxicity", Experimental Neurology, 2001, 167, 196-204.
Orlowski et al., "D-and L-Stereoisomers of Allylglycine: Convulsive Action and Inhibition of Brain L-Glutamate Decarboxylase", J Neurochem, 1977, 28, 349-353.
Orrenius et al., "Calcium Ions and Oxidative Cell Injury", Annals of Neurology, 1992, 32 (Suppl-42), S33-S42.
Osikowicz et al., "Glutamate Receptor Ligands Attenuate Allodynia and Hyperalgesia and Potentiate Morphine Effects in a Mouse Model of Neuropathic Pain", Pain, 2008, 139, 117-126.
Ossowska et al., "The Role of Glutamate Receptors in Antipsychotic Drug Action", Amino. Acids, 2000, 19(1), 87-94.
Ossowska et al., "The Striatum as a Target for Anti-Rigor Effects of an Antagonist of Mglurl, But Not an Agonist of Group II Metabotropic Glutamate Receptors", Brain Research, 2002, 950, 88-94.
O'suilleabhain, "A Randomized Trial of Amantadine in Huntington Disease", Arch Neurol, 2003, 60, 996-998.
Othmer et al., "Brain Functions and Psychiatric Disorders: A Clinical View", Diagnostic Dilemmas, Part I, the Psychiatryc Clinics of N.A., Sep. 1998, 21(3), 517-566.
Ottersen et al., "Organization of Glutamate Receptors at the Synapse", European Journal of Neuroscience, 1997, 9(11), 2219-2224.
Overstreet et al., "A 5-Ht1a Agonist and a 5-Ht2c Antagonist Reduce Social Interaction Deficit Induced by Multiple Ethanol Withdrawals in Rats", Psychopharmacology, 2003, 167, 344-352.
Ozawa et al., "Glutamate Receptors in the Mammalian Central Nervous System", Progress in Neurobiology, 1998, 54(5), 581-618.
Page et al., "Metabotropic Glutamate Receptors Inhibit Mechanosensitivity in Vagal Sensory Neurons", Gastroenterology, 2005, 128(2), 402-410.

Pajer et al., "Discovery of Blood Transcriptomic Markers for Depression in Animal Models and Pilot Validation in Subjects with Early-Onset Major Depression", Transl Psychiatry, 2012, 2(E101), 10pages.
Pajonk et al., "Comparing the Efficacy of Atypical Antipsychotics in Open Uncontrolled Versus Double-Blind Controlled Trials in Schizophrenia", Psychopharmacology (Berl.), 2002, 162(1), 29-36.
Palazzo et al., "Metabotropic and Nmda Glutamate Receptors Participate in the Cannabinoid-Induced Antinociception", Neuropharmacology, 20 01, 40(3), 319-326.
Palop et al., "Amyloid-B-lnduced Neuronal Dysfunction in Alzheimer's Disease: From Synapses Toward Neural Networks", Nature Neuroscience, 2010, 13(7), 812-818.
Palucha et al., "Chronic Imipramine Treatment Reduces Inhibitory Properties of Group II Mglu Receptors Without Affecting Their Density or Affinity", Pharmacol. Rep., 2007, 59(5), 525-530.
Palucha et al., "Metabotropic Glutamate Receptor Ligands as Possible Anxiolytic and Antidepressant Drugs", Pharmacology & Therapeutics, 2007, 115, 116-147.
Palucha et al., "The Involvement of Glutamate in the Pathophysiology of Depression", Drug News Perspect, 2005, 18(4), 262-268.
Palucha, "Are Compounds Acting at Metabotropic Glutamate Receptors the Answer To Treating Depression?", Expert Opin. Investig. Drugs, 2006, 15(12), 1545-1553.
Palucha-Poniewiera et al., "On the Mechanism of the Antidepressant-Like Action of Group II Mglu Receptor Antagonist, Mgs0039", Psychopharmacology, 2010, 212, 523-535.
Panzer, "Are SSRIs Really More Effective for Anxious Depression?", Annals of Clinical Psychiatry, 2005, 17(1), 23-29.
Papakostas et al., "Augmentation of Antidepressants with Atypical Antipsychotic Medications for Treatment-Resistant Major Depressive Disorder: A Meta-Analysis", J Clin Psychiatry 2007, 68(6), 826-831.
Papakostas et al., "Efficacy of Bupropion and the Selective Serotonin Reuptake Inhibitors in the Treatment of Major Depressive Disorder with High Levels of Anxiety (Anxious Depression): A Pooled Analysis of 10 Studies", J Clin Psychiatry, 2008, 69(8), 1287-1292.
Papakostas et al., "Fluxetine-Clonazepam Cotherapy for Anxious Depression: An Exploratory, Post-Hoc Analysis of a Randomized, Double Blind Study", International Clinical Psychopharmacology. 2010, 25, 17-21.
Papakostas etaL, "Predictors, Moderators, and Mediators (Correlates) of Treatment Outcome in Major Depressive Disorder", Dialogues Clin Neurosci., 2008, 10, 439-451.
Papakostas et al., "Severe and Anxious Depression: Combining Definitions of Clinical SubTypes to Identify Patients Differentially Responsive to Selective Serotonin Reuptake Inhibitors", European Neuropsychopharmacology, 2012, 22, 347-355.
Papakostas et al., "Testing Anxious Depression as a Predictor and Moderator of Symptom Improvement in Major Depressive Disorder During Treatment with Escitalopram", Eur Arch Psychiatry Clin Neurosci, 2011, 261, 147-156.
Parmentier et al., "A Model for the Functioning of Family 3 Gpcrs", Trends in Pharmacological Sciences, 2002, 23(6), 268-274.
Parnot et al., "Toward Understanding Gpcr Dimers", Nature Structural & Molecular Biology, 2004, 11(8), 691-692.
Parry et al., "Functionalized Pyridylboronic Acids and Their Suzuki Cross-Coupling Reactions to Yield Novel Heteroarylpyridines", J. Org. Chem., 2002, 67, 7541-7543.
Parsons et al., "Memantine: A Nmda Receptor Antagonist That Improves Memory by Restoration of Homeostasis in the Glutamatergic System—Too Little Activation Is Bad, Too Much Is Even Worse", Neuropharmacology, 2007, 53, 699-723.
Passchier et al., "Measuring Drug-Related Receptor Occupancy with Positron Emission Tomography", Methods, 2002, 27, 278-286.
Pastorino et al., "Pin1 Protects Against Alzheimer's Disease: One Goal, Multiple Mechanisms", Intech, 2013, 36 pages.
Patani et al. "Bioisosterism: A Rational Approach in Drug Design" Chemical Reviews 1996, 96, 314 7-3176.
Patil, "Activation of Mglu2/3 Receptors as a New Approach to Treat Schizophrenia: A Randomized Phase 2 Clinical Trial", Nature Medicine, 2007, 13(9), 1102-1107.

(56) References Cited

OTHER PUBLICATIONS

Patkar et al., "A Randomized, Double-Blind, Placebo-Controlled Trial of Augmentation with an Extended Release Formulation of Methylphenidate in Outpatients with Treatment-Resistant Depression", J Clin Psychopharmacol, 2006, 26, 653-656.
Paykel et al., "Response to Phenelzine and Amitriptyline in Subtypes of Outpatient Depression", Arch Gen Psychiatry, 1982, 39, 1041-1049.
Pehrson et al., "Impact of Metabotropic Glutamate 2/3 Receptor Stimulation on Activated Dopamine Release and Locomotion", Psychopharmacology, 2010, 211, 443-455.
Pellicciari et al., "Metabotropic Glutamate Receptors: Structure and New Subtype-Selective Ligands", Il Farmaco, 2001, 56(1-2), 91-94.
Pellicciari et al., "Metabotropic G-Protein-Coupled Glutamate Receptors As Therapeutic Targets", Current Opinion in Chemical Biology, 1999, 3(4), 433-440.
Pellicciari et al., "Modulation of Glutamate Receptor Pathways in the Search for New Neuroprotective Agents", Farmaco, 1998, 53(4), 255-261.
Penninx et al., "Two-Year Course of Depressive and Anxiety Disorders: Results from the Netherlands Study of Depression and Anxiety (Nesda)", Journal of Affective Disorders, 2011, 133, 76-85.
Pereira et al., "Study Pharmacologic of the Gabaergic and Glutamatergic Drugs on Seizures and Status Epilepticus Induced by Pilocarpine in Adult Wistar Rats", Neuroscience Letters, 2007, 419, 253-257.
Perkins et al., "Pharmacokinetics, Metabolism, and Excretion of the Intestinal Peptide Transporter 1 (Slc15a1)-Targeted Prodrug (1s,2s,5r,6s)-2-[(2,s)-(2-Amino)Propionyl]Aminobicyclo[3.1.0.]Hexen-2,6-Dicarboxylic Acid (Ly544344) in Ratsand Dogs: Assessment of First-Pass Bioactivation and Dose Linearity", Drug Metabolism and Disposition, 2007, 35, 1903-1909.
Perroy et al., "The C Terminus of the Metabotropic Glutamate Receptor Subtypes 2 and 7 Specifies the Receptor Signaling Pathways", Journal of Biological Chemistry, 2001, 276(49), 45800-45805.
Petroff, "Glutamate-Glutamine Cycling in the Epileptic Human Hippocampus", Epilepsia, 2002, 43(7) 703-710.
Pettmann et al., "Neuronal Cell Death", Neuron, 1998, 20(4), 633-647.
Pfeiffer et al., "Benzodiazepines and Adequacy of Initial Antidepressant Treatment for Depression", J Clin Psychopharmacol, 2011, 31, 360-364.
Piccinin et al., "Interaction Between Ephrins and Mglu5 Metabotropic Glutamate Receptors in the Induction of Long-Term Synaptic Depression in the Hippocampus", Journal of Neuroscience, 2010, 30(8), 2835-2843.
Pietraszek et al., "The Role of Group I Metabotropic Glutamate Receptors in Schizophrenia", Amino Acids, 2006, 7 pages.
Pike, "Pet Radiotracers: Crossing the Blood-Brain Barrier and Surviving Metabolism", Trends Pharmacol Sci, 2009, 30, 431-440.
Pile et al., "Mood Disorders: Regulation By Metabotropic Glutamate Receptors", Biochemical Pharmacology, 2000, 75, 997-1006.
Pin et al., "Evolution, Structure, and Activation Mechanism of Family 3/C G-Protein-Coupled Receptors", Pharmacology & Therapeutics, 2003, 98, 325-354.
Pin et al., "Get Receptive to Metabotropic Glutamate Receptors", Current Opinion in Neurobiology, 1995, 5(3), 342-349.
Pin et al., "New Perspectives for the Development of Selective Metabotropic Glutamate Receptor Ligands", European J of Pharmacology, 1999, 375, 277-294.
Pin et al., "Positive Allosteric Modulators for-Aminobutyric Acidb Receptors Open New Routes for the Development of Drugs Targeting Family 3 G-Protein-Coupled Receptors" Mol Pharmacol 2001,60, 881-884.
Pin et al., "Release of Endogenous Amino Acids From Striatal Neurons in Primary Culture", Journal of Neurochemistry, 1986, 47(2), 594-603.
Pin et al., "The Metabotropic Glutamate Receptors: Structure and Functions", Neuropharmacology, 1995, 34(1), 1-26.
Pin et al., "Alternative Splicing Generates Metabotropic Glutamate Receptors Inducing Different Patterns of Calcium Release in Xenopus Oocytes", Proceedings of the National Academy of Sciences of the USA, 1992, 89(21), 10331-10335.
Pinhasov et al., "Reduction of Submissive Behavior Model for Antidepressant Drug Activity Testing; Study Using a Video-Tracking System", Behav Pharmacol, 2005, 16, 657-664.
Pinheiro et al., "Presynaptic Glutamate Receptors: Physiological Functions and Mechanisms of Action", Nat. Rev Neurosci., 2008, 9(6), 423-436.
Pinkerton et al., "Allosteric Potentiators of the Metabotropic Glutamate Receptor 2 (Mglu2). Part 1: Identification and Synthesis of Phenyl-Tetrazolyl Acetophenones", Bioorganic & Medicinal Chemistry Letters, 2004, 14, 5329-5332.
Pinkerton et al., "Allosteric Potentiators of the Metabotropic Glutamate Receptor 2 (Mglu2). Part 2: 4-Thiopyridyl Acetophenones as Non-Tetrazole Containing Mglu2 Receptor Potentiators", Bioorganic & Medicinal Chemistry Letters, 2004, 14, 5867-5872.
Pinkerton et al., "Substituted Acetophenones as Selective and Potent Allosteric Potentiators of the Metabotropic Glutamate Receptor 2 (Mglur2)", 229th ACS National Meeting, Mar. 2005, 1 page.
Pinkerton, "Allosteric Potentiators of the Metabotropic Glutamate Receptor 2 (Mglu2). Part 3: Identification and Biological Activity of Indanone Containing Mglu2 Receptor Potentiators", Bioorganic & Medicinal Chemistry Letters, 2005, 15, 1565-1571.
Pinkerton et al., "Phenyl-Tetrazolyl Acetophenones: Discovery of Positive Allosteric Potentiators for the Metabotropic Glutamate 2 Receptor", J. Med. Chem, 2004, 47, 4595-4599.
Pittenger et al., "Stress, Depression, and Neuroplasticity: A Convergence of Mechanisms", Neuropsychopharmacology, 2008, 33(1), 88-109.
Pitts et al., "Lactate Metabolism in Anxiety Neurosis",New England Journal of Medicine, 1967, 277, 1329-1336.
Pizzi et al., "Activation of Multiple Metabotropic Glutamate Receptor Subtypes Prevents NMDA-lnduced Excitotoxicity in Rat Hippocampal Slices", European Journal of Neuroscience, 1996, 8(7), 1516-1521.
Poisik, et al., "Metabotropic Glutamate Receptor 2 Modulates Excitatory Synaptic Transmission in the Rat Globus Pallidus", Neuropharmacology, 2005, 49, 57-69.
Popik et al., "Selective Agonist of Group II Glutamate Metabotropic Receptors, Ly354740, Inhibits Tolerance to Analgesic Effects of Morphine in Mice", British Journal of Pharmacology, 2000, 130, 1425-1431.
Porsolt et al., "Behavioural Despair in Mice: A Primary Screening Test for Antidepressants", Arch. Int. Pharmacodyn., 1977, 229, 327-336.
Porsolt et al., "Behavioural Despair in Rats: A New Model Sensitive to Antidepressant Treatments", Eur. J. Pharmacol., 1978. 47(4), 379-391.
Porter et al., "(S)-Homoquisqualate: A Potent Agonist at the Glutamate Metabotropic Receptor", British Journal of Pharmacology, 1992, 106(3), 509-510.
Posluns, "An Analysis of Chlorpromazine-Induced Suppression of the Avoidance Response.", Psychopharmacol. 3: 361-373 (1962).
Posner et al., "Columbia Classification Algorithm of Suicide Assessment (C-Casa): Classification of Suicidal Events in the FDA's Pediatric Suicidal Risk Analysis of Antidepressants", American Journal of Psychiatry, 2007, 164, 1035-1043.
Potts et al., "1,2,4-Triazoles. Xii. Derivatives of the S-Triazolo[4,3-A]Pyridine Ring System", Journal of Organic Chemistry, 1966, 251-260.
Potts et al., "1,2,4-Trizoles. Xxv. the Effect of Pyridine Substitution on the Isomerization of S-Triazolo [4,3-A] Pyridines Into S-Triazolo [1,5-A] Pyridines (1)", J. Heterocycl. Chem., 1970, 7, 1019-1027.
Poyurovsky et al., "Lamotrigine Augmentation in Schizophrenia and Schizoaffective Patients with Obsessive-Compulsive Symptoms", J Psychopharmacol., 2010, 24(6), 861-866.
Prabakaran et al., "2-D Dige Analysis of Liver and Red Blood Cells Provides Further Evidence for Oxidative Stress in Schizophrenia", Journal of Proteome Research, 2007, 6, 141-149.

(56) References Cited

OTHER PUBLICATIONS

Prager et al., "The Synthesis of Peroline, 6-(3,4-Dimethoxyphenyl)-5-Hydroxy-5,6-Dihydrobenzo[C][2,7]Naphthyridin-4(3h)-One", Aust. J. Chem., 1983, 36, 1441-1453.
Pralong et al., "Cellular Perspectives On the Glutamate-Monoamine Interactions in Limbic Lobe Structures and Their Relevance for Some Psychiatric Disorders", Progress in Neurobiology, 2002, 67, 173-202.
Prezeau et al., "Functional Crosstalk Between Gpcrs: With or Without Oligomerization", Current Opinion in Pharmacology, 2010, 10, 6-13.
Prezeau et al., "Pharmacological Characterization of Metabotropic Glutamate Receptors in Several Types of Brain Cells in Primary Cultures", Mol Pharmacol, 1993, 45(4), 570-577.
Prina et al., "Co-occurrence of Anxiety and Depression Amongst Older Adults in Low and Middle Income Countries: Findings From the 10/66 Study", Psychological Medicine, Oct. 2011, 41(10), 2047-2056.
Priolo et al., "Panic-Like Attack Induced By Microinfusion Into the Locus Coeruleus of Antagonists and Inverse Agonists at Gabaa-Receptors in Rodents", Funct Neurol, 1991, 6, 393-403.
Profaci et al., "Group II Mglur Agonist Ly354740 and Naag Peptidase Inhibitor Effects on Prepulse Inhibition in Pep and D-Amphetamine Models of Schizophrenia", Psychopharmacology, 2011, 216, 235-243.
Prous Science Integrity 2007—Chemical Structure Ly-404039.
Prous Science Integrity 2007—Chemical Synthesis Ly-2140023.
Pszczolkowski et al., "Effect of Metabotropic Glutamate Receptor Agonists and Signal Transduction Modulators on Feeding by a Caterpillar", Pharmacology, Biochemistry and Behavior, 2005, 82, 678-685.
Putt et al., "An Enzymatic Assay for Poly(Adp-Ribose) Polymerase-1 (Parp-1) Via the Chemical Quantitation of Nad+: Application to the High-Throughput Screening of Small Molecules as Potential Inhibitors", Analytical Biochemistry. 2004, 326, 78-86.
Quitkin et al., "Placebo Run-in Period in Studies of Depressive Disorders: Clinical, Heuristic and Research Implications", British Journal of Psychiatry, 1998, 173, 242-248.
Raffray et al., "Apoptosis and Necrosis in Toxicology: A Continuum or Distinct Modes of Cell Death?", Pharmacology & Therapeutics, 1997, 75(3), 153-177.
Rani et al., "Thiazoline Analogues of Epiderstatin, New Inhibitiors of Cell Cycle of Tsft-210 Cells", Journal of Antibiotics, 1995, 48(10), 1179-1181.
Rao et al., "Anxious Depression: Clinical Features and Treatment", Current Psychiatry Reports, 2009, 11, 429-436.
Raskin et al., "Differential Response to Chlorpromazine, Imipramine, and Placebo. A Study of Subgroups of Hospitalized Depressed Patients", Arch Gen Psychiat, 1970, 23, 164-173.
Ravaris et al., "Phenelzine and Amitriptyline in the Treatment of Depression: A Comparison of Present and Past Studies", Arch Gen Psychiatry, 1980, 37, 1075-1080.
Recasens et al., "Metabotropic Glutamate Receptors as Drug Targets", Current Drug Targets, 2007, 8(5), 651-681.
Regier et al., "Comorbidity of Mental Disorders with Alcohol and Other Drug Abuse. Results From the Epidemiologic Catchment Area (Eca) Study", Jama, 1990, 264, 2511-2518.
Rehwald et al., "3-Amino-2(1h)-Quinolones by Cyclization of N-Acylated Anthranilic Acid Derivatives", Heterocycles, 1997, 45(3), 483-492.
Reiner et al., "Bdnf May Play a Differential Role in the Protective Effect of the Mglur2/3 Agonist Ly379258 on Striatal Projection Neurons in R6/2 Huntington's Disease Mice", Brain Research, 2012, 1473, 161-172.
Reis et al., "Reactions of Tricarbonyl(Vinylketene)Iron(0) Complexes with Imines", Orqanometallics, 1006, 14, 1586-1591.
Rensio et al., "Synthesis of Aza-, Oxa-, and Thiabicyclo[3.1. 0]Hexane Heterocycles From a Common Synthetic Intermediate", Organic Letters, 2005, 7(13), 2627-2630.

Reynolds et al., "New Approaches to the Drug Treatment of Schizophrenia", Adv. Pharmacol., 1995, 32, 461-503.
Reynolds et al., "Sleep Research in Affective Illness: State of the Art Circa", Sleep, 1987, 10, 199-215.
Rhebergen et al., "The 7-Year Course of Depression and Anxiety in the General Population" Acta Psychiatr Scand, 2011, 123, 297-306.
Ribeiro et al., "Group I Metabotropic Glutamate Receptor Signaling and Its Implication in Neurological Disease", CNS & Neurological Disorders - Drug Targets, 2010, 9, 574-595.
Richards et al., "Distribution and Abundance of Metabotropic Glutamate Receptor Subtype 2 in Rat Brain Revealed by [3h]Ly354740 Binding in Vitro and Quantitative Radioautography: Correlation with the Sites of Synthesis, Expression, and Agonist Stimulation of [35s]Gtps Binding", J Comp Neurology, 2005, 487, 15-27.
Richardson-Burns et al., Metabotropic Glutamate Receptor Mrna Expression in the Schizophrenic Thalamus, Biol. Psychiatry, 2000, 47(1), 22-28.
Rickels et al., "Efficacy of Extended-Release Venlafaxine in Nondepressed Outpatients with Generalized Anxiety Disorder", Am J Psychiatry, 2000, 157, 968-974.
Riedel et al., "Glutamate Receptor Function in Learning and Memory", Behavioural Brain Research, 2003, 140(1-2), 1-47.
Ritzen et al., "Molecular Pharmacology and Therapeutic Prospects of Metabotropic Glutamate Receptor Allosteric Modulators", Basic Clin Pharmacol Toxicol, 2005, 97, 202-213.
Robbe et al., "Role of P/Q-Ca2+ Channels in Metabotropic Glutamate Receptor 2/3-Dependent Presynaptic Long-Term Depression at Nucleus Accumbens Synapses", J Neurosci., 2002, 22(11), 4346-4356.
Robbe et al., "Metabotropic Glutamate Receptor2 3-Dependent Long-Term Depression in the Nucleus Accumbens is Blocked in Morphine Withdrawn Mice", Eur. J Neurosci., 2002, 16(11), 2231-2235.
Robbins et al., "The Neuropsychopharmacology of Fronto-Executive Function: Monoaminergic Modulation", Annu Rev Neurosci, 2009, 32, 267-287.
Robins et al., "Establishment of Diagnostic Validity in Psychiatric Illness: Its Application to Schizophrenia", Amer J Psychiat, 1970, 126(7), 107-111.
Robison et al., "The Rearrangement of Isoquinoline-N-Oxides", J Org Chem, 1957, 21, 1337-1341.
Rodd et al., "The Metabotropic Glutamate 2/3 Receptor Agonist Ly404039 Reduces Alcohol-Seeking But Not Alcohol Self-Administration in Alcohol-Preferring (P) Rats", Behavioural Brain Research, 2006, 171. 207-215.
Rodriguez et al., "Attenuation of Ketamine-Induced Hyperactivity Responses in Rats Following Administration of A Novel Metabotropic Glutamate Receptor 2 Selective Positive Modulator", Annual Meeting of the Society for Neuroscience, Oct. 2004, Abstract No. 798.8, 2 pages.
Rodriguez et al., "Relationships Among Psychosocial Functioning, Diagnostic Comorbidity, and the Recurrence of Generalized Anxiety Disorder, Panic Disorder, and Major Depression", Anxiety Disorders. 2005, 19, 752-766.
Rodriguez-Moreno et al.,, "Kainate Receptors with a Metabotropic Modus Operandi", Trends Neurosci., 2007, 30(12), 630-637.
Roma et al., "1,8-Naphthyridines Vii. New Substituted 5-Amino[L,2,4]Triazolo[4,3-A] [1 , 8]Naphthyridine-6-Carboxamides and Their Isosteric Analogues, Exhibiting Notable Anti-Inflammatory and/or Analgesic Activities, But No. Acute Gastrolesivity", European Journal of Medical Chemistry, 2008, 43, 1665-1680.
Rondard et al., "Coupling of Agonist Binding to Effector Domain Activation in Metabotropic Glutamate-Like Receptors", J Biol. Chem., 2006, 281(34), 24653-24661.
Rorick-Kehn et al., "Improved Bioavailability of the Mglu2/3 Receptor Agonist Ly354740 Using A Prodrug Strategy: In Vivo Pharmacology of Ly544344", J. Pharmacol. Exper. Therapeut., 2006, 316, 905-913.
Rorick-Kehn et al., "In Vivo Pharmacological Characterization of the Structurally Novel, Potent, Selective Mglu2/3 Receptor Agonist Ly404039 in Animal Models of Psychiatric Disorders", Psychopharmacology, 2007, 193, 121-136.

(56) References Cited

OTHER PUBLICATIONS

Rorick-Kehn et al., "Pharmacological and Pharmacokinetic Properties of a Structurally Novel, Potent, and Selective Metabotropic Glutamate 2/3 Receptor Agonist: in Vitro Characterization of Agonist (-)-(1 r,4s,5s,6s)-4-Amino-2-Sulfonylbicyclo[3.1.0]-Hexane-4,6-Dicarboxylic Acid (Ly404039)" J. Pharmacol. Exper. Therapeut., 2007, 321, 308-317.
Rorick-Kehn et al., "Pharmacological Characterization of Stress-Induced Hyperthermia in Dba/2 Mice Using Metabotropic and Ionotropic Glutamate Receptor Ligands", Psychopharmacology (Berl)., 2005, 183(2), 226-40.
Rosowsky et al., "2,4-Diaminothieno[2,3-D]Pyrimidines as Antifolates and Antimalarials. 3. Synthesis of 5,6-Disubstituted Derivatives and Related Tetracyclic Analogs", Journal of Medicinal Chemistry, 1973, 16(3), 191-194.
Ross et al., "Expression of Functional Metabotropic and Ionotropic Glutamate Receptors in Baculovirus-lnfected Insect Cells", Neuroscience Letters, 1994, 173(1-2), 139-142.
Roth et al., "G Protein-Coupled Receptor (Gpcr) Trafficking in the Central Nervous System: Relevance for Drugs of Abuse", Drug & Alcohol Dependence, 1998, 51(1-2), 73-85.
Roth et al., "Synthesis of Small Molecule Inhibitors of the Orphan Nuclear Receptor Steroidogenic Factor-1 (Nr5a1) Based on Isoquinolinone Scaffolds", Bioorg Med Chem Lett, 2008, 18, 2628-2632.
Rothman et al., "Excitatory and the NMDA Receptor", Trends in Neurosciences, 1987, 10(7), 299-302.
Rovira et al., "Modeling the Binding and Function of Metabotropic Glutamate Receptors", Jpet, 2008, 325, 443-456.
Rowe et al., "Transposition of Three Amino Acids Transforms the Human Metabotropic Glutamate Receptor (Mglur)-3 Positive Allosteric Modulation Site to Mglur2, and Additional Characterization of the Mglur2 Positive Allosteric Modulation Site", J. Pharmacol. Exper. Therapeut., 2008, 326, 240-251.
Roy et al., "A Twin Study of Generalized Anxiety Disorder and Major Depression" Psychological Medicine, 1995, 5, 1037-1049.
Roychowdhury et al., "G Protein Alpha Subunits Activate Tubulin Gtpase and Modulate Microtubule Polymerization Dynamics", J. Biol. Chem., 1999, 274(19), 13485-13490.
Roychowdhury et al., "G Protein Beta1gamma2 Subunits Promote Microtubule Assembly", J. Biol. Chem., 1997, 272(50), 31576-31581.
Rozenfeld et al., "Receptor Heteromerization and Drug Discovery", Trends in Pharmacological Sciences, 2010, 31(3), 124-130.
Rush et al., "Comorbid Psychiatric Disorders in Depressed Outpatients: Demographic and Clinical Features", Journal of Affective Disorders, 2005, 87, 43-55.
Rush et al., "Response in Relation To Baseline Anxiety Levels in Major Depressive Disorder Treated with Bupropion Sustained Release Or Sertraline", Neuropsychopharmacology, 2001,25(1), 131-138.
Rush et al., "Sequenced Treatment Alternatives to Relieve Depression (Star*D): Rationale and Design" Controlled Clinical Trials, 2004, 25, 119-142.
Russell et al., "Amyloid-B Acts as a Regulator of Neurotransmitter Release Disrupting the Interaction Between Synaptophysin and Vamp2", Pios One, 2012, 7(8), E43201, 1-14.
Ryndina, et al., "Torp-Ziegler Cyclization in the Synthesis of 3-Amino-4-Cyanopyrrole Derivatives", Chemistry of Heterocyclic Compounds. 2000, 36(12), 1409-1420.
Sackheim et al., "The Impact of Medication Resistance and Continuation Pharmacotherapy on Relapse Following Response to Electroconvulsive Therapy in Major Depression", J Clin Psychpharmacol, Apr. 1990, 10(2), 96-104.
Sagara et al., "The Activation of Metabotropic Glutamate Receptors Protects Nerve Cells from Oxidative Stress", J. Neurosci., 1998, 18(17), 6662-6671.
Sahara et al., "Cellular Localization of Metabotropic Glutamate Receptors Mglurl, 2/3, 5 and 7 in the Main and Accessory Olfactory Bulb of the Rat", Neuroscience Letters, 2001, 312(2), 59-62.
Sajdyk et al., "Measurement of Panic-Like Responses Unit 9.17 Following Intravenous Infusion of Sodium Lactate in Panic-Prone Rats", Current Protocols in Neuroscience, 2003, 9.17.1-9.17.19.
Sakamoto et al., "Condensed Heteroaromatic Ring Systems. VIII, Synthesis 3-Substituted Isocoumarins from O-Halobenzoic Acid Derivatives", Chern. Pharm. Bull., 1986, 34(7), 2754-2759.
Sakharkar et al., "Druggability of Human Disease Genes", Int J Biochem. Cell Biol., 2007, 39(6), 1156-1164.
Samadi et al., "Basal Ganglia Group II Metabotropic Glutamate Receptors Specific Binding in Non-Human Primate Model of L-Dopa-lnduced Dyskinesias", Neuropharmacology, 2008, 54(2), 258-268.
Samadi et al., "Metabotropic Glutamate Receptor II in the Brains of Parkinsonian Patients", J. Neuropathol. Exp. Neurol., 2009, 68(4), 374-382.
Sanacora et al., "Subtype-Specific Alterations of Gamma-Aminobutyric Acid and Glutamate in Patients with Major Depression", Arch Gen Psychiatry, 2004, 61, 705-713.
Sanacora et al., "Targeting the Glutamatergic System to Develop Novel, Improved Therapeutics for Mood Disorders", Nat Rev Drug Discov, May 2008, 7(5), 426-437.
Sanacora et al., "Towards A Glutamate Hypothesis of Depression: An Emerging Frontier of Neuropsychopharmacology for Mood Disorders", Neuropharmacology, 2012, 62, 63-77.
Sanders et al., "Regulation of Anxiety By Gabaa Receptors in the Rat Amygdala", Pharmacology, Biochemistry and Behavior, 1995, 52(4), 701-706.
Sanderson et al., "Syndrome Comorbidity in Patients with Major Depression or Dysthymia: Prevalence and Temporal Relationships", Am J Psychiatry, Aug. 1990, 147(8), 1025-1028.
Sanger et al., "Pharmacological Profiling of Native Group II Metabotropic Glutamate Receptors in Primary Cortical Neuronal Cultures Using a Flipr", Neuropharmacology 2012, 1-10.
Sarichelou et al., "Metabotropic Glutamate Receptors Regulate Differentiation of Embryonic Stem Cells Into Gabaergic Neurons", Cell Death. Differ., 2008, 15(4), 700-707.
Satow et al., "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Detailed Investigations with a Selective Allosteric Metabotropic Glutamate Receptor 1 Antagonist, Ftidc [4-(1 -(2-Fluoropyridine-3-YI)-5-Methyl-1h-1,2,3-Triazol-4-YI]-Nisopropyl-N-Methyl-3,6-Dihydropyridine-1(2h)-Carboxamidel", J. Pharmacol. Exper. Therapeut., 2008, 326, 577-586.
Sawamoto et al., "Cognitive Slowing in Parkinson Disease is Accompanied by Hypofunctioning of the Striatum", Neurology, 2007, 68, 1062-1068.
Sawamoto et al., "Cognitive Slowing in Parkinson's Disease: A Behavioral Evaluation Independent of Motor Slowing", J.Neurosci., 2002, 22, 5198-5203.
Scaccianoce et al., "Endogenous Activation of Group-ll Metabotropic Glutamate Receptors Inhibits the Hypothalamic-Pituitary-Adrenocortical Axis", Neuropharmacology, 2003, 44, 555-561.
Scanziani et al., "Use-Dependent Increases in Glutamate Concentration Active Presynaptic Metabotropic Glutamate Receptors", Nature, 1997, 385, 630-634.
Schaffhauser et al., "Camp-Dependent Protein Kinase Inhibits Mglur2 Coupling to G-Proteins by Direct Receptor Phosphorylation", J Neurosci., 2000, 20(15), 5663-5670.
Schaffhauser et al., "In Vitro Binding Characteristics of a New Selective Group II Metabotropic Glutamate Receptor Radioligand, [3h]Ly354740, in Rat Brain", Mol Pharmacology, 1998, 53, 228-233.
Schaffhauser et al., "In Vitro Characterization of N-(4'-(2-Methoxyphenoxy)Phenyl-N-(2,2,2-Trifluoroethylsulfonyl)Pyrid-3-Ylmethylamine (Ly487379) a Selective Mglu2 Receptor Positive Modulator", Neuropharmacology, 2002, 43, 307.
Schaffhauser et al., "Multiple Pathways for Regulation of the Kcl-lnduced [3h]-Gaba Release by Metabotropic Glutamate Receptors, in Primary Rat Cortical Cultures", Brain Res., 1998, 782(1-2), 91-104.

(56) References Cited

OTHER PUBLICATIONS

Schaffhauser et al., "Pharmacological Characterization and Identification of Amino Acids Involved in the Positive Modulation of Metabotropic Glutamate Receptor Subtype 2", Mol Pharmacol, 2003, 64, 798-810.
Schapira, "Science, Medicine, and the Future: Parkinson's Disease", Brit.Med.J., 1999, 318, 311-314.
Schiefer et al., "The Metabotropic Glutamate Receptor 5 Antagonist Mpep and the Mglur2 Agonist Ly379268 Modify Disease Progression in a Transgenic Mouse Model of Huntington's Disease", Brain Research, 2004, 1019, 246-254.
Schiffer et al., "Optimizing Experimental Protocols for Quantitative Behavioral Imaging with 18f-Fdq in Rodents", J Nucl Med, 2007, 48, 277-287.
Schlumberger et al., "Comparison of the Mglu5 Receptor Positive Allosteric Modulator Adx47273 and the Mglu2/3 Receptor Agonist Ly354740 in Tests for Antipsychotic-Like Activity", European Journal of Pharmacology, 2009, 623, 73-83.
Schlumberger et al., "Effects of a Metabotropic Glutamate Receptor Group II Agonist Ly354740 in Animal Models of Positive Schizophrenia Symptoms and Cognition", Behav Pharmacol., 2009, 20, 56-66.
Schoepp et al., "Ly354740, An Mglu2/3 Receptor Agonist as a Novel Approach to Treat Anxiety/Stress", Stress, 2003, 6(3), 189-197.
Schoepp et al., "Metabotropic Glutamate Receptors" Pharmacol Biochem Behav, 2002, 74, 255-256.
Schoepp et al., "Pharmacological Agents Acting at Subtypes of Metabotropic Glutamate Receptors", Neuropharmacology, 1999, 38, 1431-1476.
Schoepp et al., "Potent, Stereoselective, and Brain Region Selective Modulation of Second Messengers in the Rat Brain By (+)Ly354740, A Novel Group II Metabotropic Glutamate Receptor Agonist", Naunyn-Schmiedebergs Archives of Pharmacology, 1998, 358(2), 175-180.
Schoepp et al., "Preclinical Pharmacology of Mglu2/3 Receptor Agonists: Novel Agents for Schizophrenia?", CNS & Neurological Disorders, 2002, 1, 215-225.
Schoepp, "Unveiling the Functions of Presynaptic Metabotropic Glutamate Receptors in the Central Nervous System", J Pharmacol ExpTher, 2001, 299, 12-20.
Schoppa et al., "Modulation of Mepscs in Olfactory Bulb Mitral Cells by Metabotropic Glutamate Receptors" J Neurophysiol., 1997, 78(3), 1468-1475.
Schreiber et al., "Ly354740 Affects Startle Responding But Not Sensorimotor Gating or Discriminative Effects of Phencyclidine", Eur. J Pharmacol., 2000, 388(2), R3-R4.
Schulze-Osthoff et al., "Apoptosis Signaling by Death Receptors", European Journal of Biochemistry, 1998, 254(3), 439-459.
Schwartz et al., "Ago-Allosteric Modulation and Other Types of Allostery in Dimeric 7tm Receptors", J Recept. Signal. Transduct. Res., 2006, 26(1-2), 107-128.
Schwartz et al., "Allosteric Enhancers, Allosteric Agonists and Ago-Allosteric Modulators: Where Do They Bind and How Do They Act?", Trends Pharmacol. Sci., 2007, 28(8), 366-373.
Schweitzer et al., "Characterization of [(3)H]-Ly354740 Binding to Rat Mglu2 and Mglu3 Receptors Expressed in Cho Cells Using Semliki Forest Virus Vectors", Neuropharmacology, 2000, 39(10), 1700-1706.
Seddon, "Pseudopolymorph: A Polemic", Crystal Growth & Design, 2004, 4(6), 1087.
Seebahn et al., "Ranbpm is Expressed in Synaptic Layers of the Mammalian Retina and Binds to Metabotropic Glutamate Receptors",. Febs Lett., 2008, 582(16), 2453-2457.
Seedat et al., "Measuring Anxiety in Patients with Schizophrenia", J Nerv Ment Dis. Apr. 2007,195(4), 320-324.
Seeman et al., "Glutamate Receptor Mglu2 and Mglu3 Knockout Striata are Dopamine Supersensitive, with Elevated D2(High) Receptors and Marked Supersensitivity to the Dopamine Agonist (+)Phno", Synapse, 2009, 63(3), 247-251.
Seeman, "An Agonist at Glutamate and Dopamine D2 Receptors, Ly404039" Neuropharmacology, 2012, 7 pages.
Seeman, "Glutamate Agonists for Schizophrenia Stimulate D2high Receptors", Schizophrenia Research. 2008, 99, 373-374.
Semba et al., "Regional Differences in the Effects of Glutamate Uptake Inhibitor L-Trans-Pyrrolidine-2,4-Dicarboxylic Acid on Extracellular Amino Acids and Dopamine in Rat Brain: An in Vivo Microdialysis Study", General Pharmacology, 1998, 31(3), 399-404.
Semple et al., "3-Aryl Pyridone Derivatives. Potent and Selective Kappa Opioid Receptor Agonists", Bioorganic and Medicinal Chemistry Lett, 2002, 12, 197-200.
Senda et al., "Ring Transformation of Uracils to 2-Pyridones. Hydrolysis of 6-(Dimethylaminovinyl) Uracils", Heterocycles, 1978, 9(6), 1-6.
Seo et al., "Distinctive Clinical Characteristics and Suicidal Tendencies of Patients with Anxious Depression", J Nerv Ment Dis, 2011, 199, 42-48.
Seroquel XR® Highlights of Prescribing Information 2013.
Shalev, "Neurobiology of Relapse to Heroin and Cocaine Seeking: A Review", Pharmacol. Rev., 2002, 54(1), 1-42.
Sharpe et al., "Systemic Pre-Treatment with a Group II Mglu Agonist, Ly379268, Reduces Hyperalgesia in Vivo", British Journal of Pharmacology, 2002, 135, 1255-1262.
Shear et al., "Reliability and Validity of a Structured Interview Guide for the Hamilton Axiety Rating Scale (Sigh-A)", Depress Anxiety, 2001, 13(4), 166-178.
Sheffler et al., "Recent Progress in the Synthesis and Characterization of Group II Metabotropic Glutamate Receptor Allosteric Modulators", Acs Chem Neurosci, 2011, 2, 382-393.
Shekhar et al., "Ly354740, a Potent Group II Metabotropic Glutamate Receptor Agonist Prevents Lactate-Induced Panic-Like Response in Panic-Prone Rats", Neuropharmacology, 2000, 39, 1139-1146.
Shekhar et al., "Dorsomedial Hypothalamic Gaba Dysfunction Produces Physiological Arousal Following Sodium Lactate Infusions", Pharmacol Biochem Behav., Oct. 1996, 55(2), 249-256.
Shekhar et al., "Dorsomedial Hypothalamic Gaba Regulates Anxiety in the Social Interaction Test", Pharmacology, Biochemistry and Behavior, 1995, 50(2), 253-258.
Shekhar et al., "The Circumventricular Organs Form a Potential Neural Pathway for Lactate Sensitivity: Implications for Panic Disorder", Journal of Neuroscience, 1997, 17(24), 9726-9735.
Shepherd et al., "Behavioural and Pharmacological Characterisation of the Elevated 'Zero-Maze' as an Animal Model of Anxiety", Psychopharmacology, 1994, 116, 56-64.
Sherbourne et al., "Course of Depression in Patients with Comorbid Anxiety Disorders" Journal of Affective Disorders 1997, 43, 245-250.
Shi et al., "L-Homocysteine Sulfinic Acid and Other Acidic Homocysteine Derivatives are Potent and Selective Metabotropic Glutamate Receptor Agonists", J Pharmacol Exp Ther, 2003, 305(1), 131-142.
Shiba et al., "Synthesis and Binding Affinities of Methylvesamicol Analogs for the Acetylcholine Transporterand Sigma Receptor", Bioorganic and Medicinal Chemistry, 2006, 14, 2620-2626.
Shigemoto et al., "Differential Presynaptic Localization of Metabotropic Glutamate Receptor Subtypes in the Rat Hippocampus", Journal of Neuroscience, 1997, 17(19), 7503-7522.
Shigemoto et al., "Metabotropic Glutamate Receptors—Immunocytochemical and in Situ Hybridization Analysis", Ottersen Op, Storm-Mathisen J (Eds) Handbook of Chemical Neuroanatomy, Elxevier Science, 2000, 63-98.
Shigemoto et al., "Target-Cell-Specific Concentration of a Metabotropic Glutamate Receptor in the Presynaptic Active Zone", Nature, 1996, 381(6582), 523-525.
Shimazaki et al., "Blockade of the Metabotropic Glutamate 2/3 Receptors Enhances Social Memory Via the Ampa Receptor in Rats", Eur.J.Pharmacol., 2007, 575, 94-97.
Shin et al., "Metabotropic Glutamate Receptors (Mglus) and Cellular Transformation", Neuropharmacology, 2008, 55(4), 396-402.
Shin et al., "The Neurocircuitry of Fear, Stress, and Anxiety Disorders", Neuropsychopharmacology, 2010, 35(1), 169-191.
Sidique et al., "Orally Active Metabotropic Glutamate Subtype 2 Receptor Positive Allosteric Modulators: Structure-Activity Rela-

(56) References Cited

OTHER PUBLICATIONS tionships and Assessment in a Rat Model of Nicotine Dependence", J Med Chem, 2012, 55, 9434-9445.
Silver et al., "Multifunctional Pharmacotherapy: What Can We Learn From Study of Selective Serotonin Reuptake Inhibitor Augmentation of Antipsychotics in Negative-Symptom Schizophrenia?". Neurotherapeutics, 2009, 6, 86-93.
Silverstone et al., "Defining Anxious Depression: Going Beyond Comorbidity", Can J Psychiatry, 2003, 48, 675-680.
Simmons et al., "Group II Mglur Receptor Agonists are Effective in Persistent and Neuropathic Pain Models in Rats", Pharmacology, Biochemistry and Behavior, 2002, 73, 419-427.
Simon et al., "Advances in the Treatment of Anxiety: Targeting Glutamate", Journal of the American Society for Exp Neur, Jan. 2006, 3, 57-68.
Simon et al., "Comparing Anxiety Disorders and Anxiety-Related Traits in Bipolar Disorder and Unipolar Depression", Journal of Psychiatric Research, 2003, 37, 187-192.
Simonyi et al., "Chronic Ethanol-Induced Subtype- and Subregion-Specific Decrease in the Mrna Expression of Metabotropic Glutamate Receptors in Rat Hippocampus", Alcoholism: Clinical & Experimental Research, 2004, 28(9), 1419-1423.
Simonyi et al., "Expression of Groups I and I Metabotropic Glutamate Receptors in the Rat Brain During Aging", Brain Res, 2005, 1043, 95-106.
Simonyi et al., "Metabotropic Glutamate Receptor Subtype 5 Antagonism in Learning and Memory", European Journal of Pharmacology, 2010, 639, 17-25.
Simpson et al., "A Possible Role for the Striatum in the Pathogenesis of the Cognitive Symptoms of Schizophrenia", Neuron., 2010, 65(5), 585-596.
Siok et al., "Comparative Analysis of the Neurophysiological Profile of Group I Metabotropic Glutamate Receptor Activators and Diazepam: Effects On Hippocampal and Cortical Eeg Patterns in Rats", Neuropharmacology, 2012, 62, 226-236.
Skofic et al., "Syntheses of 4-2-naphthyl)pyridine derivatives from DDNP", Slovenian Chemical Society (Acta Chimica Slovencia), 2005, 52(4), 391-397.
Sladeczek et al., "The Metabotropic Glutamate Receptor (Mgr): Pharmacology and Subcellular Location", Journal of Physiology, 1992, 86(1-3), 47-55.
Slattery et al., "Potentiation of Mouse Vagal Afferent Mechanosensitivity by Ionotropic and Metabotropic Glutamate Receptors", J Physiol, 2006, 577(Pt 1), 295-306.
Sleight et al., "Radiolabelling of the Human 5-Ht2a Receptor with an Agonist, a Partial Agonist and an Antagonist: Effects On Apparent Agonist Affinities", Biochemical Pharmacology, 1996, 51, 71-76.
Smalley et al., "Pyrolysis of Aryle Azides in Acetic Anhydride", J. Chem. Soc., 1963, 5571-5572.
Smialowska et al., "The Effect of Intrahippocampal Injection of Group II and III Metobotropic Glutamate Receptor Agonists on Anxiety; the Role of Neuropeptide Y", Neuropsychopharmacology, 2007, 32(6), 1242-1250.
Smith et al., "Ionotropic and Metabotropic Gaba and Glutamate Receptors in Primate Basal Ganglia", Journal of Chemical Neuroanatomy, 2001, 22(1-2), 13-42.
Smith et al., "Is Extended Clonazepam Cotherapy of Fluoxetine Effective for Outpatients with Major Depression?", Journal of Affective Disorders, 2002, 70, 251-259.
Smith et al., "Schizophrenia (MaintenanceTreatment)", Clin Evid (Online), 2009, 1007.
Smith et al., "Short-Term Augmentation of Fluoxetine Clonazepam in the Treatment of Depression: A Double-Blind Study", Am J Psychiatry, 1998, 155, 1339-1345.
Smith, "Regulation of Glutamate Uptake in Astrocytes Continuously Exposed to Ethanol", Life Sciences, 1997, 61(25), 2499-2505.
Smits et al., "Outcomes of Acute Phase Cognitive Therapy in Outpatients with Anxious Versus Nonaxious Depression", Psychother Psychosom, 2012, 81, 153-160.

Smolders et al., "In Vivo Modulation of Extracellular Hippocampal Glutamate and Gaba Levels and Limbic Seizures by Group I and Ii Metabotropic Glutamate Receptor Ligands", Journal of Neurochemistry, 2004, 88(5), 1068-1077.
Sokolowski et al., "The Behavioral Effects of Sertraline, Fluoxetine, and Paroxetine Differ on the Differential-Reinforcement-Of-Low-Rate 72-Second Operant Schedule in the Rat", Psychopharmacology, 1999, 147, 153-161.
Spencer et al., "Novel Strategies for Alzheimer's Disease Treatment", Expert Opin. Biol. Ther., 2007, 7(12), 1853-1867.
Spiegel etaL, "Defects in G Protein-Coupled Signal Transduction in Human Disease", Annual Review of Physiology, 1996, 58, 143-170.
Spiegel et al., "Psychosis Induced By the Interaction of Memantine and Amantadine: Lending Evidence to the Glutamatergic Theory of Schizophrenia", Clinical Schizophrenia & Related Psychoses, 2007, 1(3), 273-276.
Spijker, "The Course of Anxiety and Depression in Nemesis and Nesda", Abstract AS36-04 of the 200h European Congress of Psychiatry, Mar. 2012, 1 page.
Spooren et al., "Anxiolytic-Like Effects of the Prototypical Metabotropic Glutamate Receptor 5 Antagonist 2-Methyl-6-(Phenylethynyl)Pyridine in Rodents", Journal of Pharmacology & Experimental Therapeutics, 2000, 295(3), 1267-1275.
Spooren et al., "Insight Into the Function of Group I and Group II Metabotropic Glutamate (Mglu) Receptors: Behavioural Characterization and Implications for the Treatment of CNS Disorders", Behavioural Pharmacology, 2003, 14(4), 257-277.
Spooren et al., "Lack of Effect of Ly314582 (A Group 2 Metabotropic Glutamate Receptor Agonist) on Phencyclidine-Induced Locomotor Activity in Metabotropic Glutamate Receptor 2 Knockout Mice", Eur J Pharmacol., 2000, 397, R1-R2.
Spooren et al., "Metabotropic Glutamate Receptors: Their Therapeutic Potential in Anxiety", Current Topics in Behavioral Neurosciences, 2010, 2, 391-413.
Spooren et al., "Pharmacological and Endocrinological Characterization of Stress-Induced Hyperthermia in Singly Housed Mice Using Classical and Candidate Anxiolytics (Ly314582, Mpep and Nkp608)", Eur J Pharmacol, 2002, 435, 161-170.
Srivastava et al., "Novel Anchorage of Glur2/3 to the Postsynaptic Density by the Ampa Receptor-Binding Protein Abp", Neuron, 1998, 21(3), 581-591.
Stachowicz et al., "Anxiolytic-Like Activity of Mgs0039, A Selective Group II Mglu Receptor Antagonist, Is Serotonin- and Gaba-Dependent", Pharmacological Reports, 2011, 63, 880-887.
Stahl et al., "Negative Symptoms of Schizophrenia: A Problem That Will Not Go Away ", Acta Psychiatr. Scand., 2007, 115(1), 4-11.
Steckler, "Glutamatergic Anxiolytics Are They Any Better?", (Presentation Slides), European College of Neuropsychopharmacology, 2009, 18 pages.
Steckler et al., "Effects of Mglul Receptor Blockade on Anxiety-Related Behavior in the Rat Lick Suppression Test", Psychopharmacology, 2005, 179, 198-206.
Steckler et al., "Pharmacological Treatment of PTSD—Established and New Approaches", Neuropharmacology, 2012, 62, 617-627.
Stefani et al., "Activation of Type 5 Metabotropic Glutamate Receptors Attenuates Deficits in Cognitive Flexibility Induced by NMDA Receptor Blockade", European Journal of Pharmacology, 2010, 639, 26-32.
Stefani et al., "The Modulation of Calcium Currents by the Activation of Mglurs. Functional Implications", Molecular Neurobiology, 1996, 13(1), 81-95.
Steinpreis, "The Behavioral and Neurochemical Effects of Phencyclidine in Humans and Animals: Some Implications for Modeling Psychosis", Behavioral Brain Research, 1996, 74, 45-55.
Stella et al., "4. Prodrugs: the Contrul of Drug Delivery Via Bioreversible Chemical Modification", Drug Delivery Systems: Characteristics and Biomedical Applications. New York: Oxford University Press, 1980, 67 pages.
Stella et al., "Prodrugs: Do They Have Advantages in Clinical Practice?", Drugs, 1985, 29, 455-473.
Stepulak et al., "Expression of Glutamate Receptor Subunits in Human Cancers", Histochem. Cell Biol., 2009, 12 pages.

(56) References Cited

OTHER PUBLICATIONS

Steru et al., "The Tail Suspension Test: A New Method for Screening Antidepressants in Mice", Psychopharmacology, 1985, 85, 367-370.
Stewart et al., "Discovery of Inhibitors of Cell Adhesion Molecule Expression in Human Endothelial Cell. 1. Selective Inhibition of Icam-1 and E-Selectin Expression", J Med Chem, 2001, 44, 998-1002.
Stogryn et al., "5-Hetarylmethylene-2,4-Diaminopyrimidines (1)", J. Heterocyclic Chem., Apr. 1974. 11, 251-253.
Stone et al., "Glutamateand Dopamine Dysregulation in Schizophrenia—A Synthesis and Selective Review", J Psychopharmacol., 2007, 21(4), 440-452.
Stout et al., "High-Affinity Calcium Indicators Underestimate Increases in Intracellular Calcium Concentrations Associated with Excitotoxic Glutcimate Stimulations", Neuroscience, 1999, 89(1), 91-100.
Straiker et al., "Metabotropic Suppression of Excitation in Murine Autaptic Hippocampal Neurons", J Physiol, 2007, 578(Pt 3), 773-785.
Strange, "Use of the Gtpgs ([35s]Gtpgs and Eu-Gtpgs) Binding Assay for Analysis of Ligand Potency and Efficacy at G Protein-Coupled Receptors", British Journal of Pharmacology, 2010, 161, 1238-1249.
Stroup et al., "Results of Phase 3 of the Catie Schizophrenia Trial", Schizophr Res., 2009, 107(1),1-12.
Stulz et al., "Distinguishing Anxiety and Depression in Self-Report: Purification of the Beck Anxiety Inventory and Beck Depression Inventory-ll", J Clin Psychol, 2010, 66, 927-940.
Suh et al., "Hypoglycemic Neuronal Death and Cognitive Impairment are Prevented By Poly(Adp-Ribose) Polymerase Inhibitors Administered After Hypoglycemia", Journal of Neuroscience, 2003, 23(33), 10681-10690.
Sutton et al., "Regulation of Akt and Wnt Signaling by the Group II Metabotropic Glutamate Receptor Antagonist Ly341495 and Agonist Ly379268", Journal of Neurochemistry, 2011, 117, 973-983.
Swanson et al., "A Role for Noradrenergic Transmission in the Actions of Phencyclidine and the Antipsychotic and Antistress Effects of Mglu2/3 Receptor Agonists", Annals of the New York Academy of Sciences, 2003, 1003, 309-17.
Swanson et al., "Metabotropic Glutamate Receptors as Novel Targets for Anxiety and Stress Disorders", Nature Reviews Drug Discovery, 2005, 4, 131-144.
Swanson et al., "The Group II Metabotropic Glutamate Receptor Agonist (-)-2-Oxa-4-Aminobicyclo[3.1.0.]Hexane-4,6-Dicarboxylate (Ly379268) and Clozapine Reverse Phencyclidine-Induced Behaviors in Monoamine-Depleted Rats", Journal of Pharmacology & Experimental Therapeutics, 2002, 303(3), 919-927.
Swerdlow et al., "Strain Differences in the Disruption of Prepulse Inhibition of Startle After Systemic and Intra-Accumbens Amphetamine Administration",. Pharmacol. Biochem. Behav., 2007, 87(1), 1-10.
Szapiro et al., "Facilitation and Inhibition of Retrieval in Two Aversive Tasks in Rats By Intrahippocampat Infusion of Agonists of Specific Glutamate Metabotropic Receptor Subtypes", Psychopharmacology, 2001, 156(4), 397-401.
Takahashi et al., "In Vitro Systems for the Study of Apoptosis", Advances in Pharmacology, 1997, 41, 89-106.
Takahashi et al., "Post-Treatment with an Inhibitor of Poly(Adp-Ribose) Polymerase Attenuates Cerebral Damage in Focal Ischemia", Brain Research, 1999, 829, 46-54.
Takahashi et al., "Role of the Large Extracellular Domain of Metabotropic Glutamate Receptors in Agonist Selectivity Determination", J. Biol. Chem., 1993, 268(26), 19341-19345.
Takamori et al., "Antipsychotic Action of Selective Group II Metabotropic Glutamate Receptor Agonist Mgs0008 and Mgs0028 on Conditioned Avoidance Responses in the Rat", LifeSci., 2003, 73, 1721-1728.
Takamori, "Vgluts: 'Exciting' Times for Glutamatergic Research?", Neuroscience Research, 2006, 55(4), 343-351.

Takumi et al., "The Arrangement of Glutamate Receptors in Excitatory Synapses", Annals of the New York Academy of Sciences, 1999, 868, 474-482.
Tamminga et al., "Glutamate Pharmacology and the Treatment of Schizophrenia: Current Status and Future Directions", Intl Clinical Psychopharmacology, 1995, 10(Suppl-37), 29-37.
Tamminga, "Schizophrenia and Glutamatergic Transmission", Critical Reviews in Neurobiology, 1998, 12(1-2), 21-36.
Tanabe et al., "A Family of Metabotropic Glutamate Receptors", Neuron, 1992, 8(1), 169-179.
Tandon et al., "Schizophrenia, Just the Facts, 5.Treatment and Prevention Past, Present, and Future", Schizophr Res., Jul. 2010, 122, 1-23.
Tang et al., "Metabotropic Glutamate Receptors in the Control of Neuronal Activity and as Targets for Development of Anti-Epileptogenic Drugs", Curr. Med. Chem, 2009, 16(17), 2189-2204.
Tang et al., "Prolonged Anticonvulsant Action of Glutamate Metabotropic Receptor Agonists in Inferior Colliculus of Genetically Epilepsy-Prone Rats", European Journal of Pharmacology, 1997, 327(2-3), 109-115.
Targum et al., "Redefining Affective Disorders: Relevance for Drug Development", CNS Neuroscience and Therapeutics, 2008, 14, 2-9.
Targum et al., "The Relevance of Anxious Depression as a Distinct Entity for Psychopharmacology and Drug Development", US Psychiatry, 2009, 2(1), 29-31.
Tarrier et al., "A Trial of Two Cognitive Behavioural Methods of Treating Drug-Resistant Residual Psychotic Symptoms in Schizophrenic Patients: I. Outcome", Br J Psychiatry, 1993, 162, 524-532.
Tatarczyska et al., "The Antianxiety-Like Effects of Antagonists of Group I and Agonists of Group II and III Metabotropic Glutamate Receptors After Intrahippocampal Administration", Psychopharmacology, 2001, 158, 94-99.
Taylor et al., "Stimulation of Microglial Metabotropic Glutamate Receptor Mglu2 Triggers Tumor Necrosis Factor?-!nduced Neurotoxicity in Concert with Microglial-Derived Fas Ligand", Journal of Neuroscience, 2005, 25(11), 2952-2964.
Taylor et al., "The Efficacy of Nefazodone Augmentation for Treatment-Resistant Depression with Anxiety Symptoms or Anxiety Disorder", Depression and Anxiety, 2003, 18, 83-88.
Teitler et al., "4-[125i]Iodo-(2,5-Dimethoxy)Phenylisopropylamine and [3h]Ketanserin Labeling of 5-Hydroxytryptamine2 (5ht2) Receptors in Mammalian Cells Transfected with a Rat 5ht2 Cdna: Evidence for Multiple States and Not Multiple 5ht2 Receptor Subtypes", Molecular Pharmacology, 1990, 38, 594-598.
Teran et al., "Regioselective Oxidation of 3-Substituted Pyridinium Salts", Molecules, 2000, 5, 1175-1181.
Testa et al., "Metabotropic Glutamate Receptor Mrna Expression in the Basal Ganglia of the Rat", Journal of Neuroscience, 1994, 14(5), 3005-3018.
Thase et al., "Extended Release Quetiapine Fumarate in Major Depressive Disorder: Analysis in Patients with Anxious Depression", Depression and Anxiety, 2012, 29, 574-586.
Thase, "Augmentation Strategies for Depression: History and Concepts", CNS Spectr, 2007, 12(12), (Suppl 22), 3-5.
Thase, "Depression and Sleep: Pathophysiology and Treatment", Dialogues Clin Neurosci, 2006, 8, 217-226.
Thathiah et al., "The Role of G Protein-Coupled Receptors in the Pathology of Alzheimer's Disease", Nature Reviews Neuroscience, 2011, 12, 73-87.
Theberge, "Glutamate and Glutamine in the Anterior Cingulate and Thalamus of Medicated Patients with Chronic Schizophrenia and Healthy Comparison Subjects Measured with 4.0-T Proton MRS", Am. J. Psychiatry, 2003, 160, 2231-2233.
Theberge, "Glutamate and Glutamine Measured with 4.0t Proton Mrs in Never-Treated Patients with Schizophrenia and Healthy Volunteers", Am. J. Psychiatry, 2002, 159, 1944-1946.
Thompson et al., "Activation of Group II and Group III Metabotropic Glutamate Receptors By Endogenous Ligand(S) and the Modulation of Synaptic Transmission in the Superficial Superior Colliculus", Neuropharmacology, 2004, 47(6), 822-832.
Thomsen et al., "Actions of Phenylglycine Analogs at Subtypes of the Metabotropic Glutamate Receptor Family", European Journal of Pharmacology, 1994, 267(1), 77-84.

(56) References Cited

OTHER PUBLICATIONS

Thomsen et al., "Roles of Metabotropic Glutamate Receptor Subtypes in Modulation of Pentylenetetrazole-Induced Seizure Activity in Mice", Neuropharmacology, 1998, 37(12), 1465-1473.
Tiihonen et al., "The Efficacy of Lamotrigine in Clozapine-Resistant Schizophrenia: A Systematic Review and Meta-Analysis", Schizophr Res. 2009, 109(1-3), 10-14.
Tilakaratne et al., "Chronic Fluoxetine or Desmethylimipramine Treatment Alters 5-Ht2 Receptor Mediated C-Fos Gene Expression", European Journal of Pharmacology, 1995, 290(3), 263-266.
Tizzano et al., "Induction or Protection of Limbic Seizures in Mice by Mglur Subtype Selective Agonists", Neuropharmacology, 1995, 34(8), 1063-1067.
Tizzano et al., "The Anxiolytic Action of Mglu2/3 Receptor Agonist, Ly354740, in the Fear-Potentiated Startle Model in Rats is Mechanistically Distinct From Diazepam", Pharmacology, Biochemistry and Behavior, 2002, 73, 367-374.
Tokita et al., "Roles of Glutamate Signaling in Preclinical and/or Mechanistic Models of Depression", Pharmacology, Biochemistry and Behavior, 2012, 100, 688-704.
Tokunaga et al., "Neuroimaging and Physiological Evidence for Involvement of Giutamatergic Transmission in Regulation of the Striatal Dopaminergic System", Journal of Neuroscience, 2009, 29(6), 1887-1896.
Tolchard et al., "Modulation of Synaptic Transmission in the Rat Ventral Septal Area by the Pharmacological Activation of Metabotropic Glutamate Receptors", European Journal of Neuroscience, 2000, 12(5), 1843-1847.
Tollefson et al., "Fluoxetine, Placebo, and Tricyclic Antidepressants in Major Depression with and without Anxious Features", J Clin Psychiatry, 1994, 55(2), 50-59.
Toms et al., "Latest Eruptions in Metabotropic Glutamate Receptors", Trends in Pharmacological Sciences, 1996, 17(12), 429-435.
Tong et al., "Signal Transduction in Neuronal Death", Journal of Neurochemistry, 1998, 71(2), 447-459.
Trabanco et al., "lmidazo[1,2-A]Pyridines: Orally Active Positive Allosteric Modulators of the Metabotropic Glutamate 2 Receptor", J Med Chem, 2012, 55, 2688-2701.
Trabanco et al., "Mglur2 Positive Allosteric Modulators (Pams): A Patent Review (2009—Present)", Expert Opin. 2013, 19 pages.
Trabanco et al., "New Positive Allosteric Modulators of the Metabotropic Glutamate Receptor 2 (Mglur2). Identification and Synthesis of N-Propyl-5-Substituted Isoquinolones", Med Chem Commun, 2011, 2, 132-139.
Trabanco et al., "New Positive Allosteric Modulators of the Metabotropic Glutamate Receptor 2 (Mglur2): Identification and Synthesis of N-Propyl-8-Chloro-6-Substituted Isoquinolones", Bioorganic & Medicinal Chemistry Letters, 2011, 21, 971-976.
Trabanco et al., "Progress in the Developement of Positive Allosteric Modulators of the Metabotropic Glutamate Receptor 2", Current Medicinal Chemistry, 2011, 18, 47-68.
Trabanco et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8689.
Tresadern et al., "Scaffold Hopping From Pyridonesto lmidazo[1,2-A]Pyridines. New Positive Allosteric Modulators of Metabotropic Glutamate 2 Receptor", Bioorganic & Medicinal Chemistry Letters, 2010, 20, 175-179.
Trettel et al., "Endocannabinoid Signalling Selectively Targets Perisomatic Inhibitory Inputs to Pyramidal Neurones in Juvenile Mouse Neocortex", Journal of Physiology, 2004, 556(Pt 1), 95-107.
Treutlein et al., "Dissection of Phenotype Reveals Possible Association Between Schizophrenia and Glutamate Receptor Delta 1 (Grid1) Gene Promoter", Schizophr. Res., 2009, 111(1-3), 123-130.
Trivedi et al., "Adjunctive Aripiprazole in Major Depressive Disorder: Analysis of Efficacy and Safety in Patients with Anxious and Atypical Features", J Clin Psychiatry, 2008, 69, 1928-1936.
Trivedi et al., "Evaluation of Outcomes with Citalopram for Depression Using Measurement-Based Care in Star*D: Implications for Clinical Practice", Am J Psychiatry, 2006; 163, 28-40.
Trofimova et al., "The Lability of Behavior as a Marker of Comorbid Depression and Anxiety", Advances in Bioscience and Biotechnology, 2010, 1, 190-199.
Trullas et al., "Functional Antagonists at the NMDA Receptor Complex Exhibit Antidepressant Actions", Eur J Pharmacol, Aug. 1990, 185(1), 1-10.
Tsai et al., "Immunocytochemical Distribution of N-Acetylaspartylglutamate in the Rat Forebrain and Glutamatergic Pathways", Journal of Chemical Neuroanatomy, 1993, 6(5), 277-292.
Tsai, "Central N-Acetyl Aspartylglutamate Deficit: A Possible Pathogenesis of Schizophrenia", Med Sci. Monit., 2005, 11(9), Hy39-Hy45.
Tsai, "Glutamatergic Mechanisms in Schizophrenia", Ann. Rev. Pharmacol. Toxicol., 2002, 42, 165-179.
Tsiveriotis et al., "Nickel(ll) and Cobalt(ll) Complexes of 2,4-Diaminothieno[2,3-D]-Pyrimidines", Transition Metal Chemistry, 1994, 19, 335-339.
Tsunoka et al., "Association Analysis of Grm2 and Htr2a with Methamphetamine-Induced Psychosis and Schizophrenia in the Japanese Population", Progress in NeuroPsychopharmacology & Biological Psychiatry, 2010, 34(4), 639-644.
Tsunoka et al., "Association Analysis of Group II Metabotropic Glutamate Receptor Genes (Grm2 and Grm3) with Mood Disorders and Fluvoxamine Response in a Japanese Population", Progress in Neuro-Psychopharmacology & Biological Psychiatry, 2009, 33(5), 875-879.
Tuominen et al., "Glutamatergic Drugs for Schizophrenia", The Cochrane Collaboration, Cochrane Database Syst Rev., Apr. 2006, 1, 8 pages.
Tuominen, "Glutamatergic Drugs for Schizophrenia: A Systematic Review and Meta-Analysis", Schiz. Res., 2005, 72, 225-234.
Turck et al., "Advances in the Directed Metallation of Azines and Diazines (Pyridines, Pyrimidines, Pyrazines, Pyridazines, Quinolines, Benzodiazines and Carbolines). Part 2: Metallation of Pyrimidines, Pyrazines, Pyridazines and Benzodiazines", Tetrahedron, 2001, 57(21), 4489-4505.
Tutonda et al., "Diels-Alder Reactions of the Heterodiene System in 2(1h)-Pyrazinones", Tetrahedron Letters, 1986, 27, 22, 2509-2512.
Tyrer, "The Case for Cothymia: Mixed Anxiety and Depression as a Single Diagnosis", British Journal of Psychiatry, 2001, 179, 191-193.
Uher et al., "Differential Efficacy of Escitalopram and Nortriptyline on Dimensional Measures of Depression", British Journal of Psychiatry, 2009, 194, 252-259.
Uher et al., "Melancholic, Atypical and Anxious Depression Subtypes and Outcome of Treatment with Escitalopram and Nortriptyline", Journal of Affective Disorders, 2011, 132, 112-120.
Um et al., "Alzheimer Amyloid-B Oligomer Bound to Postsynaptic Prion Protein Activates Fyn to Impair Neurons", Nature Neuroscience, 2012, 15(9), 1227-1235.
Undine et al., "Molecular Mechanisms of Schizophrenia", Cell Physiol Biochem, 2007, 20, 687-702.
Ung et al., "Synthesis and Biological Activities of Conformationally Restricted Cyclopentenyl-Glutamate Analogues", Journal of Organic Chemistry, 2002, 67(1), 227-233.
Urwyler, "Allosteric Modulation of Family C G-Protein-Coupled Receptors From Molecular Insights to Therapeutic Perspectives", Pharmacol Rev, 2011, 63, 59-126.
Uslaner et al., "Combined Administration of an Mglu2/3 Receptor Agonist and A 5-Ht 2a Receptor Antagonist Markedly Attenuate the Psychomotor-Activating and Neurochemical Effects of Psychostimulants", Psychopharmacology (Berl), 2009, 206(4), 641-651.
Uys et al., "Glutamate: the New Frontier in Pharmacotherapy for Cocaine Addiction", CNS & Neurological Disorders—Drug Targets, 2008, 7, 482-491.

(56) References Cited

OTHER PUBLICATIONS

Vaccarino et al., "Symptoms of Anxiety in Depression: Assessment of Item Performance of the Hamilton Anxiety Rating Scale in Patients with Depression", Depression and Anxiety, 2008, 25, 1006-1013.
Valentine et al., "Targeting Glial Physiology and Glutamate Cycling in the Treatment of Depression", Biochem. Pharmacol., 2009, 78(5), 431-439.
Vales et al., "The Difference in Effect of Mglu2/3 and Mglu5 Receptor Agonists on Cognitive Impairment Induced By Mk-801", European Journal of Pharmacology, 2010, 639, 91-98.
Valproate Information Available from Http://Www. Fda.Gov/Drugs/Drugsafety/Postmarketdrugsafetyinformationforpatientsandproviders/Ucm192645.Htm, 2011, 2 pages.
Van Beljouw et al., "The Course of Untreated Anxiety and Depression, and Determinants of Poor On-Year Outcome: A One-Year Cohort Study", BMC Psychiatry, 2010, 10, 86.
Van Berckel et al., "Modulation of Amphetamine-Induced Dopamine Release by Group Ii Metabotropic Glutamate Receptor Agonist Ly354740 in Non-Human Primates Studied with Positron Emission Tomography", Neuropsychopharmacology, 2006, 31, 967-977.
Van Den Pol, "Presynaptic Metabotropic Glutamate Receptors in Adult and Developing Neurons: Autoexcitation in the Olfactory Bulb", Journal of Comparative Neurology, 1995, 359(2), 253-271.
Van Tol et al., "Regional Brain Volume in Depression and Anxiety Disorders", Arch Gen Psychiatry, 2010, 67(10), 1002-1011.
Van Valkenberg et al., "Anxious Depressions. Clinical, Family History, and Naturalistic Outcome—Comparisons with Panic and Major Depressive Disorders", Journal of Affective Disorders, 1984, 6(1), 67-82.
Van Vliet et al., "Adaptive Changes in the No. of Gs- and Gi-Proteins Underlie Adenylyl Cyclase Sensitization in Morphine-Treated Rat Striatal Neurons", European Journal of Pharmacology, 1993, 245(1), 23-29.
Vanallan et al., "Reactions of Some 4-Methylene-4h-Pyran Derivatives with Primary and Secondary Amines", Journal of Heterocyclic Chemistry, 1970, 7, 495-507.
Vandergrift et al., "The Selective Mglu2/3 Receptor Agonist Ly354740 Attenuates Morphine-Withdrawal-Induced Activation of Locus Coeruleus Neurons and Behavioral Signs of Morphine Withdrawal", Neuropharmacology, 1999, 38, 217-222.
Vandesompele et al., "Accurate Normalization of Real-Time Quantitative Rt-Pcr Data By Geometric Averaging of Multiple Internal Control Genes", Genome Biology, 2002, 3(7), 1-12.
Varney et al., "Metabotropic Glutamate Receptor Involvement in Models of Acute and Persistent Pain: Prospects for the Development of Novel Analgesics", Current Drug Targets- CNS & Neurological Disorders, 2002, 1, 283-296.
Vasilieva, "Clinical-Dynamic Characteristics of Depressive Disorders Comorbid with Anxiety Disorders", Abstract P01-109 of 18th European Congress of Psychiatry, 2010, 1 page.
Vaughan et al., "Reactivity of 3-Alkyl-4-Arylazomethylene-3,4-Dihydro-1,2,3-Benzotriazines : in Protic Solvents: 1,4-Addition Reactions and Dimroth Rearrangement", Journal of Heterocyclic Chemistry, Nov. 1991, 1709-1713.
Ver Donck et al., "Low Dose Subchronic Phencyclidine (PCP) Pretreatment Potentiates Acute PCP-lnduced Hyperlocomotion in Adult Rats: A Model of Schizophrenia?", Presentation Abstract, Society for Neuroscience, 2011, 2 pages.
Verhagen et al., "Effect of the 5-Httlpr Polymorphism in the Serotonin Transporter Gene on Major Depressive Disorder and Related Comorbid Disorders", Psychiatric Genetics, 2009, 19, 39-44.
Verma et al., "Regulation of Striatal Dopamine Release by Metabotropic Glutamate Receptors", Synapse 1998, 28(3), 220-226.
Vernon et al., "Additive Neuroprotection by Metabotropic Glutamate Receptor Subtype-Selective Ligands in aRat Parkinson's Model", Neuroreport, 2008, 19(4), 475-478.
Versiani et al., "Fluoxetine Versus Amitriptyline in the Treatment of Major Depression with Associated Anxiety (Anxious Depression): A Double-Blind Comparison", International Clinical Psychopharmacology, 1999, 14, 321-327.
Vezina et al., "Metabotropic Glutamate Receptors and the Generation of Locomotor Activity: Interactions with Midbrain Dopamine", Neuroscience & Biobehavioral Reviews, 1999, 23(4), 577-589.
Vilsmaier et al., "Diastereoselective Syntheses of N-Protected Derivatives of La,5a,6fi-6-Amino-3-Azabicyclo [3.101]Hexane: A Route to Trovafloxacin 6fl-Diastereomer", Synthesis, 1998, 739-744.
Vinson et al., "Metabotropic Glutamate Receptors as Therapeutic Targets for Schizophrenia", Neuropharmacology, 2012, 62, 1461-1472.
Vippagunta et al., "Crystalline Solids", Adv. Drug Deliv. Rev., 2001, 48, 3-26.
Vogel et al., "A Simple and Reliable Conflict Procedure for Testing Anti-Anxiety Agents", Psychopharmacologia, 1971, 21, 1-7.
Vogel et al., "Drug Effects on Rem Sleep and on Endogenous Depression", Neuroscience & Biobehavioral Reviews, 1990, 14, 49-63.
Vollenweider et al., "A Systems Model of Altered Consciousness: Integrating Natural and Drug-Induced Psychoses", Brain Res. Bull., 2001, 56, 495-507.
Vollenweider et al., "Differential Psychopathology and Patterns of Cerebral Glucose Utilization Produced by (S)- and (R)-Ketamine in Healthy Volunteers Using Positron Emission Tomography (Pet)", Eur Neuropsychopharmacol, 1997, 7, 25-38.
Vollenweider et al., "Effect of Clozapine and Ketanserin on S-Ketamine-lnduced Brain Activation and Psychotic Symptoms in Healthy Humans", Abstract, Symposia, 28th Cinp World Congress of Neuropsychopharmacology, 2012, 2 pages.
Vollenweider et al., "Metabolic Hyperfrontality and Psychopathology in the Ketamine Model of Psychosis Using Positron Emission Tomography (Pet) and [18f]fluorodeoxyglucose (Fdg)" Eur Neuropsychopharmacol, 1997, 7, 9-24.
Vollenweider et al., "Psilocybin induces Schizophrenia-Like Psychosis in Humans Via a Serotonin-2 Agonist Action", Neuroreport, 1998, 9, 3897-3902.
Vollenweider, "Positron Emission Tomography and Fluorodeoxyglucose Studies of Metabolic Hyperfrontality and Psychopathology in the Psilocybin Model of Psychosis", Neuropsychopharmacology, 1997, 16, 357-372.
Wachtel et al., "Glutamate: A New Target in Schizophrenia?", Trends in Pharmacological Sciences, 1990, 11(6), 219-220.
Wadenberg, "Conditioned Avoidance Response in the Development of New Antipsychotics", Curr Pharm Des, 2010, 16, 358-370.
Wadenberg et al., "The Conditioned Avoidance Response Test Re-Evaluated: Is it a Sensitive Test for the Detection of Potentially Atypical Antipsychotics?", Neurosci. Biobehav. Rev., 1999, 23, 851-862.
Wainer, "Finding Time for Allosteric Interactions", Nature Biotechnology, 2004, 22(11), 1376-1377.
Wakefield, "Fluorinated Pharmaceuticals: Fluorinated Compounds are of Increasing Interest as Pharmaceuticals, and an Extensive Range of Techniques for Making Them is Now Available", Innovations in Pharmaceutical Technology, 2003, 74-78.
Walker et al., "Group II Metabotropic Glutamate Receptors Within the Amygadale Regulate Fear as Assessed with Potentiated Startle in Rats", Behav Neurosci, 2002, 116, 1075-1083.
Walker et al., "The Role of Amygdala Glutamate Receptors in Fear Learning, Fear-Potentiated Startle, and Extinction", Pharmacol. Biochem. Behav., 2002, 71(3), 379-392.
Wang et al., "A Simple and Effcient Automatable One Step Synthesis of Triazolopyridines Form Carboxylic Acids", Tetrahedron Letters, 2007, 48, 2237-2240.
Wang et al., "Allosteric Modulators of G Protein-Coupled Receptors: Future Therapeutics for Complex Physiological Disorders", J Pharmacol. Exp. Ther., 2009, 331(2), 340-348.
Wang et al., "Development of Metabotropic Glutamate Receptor Ligands for Neuroimaging", Curr Med Imaging Rev, 2007, 3, 186-205.

(56) References Cited

OTHER PUBLICATIONS

Wang et al., "Radiosynthesis of Pet Radiotracer as a Prodrug for Imaging Group II Metabotropic Glutamate Receptors in Vivo", Bioorganic & Medicinal Chemistry Letters, 2012, 22, 1958-1962.
Warden et al., "The Star*D Project Results: A Comprehensive Review of Findings", Current Psychiatry Reports, 2007, 9, 449-459.
Warnock et al.,, "In Vivo Evidence for Ligand-Specific Receptor Activation in the Central CRF System, As Measured By Local Cerebral Glucose Utilization", Peptides, 2009, 30, 947-954.
Watanabe et al., "Mglur2 Postsynaptically Senses Granule Cell Inputs At Golgi Cell Synapses" Neuron, 2003, 39, 821-829.
Watanabe et al., "Pd/P(T-Bu)3-Catalyzed Synthesis of Aromatic Amines", Journal of Tosoh Research, 1999, 43, 38-50.
Watkins, "L-Glutamate as a Central Neurotransmitter: Looking Back", Biochem Soc Trans, 2000, 28, 297-310.
Watkins et al., "Structure-Activity Relationships in the Development of Excitatory Amino Acid Receptor Agonists and Competitive Antagonists", Trends in Pharmacological Sciences, 1990, 11(1), 25-33.
Webb et al., "Apoptosis: An Overview of the Process and its Relevance in Disease", Advances in Pharmacology, 1997, 41, 1-34.
Weinberger et al., "Schizophrenia Drug Says Goodbye To Dopamine", Nature Medicine, 2007, 13, 1018-1019.
Weinberger, "The Biological Basis of Schizophrenia: New Directions", Journal of Clinical Psychiatry, 1997, 58(Suppl 10), 22-27.
Weiner et al., "5-Hydroxytryptamine2a Receptor Inverse Agonists as Antipsychotics", Journal of Pharmacology & Experimental Therapeutics, 2001, 299(1), 268-276.
Weisstaub, "Cortical 5-Ht2a Receptor Signaling Modulates Anxiety-Like Behaviors in Mice", Science, 2006, 313, 536-540.
Wenner et al., "Derivatives of 2-Pyridone", Journal of Organic Chemistry, 1946, 11, 751-759.
Wheeler et al., "(2s,1's,2'r,3'r)-2(2'-Carboxy-3'-Hydroxymethyl-Cyclopropyl)Glycine-[3h], a Potent and Selective Radioligand for Labeling Group 2 and 3 Metabotropic Glutamate Receptors", Bioorganic & Medicinal Chemistry Letters, 2005, 15, 349-351.
Whitehouse et al., "Clinical Trial Designs for Demonstrating Disease-Course-Altering Effects in Dementia", Alzheimer Disease and Associated Disorders, 1998, 12, 281-294.
Wicke et al., "Effects of Metabotropic Glutamate Receptor (Mglur) 2/3 Agonists and Antagonist on Rat Sleep Eeg", Program No. 839.2/M9, Neuroscience Meeting Planner, Society for Neuroscience, 2009, 2 pages.
Wieronska et al., "Anxiolytic Action of Group II and III Metabotropic Glutamate Receptors Agonists Involves Neuropeptide Y in the Amygdala", Pharmacol. Rep., 2005, 57(6), 734-743.
Wieronska et al., "Glutamate-Based Anxiolytic Ligands in Clinical Trials", Expert Opin Investig Drugs, 2013, 22(8), 1007-1022.
Wieronska et al., "Metabotropic Glutamate Receptor 4 Novel Agonist Lsp1-2111 with Anxiolytic, but not Antidepressant-Like Activity, Mediated by Serotonergic and Gabaergic Systems", Neuropharmacology, 2010, 59, 627-634.
Wieronska et al., "Metabotropic Glutamate Receptors in the Tripartite Synapse as a Target for New Psychotropic Drugs", Neurochem. Int, 2009, 55(1-3), 85-97.
Wieronska et al., "On the Mechanism of Anti-Hyperthermic Effects of Ly379268 and Ly487379, Group II Mglu Receptors Activators, in the Stress-Induced Hyperthermia in Singly Housed Mice", Neuropharmacology, 2012, 62, 322-331.
Wieronska et al., "Opposing Efficacy of Group ill Mglu Receptor Activators, Lsp1-2111 and Amn082, in Animal Models of Positive Symptoms of Schizophrenia", Psychopharmacology, Sep. 2011, 14 pages.
Wiethoff et al., "Prevalence and Treatment Outcome in Anxious Versus Nonanxious Depression: Results From the German Algorithm Project", J Clin Psychiatry, 2010, 71(8), 1047-1054.
Wikipedia, "Allosteric Regulation", 2010, 1-4.
Wiley et al., "2-Pyrones. XVIII. 5-Aroyl-2-Pyridones", J. Am. Chem. Soc., Jun. 1956, 78, 2393-2398.

Rwilliams et al., "Characterization of Polyamines Having Agonist, Antagonist, and Inverse Agonist Effects at the Polyamine Recognition Site of the NMDA Receptor", Neuron, 1990, 5(2), 199-208.
Williams et al., "International Study to Predict Optimized Treatment for Depression (Ispot-D), A Randomized Clinical Trial: Rationale and Protocol", Trials, 2011, 12(4), 17 pages.
Wilsch et al., "Metabotropic Glutamate Receptor Agonist DCG-IV as NMDA Receptor Agonist in Immature Rat Hippocampal Neurons", European Journal of Pharmacology, 1994, 262(3), 287-291.
Wilson et al., "Antidepressants and Sleep: A Qualitative Review of the Literature", Drugs, 2005, 65, 927-947.
Winter et al., "Serotonergic/Glutamatergic Interactions: The Effects of Mglur2/3 Receptor Ligands in Rats Trained with LSD and PCP as Discriminative Stimuli.", Psychopharmacol. (Berl), 2004, 172, 233-240.
Wischhof et al., "Pre-Treatment with the Mglu2/3 Receptor Agonist Ly379268 Attenuates DOI-Induced Impulsive Responding and Regional C-Fos Protein Expression", Psychopharmacology, Aug. 2011, 14 pages.
Witkin etaL, "Metabotropic Glutamate Receptors in the Control of Mood Disorders", CNS & Neurological Disorders—Drug Targets, 2007, 6, 87-100.
Wittchen et al., "Disabilities and Quality of Live in Pure and Comorbid Generalized Anxiety Disorder and Major Depression in a National Survey", Inti Clinical Psychopharmacology, 2000, 15, 319-328.
Wittchen et al., "DSM-III-R Generalized Anxiety Disorder in the National Comorbidity Survey", Arch Gen Psychiatry. 1994, 51, 355-364.
Wittmann et al., "Dopamine Modulates the Function of Group II and Group III Metabotropic Glutamate Receptors in the Substantia Nigra Pars Reticulata", J Pharmacol. Exp. Ther., 2002, 302(2), 433-441.
Wong et al., "The Role of Imaging in Proof of Concept for CNS Drug Discovery and Development", Neuropsychopharmacology, 2009, 34, 187-203.
Woolley et al., "The Mglu2 but not the Mglu3 Receptor Mediates the Actions of the Mglur2/3 Agonist, Ly379268, in Mouse Models Predictive of Antipsychotic Activity", Psychopharmacology, 2008, 196, 431-440.
World Health Organization, "Mental Health: New Understanding, New Hope", 2001, 169 pages.
Wright e al., "[3h]Ly341495 Binding To Group II Metabotropic Glutamate Receptors in Rat Brain", Journal of Pharmacology & Experimental Therapeutics, 2001, 298(2), 453-460.
Wroblewska et al., "N-Acetylaspartylglutamate Activates Cyclic Amp-Coupled Metabotropic Glutamate Receptors in Cerebellar Astrocytes", Glia, 1998, 24(2), 172-179.
Xi et al., "Group II Metabotropic Glutamate Receptors Modulate Extracellular Glutamate in the Nucleus Accumbens", Journal of Pharmacology & Experimental Therapeutics, 2002, 300(1), 162-171.
Xiao et al., "Desensitization of G-Protein-Coupled Receptors. Agonist-Induced Phosphorylation of the Chemoattractant Receptor Car1 Lowers its Intrinsic Affinity for Camp", J. Biol. Chem., 1999,2 74(3), 1440-1448.
Xiao et al., "Metabotropic Glutamate Receptor Activation Causes a Rapid Redistribution of Ampa Receptors", Neuropharmacology, 2001, 41(6), 664-671.
Xu et al., "Neurotransmitter Receptors and Cognitive Dysfunction in Alzheimer's Disease and Parkinson's Disease", Progress in Neurobiology, 2012, 97, 1-13.
Yakovidis et al., "Copper(II) Complexes of Thieno[2,3-D] Pyrimidine Derivatives", Inorganica Chimica Acta, 1988, 151, 165-167.
Yalyaheva et al.."Chemical Abstract", Heterocycles, 1987, 2 pages.
Yanamala et al., "Preferential Binding of Allosteric Modulators to Active and Inactive Conformational States of Metabotropic Glutamate Receptors", BMC Bioinformatics, 2008, 9(Suppl 1), S16.
Yao et al., "Enhancement of Glutamate Uptake Mediates the Neuroprotection Exerted By Activating Group II or III Metabotropic Glutamate Receptors on Astrocytes", Journal of Neurochemistry, 2005, 92(4), 948-961.

(56) References Cited

OTHER PUBLICATIONS

Yasuhara et al., "Metabotropic Glutamate Receptors: Potential Drug Targets for Psychiatric Disorders", Open Medicinal Chemistry Journal, 2010, 4, 20-36.
Ye et al., "Metabotropic Glutamate Receptor Agonists Reduce Glutamate Release From Cultured Astrocytes", Glia, 1999, 25(3), 270-281.
Yokoi et al., "Impairment of Hippocampal Mossy Fiber Ltd in Mice Lacking Mgiur2", Science, 1996, 273, 645-647.
Young et al., "Biomarkers of Oxidative Stress in Schizophrenic and Control Subjects", Prostaglandins Leukot. Essent. Fatty Acids, 2007, 76(2), 73-85.
Young et al., "Evidence for a Role of Metabotropic Glutamate Receptors in Sustained Nociceptive Inputs to Rat Dorsal Horn Neurons," Neuropharmacoloqy, 1994, 33(1), 141-144.
Young et al., "The Involvement of Metabotropic Glutamate Receptors and Their Intracellular Signalling Pathways in Sustained Nociceptive Transmission in Rat Dorsal Horn Neurons", Neuropharmacology, 1995, 34(8), 1033-1041.
Yousif et al., "Studies On Tertiary Amine Oxides. LXXV. Reactions of Aromatic N-Oxides with Meldrum's Acid in the Presence of Acetic Anhydride", Chem. Pharm. Bull., 1982, 30(5), 1680-1691.
Yuan et al., "Glutamate-Induced Swelling of Cultured Astrocytes is Mediated by Metabotropic Glutamate Receptor", Science in China, Series C, Life Sciences, 1996, 39(5), 517-522.
Yucel et al., "Anterior Cingulate vols. in Never-Treated Patients with Major Depressive Disorder", Neuropsychopharmacology, 2008, 33, 3157-3163.
Yui et al., "Studies of Amphetamine or Methamphetamine Psychosis in Japan: Relation of Methamphetamine Psychosis To Schizophrenia", Annals New York Academy of Sciences, 2000, 914, 1-12.
Yuzwa et al., "O-GlcNAc and neurodegeneration: biochemical mechanisms and potential roles in Alzheimer's disease and beyond", Chem. Soc. Rev., 2014, 43, 6839-6858.
Yuzaki et al., "Pharmacological and Immunocytochemical Characterization of Metabotropic Glutamate Receptors in Cultured Purkinje Cells", J. Neurosci., 1992, 12(11), 4253-4263.
Zarate et al., "An Open-Label Trial of Riluzole in Patients with Treatment-Resistant Major Depression", Am J Psychiatry, 2004, 161, 171-174.
Zeilhofer et al., "Differential Effects of Ketamine Enantiomers on NMDA Receptor Currents in Cultured Neurons", Eur J Pharmacol, 1992, 213, 155-158.
Zhang et al., "1-[(1-Methyl-1h-Imidazol-2-YI)Methyl]-4-Phenylpiperidines as Mglur2 Positive Allosteric Modulators for the Treatment of Psychosis", J Med Chem, 2011, 54, 1724-1739.
Zhang et al., "3-(lmidazolyl Methyl)-3-Aza-Bicyclo[3.1.0]Hexan-6-YI)Methyl Ethers: a Novel Series of Mglur2 Positive Allosteric Modulators", Bioorg Med Chem Lett, 2008, 18, 5493-5496.
Zhang et al., "Neuroprotective Effects of Poly(Adp-Ribose) Polymerase Inhibition on Focal Cerebral Ischemia", Biology of Nitric Oxide, Portland Press Proceedings, 1998, 15, 125.
Zhao et al., "Activation of Group II Metabotropic Glutamate Receptors Attenuates Both Stress and Cue-Induced Ethanol-Seeking and Modulates C-Fos Expression in the Hippocampus and Amygdala", Journal of Neuroscience, 2006, 26(39), 9967-9974.
Zhu et al., "Rapid Enhancement of High Affinity Glutamate Uptake by Glucocorticoids in Rat Cerebral Cortex Synaptosomes and Human Neuroblastoma Clone Sk—N—Sh: Possible Involvement of G-Protein", Biochemical & Biophysical Research Communications, 1998, 247(2), 261-265.
Zhu, "The Competitive and Noncompetitive Antagonism of Receptor-Mediated Drug Actions in the Presence of Spare Receptors", Journal of Pharmacological & Toxicological Methods, 1993, 29(2), 85-91.
Zimmerman et al., "Frequency of Anxiety Disorders in Psychiatric Outpatients with Major Depressive Disorder". Am J Psychiatry, 2000, 157, 1337-1340.
Zuena et al., "Prenatal Restraint Stress Generates Two Distinct Behavioral and Neurochemical Profiles in Male and Female Rats", lios. One, 2008, 3(5), E2170.
Zusso et al., "Cerebellar Granular Cell Cultures as an In Vitro Model for Antidepressant Drug-Induced Meurogenesis", Critical Reviews in Neurobiology, 2004, 16(182), 59-65.
Zwart et al., "Sazetidine-A is a Potent and Selective Agonist at Native and Recombinant A4B2Nicotinic Acetylcholine Receptors", Mol Pharmacol, 2008, 73, 1838-1843.
Schmidt, Current Neurol Neurosci Rep 2016, 95, p. 1-5.
You et al. Seizure, 21, 2012, 153-159.
Silverman, The Organic Chemistry of Drug Design and Drug Action, 1992.
Patani et al. (Chern Rev, 1996, 96, 3147-3176).
FDA Document, 2009.
Pitkänen et al., "Epileptogenesis", Cold Spring Harb. Perspect. Med, 2015, Vol. 5, No. 10, a022822, 18 sheets.

\* cited by examiner

US 11,369,606 B2

COMBINATIONS COMPRISING POSITIVE ALLOSTERIC MODULATORS OR ORTHOSTERIC AGONISTS OF METABOTROPIC GLUTAMATERGIC RECEPTOR SUBTYPE 2 AND THEIR USE

CROSS REFERENCE TO RELATED APPLICATIONS

This application is a continuation application of U.S. patent application Ser. No. 15/112,818, filed Jul. 20, 2016, now U.S. Pat. No. 10,537,573, which is a § 371 national stage application of PCT Application No. PCT/EP2015/051029, filed Jan. 20, 2015, which claims priority from U.S. Provisional Patent Application Ser. No. 61/929,1795, filed Jan. 21, 2014, European Patent Application No. 14153887.6, filed Feb. 4, 2014, European Patent Application No. 14153880.1, filed Feb. 4, 2014, European Patent Application No. 14183324.4, filed Sep. 3, 2014, European Patent Application No. 14187429.7, filed Oct. 2, 2014 and U.S. Provisional Patent Application No. 62/091,668, filed Dec. 15, 2014, the entire disclosures of which are hereby incorporated in their entirety.

FIELD OF THE INVENTION

The present invention relates to combinations comprising a positive allosteric modulator ("PAM") of metabotropic glutamatergic receptor subtype 2 ("mGluR2") or a pharmaceutically acceptable salt or a solvate thereof, or an orthosteric agonist of metabotropic glutamatergic receptor subtype 2 compound or a pharmaceutically acceptable salt or a solvate thereof, and a synaptic vesicle protein 2A ("SV2A") ligand.

BACKGROUND OF THE INVENTION

Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at approximately 0.3 to 0.5 percent in different populations throughout the world, with the prevalence of epilepsy estimated at 5 to 10 people per 1000.

An essential step in the evaluation and management of a patient with a seizure is to determine the type of seizure that has occurred. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 s. Consciousness is briefly impaired, but there is usually no postictal confusion. Myoclonic seizures are characterized by a sudden and brief muscle contraction that may involve one part of the body or the entire body.

The synaptic vesicle protein 2A ("SV2A") has been identified as a broad spectrum anticonvulsant target in models of partial and generalized epilepsy. Studies performed in animal models and human tissue suggest that changes in the expression of SV2A are implicated in epilepsy (for a review see for instance: (a) Mendoza-Torreblanca et al. "Synaptic vesicle protein 2A: basic facts and role in synaptic function" European Journal of Neuroscience 2013, pp. 1-11; (b) Kaminski R M, et al. "Targeting SV2A for Discovery of Antiepileptic Drugs". In: Noebels J L, Avoli M, Rogawski M A, et al., editors. Jasper's Basic Mechanisms of the Epilepsies [Internet]. 4th edition. Bethesda (Md.): National Center for Biotechnology Information (US); 2012. Available from: http://www.ncbi.nlm.nih.gov/books/NBK98183/).

The exact role of SV2A remains unclear but studies suggest that changes in the expression of SV2A affect synaptic function (Nowack et al. "Levetiracetam reverses synaptic deficits produced by overexpression of SV2A" PLoS One 2011, Volume 6 (12), e29560). It has also been suggested that SV2A is a key player in exocytosis and is involved in neurotransmission (Crowder et al. "Abnormal neurotransmission in mice lacking synaptic vesicle protein 2A (SV2A)" Proc Nat Acad Sci USA 1999, 96, pp. 15268-15273) and studies in knock-out mice suggest that lack of SV2A results in an imbalance between glutamatergic and GABAergic neurotransmission (Venkatesan et al. "Altered balance between excitatory and inhibitory inputs onto CA pyramidal neurons from SV2A-deficient but not SV2B-deficient mice" J Neurosci Res 2012, 90, pp. 2317-2327). Decreased expression of SV2A may be a consequence of seizure activity and may be involved in the progression of epilepsy (van Vliet et al. "Decreased expression of synaptic vesicle protein 2A, the binding site for levetiracetam, during epileptogenesis and chronic epilepsy" Epilepsia 2009, 50, pp. 422-433; Feng et al. "Down-regulation of synaptic vesicle protein 2A in the anterior temporal neocortex of patients with intractable epilepsy" J Mol Neurosci 2009, 39, pp. 354-359; Toering et al. "Expression patterns of synaptic vesicle protein 2A in focal cortical dysplasia and TSC-cortical tubers" Epilepsia 2009, 50, pp. 1409-1418) and epileptogenesis in patients with brain tumours (de Groot et al. "Expression of synaptic vesicle protein 2A in epilepsy-associated brain tumors and in the peritumoral cortex" Neuro-Oncology 2010, 12, pp. 265-273).

SV2A ligands include levetiracetam (Lynch et al. "The synaptic vesicle protein SV2A is the binding site for the antiepileptic drug levetiracetam" Proc. Natl. Acad. Sci. USA 2004, Vol. 101, pp. 9861-9866), brivaracetam and seletracetam (Kaminski R M, et al. "Targeting SV2A for Discovery of Antiepileptic Drugs". In: Noebels J L, Avoli M, Rogawski M A, et al., editors. Jasper's Basic Mechanisms of the Epilepsies [Internet]. 4th edition. Bethesda (Md.): National Center for Biotechnology Information (US); 2012. Available from: http://www.ncbi.nlm.nih.gov/books/NBK98183/; Nowack et al. "Levetiracetam reverses synaptic deficits produced by overexpression of SV2A" PLoSone December 2011, Vol. 6(12), e29560).

Levetiracetam, (−)-(S)-α-ethyl-2-oxo-1-pyrrolidine acetamide or (S)-2-(2-oxopyrrolidin-1-yl)butanamide,

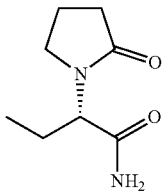

is an antiepileptic drug. It showed no activity in traditional acute models (maximal electroshock and pentylenetetrazol seizure tests) but was found potent in chronic epilepsy models and in genetic models of generalized epilepsy. It has shown a high safety margin compared to other antiepileptic drugs (Klitgaard "Levetiracetam: the preclinical profile of a new class of antiepileptic drugs" Epilepsia 2001, 42 (Supplement 4), pp. 13-18). It is commercialized under the trademark Keppra®, available as tablets, as an oral solution, and as a concentrate made up into a solution for infusion. Keppra® has been approved in Europe as a monotherapy in patients from 16 years of age with newly diagnosed epilepsy, in the treatment of partial-onset seizures (fits) with or without secondary generalization and as an add-on therapy for use with other anti-epileptic drugs in the treatment of partial-onset seizures with or without generalization in patients from 1 month of age; myoclonic seizures in patients from 12 years of age with juvenile myoclonic epilepsy; and primary generalized tonic-clonic seizures in patients from 12 years of age with idiopathic generalized epilepsy (www.ema.europa.eu). Keppra® has also been approved in the USA as an add-on therapy for the treatment of partial onset seizures in patients from 1 month of age; myoclonic seizures in patients 12 years of age and older with juvenile myoclonic epilepsy; and primary generalized tonic-clonic seizures in patients 6 years of age and older with idiopathic generalized epilepsy. Keppra XR®, available as extended-release tablets, has been approved in the USA for the add-on treatment of partial onset seizures in patients 16 years of age and older with epilepsy (http://www.accessdata.fda.gov/scripts/cder/drugsatfda/index.cfm).

Brivaracetam, the 4-n-propyl analog of levetiracetam, (2S)-2-[(4R)-oxo-4-propyl-pyrrolidin-1-yl]butanamide,

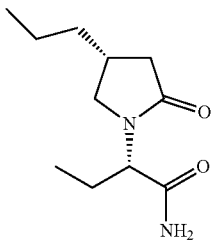

is in clinical trials and investigated as monotherapy in partial onset seizures and post-herpetic neuralgia and as add-on therapy in refractory partial onset seizures, Unverricht-Lundborg disease in adolescents and adults and in photosensitive epilepsy (www.clinicaltrials.gov).

Seletracetam, (2S)-2-[(4S)-4-(2,2,-difluorovinyl)-2-oxo-pyrrolidin-1-yl]butanamide,

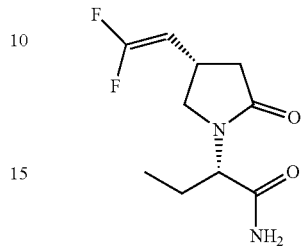

has been tested in clinical trials.

Processes for the preparation of the three compounds are known in the literature. For instance, processes for making Levetiracetam are disclosed for instance, in EP 0 162 036 and in GB 2 225 322. A process for the preparation of Brivaracetam is disclosed for instance in WO 01/62726. A process for the preparation of Seletracetam is known for instance from WO2005/121082. Alternative processes for making the three compounds are disclosed in EP1806339.

Antiepileptic drugs have found usefulness in neurological and psychiatric disorders, including neuropathic pain, migraine, essential tremor and in anxiety, schizophrenia and bipolar disorder (Landmarck "Antiepileptic drugs in non-epilepsy disorders. Relations between mechanisms of action and clinical efficacy" CNS Drugs 2008, Vol. 22(1), pp. 27-47; Calabresi et al. "Antiepileptic drugs in migraine: from clinical aspects to cellular mechanisms" Trends in Pharmacological Sciences 2007, Vol. 28(4), pp. 188-195; Rogawski and Loscher "The neurobiology of antiepileptic drugs for the treatment of nonepileptic conditions" Nat Med 2004, Vol. 10, pp. 685-692).

Levetiracetam has been found effective or potentially effective in a wide-spectrum of neuropsychiatric disorders including mood disorders (Muralidharan and Bhagwagar "Potential of levetiracetam in mood disorders: a preliminary review" CNS Drugs 2006, Vol. 20, pp. 969-979; Mula et al. "The role of anticonvulsant drugs in anxiety disorders: a critical review of the evidence" J Clin Pshycopharmacol 2007, Vol. 27, pp. 263-272), anxiety disorders (Kinrys et al. "Levetiracetam as adjunctive therapy for refractory anxiety disorders" J Clin Psychiatry 2007, Vol. 68, pp. 1010-1013; Zhang et al. "Levetiracetam in social phobia: a placebo controlled pilot study" J Psychopharmacol 2005, Vol. 19, pp. 551-553; Kinrys et al. "Levetiracetam for treatment-refractory posttraumatic stress disorder" J Clin Psychiatry 2006, Vol. 67, pp. 211-214), pain (Enggaard et al. "Specific effect of levetiracetam in experimental human pain models" Eur J Pain 2006, Vol. 10, pp. 193-198; Dunteman "Levetiracetam as an adjunctive analgesic in neoplastic plexopathies: case series and commentary" J Pain Palliative Care Pharmacother 2005, Vol. 19, pp. 35-43; Price "Levetiracetam in the treatment of neuropathic pain: three case studies" Clin J Pain 2004, Vol. 20, pp. 33-36), movement disorders (Bushara et al. "The effect of levetiracetam on essential tremor" Neurology 2005, Vol. 64, pp. 1078-1080; McGavin et al "Levetiracetam as a treatment for tardive dyskinesia: a case report" Neurology 2003, Vol. 61, pp. 419; Woods et al. "Effects of levetiracetam on tardive dyskinesia: a randomized, double-blind, placebo-controlled study" J Clin Psychiatry 2008, Vol. 69, pp. 546-554; Zivkovic et al. "Treatment of tardive dyskinesia with levetiracetam in a transplant patient" Acta Neurol Scand 2008, Vol. 117, pp. 351-353; Striano et al. "Dramatic response to levetiracetam in post-ischaemic Holmes' tremor" J Neurol Neurosurg Psychiatry 2007, Vol. 78, pp. 438-439) and it is suspected to show potentially beneficial effects in cognitive functioning (Piazzini et al. "Levetiracetam: An improvement of attention and of oral fluency in patients with partial epilepsy" Epilepsy Research 2006, Vol. 68, pp. 181-188; de Groot et al. "Levetiracetam improves verbal memory in high-grade glioma patients" Neuro-oncology 2013, Vol. 15(2), pp. 216-223; Bakker et al. "Reduction of hippocampal hyperactivity improves cognition in amnestic mild cognitive impairment" Neuron 2012, Vol. 74, pp. 467-474; for a review: Eddy et al. "The cognitive impact of antiepileptic drugs" Ther Adv Neurol Disord 2011, Vol. 4(6), pp. 385-407 and references cited therein; Wheless "Levetiracetam in the treatment of childhood epilepsy" Neuropsychiatric Disease and Treatment 2007, Vol. 3(4), pp. 409-421), and behavioral symptoms in dementia (Dolder and Nealy "The efficacy and safety of newer anticonvulsants in patients with dementia" Drugs Aging 2012, Vol. 29(8), pp. 627-637). Animal data and some preliminary clinical trials suggest that levetiracetam may have potential for restraining post-traumatic epilepsy, such as those caused by status epilepticus, traumatic brain injury and ischemic stroke, and it appears to have neuroprotective effects. The potential of levetiracetam in easing epileptogenesis or cognitive dysfunction remains to be ascertained by conclusive animal and clinical studies (for reviews: Loscher and Brandt "Prevention or modification of epileptogenesis after brain insults: experimental approaches and translational research" Pharmacol Rev 2010, Vol. 62, 668-700; Shetty "Prospects of levetiracetam as a neuroprotective drug against status epilepticus, traumatic brain injury and stroke" Front. Neur.2013, 4:172. Doi: 10.3389/fneur.2013.00172) as it has displayed antiepileptogenic activity in the kindling model in mice and rats. It has also been suggested that levetiracetam inhibits glutamate release (Lee et al. "Levetiracetam inhibits glutamate transmission through presynaptic P/Q-type calcium channels on the granule cells of the dentate gyrus" British Journal of Pharmacology 2009, Vol. 158, pp. 1753-1762).

Seletracetam and Brivaracetam, have been found to reduce the severity of dystonia in the $dt^{sz}$ mutant hamster model and may be helpful in some patients suffering from dyskinetic and dystonic movement disorders (Hamann et al. "Brivaracetam and seletracetam, two new SV2A ligands, improve paroxysmal dystonia in the $dt^{sz}$ mutant hamster" European Journal of Pharmacology 2008, Vol. 601, pp. 99-102). Positive allosteric modulators of mGluR2 have emerged recently as promising novel therapeutic approaches for the treatment of several CNS disorders, including epilepsy, and some mGluR2 PAMs are currently undergoing clinical trials for the treatment of schizophrenia, and anxiety-depression (www.clinicaltrials.gov, see for instance: JNJ-40411813/ADX71149 by Addex Therapeutics and Janssen Pharmaceuticals, Inc.). The initial suggestion that drugs that dampen glutamatergic transmission may be efficacious in the treatment of epilepsy came from acute non-clinical studies with mixed mGlu2/3 receptor agonists (Moldrich et al. "Glutamate metabotropic receptors as targets for drug therapy in epilepsy" Eur J Pharmacol. 2003, Vol. 476, pp. 3-16). LY379268 and LY389795, two mGlu2/3 receptor agonists, were found ineffective in blocking MES seizures up to doses producing motor impairment but were found effective in the 6 Hz model in a dose-dependent manner (Barton et al. "Comparison of the effect of glutamate receptor modulators in the 6 Hz and maximal electroshock seizure models" Epilepsy Research 2003, Vol. 56, pp. 17-26). Continued administration of an mGlu2/3 agonist paradoxically induced seizure activity in long-term toxicology studies (Dunayevich et al. "Efficacy and tolerability of an mGlu2/3 agonist in the treatment of generalized anxiety disorder" Neuropsychopharmacology. 2008, Vol. 33(7), pp. 1603-10). This paradoxical effect may be related to agonist-induced changes in the sensitivity of the receptor system (tachyphylaxis), but has not been reported however in preclinical models of epilepsy. Positive allosteric modulators, in contrast, modulate ongoing neurotransmission but are not directly stimulatory, thereby reducing the risk for tachyphylaxis.

Prior to seizure activity, increases in extracellular glutamate are measured in human hippocampus and the increase is sustained during epileptogenic activity (During and Spencer "Extracellular hippocampal glutamate and spontaneous seizure in the conscious human brain" Lancet 1993, Vol. 341(8861), pp. 1607-10), thus lending support to the idea that a reduction in glutamate levels may be of benefit in the treatment of epilepsy. In fact, during seizure activity glutamate levels increase to potentially neurotoxic levels. Seizure activity results in progressive structural damage in human brain inducing further abnormalities in glutamate metabolism (Petroff et al. "Glutamate-glutamine cycling in the epileptic human hippocampus" Epilepsia 2002, Vol. 43(7), pp. 703-10). Thus, an mGluR2 positive allosteric modulator or an mGluR2 orthosteric agonist may be expected to protect against seizure-induced neuronal damage.

WO2009/033704 and WO2010/130424 disclose mGluR2 positive allosteric modulators, uses thereof and processes for synthesizing the compounds. WO1997/18199 and WO2003/104217 disclose excitatory amino acid receptor modulator compounds that later were shown to have mGlu2/3 orthosteric agonist activity (see for example Rorick-Kehn et al. (2007) The Journal of Pharmacology and Experimental therapeutics Vol. 321, No. 1, pp. 308-317), further scientific and patent literature disclose additional examples of compounds having mGlu2/3 orthosteric agonist activity, and WO2008/150233 discloses compounds with mGluR2 allosteric activator activity.

Currently available anti-epileptic drugs do not solely affect glutamatergic transmission. Their mechanism of action is generally conceptualized as altering the balance between excitatory (glutamate-mediated) and inhibitory (GABA-mediated) transmission (Johannessen Landmark "Antiepileptic drugs in non-epilepsy disorders: relations between mechanisms of action and clinical efficacy" CNS Drugs 2008, Vol. 22(1), pp. 27-47).

A significant limiting factor in the use of SV2A ligands is tolerability and side-effect profile. For example the effective dose of levetiracetam for partial onset seizures is dosed at 1000 mg, 2000 mg, and 3000 mg, given as twice-daily. The side effects reported for levetiracetam include aggressive or angry behavior, anxiety, change in personality, chills, cough or hoarseness, crying, depersonalization, diarrhea, dry mouth, euphoria, fever, general feeling of discomfort or illness, headache, hyperventilation, irregular heartbeats, irritability, joint pain, loss of appetite, lower back or side pain, mental depression, muscle aches and pains, nausea, painful or difficult urination, paranoia, quick to react or overreact emotionally, rapidly changing moods, restlessness, shaking, shivering, shortness of breath, sleepiness or unusual drowsiness, sore throat, stuffy or runny nose, sweating, trouble sleeping, unusual tiredness or weakness and vomiting. Thus, there is still a need to provide an effective treatment with a lower effective dose of levetiracetam and a more favourable side effect profile for the treatment of epilepsy and related disorders, not only in the adult but also in the pediatric population.

BRIEF DESCRIPTION OF THE FIGURES

In FIG. 2, the ratio of LEV to Co. No. 1 is depicted as follows:

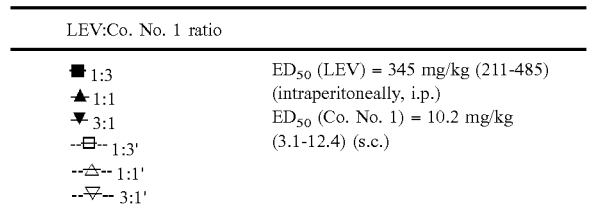

Figure 3:
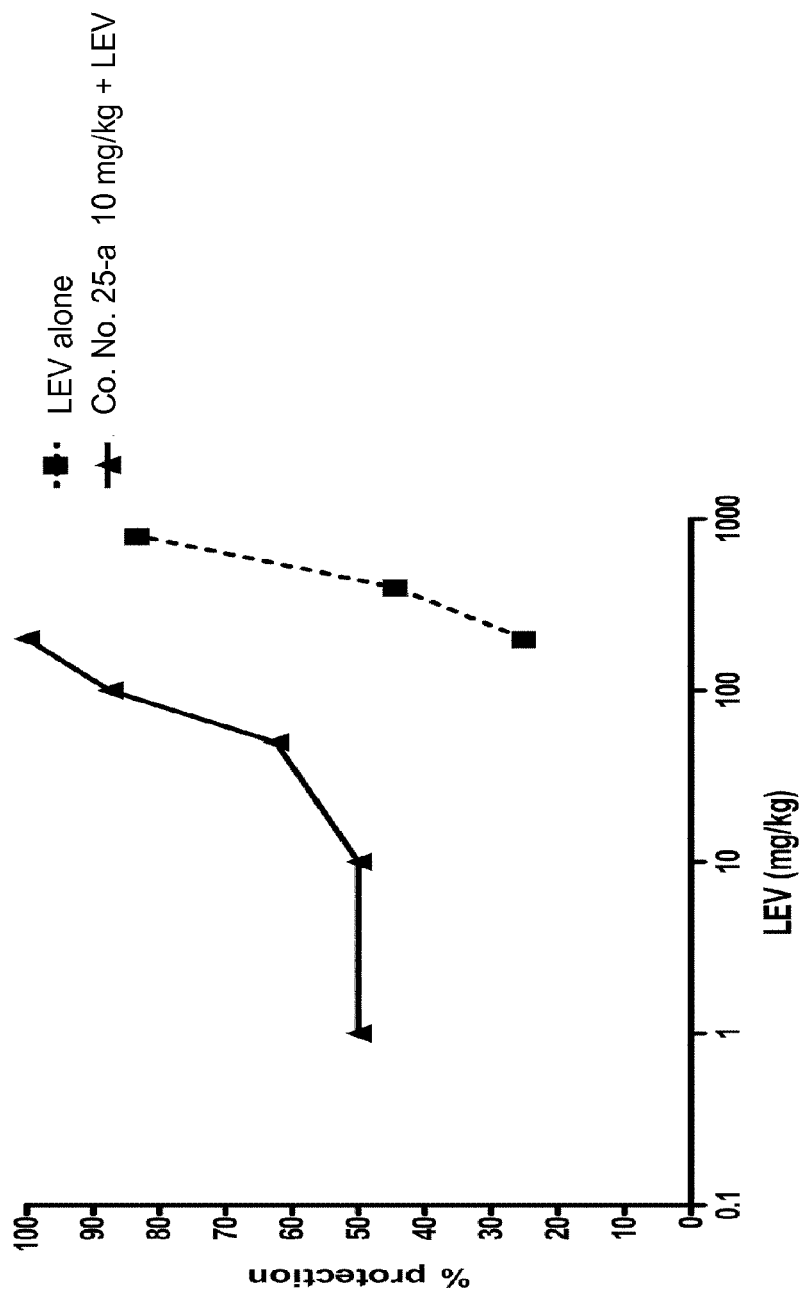

FIG. 3: Combination Studies for Co. No. 25-a with levetiracetam (LEV) in the 6 Hz Assay (44 mA). At a dose of 10 mg/kg s.c., Co. No. 25-a increases the potency of LEV, leading to an approximate 70-fold shift in the $ED_{50}$. This suggests a positive pharmacodynamic relationship.

Figure 4:
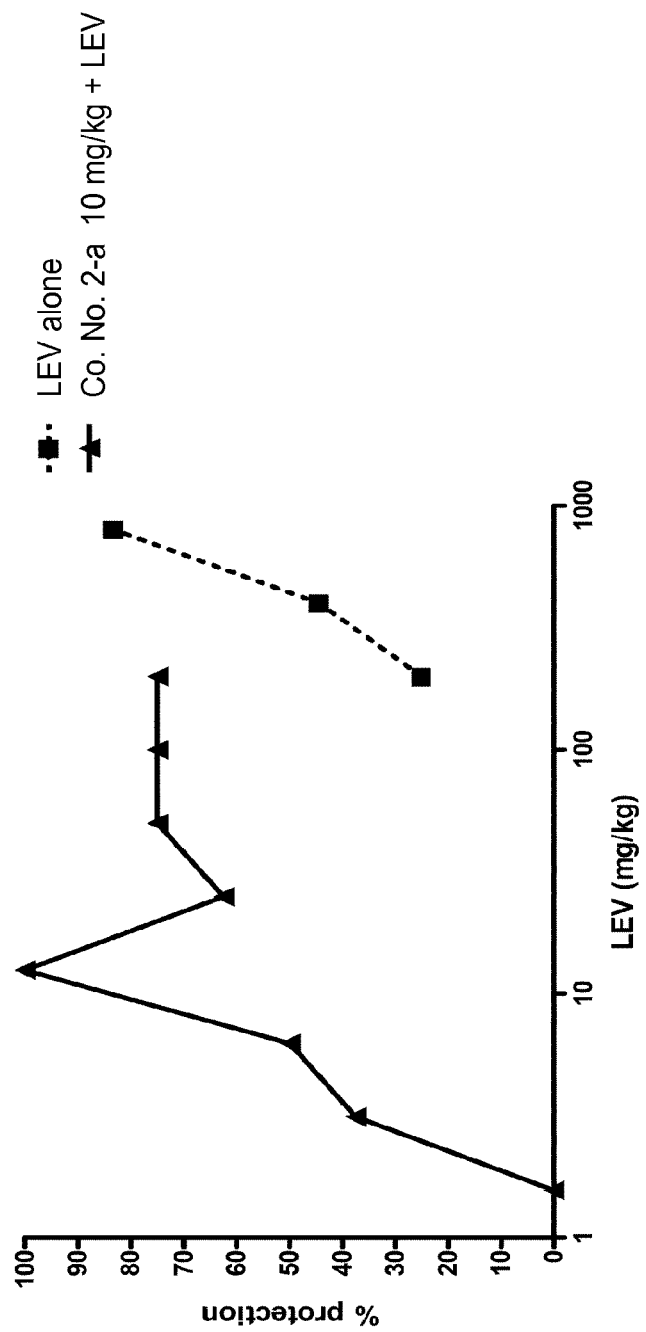

FIG. 4: Combination Studies for Co. No. 2-a with levetiracetam (LEV) in the 6 Hz Assay (44 mA). At a dose of 10 mg/kg s.c., Co. No. 2-a increases the potency of LEV, leading to an approximate 35-fold shift in the $ED_{50}$. This suggests a positive pharmacodynamic relationship.

Figure 5:
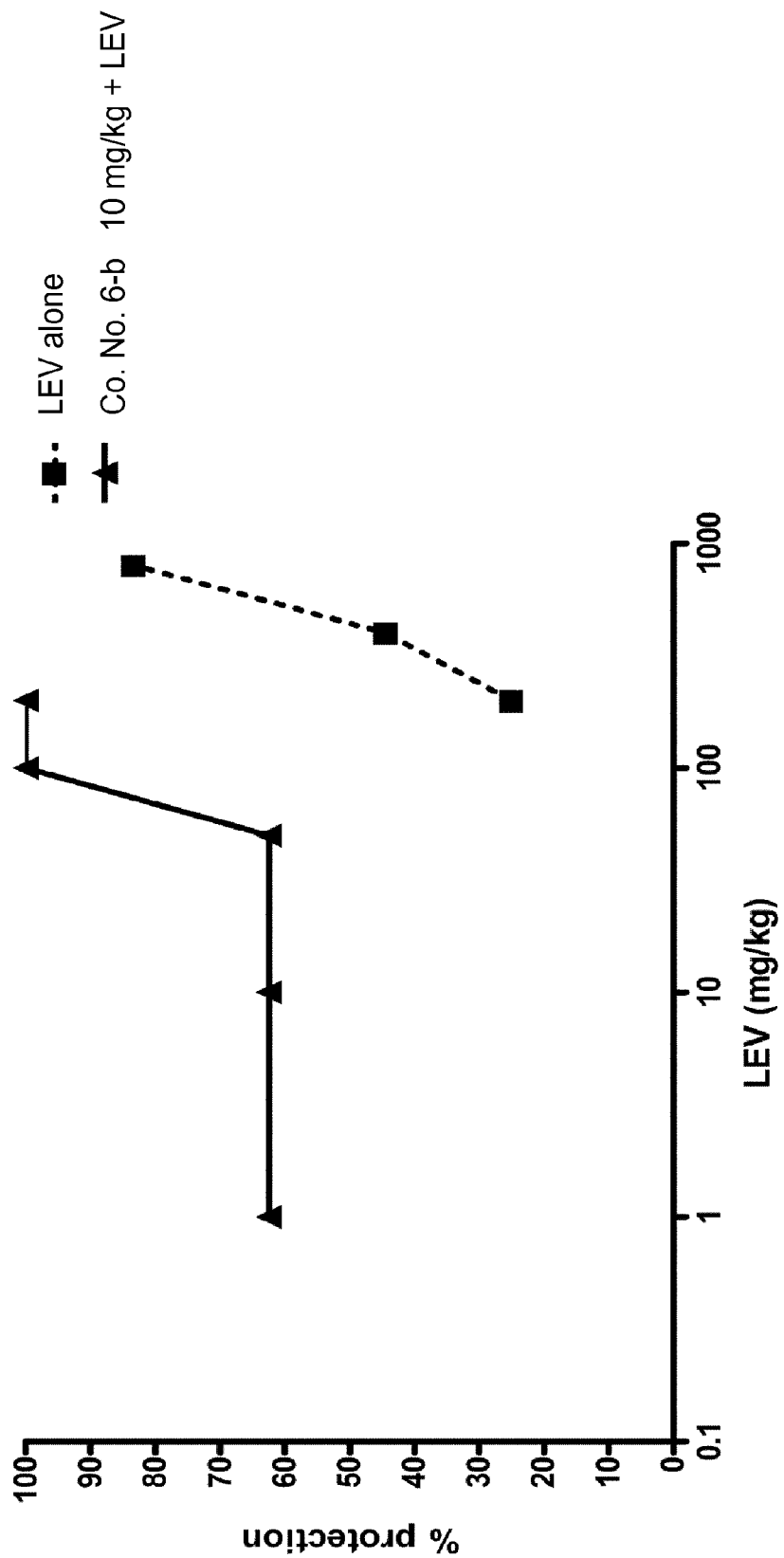

FIG. 5: Combination Studies for Co. No. 6-b with levetiracetam (LEV) in the 6 Hz Assay (44 mA). At a dose of 10 mg/kg p.o., Co. No. 6-b increases the potency of LEV, leading to an approximate 100-fold shift in the $ED_{50}$. This suggests a positive pharmacodynamic relationship.

Figure 6:
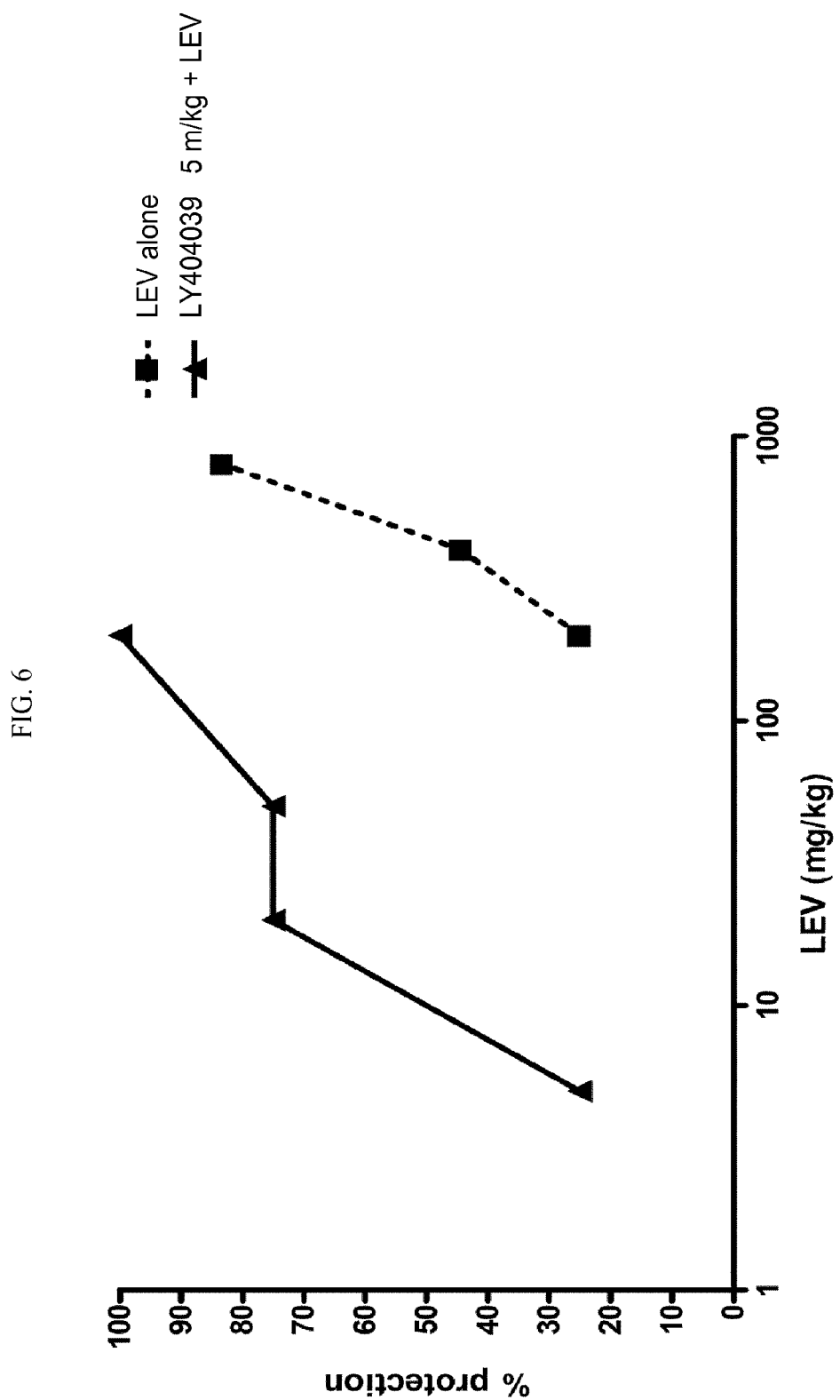

FIG. 6: Combination Studies for LY-404039 with levetiracetam (LEV) in the 6 Hz Assay (44 mA). At a dose of 5 mg/kg s.c., LY-404039 increases the potency of LEV, leading to an approximate 27-fold shift in the $ED_{50}$. This suggests a positive pharmacodynamic relationship.

DESCRIPTION OF THE INVENTION

The present invention relates to a combination comprising
(a) a synaptic vesicle protein 2A ("SV2A") ligand; and
(b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof.

In a particular embodiment, the invention as described herein relates to a pharmaceutical combination, in particular a pharmaceutical combination product, comprising
(a) a synaptic vesicle protein 2A ("SV2A") ligand; and
(b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof; and
(c) at least one pharmaceutically acceptable carrier.

In a further embodiment, the invention relates to the combination described herein for use as a medicament.

A further embodiment of this invention relates to the use of the combination described herein for the manufacture of a medicament or a pharmaceutical product for the treatment or prevention of epilepsy and related disorders; neuropathic pain; migraine or resistant headache and bipolar and related disorders.

A further embodiment of this invention relates to the use of the combination described herein for the manufacture of a medicament or a pharmaceutical product for neuroprotection.

A further embodiment of this invention relates to the use of the combination described herein for the manufacture of a medicament or a pharmaceutical product for the prevention of epileptogenesis.

A further embodiment relates to the treatment or prevention of epilepsy and related disorders; neuropathic pain; migraine or resistant headache; and bipolar and related disorders of a subject comprising administering concurrently or sequentially to the subject in need thereof a synaptic vesicle protein 2A ("SV2A") ligand; and a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof, in amounts that would be therapeutically effective when the SV2A ligand and mGluR2 compound are administered together.

A further embodiment relates to a combination as described herein for neuroprotection; or to a combination as described herein for use in neuroprotection.

A further embodiment relates to a combination as described herein for the prevention of epileptogenesis; or to a combination as described herein for use in the prevention of epileptogenesis.

In a further embodiment the invention relates to a method of treating or preventing epilepsy and related disorders; neuropathic pain; migraine or resistant headache; bipolar and related disorders in patients comprising administering a fixed dose combination of
(a) a synaptic vesicle protein 2A ("SV2A") ligand; and
(b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof, in amounts that would be therapeutically effective when the SV2A ligand and mGluR2 compound are administered together.

In a further embodiment the invention relates to a method of neuroprotection with a combination as defined herein.

In a further embodiment the invention relates to a method of anti-epileptogenesis with a combination as defined herein.

A further embodiment relates to a method for the treatment or prevention of epilepsy and related disorders; neuropathic pain; migraine or resistant headache; bipolar and related disorders said method comprising administering a therapeutically effective amount of a combination or a combination product comprising
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
to a subject in need thereof, such as a warm-blooded animal, in particular a human.

A further embodiment relates to a method of neuroprotection, said method comprising administering a therapeutically effective amount of a combination or a combination product comprising
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
to a subject in need thereof, such as a warm-blooded animal, in particular a human.

A further embodiment relates to a method of anti-epileptogenesis, said method comprising administering a therapeutically effective amount of a combination or a combination product comprising
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
to a subject in need thereof, such as a warm-blooded animal, in particular a human.

In an additional embodiment, the present invention relates to a pharmaceutical product or a commercial package comprising a combination according to the invention as described herein, in particular together with instructions, for simultaneous, separate or sequential use thereof in the treatment or prevention of epilepsy and related disorders; neuropathic pain; migraine or resistant headache bipolar; and related disorders.

In an additional embodiment, the present invention relates to a pharmaceutical product or a commercial package comprising a combination according to the invention as described herein, in particular together with instructions, for simultaneous, separate or sequential use thereof in neuroprotection.

In an additional embodiment, the present invention relates to a pharmaceutical product or a commercial package comprising a combination according to the invention as described herein, in particular together with instructions, for simultaneous, separate or sequential use thereof in anti-epileptogenesis.

In a further embodiment the invention relates to a combination comprising a quantity which is jointly therapeutically effective against epilepsy and related disorders; neuropathic pain; migraine or resistant headache; bipolar and related disorders; of
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
   and at least one pharmaceutically acceptable carrier.

In a further embodiment the invention relates to a combination comprising a quantity which is jointly therapeutically effective as neuroprotectant, of
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
   and at least one pharmaceutically acceptable carrier.

In a further embodiment the invention relates to a combination comprising a quantity which is jointly therapeutically effective in the prevention of epileptogenesis, of
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
   and at least one pharmaceutically acceptable carrier.

In a further embodiment, the invention relates to the use of
   (a) a synaptic vesicle protein 2A ("SV2A") ligand; and
   (b) a positive allosteric modulator ("PAM") of metabotropic glutamatergic receptor subtype 2 ("mGluR2") compound or a pharmaceutically acceptable salt or a solvate thereof, or an orthosteric agonist of metabotropic glutamatergic receptor subtype 2 compound or a pharmaceutically acceptable salt or a solvate thereof,
   for the preparation of a combination product according to the present invention.

The (b) components of the combination of the invention are in general referred to herein as "mGluR2 compounds" or "mGluR2 PAM/agonist compounds", or "positive allosteric modulator of mGluR2/mGluR2 orthosteric agonist compound" meaning that the compounds have mainly activity at the metabotropic glutamatergic receptor subtype 2, and are in particular selected from positive allosteric modulators (PAMs) of metabotropic glutamatergic receptor subtype 2, and orthosteric agonists of metabotropic glutamatergic receptor subtype 2. A skilled person will be familiar with the large homology of mGluR2 and mGluR3, due to which some mGluR2 orthosteric agonists also display activity as mGluR3 orthosteric agonists. Such is the case for example, of (−)-(1R,4S,5S,6S)-4-amino-2-sulfonylbicyclo[3.1.0]-hexane-4,6-dicarboxylic acid (also known as LY-404,039 [CAS 635318-11-5]), with a $K_i$=149 nM (mGlu2 receptor) and $K_i$=92 nM (mGlu3 receptor), 100-fold selectivity for mGlu2 and mGlu3 over mGlu4a, -6, -7a, and -8a, and no activity at mGlu1a and mGlu5a (Rorick-Kehn et al. (2007) The Journal of Pharmacology and Experimental Therapeutics Vol. 321, No. 1, pp. 308-317). The term "mGluR2 compounds" or "mGluR2 PAM/agonist compounds", or "positive allosteric modulator of mGluR2/mGluR2 orthosteric agonist compound" does therefore not exclude compounds displaying some other additional minor activity in vitro or in vivo.

The mGluR2 PAM compounds of the combination of the invention are in particular selected from those disclosed in WO2010/130424. A particular subgroup of said compounds disclosed in WO2010/130424 can be defined by the following Formula (I)

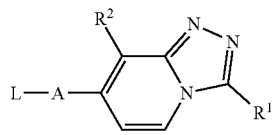

(I)

or a stereoisomeric form thereof, wherein
$R^1$ is selected from the group consisting of $(C_{3-7}cycloalkyl)C_{1-3}alkyl$-, mono- or polyhalo$C_{1-4}$alkyl, and $(C_{1-4}alkyl)$—O—$(C_{1-4}alkyl)$;
$R^2$ is halo or polyhalo$C_{1-4}$alkyl;
A is a covalent bond or a —$CH_2$—;
L is selected from the radicals (a), (b) and (c):

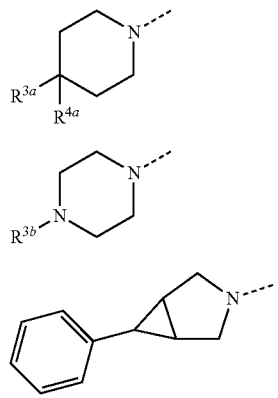

(a)

(b)

(c)

wherein
$R^{3a}$ is selected from unsubstituted phenyl or phenyl substituted with 1 or 2 halo substituents;
$R^{4a}$ is selected from the group of hydrogen, $C_{1-3}$alkyl and halo;
or $R^{3a}$—C—$R^{4a}$ together represent a radical of formula (a-1)

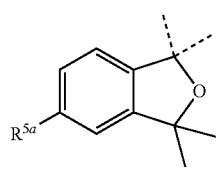

(a-1)

wherein $R^{5a}$ is hydrogen or halo;

$R^{3b}$ is selected from the group of phenyl substituted with 1 or 2 halo substituents, pyridinyl substituted with 1 or 2 halo substituents, unsubstituted pyrimidinyl and pyrimidinyl substituted with 1 or 2 $C_{1-3}$alkyloxy substituents;

or a pharmaceutically acceptable salt or a solvate thereof.

Thus, according to a particular embodiment of the invention, the positive allosteric modulator ("PAM") of metabotropic glutamatergic receptor subtype 2 ("mGluR2") compound is a compound of Formula (I) as defined herein.

In a particular embodiment, the compounds of Formula (I) are as defined herein wherein $R^1$ is selected from the group consisting of cyclopropylmethyl-, 2,2,2-trifluoroethyl, and $CH_3$—O—$CH_2$—;

$R^2$ is chloro or $CF_3$;

A is a covalent bond or a —$CH_2$—;

L is selected from the radicals (a), (b) and (c):

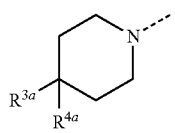

(a)

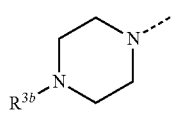

(b)

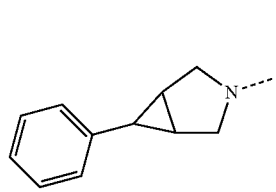

(c)

wherein $R^{3a}$ is selected from unsubstituted phenyl or phenyl substituted with 1 or 2 fluoro substituents;

$R^{4a}$ is selected from the group of hydrogen, methyl and fluoro;

or $R^{3a}$—C—$R^{4a}$ together represent a radical of formula (a-1)

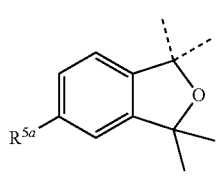

(a-1)

wherein $R^{5a}$ is hydrogen or fluoro;

$R^{3b}$ is selected from the group of phenyl substituted with 1 or 2 fluoro substituents, pyridinyl substituted with 1 or 2 fluoro substituents, unsubstituted pyrimidinyl and pyrimidinyl substituted with 1 or 2 methoxy substituents;

or a pharmaceutically acceptable salt or a solvate thereof.

In a particular embodiment, the compounds of Formula (I) are as defined herein wherein (i) when A is CH$_2$; and R$^2$ is trifluoromethyl; then
R$^1$ is cyclopropylmethyl-; and
L is selected from

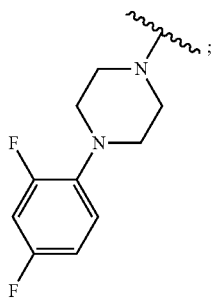 (L-a)

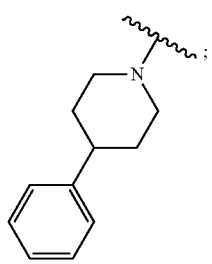 (L-b)

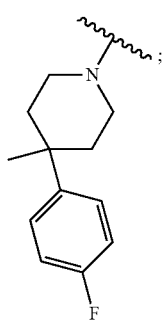 (L-c)

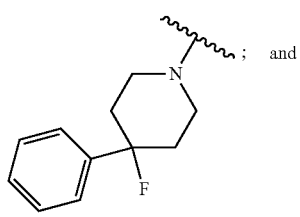 (L-d) and

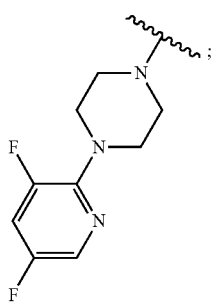 (L-e)

(ii) when A is CH$_2$; and R$^2$ is chloro; then
R$^1$ is cyclopropylmethyl-; and
L is

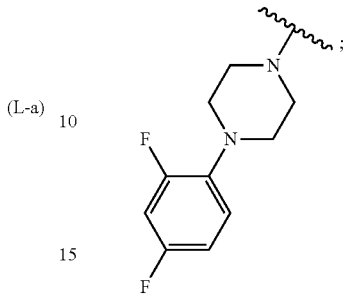 (L-a)

(iii) when A is a covalent bond; and R$^2$ is trifluoromethyl; then
R$^1$ is cyclopropylmethyl; and
L is selected from

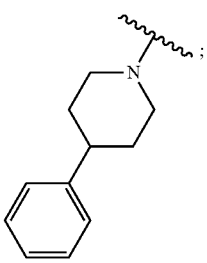 (L-b)

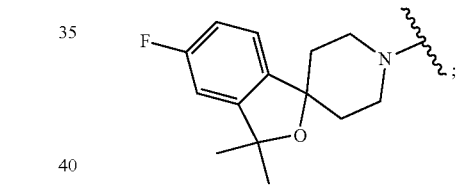 (L-e)

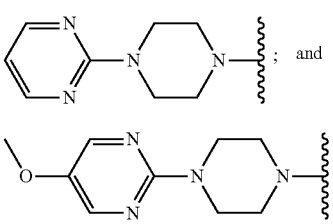 (L-f) and (L-g)

(iv) when A is a covalent bond and R$^2$ is Cl; then
(iv-a) R$^1$ is cyclopropylmethyl and L is

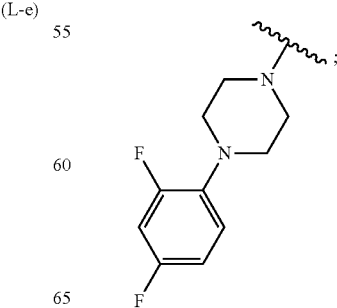 (L-a)

or (iv-b) R¹ is 2,2,2-trifluoroethyl and L is selected from (L-d)

(L-h)

(v) when A is $CH_2$ and R¹ is —$CH_2$—O—$CH_3$; then R² is —$CF_3$ and L is (L-i)

rac-(2aα, 3α, 3aα)

or a pharmaceutically acceptable salt or a solvate thereof.

The compounds of Formula (I) are disclosed in WO2010/130424 and may be prepared according to the processes described therein, which are hereby incorporated by reference in their totality.

Particular compounds of Formula (I) include

Co. No. 1 or a hydrochloride salt thereof (Co. No. 1a)

Co. No. 2 or a hydrochloride salt thereof (•HCl) (Co. No. 2a)

Co. No. 3

Co. No. 4

Co. No. 5

Co. No. 6 or a hydrochloride salt thereof (Co. No. 6a)

Co. No. 7

Co. No. 8

-continued

Co. No. 9

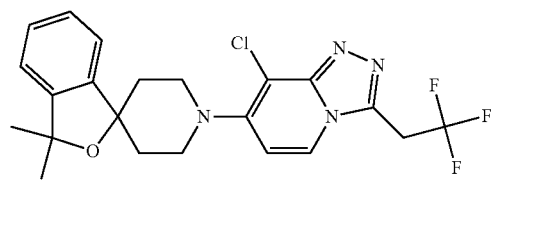

Co. No. 10

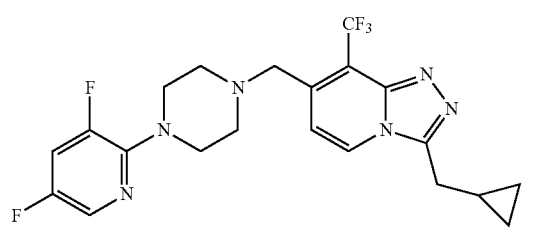

Co. No. 11

Co. No. 12

Co. No. 13

Co. No. 14

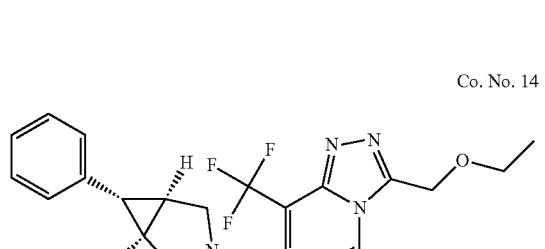

rac - (2aα, 3a, 3aα)

In an embodiment of the invention, the compound of Formula (I) is

Co. No. 1

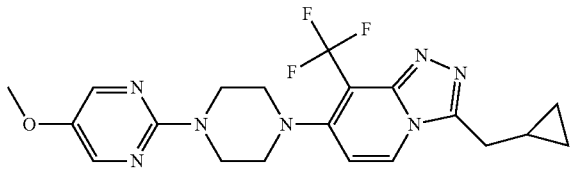

or a pharmaceutically acceptable salt thereof, preferably a hydrochloride salt thereof.

In an additional embodiment of the invention, the compound of Formula (I) is

Co. No. 2

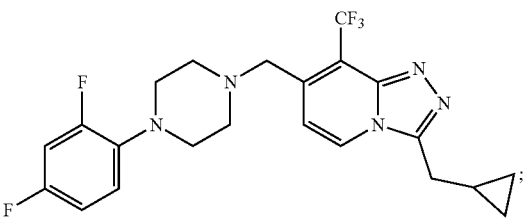

or a pharmaceutically acceptable salt thereof, preferably a hydrochloride salt thereof (.HCl).

The mGluR2 PAM compounds of the combination of the invention are also in particular selected from those disclosed in WO2009/033704. Said compounds disclosed in WO2009/033704 can be defined by the following Formula (I-A)

(I-A)

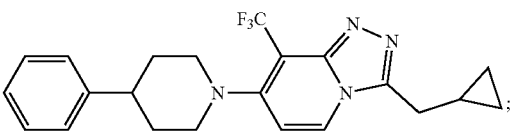

and the stereochemically isomeric forms thereof, wherein
$R^1$ is $C_{1-6}$alkyl; or $C_{1-3}$alkyl substituted with $C_{3-7}$cycloalkyl, phenyl, or phenyl substituted with halo, trifluoromethyl or trifluoromethoxy;
$R^2$ is halo, trifluoromethyl, $C_{1-3}$alkyl or cyclopropyl;
$R^3$ is hydrogen, fluoro, hydroxyl, hydroxyC$_{1-3}$alkyl, hydroxyC$_{1-3}$alkyloxy, fluoroC$_{1-3}$alkyl, fluoroC$_{1-3}$alkyloxy or cyano; and
Ar is unsubstituted phenyl; or phenyl substituted with n radicals $R^4$, wherein n is 1, 2 or 3;
$R^4$ is selected from the group consisting of hydrogen, halo, $C_{1-3}$alkyl, hydroxyC$_{1-3}$alkyl, polyhaloC$_{1-3}$alkyl, cyano, hydroxyl, amino, carboxyl, $C_{1-3}$alkyloxyC$_{1-3}$alkyl, $C_{1-3}$alkyloxy, polyhaloC$_{1-3}$alkyloxy, $C_{1-3}$alkylcarbonyl, mono- and di($C_{1-3}$alkyl)amino, and morpholinyl; or
two vicinal $R^4$ radicals taken together form a bivalent radical of formula —N=CH—NH—  (i), —CH=CH—NH—  (ii), or —O—CH$_2$—CH$_2$—NH—  (iii); or R³ and a R⁴ radical in ortho position taken together form a bivalent radical of formula —CH₂—O—  (iv), or —O—CH₂—  (v);

and the pharmaceutically acceptable salts and the solvates thereof.

In a particular embodiment, the compounds of Formula (I-A) are as defined herein wherein R¹ is $C_{1-6}$alkyl; or $C_{1-3}$alkyl substituted with $C_{3-7}$cycloalkyl, phenyl, or phenyl substituted with halo, trifluoromethyl or trifluoromethoxy;

R² is halo, trifluoromethyl, $C_{1-3}$alkyl or cyclopropyl;

R³ is hydrogen, fluoro, hydroxyl, hydroxy$C_{1-3}$alkyl, hydroxy$C_{1-3}$alkyloxy, fluoro$C_{1-3}$alkyl, fluoro$C_{1-3}$alkyloxy or cyano; and Ar is unsubstituted phenyl, or phenyl substituted with n radicals R⁴, wherein n is 1, 2 or 3;

R⁴ is selected from the group consisting of hydrogen, halo, $C_{1-3}$alkyl, hydroxy$C_{1-3}$alkyl, polyhalo$C_{1-3}$alkyl, cyano, hydroxyl, amino, carboxyl, $C_{1-3}$alkyloxy$C_{1-3}$alkyl, $C_{1-3}$alkyloxy, polyhalo$C_{1-3}$alkyloxy; $C_{1-3}$alkylcarbonyl, mono- and di($C_{1-3}$alkyl)amino, and morpholinyl; or two vicinal R⁴ radicals taken together form a bivalent radical of formula —N=CH—NH—  (i), —CH=CH—NH—  (ii), or —O—CH₂—CH₂—NH—  (iii);

and the pharmaceutically acceptable salts and solvates thereof.

In a particular embodiment, the compounds of Formula (I-A) are as defined herein wherein R¹ is $C_{1-6}$alkyl; or $C_{1-3}$alkyl substituted with $C_{3-7}$cycloalkyl, phenyl or phenyl substituted with halo, trifluoromethyl or trifluoromethoxy;

R² is halo, trifluoromethyl, $C_{1-3}$alkyl or cyclopropyl;

R³ is hydrogen, fluoro, hydroxyl, hydroxy$C_{1-3}$alkyl, hydroxy$C_{1-3}$alkyloxy, fluoro$C_{1-3}$alkyl, fluoro$C_{1-3}$alkyloxy or cyano; and Ar is unsubstituted phenyl;

and the pharmaceutically acceptable salts and solvates thereof.

In an additional embodiment, the compounds of Formula (I-A) are as defined herein wherein R¹ is 1-butyl, 2-methyl-1-propyl, 3-methyl-1-butyl, (cyclopropyl)methyl or 2-(cyclopropyl)-3-ethyl;

R³ is hydrogen, fluoro or cyano; and

Ar is unsubstituted phenyl;

and the pharmaceutically acceptable salts and solvates thereof.

In an additional embodiment, the compounds of Formula (I-A) are as defined herein wherein R¹ is 1-butyl, 3-methyl-1-butyl, (cyclopropyl)methyl or 2-(cyclopropyl)-1-ethyl;

R² is chloro;

R³ is hydrogen or fluoro; and

Ar is unsubstituted phenyl;

and the pharmaceutically acceptable salts and the solvates thereof.

In a further embodiment, the compounds of Formula (I-A) are as defined herein wherein R¹ is $C_{1-6}$alkyl; or $C_{1-3}$alkyl substituted with $C_{3-7}$cycloalkyl, phenyl, or phenyl substituted with halo, trifluoromethyl or trifluoromethoxy;

R² is halo, trifluoromethyl, $C_{1-3}$alkyl or cyclopropyl;

R³ is hydrogen, fluoro, hydroxyl, hydroxy$C_{1-3}$alkyl, hydroxy$C_{1-3}$alkyloxy, fluoro$C_{1-3}$alkyl, fluoro$C_{1-3}$alkyloxy or cyano; and Ar is phenyl substituted with n radicals R⁴, wherein n is 1, 2, or 3;

R⁴ is selected from the group consisting of halo, $C_{1-3}$alkyl, hydroxy$C_{1-3}$alkyl, $C_{1-3}$alkyloxy, polyhalo$C_{1-3}$alkyloxy, $C_{1-3}$alkylcarbonyl, mono- and di($C_{1-3}$alkyl)amino, and morpholinyl; or two vicinal R⁴ radicals taken together form a bivalent radical of formula —N=CH—NH—  (i), —CH=CH—NH—  (ii), or —O—CH₂—CH₂—NH—  (iii); or R³ and a R⁴ radical in ortho position taken together form a bivalent radical of formula —CH₂—O—  (iv),

—O—CH₂—  (V);

and the pharmaceutically acceptable salts and solvates thereof.

In an additional embodiment, the compounds of Formula (I-A) are as defined herein wherein R¹ is 1-butyl, 2-methyl-1-propyl, 3-methyl-1-butyl, (cyclopropyl)methyl or 2-(cyclopropyl)-1-ethyl;

R³ is hydrogen, fluoro or cyano; and

Ar is phenyl substituted with halo, trifluoromethyl, morpholinyl or hydroxy$C_{1-3}$alkyl;

and the pharmaceutically acceptable salts and solvates thereof.

In an additional embodiment, the compounds of Formula (I-A) are as defined herein wherein R¹ is 1-butyl, 3-methyl-1-butyl, (cyclopropyl)methyl or 2-(cyclopropyl)-1-ethyl;

R² is chloro;

R³ is hydrogen or fluoro; and

Ar is phenyl substituted with at least one halo group;

and the pharmaceutically acceptable salts and solvates thereof.

In an additional embodiment, the compounds of Formula (I-A) are as defined herein wherein R¹ is 1-butyl, 3-methyl-1-butyl, (cyclopropyl)methyl or 2-(cyclopropyl)-1-ethyl;

R² is chloro;

R³ is hydrogen or fluoro; and

Ar is phenyl substituted with at least two fluoro groups;

and the pharmaceutically acceptable salts and solvates thereof.

The compounds of Formula (I-A) are disclosed in WO2009/033704 and may be prepared according to the processes described therein, which are hereby incorporated by reference in their totality.

Particular compounds of Formula (I-A) include

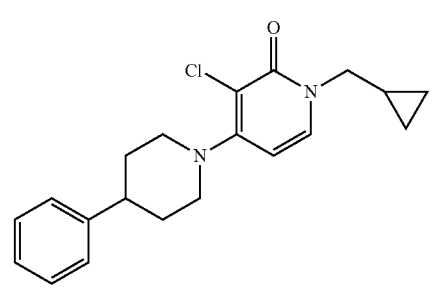

Co. No. 1-a

Co. No. 2-a
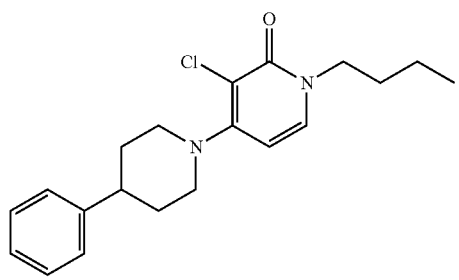
Co. No. 3-a
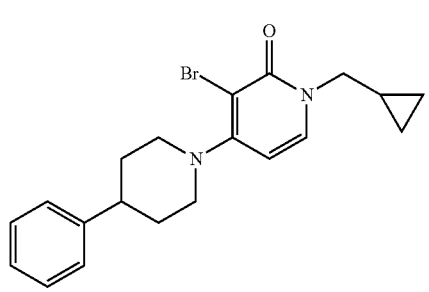
Co. No. 4-a
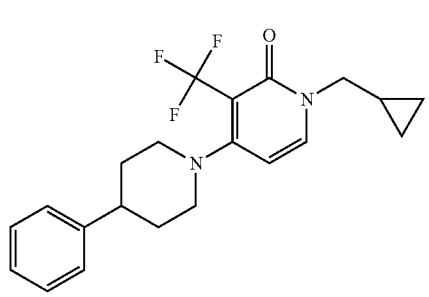
Co. No. 5-a
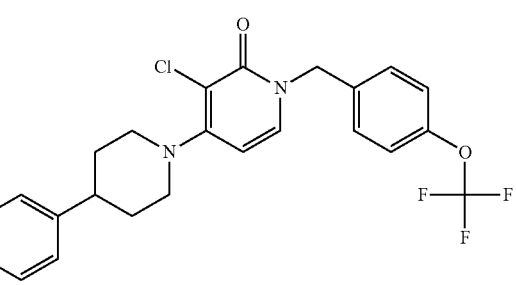
Co. No. 6-a
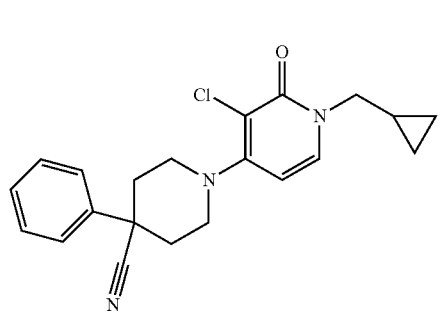
Co. No. 7-a
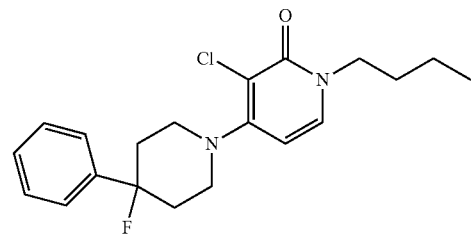
Co. No. 8-a
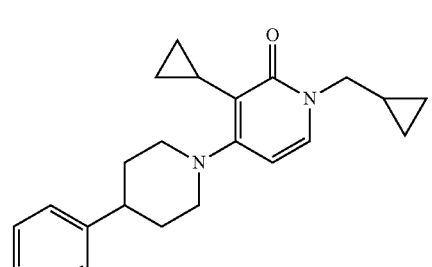
Co. No. 9-a
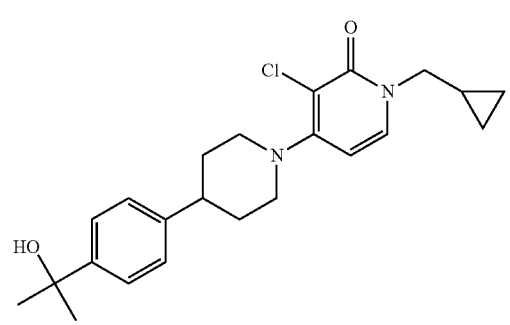
Co. No. 10-a
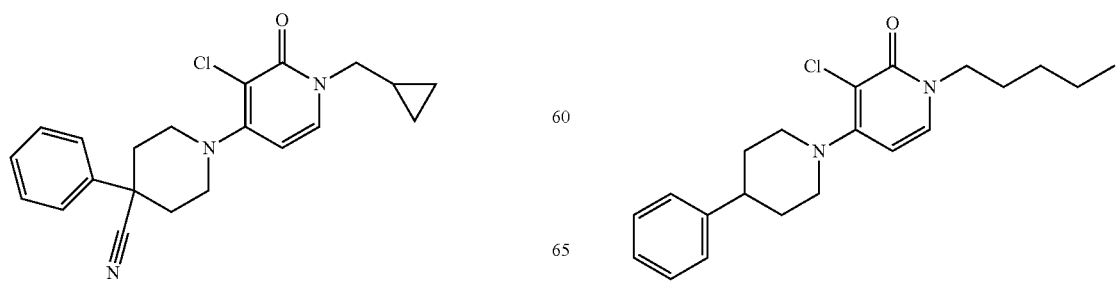
Co. No. 11-a
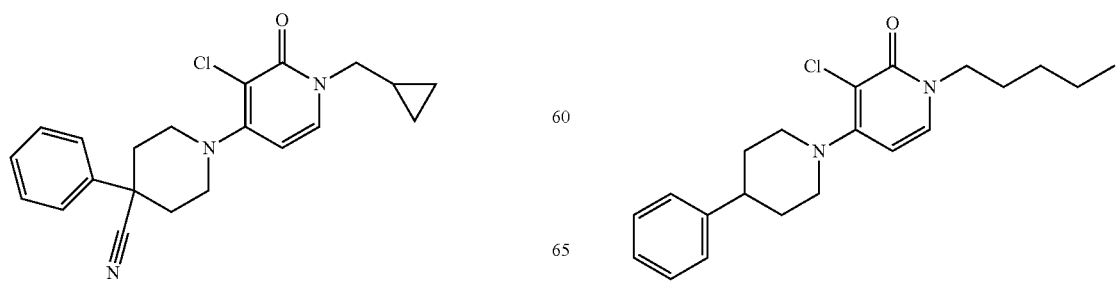

Co. No. 12-a
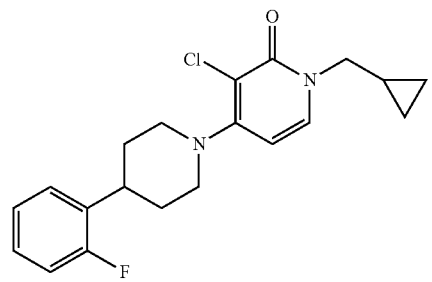
Co. No. 13-a
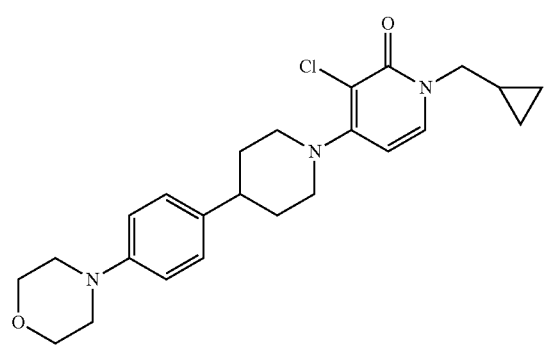
Co. No. 14-a
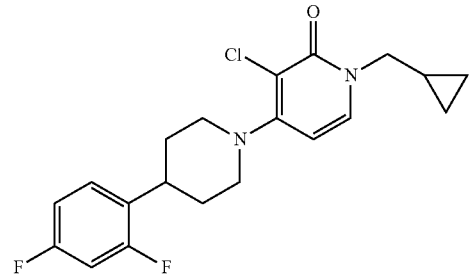
Co. No. 15-a
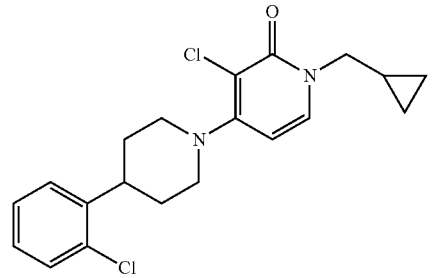
Co. No. 16-a
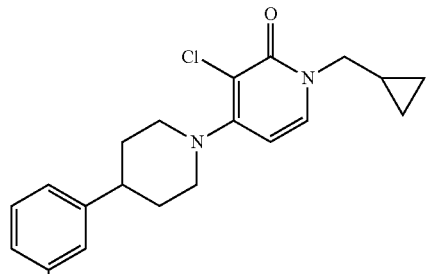
Co. No. 17-a
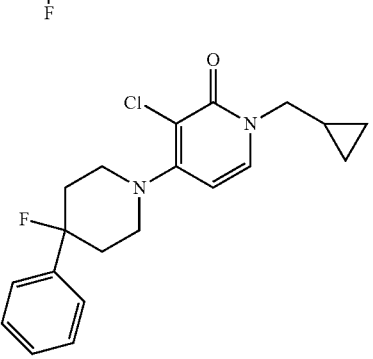
Co. No. 18-a
Co. No. 19-a
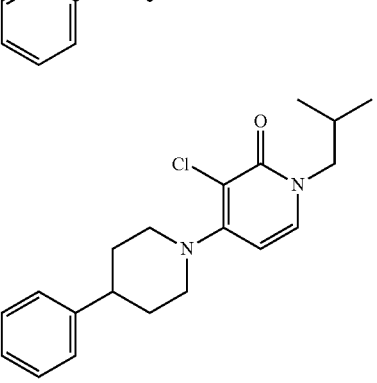
Co. No. 20-a
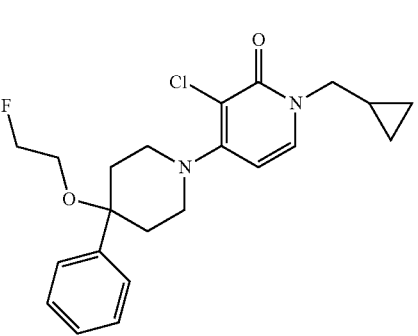

-continued
Co. No. 21-a
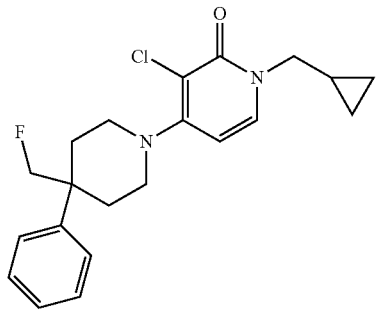
Co. No. 22-a
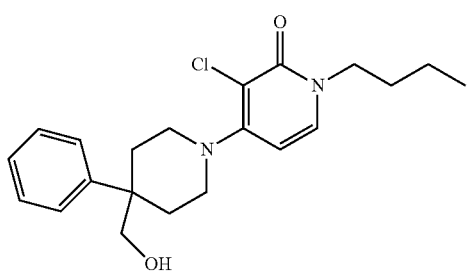
Co. No. 23-a
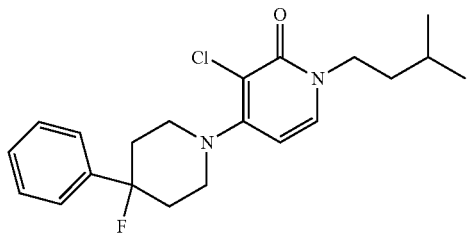
Co. No. 24-a
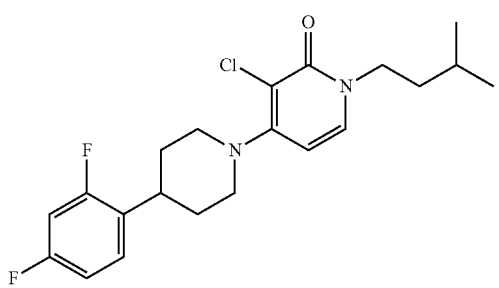
Co. No. 25-a
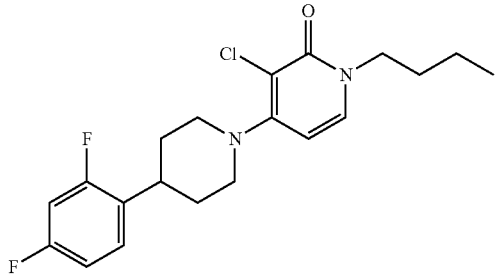
-continued
Co. No. 26-a
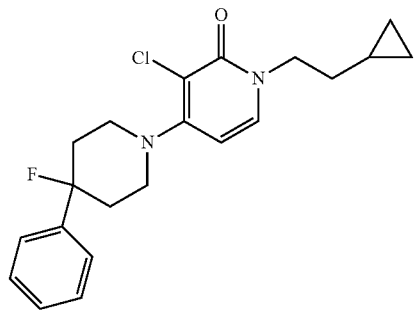
Co. No. 27-a
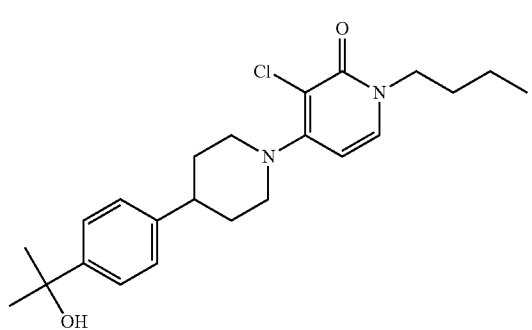
Co. No. 28-a
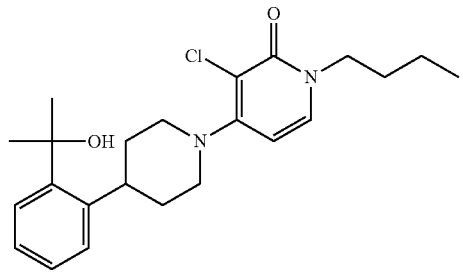
Co. No. 29-a
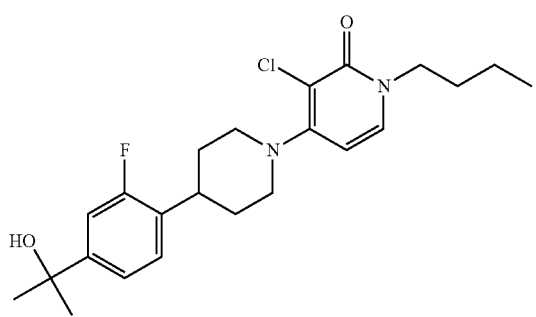
Co. No. 30-a
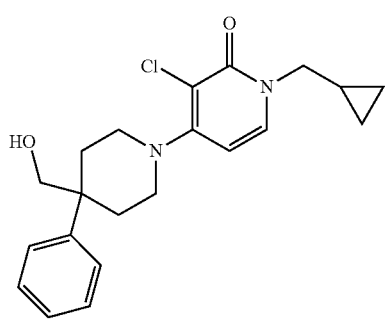

Co. No. 31-a

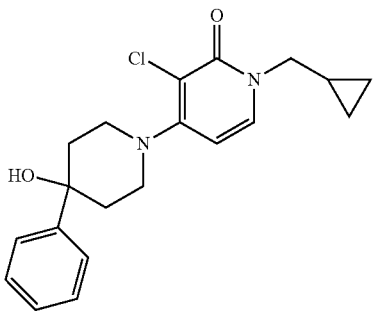

Co. No. 32-a

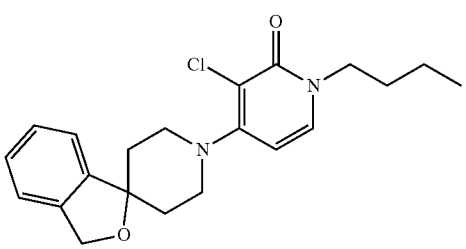

Co. No. 33-a

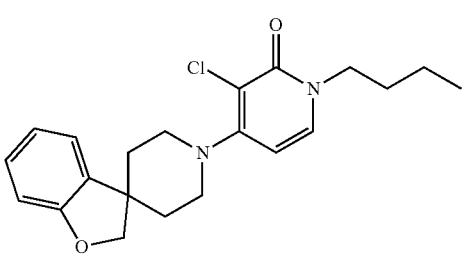

and the pharmaceutically acceptable salts and the solvates thereof.

In an embodiment of the invention, the compound of Formula (I-A) is

Co. No. 2-a

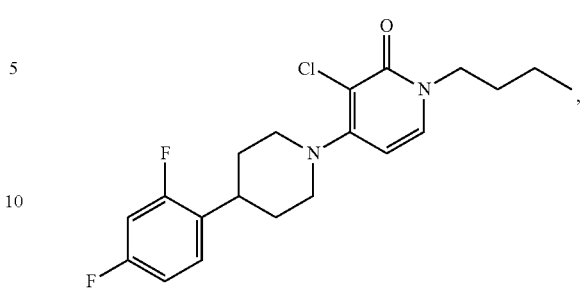

or

Co. No. 25-a or a pharmaceutically acceptable salt or a solvate thereof.

The mGluR2 PAM compounds of the combination of the invention are also in particular selected from those disclosed in PCT/EP2014/068676. Said compounds disclosed in PCT/EP2014/068676 can be defined by the following Formula (I-B)

(I-B)

and the stereochemically isomeric forms thereof, wherein
R$^1$ is selected from the group consisting of C$_{1-6}$alkyl, (C$_{3-8}$cycloalkyl)C$_{1-3}$alkyl, and (C$_{1-3}$alkyloxy)C$_{1-3}$alkyl;

each R$^2$ is independently selected from F, Cl, C$_{1-3}$alkyl, C$_{1-3}$alkyloxy, mono- or polyhaloC$_{1-3}$alkyl, and mono- or polyhaloC$_{1-3}$alkyloxy;

n is an integer selected from 1, 2, and 3;
and the pharmaceutically acceptable salts and the solvates thereof.

The mGluR2 PAM compounds of the combination of the invention are in particular selected from compounds of Formula (I-B) as defined hereinabove, and stereoisomeric forms thereof, wherein R$^1$ is selected from the group consisting of CH$_3$CH$_2$, CH$_3$CH$_2$CH$_2$, (cyclopropyl)methyl, (cyclobutyl)methyl, ethyloxymethyl and methyloxymethyl; and the rest of variables are as defined herein; and the pharmaceutically acceptable salts and the solvates thereof.

In a further embodiment, the mGluR2 PAM compounds of the combination of the invention are in particular selected from compounds of Formula (I-B) as defined hereinabove, and stereoisomeric forms thereof, wherein R$^1$ is selected from the group consisting of CH$_3$CH$_2$, (cyclopropyl)methyl, (cyclobutyl)methyl and methyloxymethyl; and the rest of variables are as defined herein; and the pharmaceutically acceptable salts and the solvates thereof.

In a further embodiment, the mGluR2 PAM compounds of the combination of the invention are in particular selected from compounds of Formula (I-B) as defined hereinabove, and stereoisomeric forms thereof, wherein R$^1$ is selected from the group consisting of CH$_3$CH$_2$, (cyclopropyl)methyl, (cyclobutyl)methyl and ethyloxymethyl; and the rest of variables are as defined herein; and the pharmaceutically acceptable salts and the solvates thereof.

Thus, according to a particular embodiment of the invention, the positive allosteric modulator ("PAM") of metabotropic glutamatergic receptor subtype 2 ("mGluR2") compound is a compound of Formula (I-B) as defined herein.

In an additional embodiment, the compounds of Formula (I-B) are as defined herein, wherein
each $R^2$ is independently selected from F, Cl, $CH_3$, $CH_3O$ and $CF_3$; and the pharmaceutically acceptable salts and the solvates thereof.

In a further embodiment, the compounds of Formula (I-B) are as defined herein having the Formula (I—Ba)

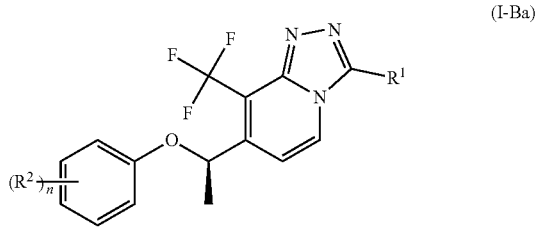

(I-Ba)

wherein the variables are as defined in Formula (I-B) herein, and the pharmaceutically acceptable salts and the solvates thereof.

In a further embodiment, the compounds of Formula (I-B) are as defined herein having the Formula (I-Bb)

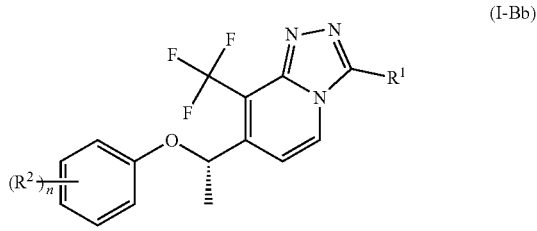

(I-Bb)

wherein the variables are as defined in Formula (I-B) herein, and the pharmaceutically acceptable salts and the solvates thereof.

Particular compounds of formula (I-B) include
3-(Cyclopropylmethyl)-7-[1-(4-fluorophenoxy)ethyl]-8-(trifluoromethyl)[1,2,4]triazolo-[4,3-a]pyridine;
3-(Cyclopropylmethyl)-7-[(1*R)-1-(4-fluorophenoxy) ethyl]-8-(trifluoromethyl) [1,2,4]triazolo[4,3-a]pyridine;
3-(Cyclopropylmethyl)-7-[(1*S)-1-(4-fluorophenoxy) ethyl]-8-(trifluoromethyl)[1,2,4]triazolo[4,3-a]pyridine;
3-(Cyclopropylmethyl)-7-[(1S)-1-(2,4-difluorophenoxy) ethyl]-8-(trifluoromethyl) [1,2,4]triazolo[4,3-a]pyridine;
3-(Cyclopropylmethyl)-7-[(1R)-1-(2,4-difluorophenoxy) ethyl]-8-(trifluoromethyl)[1,2,4]triazolo[4,3-a]pyridine;
3-(Cyclopropylmethyl)-7-[1-(2,4-difluorophenoxy)ethyl]-8-(trifluoromethyl)[1,2,4]triazolo-[4,3-a]pyridine;
3-(Cyclopropylmethyl)-7-[(1S)-1-(3,5-difluorophenoxy) ethyl]-8-(trifluoromethyl)[1,2,4]triazolo[4,3-a]pyridine;
3-(Cyclopropylmethyl)-7-[(1S)-1-(3,4-difluorophenoxy) ethyl]-8-(trifluoromethyl)[1,2,4]triazolo[4,3-a]pyridine;
3-(Cyclopropylmethyl)-7-[(1S)-1-(2,3-difluorophenoxy) ethyl]-8-(trifluoromethyl)[1,2,4]triazolo[4,3-a]pyridine;
3-(Cyclopropylmethyl)-7-[(1S)-1-(2,5-difluorophenoxy) ethyl]-8-(trifluoromethyl)[1,2,4]triazolo[4,3-a]pyridine;
3-(Cyclopropylmethyl)-7-[(1S)-1-(2,6-difluorophenoxy) ethyl]-8-(trifluoromethyl)[1,2,4]triazolo[4,3-a]pyridine;
3-(Cyclopropylmethyl)-7-[(1S)-1-(4-fluoro-2-methoxyphenoxy)ethyl]-8-(trifluoromethyl)[1,2,4]triazolo[4,3-a]pyridine;
3-(Cyclobutylmethyl)-7-[1-(2,4-difluorophenoxy)ethyl]-8-(trifluoromethyl)[1,2,4]triazolo-[4,3-a]pyridine;
7-[(1S)-1-(2-Chloro-4-methylphenoxy)ethyl]-3-(cyclopropylmethyl)-8-(trifluoromethyl)[1,2,4]triazolo[4,3-a]pyridine;
3-(Cyclopropylmethyl)-7-[(1S)-1-(4-fluoro-2-methylphenoxy)ethyl]-8-(trifluoromethyl)[1,2,4]triazolo[4,3-a]pyridine;
3-(Cyclopropylmethyl)-8-(trifluoromethyl)-7-[(1S)-1-(2,4,6-trifluorophenoxy)ethyl][1,2,4]triazolo[4,3-a]pyridine;
7-[1-(2,4-Difluorophenoxy)ethyl]-3-(ethoxymethyl)-8-(trifluoromethyl)[1,2,4]triazolo-[4,3-a]pyridine;
3-Ethyl-8-(trifluoromethyl)-7-[1-(2,4,6-trifluorophenoxy) ethyl][1,2,4]triazolo[4,3-a]pyridine;
7-[1-(2,4-Difluorophenoxy)ethyl]-3-ethyl-8-(trifluoromethyl)[1,2,4]triazolo[4,3-a]pyridine;
3-(Cyclobutylmethyl)-7-[(1*R)-1-(2,4-difluorophenoxy) ethyl]-8-(trifluoromethyl) [1,2,4]triazolo[4,3-a]pyridine;
3-(Cyclobutylmethyl)-7-[(1*S)-1-(2,4-difluorophenoxy) ethyl]-8-(trifluoromethyl)[1,2,4]triazolo[4,3-a]pyridine;
3-(Ethoxymethyl)-8-(trifluoromethyl)-7-[(1*R)-1-(2,4,6-trifluorophenoxy)ethyl][1,2,4]triazolo[4,3-a]pyridine;
3-(Ethoxymethyl)-8-(trifluoromethyl)-7-[(1*S)-1-(2,4,6-trifluorophenoxy)ethyl][1,2,4]triazolo[4,3-a]pyridine;
7-[(1*S)-1-(2,4-Difluorophenoxy)ethyl]-3-(ethoxymethyl)-8-(trifluoromethyl) [1,2,4]triazolo[4,3-a]pyridine;
7-[(1*R)-1-(2,4-Difluorophenoxy)ethyl]-3-(ethoxymethyl)-8-(trifluoromethyl)[1,2,4]triazolo[4,3-a]pyridine;
7-[(1*R)-1-(2,4-Difluorophenoxy)ethyl]-3-ethyl-8-(trifluoromethyl) [1,2,4]triazolo-[4,3-a]pyridine;
7-[(1*S)-1-(2,4-Difluorophenoxy)ethyl]-3-ethyl-8-(trifluoromethyl)[1,2,4]triazolo-[4,3-a]pyridine;
7-[1-(2,4-Difluorophenoxy)ethyl]-3-propyl-8-(trifluoromethyl)[1,2,4]triazolo[4,3-a]pyridine;
3-Ethyl-8-(trifluoromethyl)-7-[(1*R)-1-(2,4,6-trifluorophenoxy)ethyl]-[1,2,4]triazolo-[4,3-a]pyridine;
3-Ethyl-8-(trifluoromethyl)-7-[(1*S)-1-(2,4,6-trifluorophenoxy)ethyl]-[1,2,4]triazolo-[4,3-a]pyridine;
7-[(1*R)-(2,4-difluorophenoxy)ethyl]-3-propyl-8-(trifluoromethyl)-[1,2,4]triazolo[4,3-a]pyridine; and
7-[(1*S)-(2,4-difluorophenoxy)ethyl]-3-propyl-8-(trifluoromethyl)-[1,2,4]triazolo[4,3-a]pyridine.

Included within the scope of this list are stereoisomeric forms, the pharmaceutically acceptable salts and the solvates thereof.

In an additional embodiment, the compound may be selected from
3-(Cyclopropylmethyl)-7-[(1S)-1-(2,4-difluorophenoxy) ethyl]-8-(trifluoromethyl)[1,2,4]triazolo[4,3-a]pyridine hydrochloride salt.

The orthosteric agonists of mGluR2/mGluR2/3 of the combination of the invention include, but are not limited to, for example, LY-404039; LY-2969822; LY-2934747; LY-379268; DCG-IV; LY-354740; LY-314582; LY-544344; LY-2140023; LY-181837; LY-389795; LY-446433; LY-450477; LY-395756; LY-566332; LY-541850; LY-2300559; LY-404040; LY-281223; LY-2979165; talaglumetad; MGS008; MGS0022; MGS0028; MGS0039; (−)-2-oxa-4-aminobicyclo[3.1.0]hexane-4,6-dicarboxylate; (+)-4-amino-2-sulfonylbicyclo[3.1.0]hexane-4,6-dicarboxylic acid; (+)-2-amino-4-fluorobicyclo-[3.1.0]hexane-2,6-dicarboxylic acid; 1 S,2R,5S,6S-2-amino-6-fluoro-4-oxobicyclo-[3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R,3R,5S,6S-2-amino-3-fluorobicyclo[3.1.0]hexane-2,6-dicarboxylic acid; 1S,2R,3S,5S, 6S-2-amino-6-fluoro-3-hydroxybicyclo[3.1.0]hexane-2,6-dicarboxylic acid; (+)-4-amino-2-sulfonylbicyclo-[3.1.0] hexane-4,6-dicarboxylic acid; (+)-2-amino-4-fluorobicyclo [3.1.0]hexane-2,6-dicarboxylic acid; 1S,2R,5S,6S-2-amino-6-fluoro-4-oxobicyclo[3.1.0]hexane-2,6-dicarboxylic acid; 1 S,2R,4S,5S,6S-2-amino-6-fluoro-4-hydroxybicyclo[3.1.0] hexane-2,6-dicarboxylic acid; 1S,2R,3R,5S,6S-2-amino-3- fluorobicyclo[3.1.0]hexane-2,6-dicarboxylic acid; or 1S,2R, 3S,5S,6S-2-amino-6-fluoro-3-hydroxybicyclo-[3.1.0] hexane-2,6-dicarboxylic acid.

A particular group of mGluR2 agonists include LY-379268; DCG-IV; LY-354740; LY-404039; LY-2969822; LY-2934747; LY-544344; and LY-2140023.

The orthosteric agonists of metabotropic glutamatergic receptor subtype 2 of the combination of the invention are in particular further selected from those disclosed in WO1997/18199 and WO2003/104217, incorporated herein in their entirety. Particular compounds disclosed therein are (−)-(1R, 4S,5S,6S)-4-amino-2-sulfonylbicyclo[3.1.0]-hexane-4,6-dicarboxylic acid (also known as LY-404039)

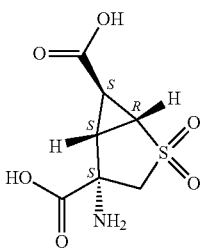

or a salt or a solvate thereof, and (1R,4S,5S,6S)-4-[[(2S)-2-amino-4-(methylthio)-1-oxobutyl]amino]-2-thiabicyclo [3.1.0]hexane-4,6-dicarboxylic acid 2,2-dioxide (also known as LY-2140023 [CAS 635318-55-7])

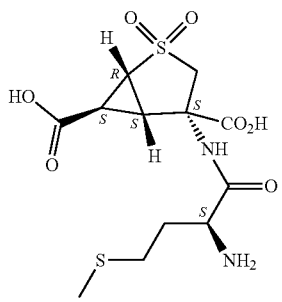

or a salt or a solvate thereof, for example the monohydrate thereof.

The names of the compounds of the present invention were generated according to the nomenclature rules agreed upon by the Chemical Abstracts Service (C.A.S.) using Advanced Chemical Development, Inc., software (ACD/Name product version 10.01.0.14105, October 2006). In case of tautomeric forms, the name of the depicted tautomeric form of the structure was generated. However it should be clear that the other non-depicted tautomeric form is also included within the scope of the present invention.

As used herein, the notation "$C_{1-3}$alkyl", "$C_{1-4}$alkyl" or "$C_{1-6}$alkyl" as a group or part of a group defines a saturated, straight or branched, hydrocarbon radical having from 1 to 3 or from 1 to 4 or from 1 to 6 carbon atoms, such as methyl, ethyl, 1-propyl, 1-methylethyl, butyl, 1-methylpropyl, 2-methyl-1-propyl, 1,1-dimethylethyl, 3-methyl-1-butyl, 1-pentyl, 1-hexyl and the like.

The notation "$C_{3-7}$cycloalkyl" or "$C_{3-8}$cycloalkyl" as a group or part of a group defines a saturated, cyclic hydrocarbon radical having from 3 to 7 or from 3 to 8 carbon atoms, such as cyclopropyl, cyclobutyl, cyclopentyl, cyclohexyl, cycloheptyl, and cyclooctyl.

The notation "halo" or "halogen" as used herein as a group or part of a group refers to fluoro, chloro, bromo or iodo, with fluoro or chloro being preferred.

The notation "mono- and polyhalo$C_{1-3}$alkyl" or "mono- and polyhalo$C_{1-4}$alkyl" shall denote $C_{1-3}$alkyl or $C_{1-4}$alkyl respectively, as defined before, substituted with 1, 2, 3 or where possible with more halo atoms as defined before.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

As used herein, unless otherwise noted, the term "antiepileptic agent" and the abbreviation "AED" will be used interchangeably with the term "anticonvulsant agent", and as used herein, refer to an agent capable of treating, inhibiting or preventing seizure activity or ictogenesis when the agent is administered to a subject or patient.

As used herein, unless otherwise noted, the term "synaptic vesicle protein 2A ligand" and the abbreviation "SV2A ligand" will be used interchangeably. Examples of SV2A ligands include, but are not limited to, the compounds included in the publications GB 1,039,113; GB 1,309,692; EP 1 262 036; EP 1 806 339; WO 2001/062726; US 2002/094787; WO 2004/087658; WO 2005/121082; WO 2005/054188; WO 2006/128692; WO 2006/128693; WO 2007/065595; WO 2008/132139, and WO 2008/132142; WO 2011/047860; WO 2012/143116; and WO 2012/143117. Suitable particular examples of SV2A ligands include, but are not limited to: levetiracetam, brivaracetam and seletracetam.

Therefore, in an embodiment of the invention, the SV2A ligand is selected from levetiracetam, brivaracetam and seletracetam.

In a particular embodiment, the SV2A ligand is levetiracetam.

In a particular embodiment, the SV2A ligand is brivaracetam.

Processes for the preparation of the above SV2A ligands are known from the literature and described for instance in EP 1 806 339; in EP 0 162 036 and in GB 2 225 322 (levetiracetam); in WO 01/62726 (brivaracetam); and in WO 2005/121082 (seletracetam); such processes are hereby incorporated by reference in their totality.

In an additional embodiment, the combination according to the invention comprises (a) a SV2A ligand selected from levetiracetam or brivaracetam; and (b)

Co. No. 1

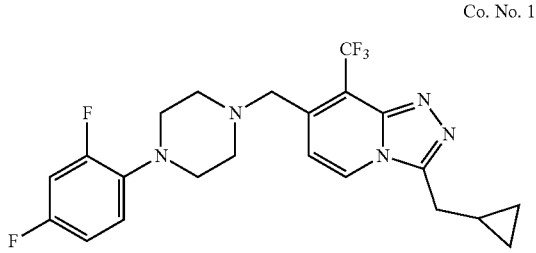 [SMILES: Fc1ccc(N2CCN(Cc3ccn4c(CC5CC5)nnc4c3C(F)(F)F)CC2)c(F)c1]

or a pharmaceutically acceptable salt thereof, preferably a hydrochloride salt thereof, or a solvate thereof.

In an additional embodiment, the pharmaceutical composition according to the invention comprises (a) a pharmaceutically effective amount of levetiracetam or brivaracetam; and (b) a pharmaceutically effective amount of

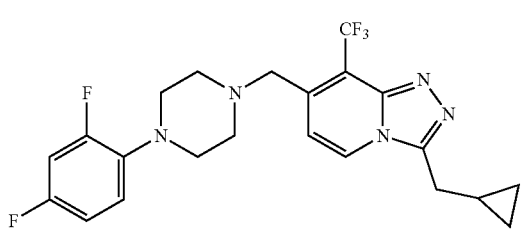

(Co. No. 1)

or a pharmaceutically acceptable salt thereof, preferably a hydrochloride salt thereof, or a solvate thereof.

In an additional embodiment, the combination according to the invention comprises (a) a pharmaceutically effective amount of levetiracetam or brivaracetam; and (b) a pharmaceutically effective amount of

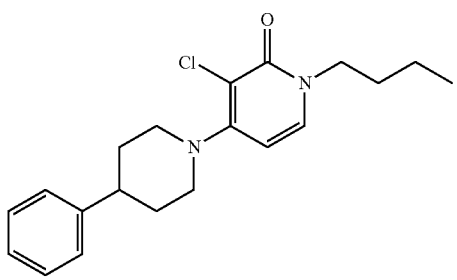

(Co. No. 2-a)

or a pharmaceutically acceptable salt, or a solvate thereof.

In an additional embodiment, the pharmaceutical composition according to the invention comprises (a) a pharmaceutically effective amount of levetiracetam or brivaracetam; and (b) a pharmaceutically effective amount of

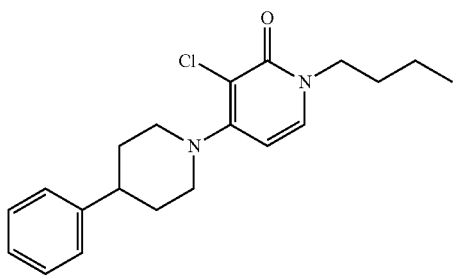

(Co. No. 2-a)

or a pharmaceutically acceptable salt, or a solvate thereof.

In an additional embodiment, the combination according to the invention comprises (a) a pharmaceutically effective amount of levetiracetam or brivaracetam; and (b) a pharmaceutically effective amount of

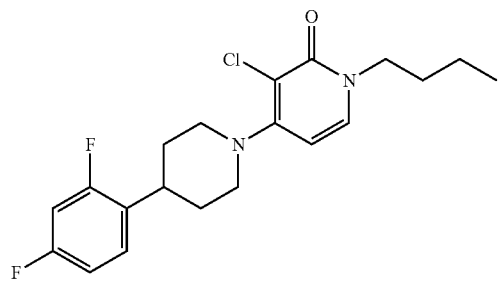

(Co. No. 25-a)

or a pharmaceutically acceptable salt, or a solvate thereof.

In an additional embodiment, the pharmaceutical composition according to the invention comprises (a) a pharmaceutically effective amount of levetiracetam or brivaracetam; and (b) a pharmaceutically effective amount of

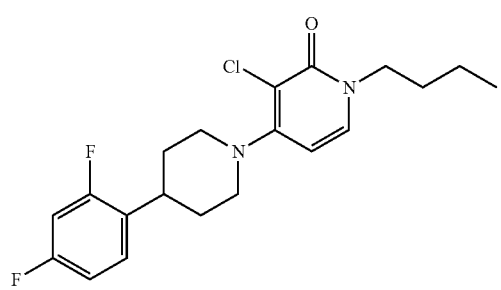

(Co. No. 25-a)

or a pharmaceutically acceptable salt, or a solvate thereof.

In an additional embodiment, the combination according to the invention comprises (a) a pharmaceutically effective amount of levetiracetam or brivaracetam; and (b) a pharmaceutically effective amount of

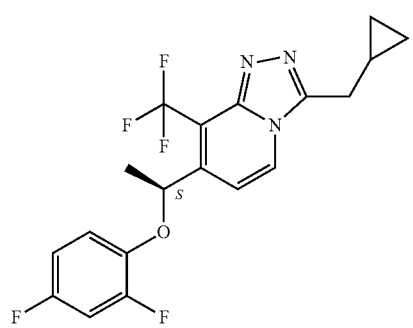

(Co. No. 6-b)

or a pharmaceutically acceptable salt thereof, in particular the hydrochloride salt thereof, or a solvate thereof.

In an additional embodiment, the pharmaceutical composition according to the invention comprises (a) a pharmaceutically effective amount of levetiracetam or brivaracetam; and (b) a pharmaceutically effective amount of

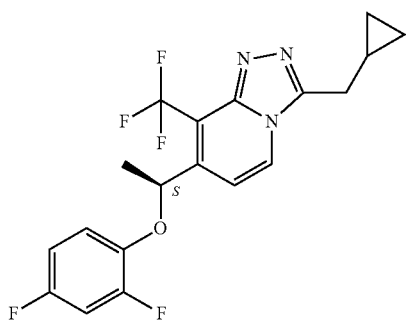

(Co. No. 6-b)

or a pharmaceutically acceptable salt thereof, in particular the hydrochloride salt thereof, or a solvate thereof.

In an additional embodiment, the combination according to the invention comprises (a) a pharmaceutically effective amount of levetiracetam or brivaracetam; and (b) a pharmaceutically effective amount of LY-404039 or a pharmaceutically acceptable salt thereof, in particular the hydrochloride salt thereof, or a solvate thereof.

In an additional embodiment, the pharmaceutical composition according to the invention comprises (a) a pharmaceutically effective amount of levetiracetam or brivaracetam; and (b) a pharmaceutically effective amount of LY-404039 or a pharmaceutically acceptable salt thereof, in particular the hydrochloride salt thereof, or a solvate thereof.

In an additional embodiment, the combination according to the invention comprises (a) a pharmaceutically effective amount of levetiracetam or brivaracetam; and (b) a pharmaceutically effective amount of LY-2140023 or a pharmaceutically acceptable salt or a solvate thereof, in particular the monohydrate thereof.

In an additional embodiment, the pharmaceutical composition according to the invention comprises (a) a pharmaceutically effective amount of levetiracetam or brivaracetam; and (b) a pharmaceutically effective amount of LY-2140023 or a pharmaceutically acceptable salt or a solvate thereof, in particular the monohydrate thereof.

The combination product of the present invention, in particular, the pharmaceutical composition according to the invention, is especially appropriate for the treatment of epilepsy and related disorders.

It will be appreciated that some of the mGluR2 compounds, in particular the mGluR2 PAM/agonist compounds of the invention and their pharmaceutically acceptable addition salts and solvates thereof may contain one or more centres of chirality and exist as stereoisomeric forms.

The term "compounds of the invention" as used herein, is meant to include the mGluR2 PAM compounds, in particular the compounds of Formula (I)/(I-A)/(I-B), and the mGluR2 agonist compounds as disclosed herein, and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "mGluR2 compound" and "mGluR2 PAM/agonist compound" are meant to include the stereoisomers thereof and the tautomeric forms thereof. The terms "stereoisomers", "stereoisomeric forms" or "stereochemically isomeric forms" hereinbefore or hereinafter are used interchangeably. The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible. The meaning of all those terms, i.e. enantiomers, diastereomers, racemates, E isomers, Z isomers, cis isomers, trans isomers and mixtures thereof are known to the skilled person. The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a mGluR2 compound is for instance specified as (R), this means that the compound is substantially free of the (S) isomer; when a mGluR2 compound is for instance specified as E, this means that the compound is substantially free of the Z isomer; when a mGluR2 compound is for instance specified as cis, this means that the compound is substantially free of the trans isomer.

Some of the mGluR2 compounds may also exist in their tautomeric form. Such forms in so far as they may exist, although not explicitly indicated in the above formula are intended to be included within the scope of the present invention.

It follows that a single compound may exist in both stereisomeric and tautomeric forms.

For use in medicine, the salts of the compounds of this invention refer to non-toxic "pharmaceutically acceptable salts" (salts of the compounds of the present invention wherein the counterion is pharmaceutically acceptable). Other salts may, however, be useful in the preparation or purification of compounds according to this invention or of their pharmaceutically acceptable salts, and may encompass acids and bases which are non-pharmaceutically acceptable. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of the invention are able to form. Suitable pharmaceutically acceptable salts of the compounds include acid addition salts which may, for example, be formed by mixing a solution of the compound with a solution of a pharmaceutically acceptable acid such as for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said salt forms can be converted by treatment with an appropriate base into the free base form. Furthermore, where the compounds of the invention carry an acidic moiety, suitable pharmaceutically acceptable salts thereof may include organic and inorganic bases. Appropriate base salt forms comprise, for example, the ammonium salts, the alkali and alkaline earth metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely, the salt form can be converted by treatment with acid into the free acid form.

The term "solvate" comprises the solvent addition forms as well as the salts thereof, which the compounds of Formula (I) are able to form. Examples of such solvent addition forms are e.g. hydrates, alcoholates and the like.

Preparation of the Compounds of Formula (I-B)

The compounds of Formula (I-B) according to the invention can generally be prepared by a succession of steps, each of which is known to the skilled person. In particular, the compounds can be prepared according to the following synthesis methods.

The compounds of Formula (I-B) may be synthesized in the form of racemic mixtures of enantiomers which can be separated from one another following art-known resolution procedures. The racemic compounds of Formula (I-B) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I-B) involves liquid chromatography or supercritical fluid chromatography (SFC) using a chiral stationary phase. Said pure stereochemically isomeric forms may also be derived from the corresponding pure stereochemically isomeric forms of the appropriate starting materials, provided that the reaction occurs stereospecifically.

A. Preparation of the final compounds of Formula (I-B)

Final compounds according to Formula (I-B), can be prepared by reacting an intermediate compound of Formula (II) with a compound of Formula (III) according to reaction scheme (1), a reaction that is performed under classical Mitsunobu conditions. The reaction is preferably conducted with a phosphine and an azodicarboxylic ester or amide in tetrahydrofuran, 1,4-dioxane, diethyl ether, toluene, benzene, dichloromethane, or mixtures thereof, at −30 to 150° C., under thermal heating or microwave irradiation. Phosphines often used are triphenylphosphine and tributylphosphine which are usually combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethyylamide), azodicarboxylic acid dipiperidide, or azodicarboxylic acid dimorpholide. In reaction scheme (1), all variables are as defined in Formula (I-B)

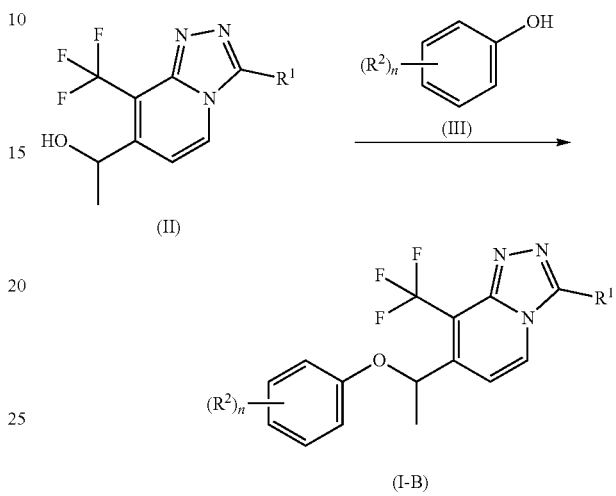

B. Preparation of the Intermediates

Experimental Procedure 2

Intermediate compounds according to Formula (II) can be prepared by subjecting an intermediate of Formula (IV) to conditions that are known to those skilled in the art. This is illustrated in reaction scheme (2) wherein all variables are defined as mentioned hereinabove. Methods accomplishing these transformations are well known to those skilled in the art. Treatment of the aldehyde of formula (IV) with an organometallic such as methyl lithium or methyl magnesium bromide gives a compound of formula (II). A suitable solvent for this reaction is an ether such as tetrahydrofuran and the reaction is usually carried out at a temperature between −78° C. and 40° C. In reaction scheme (2), all variables are defined as in Formula (I-B).

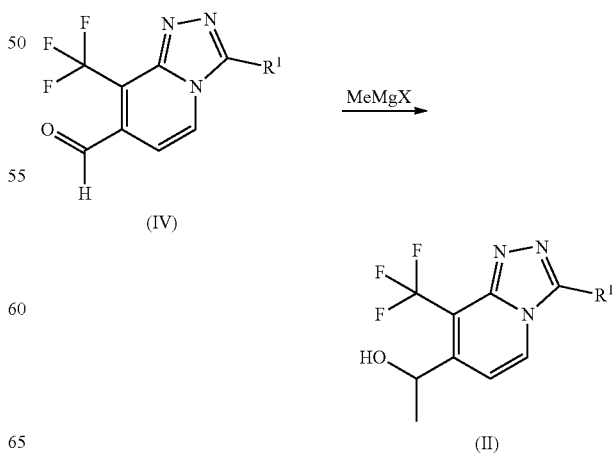

Experimental Procedure 3

Intermediate compounds according to Formula (IV) can be prepared by reacting an intermediate of Formula (V) under dihydroxylation and oxidative cleavage conditions that are known to those skilled in the art and can be realized for example with oxone, osmium tetroxide. The process may be carried out optionally in a solvent such as 1,4-dioxane, water and generally at temperatures between about −100° C. and about 100° C. A summary of such methods is found in "Comprehensive Organic Transformations", VCH Publishers, (1989), R. C. Larock, pp. 595-596. This is illustrated in reaction scheme (3) wherein all variables are defined as mentioned hereinabove.

Reaction Scheme 3

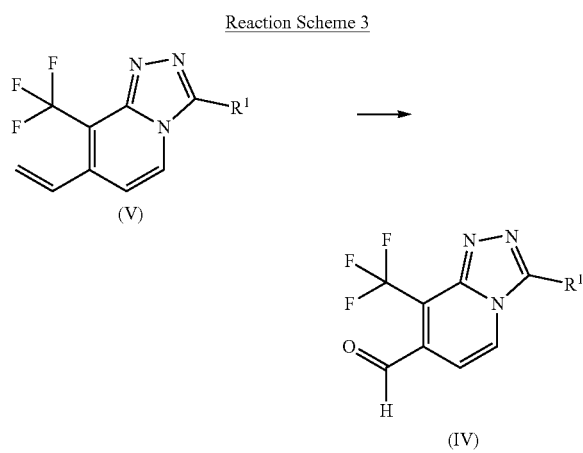

Experimental Procedure 4

Intermediate compounds according to Formula (V) can be prepared by coupling reactions, such as Stille or Suzuki reactions of an intermediate of Formula (VI) with a compound of Formula (VII) under conditions that are known to those skilled in the art. The process may be carried out optionally in a solvent such as 1,4-dioxane, water and generally at temperatures between about r.t. and about 200° C. in the presence of a base. This is illustrated in reaction scheme (4) wherein all variables are defined as mentioned hereabove, wherein M is trialkyltin, boronic acid or boronate ester, and a palladium catalyst and halo is chloro, bromo or iodo.

Reaction Scheme 4

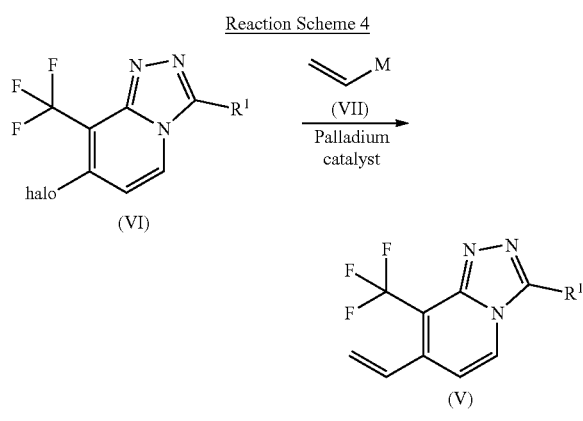

Experimental Procedure 5

Intermediate compounds according to Formula (VI) can be prepared following art known procedures by cyclization of an intermediate compound of Formula (VIII) in the presence of a halogenating agent such as for example phosphorus (V) oxychloride (POCl$_3$) in a suitable solvent such as, for example, dichloroethane, stirred under microwave irradiation, for a suitable period of time that allows the completion of the reaction, as for example 5 min at a temperature between 140-200° C. In reaction scheme (5), R$^1$ is defined as in Formula (I-B) and halo is chloro, bromo or iodo.

Reaction Scheme 5

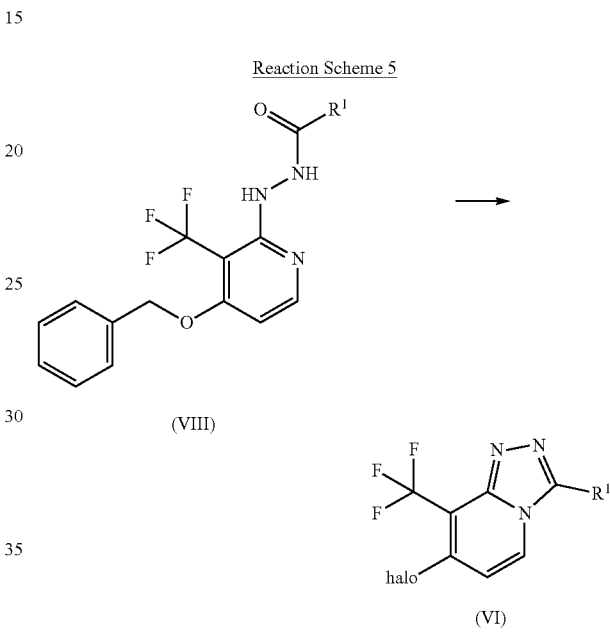

Experimental Procedure 6

Intermediate compounds according to Formula (VIII) can be prepared by art known procedures by reaction of a hydrazine intermediate of Formula (IX) with acid halides of Formula (X). The reaction can be carried out using an inert-solvent, such as for example DCM, in the presence of a base such as for example triethylamine, for example at r.t. for a suitable period of time that allows completion of the reaction, for example 20 min. In reaction scheme (6), R$^1$ is defined as in Formula (I-B).

Reaction Scheme 6

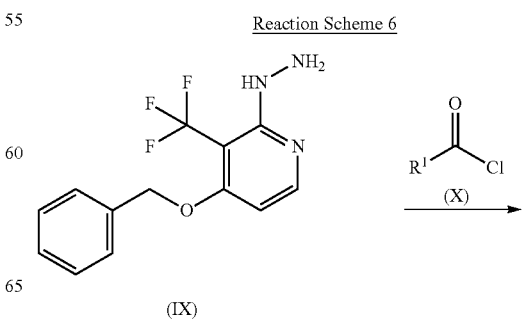

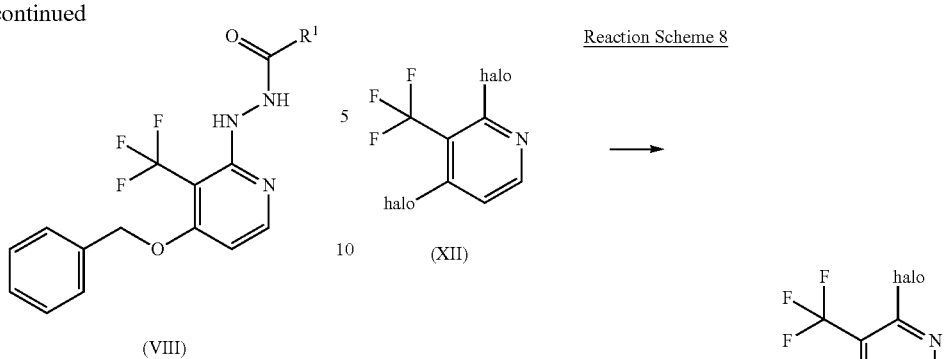

(VIII)

Experimental Procedure 7

Intermediate compounds according to Formula (IX) can be prepared by reacting an intermediate compound of Formula (XI) with hydrazine according to reaction scheme (7), a reaction that is performed in a suitable reaction-inert solvent, such as, for example, ethanol, THF or 1,4-dioxane under thermal conditions such as, for example, heating the reaction mixture for example at 160° C. under microwave irradiation for 30 min or classical thermal heating at 70° C. for 16 h. In reaction scheme (7), halo is chloro, bromo or iodo.

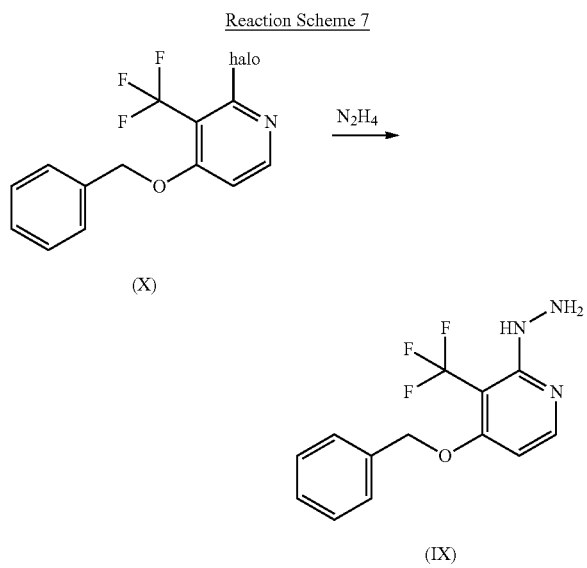

Experimental Procedure 8

Intermediate compounds according to Formula (XI) can be prepared by reacting an intermediate compound of Formula (XII) with benzyl alcohol according to reaction scheme (8), a reaction that is performed in a suitable reaction-inert solvent, such as, for example, N,N-dimethylformamide in the presence of a suitable base, such as for example sodium hydride at r.t. for a suitable period of time that allows the completion of the reaction, such as for example 1 h. In reaction scheme (8), halo is chloro, bromo or iodo.

Reaction Scheme 8

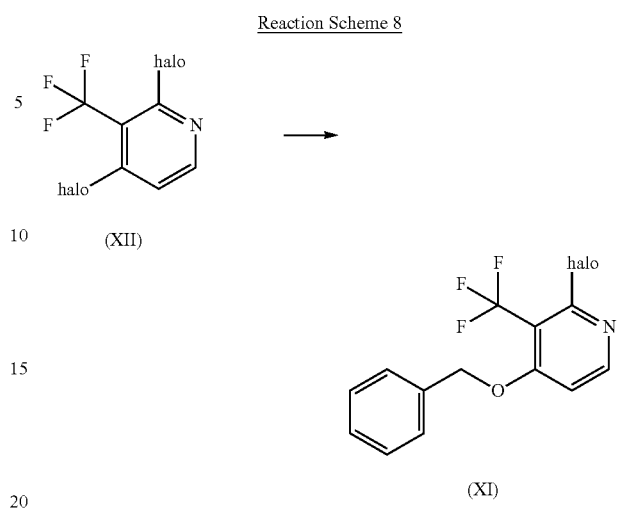

Experimental Procedure 9

Intermediate compounds of Formula (XII), can be prepared by reacting an intermediate of Formula (XIII), with a suitable trifluoromethylating agent, such as for example fluorosulfonyl(difluoro)acetic acid methyl ester, according to reaction scheme (9). This reaction is performed in a suitable reaction-inert solvent such as, for example, N,N-dimethylformamide in the presence of a suitable coupling agent such as for example, copper(I) iodide, under thermal conditions such as, for example, heating the reaction mixture for example at 160° C. under microwave irradiation for 45 min. In reaction scheme (9), halo is chloro, bromo or iodo.

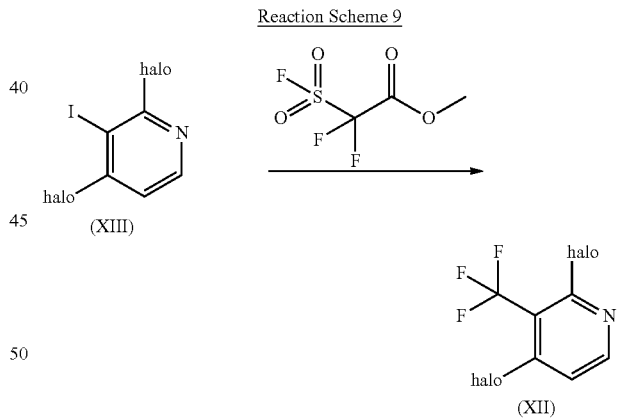

The starting materials according to Formulae (II), (VII), (X) or (XIII) are compounds that are either commercially available or may be prepared according to conventional reaction procedures generally known to those skilled in the art.

As used herein, the term "composition" is intended to encompass a product comprising the specified ingredients in the specified amounts, as well as any product which results, directly or indirectly, from combinations of the specified ingredients in the specified amounts.

As used herein, the term "subject" refers to an animal, preferably a mammal, most preferably a human adult, child or infant, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the symptoms of the disease or disorder being treated; and/or reduction of the severity of one or more of the symptoms of the disease being treated.

The combination of compounds (a) SV2A ligand and (b) positive allosteric modulator ("PAM") of metabotropic glutamatergic receptor subtype 2 ("mGluR2") or a pharmaceutically acceptable salt or a solvate thereof, or orthosteric agonist of metabotropic glutamatergic receptor subtype 2 or a pharmaceutically acceptable salt or a solvate thereof, whether the compounds (a) and (b) are given simultaneously, separately or sequentially, may be beneficial compared to the effect of the compounds (a) or (b) administered alone. In particular, there may be at least one beneficial effect, e.g. a mutual enhancement of the effect of the compounds (a) and (b), a more than additive effect, in particular a synergic effect; additional advantageous effects, include for example, a significantly reduced effective dose for the combination of (a) and (b); a further therapeutic effect not observed for any of the compounds (a) or (b) alone, a more beneficial side effect profile, or a combined therapeutic effect in a non-effective dosage of one or both of (a) and (b).

As defined herein, the term "fixed-dose ratio of (a) synaptic vesicle protein 2A ligand to (b) compound of Formula (I) of 1:1, calculated on the $ED_{50}$ values of the individual compounds (a) and (b)" refers to compositions comprising compounds (a) and (b) in a dose corresponding to 50% of the respective $ED_{50}$ dose of the individual compounds (a) and (b) or a multiple of this fixed-dose ratio. The term "fixed-dose ratio of (a) synaptic vesicle protein 2A ligand:(b) compound of Formula (I) of 3:1, calculated on the $ED_{50}$ values of the individual compounds (a) and (b)" refers to compositions comprising (b) the compound of Formula (I) in a dose corresponding to 75% of the respective $ED_{50}$ dose and compound (a) in a dose corresponding to 25% of the respective $ED_{50}$ dose of compound (a) or a multiple of this fixed-dose ratio, and so on.

Thus, in another embodiment of the invention, (a) the SV2A ligand and (b) the compound of Formula (I) are present in the pharmaceutical composition in a fixed-dose ratio of (a):(b) of about 1:10 to about 10:1, preferably about 1:5 to about 5:1, more preferably about 1:3 to about 3:1, in another embodiment of about 1:1 to about 3:1; in an alternate embodiment of 1:3; in yet another embodiment of 1:1; further embodiment of 3:1; wherein the fixed-dose ratio is calculated on the $ED_{50}$ values of the individual compounds (a) and (b).

Wherein the present invention is directed to co-therapy or combination therapy, comprising administration of (a) synaptic vesicle protein 2A ("SV2A") ligand; and (b) a mGluR2 PAM/agonist compound, in particular a compound of Formula (I)/(I-A)/(I-B) as defined herein, pharmaceutically or therapeutically effective amount shall mean that amount of the combination of agents taken together so that the combined effect elicits the desired biological or medicinal response. For example, the therapeutically effective amount of co-therapy comprising administration of (a) a SV2A ligand as defined herein and (b) a mGluR2 PAM/agonist compound, in particular a compound of Formula (I)/(I-A)/(I-B) as defined herein would be the amount of the (a) a SV2A ligand as defined herein and the amount of (b) a mGluR2 PAM/agonist compound, in particular compound of Formula (I)/(I-A)/(I-B) that when taken together or sequentially have a combined effect that is therapeutically effective. Further, it will be recognized by one skilled in the art that in the case of co-therapy with a therapeutically effective amount, as in the example above, the amount of the mGluR2 PAM/agonist compound, in particular the compound of Formula (I)/(I-A)/(I-B), and/or the amount of the suitable SV2A ligand individually may or may not be therapeutically effective.

The present invention provides methods of prevention or treatment comprising administering to a subject in need thereof, co-therapy with a therapeutically effective amount of a SV2A ligand and a therapeutically effective amount of a mGluR2 PAM/agonist compound, in particular a compound of formula (I)/(I-A)/(I-B), as described herein. In order to accomplish this objective the compounds or compositions of this invention must be used in the correct therapeutically effective amount or dose, as described below.

Optimal dosages and schedules to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that a therapeutically effective dosage of the compounds of the present invention can include repeated doses within a prolonged treatment regimen that will yield clinically significant results.

The amounts of the mGluR2 PAM/agonist compound, in particular of the compound of Formula (I)/(I-A)/(I-B), in the combinations of the invention that are administered on a daily basis may vary from about 0.01 to about 2000 mg. Examples of daily amounts of the compound of Formula (I)/(I-A)/(I-B) are 0.01, 0.05, 0.1, 0.5, 1.0, 2.5, 5.0, 10.0, 15.0, 25.0, 50.0, 100, 150, 200, 250, 300, 400, 500, 750 and 1000 milligrams for the symptomatic adjustment of the dosage to the patient to be treated. An effective amount of the drug is ordinarily supplied at a dosage level of from about 0.01 mg/kg to about 150.0 mg/kg of body weight per day or any range therein. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1, 2, 3 or 4 times per day. The amounts of SV2A ligand that are administered on a daily basis may vary from about 0.01 to about 7000 mg, preferably will be between 250 and 5000 mg and more preferably will be between 500 and 3000 mg. Examples of daily amount of the SV2A ligand are 2.5, 5.0, 10.0, 15.0, 25.0, 50.0, 100, 150, 200, 250, 500, 750, 1000, 1500 and 3000 milligrams for the symptomatic adjustment of the dosage of the patient to be treated. An effective amount of the drug is ordinarily supplied at a dosage level of from about 0.01 mg/kg to about 150.0 mg/kg of body weight per day or any range therein. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1, 2, 3 or 4 times per day. All amounts mentioned in this and the following paragraphs refer to the free form (i.e. non-salt form). The above values represent free-form equivalents, i.e. quantities as if the free form would be administered. If salts are administered the amounts need to be calculated in function of the molecular weight ratio between the salt and the free form.

The above mentioned daily doses are calculated for an average body weight of about 70 kg and should be recalculated in case of paediatric applications, or when used with patients with a substantially diverting body weight.

The dosages may be presented as one, two, three or four or more sub-doses administered at appropriate intervals throughout the day. The dosage used preferably corresponds to the daily amount of the mGluR2 PAM/agonist compound, in particular of the compound of Formula (I)/(I-A)/(I-B), or of the SV2A ligand, mentioned above, or a sub-dose thereof, such as ½, ⅓, ¼ thereof. A dosage form may contain the mGluR2 PAM/agonist compound, in particular the compound (I)/(I-A)/(I-B), or the SV2A ligand or both together, in an amount equal to the ranges or quantities mentioned in the previous paragraphs, for example a dosage form may contain 10 mg, 25 mg, 50 mg, 100 mg, 150 mg, or 200 mg of mGluR2 PAM/agonist compound, in particular of compound (I)/(I-A)/(I-B), 10 mg, 25 mg, 50 mg, 100 mg or 250 mg, of SV2A ligand, either in separate formulations or in a combined formulation. In one embodiment, the mGluR2 PAM/agonist compound, in particular the compound of Formula (I)/(I-A)/(I-B), is administered once daily (q.d.), in particular as one dose per day, and the SV2A ligand is administered once or twice daily (q.d. or b.i.d.), in particular as one or as two doses per day. In the instance where both compounds are to be administered once daily, this can be accomplished by administering two separate doses, one with the mGluR2 PAM/agonist compound, in particular the compound of Formula (I)/(I-A)/(I-B), one with the SV2A ligand, or by administering a combined dose containing the mGluR2 PAM/agonist compound, in particular the compound of Formula (I)/(I-A)/(I-B), and SV2A ligand.

The combinations of the invention may be administered once, twice, three, four, or if desired, multiple times daily. In one embodiment, the combination is administered once daily. In another embodiment, the combination is administered twice daily, or three times per day. Administration of dosages may be by separate dosage forms, i.e. dosage forms only containing mGluR2 PAM/agonist compound, in particular compound of Formula (I)/(I-A)/(I-B), or only SV2A ligand; or by combined dosage forms containing active ingredients mGluR2 PAM/agonist compound, in particular compound of Formula (I)/(I-A)/(I-B), and SV2A ligand. Also, a mix of using a combined dosage form and separate dosage forms can be used. Dosage forms that can be administered are described hereinafter, oral dosage forms, in particular tablets or capsules being preferred.

Active ingredients may be formulated in pharmaceutical compositions either separately or as a combined pharmaceutical composition. In the latter instance, there is provided a pharmaceutical composition comprising a therapeutically effective amount of the mGluR2 PAM/agonist compound, in particular of the compound of Formula (I)/(I-A)/(I-B), or a pharmaceutically acceptable salt thereof, and the SV2A ligand, the foregoing being as specified herein, and a pharmaceutically acceptable carrier.

In a further aspect, this invention relates to a process for preparing a pharmaceutical composition as specified herein, which comprises intimately mixing a pharmaceutically acceptable carrier with a therapeutically effective amount of the mGluR2 PAM/agonist compound, in particular of the compound of Formula (I)/(I-A)/(I-B), or a pharmaceutically acceptable salt or a solvate thereof, and a therapeutically effective amount of at least one SV2A ligand.

The combinations provided herein may also be formulated as a combined preparation for simultaneous, separate or sequential use in the prevention or treatment of epilepsy and related disorders; neuropathic pain; migraine or resistant headache; bipolar and related disorders; in neuroprotection; or in the prevention of epileptogenesis. In such a case, the mGluR2 PAM/agonist compound, in particular the compound of Formula (I)/(I-A)/(I-B), is formulated in a pharmaceutical composition containing other pharmaceutically acceptable excipients, and the SV2A ligand is formulated separately in a pharmaceutical composition containing other pharmaceutically acceptable excipients. Conveniently, these separate pharmaceutical compositions can be part of a kit for simultaneous, separate, or sequential use.

The individual components of the combination of the present invention can be administered simultaneously or separately at different times during the course of therapy or concurrently in divided or single combination forms.

Therefore, the mGluR2 PAM/agonist compounds, in particular the compounds of Formula (I)/(I-A)/(I-B), and the SV2A ligand, individually or combined, may be formulated into various pharmaceutical compositions suitable for administration purposes. In these, a therapeutically effective amount of the particular compound, or of both two compounds, is combined with a pharmaceutically acceptable carrier, which carrier may take a wide variety of forms depending on the form of preparation desired for administration. Pharmaceutical compositions may be prepared as medicaments to be administered orally, parenterally (including subcutaneously (s.c.), intramuscularly (i.m.), and intravenously (i.v.)), rectally, transdermally, bucally, or nasally. The pharmaceutical compositions may also be prepared to be administered directly to the nervous system by routes including, but not limited to, intracerebral, intraventricular, intracerebroventricular, intrathecal, intracisternal, intraspinal and/or peri-spinal route by delivery via intracranial or intravertebral needles and/or catheters with or without pump devices. Suitable compositions for oral administration include powders, granulates, aggregates, tablets, compressed or coated pills, dragees, sachets, hard or gelatin capsules, syrups and suspensions. Suitable compositions for parenteral administration include aqueous or non-aqueous solutions or emulsions, while for rectal administration suitable compositions for administration include suppositories with a hydrophilic or hydrophobic vehicle. For topical administration suitable transdermal delivery systems can be used and for nasal delivery suitable aerosol delivery systems can be used.

For example, in preparing the compositions for oral administration, any of the usual pharmaceutical media may be employed such as, for example, water, glycols, oils, alcohols and the like in the case of oral liquid compositions such as suspensions, syrups, elixirs, emulsions and solutions; or solid carriers such as starches, sugars, kaolin, lubricants, binders, disintegrating agents and the like in the case of solid compositions. For parenteral compositions, the carrier will usually comprise sterile water, at least in large part, though other ingredients, such as solubilizers, emulsifiers or further auxiliaries may be added thereto. Injectable solutions may be prepared in which the carrier comprises saline solution, glucose solution or a mixture of both. Injectable suspensions may also be prepared in which case appropriate liquid carriers, suspending agents and the like may be employed. Also included are solid form preparations intended to be converted, shortly before use, to liquid form preparations such as powders for reconstitution. In the compositions suitable for percutaneous administration, the carrier optionally comprises a skin penetration enhancing agent and/or a wetting agent, optionally combined with suitable skin-compatible additives in minor proportions. The mGluR2 PAM/agonist compound, in particular the compound of Formula (I)/(I-A)/(I-B), or SV2A ligand, or combinations thereof, may also be administered via oral inhalation or insufflation by formulations suited for this type of administration such as a solution, a suspension or a dry powder. Suitable pharmaceutical compositions for administration in the form of aerosols or sprays are, for example, suspensions of the mGluR2 PAM/agonist compound, in particular of the compound of Formula (I)/(I-A)/(I-B), or SV2A ligand, or both, in a pharmaceutically acceptable liquid carrier, such as ethanol or water, or a mixture thereof. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

The pharmaceutical compositions may contain the active ingredient mGluR2 PAM/agonist compound, in particular compound of Formula (I)/(I-A)/(I-B), or the SV2A ligand, or both combined in a concentration of about 0.1% to about 50%, or about 1% to about 30%, or about 3% to about 20%, or about 5% to about 20%, all percentages being by weight, wherein the total of all components in said pharmaceutical compositions does not exceed 100%. In the compositions containing both two compounds mGluR2 PAM/agonist compound, in particular compound of Formula (I)/(I-A)/(I-B), and SV2A ligand, the mGluR2 PAM/agonist compound, in particular the compound of Formula (I)/(I-A)/(I-B), is present in a concentration of about 0.1% to about 50%, or about 1% to about 30%, or about 3% to about 20%, or about 5% to about 20%; and the SV2A ligand is present in a concentration of about 3% to about 50%, or about 5% to about 50%, or about 10% to about 50%, or about 10% to about 40%, or about 10% to about 30%, wherein the total of all components in said pharmaceutical compositions does not exceed 100%.

The pharmaceutical compositions may be conveniently presented in unit dosage form for ease of administration and uniformity of dosage. Examples include tablets (including scored or coated tablets), capsules, pills, suppositories, powder packets, wafers, injectable solutions or suspensions and the like, and segregated multiples thereof. Of interest are solid dosage forms for oral administration such as tablets or capsules.

The solid dosage forms in unit dose form may be packed in any known package, blister packs being preferred, in particular for tablets and capsules. Where the mGluR2 PAM/agonist compound, in particular the compound of Formula (I)/(I-A)/(I-B), and SV2A ligand are formulated separately, they could be packed in separate blisters, but one blister could as well comprise unit dose forms of the mGluR2 PAM/agonist compound, in particular of the compound of Formula (I)/(I-A)/(I-B), and of the SV2A ligand, for example one row with units of mGluR2 PAM/agonist compound, in particular of compound of Formula (I)/(I-A)/(I-B), and another with SV2A ligand. Other possibilities may be possible as well.

The combinations of this invention may be used to treat or prevent epilepsy and related disorders; neuropathic pain; migraine or resistant headache; and bipolar and related disorders; or they may be used as a neuroprotectant or to prevent epileptogenesis.

As used herein, the term "treatment" is intended to refer to all processes, wherein there may be a slowing, interrupting, arresting or stopping of the progression of a disease or an alleviation of symptoms, but does not necessarily indicate a total elimination of all symptoms As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), partial-onset seizures with or without generalization, myoclonic seizures, primary generalized tonic-clonic seizures in particular in patients with idiopathic generalized epilepsy, seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), status epilepticus (convulsive or non convulsive), essential tremor, restless limb syndrome, and the like. Preferably, the disorder is selected from epilepsy (regardless of type, underlying cause or origin), essential tremor or restless limb syndrome. More preferably, the disorder is epilepsy (regardless of type, underlying cause or origin) or essential tremor. A particular example of epilepsy is refractory epilepsy, also referred to as treatment or therapy resistant epilepsy. This term is often used when patients have failed three or more anti-epileptic drugs (AEDs). Refractory epilepsy also includes refractory partial epilepsy and refractory generalized epilepsy (including idiopathic or symptomatic).

As used herein, the term "neuropathic pain" includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome and other chronic and debilitating condition-associated pain syndromes.

As used herein, the term "migraine" shall mean a chronic, episodic and debilitating clinical condition that is diagnosed by the presence of moderate to severe pulsating unilateral headaches lasting between 4 and 72 h, which includes migraine without aura and migraine with aura. As used herein, "migraine without aura" shall mean at least five attacks fulfilling the following criteria: (a) the headache attack lasts 4-72 hours with the headache having at least two of the following features: unilateral location, pulsating quality, moderate or severe intensity with direct influence on activities of daily living, and aggravation by walking up stairs or similar routines: and (b) during the headache at least one of the following occurs: nausea and/or vomiting, and photophobia and phonophobia. As used herein, "migraine with aura" shall mean at least two attacks accompanied by at least 3 of the 4 following features: (a) one or more fully reversible aura symptoms: (b) at least one aura symptom which develops gradually over more than four minutes or two or more symptoms which occur in succession; (c) no aura symptom which lasts more than 60 minutes; (d) a headache occurs prior to, simultaneously with or following the aura, with a free interval between aura and headache of less than about 60 minutes.

As used herein, the term "bipolar and related disorders" shall include bipolar disorder I (e.g. single manic episode, most recent episode hypomanic, most recent episode manic, most recent episode mixed, most recent episode depressed and most recent episode unspecified), bipolar disorder II, cyclothymic disorder and bipolar disorder not otherwise specified (as these terms are defined by their diagnostic criteria, in the Diagnostic and Statistical manual of Mental Disorders 4th Edition, Text Revision, American Psychiatric Association, 2000 (DSM-IV-TR) or in the $5^{th}$ Edition, Text Revision, American Psychiatric Association, 2013 (DSM-5™). Preferably, the bipolar disorder is characterized by depressive and manic (or hypomanic) phases, wherein the phases cycle. Preferably, the bipolar disorder is bipolar disorder I or bipolar disorder II. As used herein "mania" shall include mania or a manic mood phase, regardless of underlying cause. As used herein, the term "bipolar mania" is intended to mean the mania associated with, characteristic of or symptomatic of a bipolar disorder. Thus, methods of treating bipolar mania of the present invention are directed to methods which treat the mania and/or manic phase of bipolar disorders. As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders. As used herein, unless otherwise noted the terms "cycling" or "bipolar cycling" shall refer to the alteration of mood between depressive and manic phases characteristic of bipolar disorders. Thus, the present invention includes methods for the stabilization of said cycling, including, but not limited to, decreasing the frequency of the cycling and/or decreasing the magnitude of the manic and/or depressive phases.

Thus, in an embodiment, the pharmaceutical composition of the present invention may be used for mood stabilization, in particular mood stabilization for manic depression.

As used herein, the term "epileptogenesis" refers to the gradual process by which epilepsy develops. This process may occur following brain insults or a variety of conditions, including neurodegenerative diseases, traumatic brain injury, stroke, brain tumor, infections of the central nervous system, and status epilepticus; or it may occur following gene mutations.

As used herein, the term "anxiety" refers in particular to generalized anxiety disorder.

As used herein, the term "about" has its conventional meaning. In particular embodiments, when in relation to a numerical value, it may be interpreted to mean the numerical value ±10%, or ±5%, or ±2%, or ±1%, or ±0.5%, or +0.1%. In other embodiments, the precise value is meant, i.e. by leaving out the word "about".

"And/or" means that each one or both or all of the components or features of a list are possible variants, especially two or more thereof in an alternative or cumulative way.

As used herein, the term "a", "an", "the" and similar terms used in the context of the present invention (especially in the context of the claims) are to be construed to cover both the singular and plural unless otherwise indicated herein or clearly contradicted by the context.

EXAMPLES

The following Examples are set forth to aid in the understanding of the invention, and are not intended and should not be construed to limit in any way the invention set forth in the claims which follow thereafter.

A) Compounds of Formula (I-B)—Chemistry and In Vitro Testing

Several methods for preparing the compounds of Formula (I-B) of this invention are illustrated in the following Examples. Unless otherwise noted, all starting materials were obtained from commercial suppliers and used without further purification.

Hereinafter, "aq." means aqueous; "DCE" means 1,2-dichloroethane, "DCM" means dichloromethane; "DIPE" means diisopropylether; "DIPEA" means N,N-diisopropylethylamine; "DMF" means N,N-dimethylformamide; "ES" means electrospray; "$Et_3N$" means triethylamine; "$Et_2O$" means diethyl ether; "EtOAc" means ethyl acetate; "h" means hours; "HPLC" means high performance liquid chromatography; "HRMS" means high-resolution mass spectra/spectrometry; "l" or "L" means liter; "LRMS" means low-resolution mass spectrometry/spectra; "MeOH" means methanol; "min" means minute(s); "mp" means melting point; "$Pd(PPh_3)_4$" means tetrakis(triphenylphosphine)palladium(0); "RP" means reverse phase; "r.t." means room temperature; "s" means seconds; "sat." means saturated; "SFC" means supercritical fluid chromatography; "sol." means solution; "THF" means tetrahydrofuran.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from Merck, on irregular silica gel, particle size 15-40 µm (normal phase disposable flash columns) on a SPOT or LAFLASH system from Armen Instrument.

The absolute stereochemical configuration for some of the compounds was determined using vibrational circular dichroism (VCD). They were measured on a Bruker Equinox 55 equipped with a PMA 37, in a KBr liquid cell using $CD_2Cl_2$ as solvent (PEM: 1350 cm-1, LIA: 1 mV, resolution: 4 cm$^{-1}$). A description on the use of VCD for the determination of absolute configuration can be found in Dyatkin A. B. et. al, Chirality, 14:215-219 (2002).

Whenever the notation "RS" is indicated herein, it denotes that the compound is a racemic mixture, unless otherwise indicated. The stereochemical configuration for some compounds has been designated "R" or "S" when the mixture was separated; for some compounds, the stereochemical configuration has been designated as "*R" or "*S" when the absolute stereochemistry is undetermined although the compound itself has been isolated as a single stereoisomer and is enantiomerically pure. The enantiomeric excess of compounds reported herein was determined by analysis of the racemic mixture by supercritical fluid chromatography (SFC) followed by SFC comparison of the separated enantiomer(s).

Preparation of Intermediates

Description 1—Intermediate 1

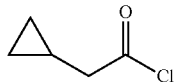

Cyclopropylacetic acid ([CAS 5239-82-7], 50 g, 500 mmol) was dissolved in CH$_2$Cl$_2$ (300 mL) then SOCl$_2$ (100 mL) was added. The reaction mixture was stirred at 60° C. for 2 h and then the solvent was evaporated to yield intermediate 1 (53 g, 90%), which was used without further purification.

Description 2—Intermediate 2

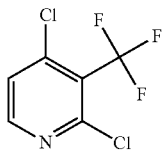

To a solution of 2,4-dichloro-3-iodopyridine ([CAS 343781-36-2], 290 g, 1058 mmol) in DMF (1.7 L) was added methyl 2,2-difluoro-2-(fluorosulfonyl)acetate ([CAS 680-15-9], 403 g, 2098 mmol) and CuI (403 g, 2.13 mol), the reaction was then heated at 100° C. for 5 h.

The reaction was cooled and filtered. The filtrate was diluted with H$_2$O and extracted with Et$_2$O and washed with a NH$_3$ solution. The organic layer was dried (Na$_2$SO$_4$), filtered and concentrated in vacuo to yield intermediate 2 (160 g), which was used without further purification.

Description 3—Intermediate 3

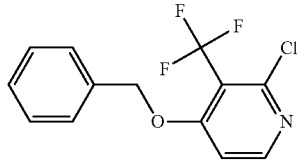 [SMILES: FC(F)(F)c1c(OCc2ccccc2)ccnc1Cl]

To a solution of NaH (60% in oil, 24 g, 600 mmol) in DMF (2 L) at 0° C. was added benzyl alcohol (35 g, 325 mmol), then the reaction was stirred for 2 min. Intermediate 2 (160 mg, 741 mmol) was added in one portion, and stirred at 0° C. for 1 h. The reaction was diluted by the addition of H$_2$O and extracted with Et$_2$O. The organic layer was dried (Na$_2$SO$_4$), filtered and concentrated in vacuo. The residue was purified by column chromatography over silica gel (eluent: petroleum ether/EtOAc=20/1). The pure fractions were collected and the solvent was evaporated to yield intermediate 3 (100 g, 38%).

Description 4—Intermediate 4

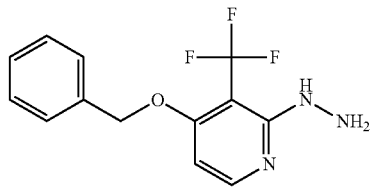 [SMILES: NNc1nccc(OCc2ccccc2)c1C(F)(F)F]

To a solution of intermediate 3 (100 g, 277 mmol) in 1,4-dioxane (1.5 L) was added NH$_2$NH$_2$ hydrate (85% solution in water, 300 g, 9.11 mol), the reaction was then heated in sealed tube at 160° C. for 2 h. The mixture was concentrated in vacuo, dissolved in DCM, washed with NaHCO$_3$. The organic layer was dried (Na$_2$SO$_4$), filtered and concentrated in vacuo to yield intermediate 4 (90 g, 90%), which was used without further purification.

Description 5—Intermediate 5

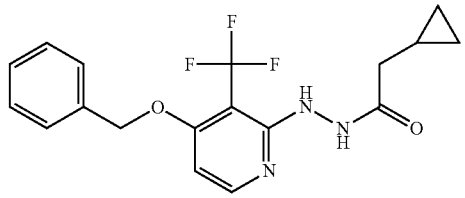 [SMILES: O=C(CC1CC1)NNc1nccc(OCc2ccccc2)c1C(F)(F)F]

To a solution of intermediate 4 (90 g, 318 mmol) in CH$_2$Cl$_2$ (1.5 L) was added triethylamine (64.3 g, 636 mmol), the mixture was cooled to 0° C., then a solution of intermediate 1 (53 g, 449 mmol) in CH$_2$Cl$_2$ was added. The solution was stirred at RT for 1 h. The reaction mixture was washed with a sat. aq. sol. of NaHCO$_3$, and extracted with CH$_2$Cl$_2$. The organic layer was dried (Na$_2$SO$_4$), filtered and concentrated in vacuo to yield intermediate 5 (104.4 g, 90%).

The following intermediates were synthesized following a synthetic sequence analogous to that reported in Description 5 (D5).

| Intermediate | Acid chloride | Conditions |
|---|---|---|
| Intermediate 6 | propionyl chloride ([CAS 79-03-8]) | Addition run at RT. |

| Intermediate | Acid chloride | Conditions |
|---|---|---|
| Intermediate 7 | cyclobutaneacetyl chloride ([CAS 59543-38-3]) | Conditions as in D5. |
| Intermediate 8 | 2-ethoxy-acetyl chloride ([CAS 14077-58-8]) | Conditions as in D5. |
| Intermediate 25 | butyryl chloride ([CAS 141-75-3]) | Conditions as in D5. |

Description 6

(a) Intermediate 9

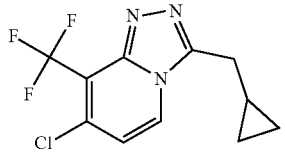 [SMILES: FC(F)(F)c1c(Cl)ccn2c(CC3CC3)nnc12]

To a solution of intermediate 5 (101 g, 277 mmol) in CH₃CN (1.2 L) were added phosphorus(V) oxychloride (84.7 g, 553 mmol) and N,N-diisopropylethylamine (71.3 g, 553 mmol). The reaction mixture was stirred at 90° C. for 38 h. The reaction was then diluted with DCM and washed with a Na₂CO₃ solution. The organic layer was dried (Na₂SO₄), filtered and concentrated in vacuo. The residue was purified by column chromatography over silica gel (eluent: petroleum ether/EtOAc=4/1). The pure fractions were collected and the solvent was evaporated to yield intermediate 9 (31.39 g, 41%).

(b) Intermediate 10

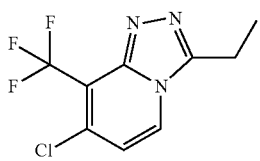 [SMILES: CCc1nnc2c(C(F)(F)F)c(Cl)ccn12]

The reaction was performed in 4 batches then combined for work up and purification. To a solution of intermediate 6 (7 g, 20.6 mmol) in DCE (50 mL), was added N,N-diisopropylethylamine (3.96 mL, 22.69 mmol) and then phosphorus oxychloride (2.12 mL, 22.69 mmol) and the reaction mixture was heated in a microwave at 150° C. for 5 min. Then DCM was added and the organic layer was washed with a sat. sol. of NaHCO₃, dried (Na₂SO₄) and concentrated in vacuo to afford the desired compound, which was purified by column chromatography (gradient elution: DCM 100% to MeOH.NH₃ 2% in DCM) to yield intermediate 10 (2.5 g, 49%).

The following intermediates were synthesized following a synthetic sequence analogous to that reported in Description 6(a) or (b)

| Intermediate | Starting material | Conditions |
|---|---|---|
| 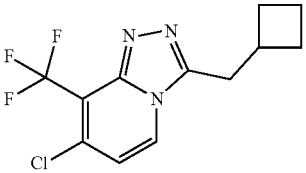

Intermediate 11 | Intermediate 7 | Reaction performed as in (a) but in $CH_3CN$. After the reaction was complete, the reaction mixture was poured into ice/water then washed with $NaHCO_3$ sat. sol. And extracted with DCM, dried ($Na_2SO_4$), filtered and concentrated. Purification was performed in Spot (Si cartridge, eluent DCM/EtOAc up to 10-20%). |
| 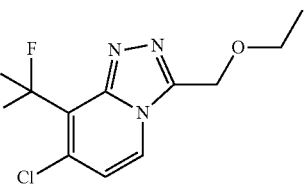

Intermediate 12 | Intermediate 8 | Reaction performed as in (b). Purification by flash column chromatography (silica; EtOAc in DCM 0/100 to 40/60). |
| 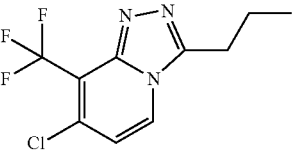

Intermediate 26 | Intermediate 25 | Reaction performed as in (a). Purification by flash column chromatography (silica; MeOH in $CH_2Cl_2$, from 0/100 to 4/96). |

Description 7—Intermediate 13

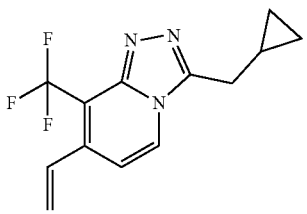 [SMILES: C=Cc1ccn2c(CC3CC3)nnc2c1C(F)(F)F]

(Ph$_3$P)$_4$Pd (2.096 g, 1.81 mmol) was added to a stirred solution of intermediate 9 (10 g, 36.28 mmol) and 4,4,5,5-tetramethyl-2-vinyl-1,3,2-dioxoborolane ([CAS 75927-49-0], 7.77 mL, 43.53 mmol) in deoxygenated dioxane (30 mL) and a deoxygenated NaHCO$_3$ saturated solution (30 mL) under nitrogen. The mixture was stirred at 100° C. for 18 h. The mixture was diluted with EtOAc/water and filtered through a pad of diatomaceous earth. The filtrate was treated with brine and extracted with EtOAc. The organic layer was separated, dried (Na$_2$SO$_4$), filtered and the solvents evaporated in vacuo. The crude product was purified by flash column chromatography (silica; EtOAc in CH$_2$Cl$_2$ 0/100 to 5/95). The desired fractions were collected and concentrated in vacuo to yield intermediate 13 (6.08, 63%) as a yellow solid.

The following intermediates were synthesized following a synthetic sequence analogous to that reported in Description 7.

| Intermediate | Starting material | Conditions |
|---|---|---|
| 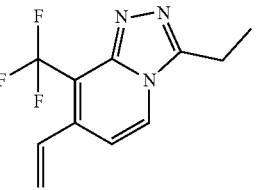

Intermediate 14 | Intermediate 10 | Reaction performed at 150° C. Purification by flash column chromatography (silica; 7N solution of ammonia in methanol in DCM 0/100 to 1/9). |

-continued

| Intermediate | Starting material | Conditions |
|---|---|---|
| 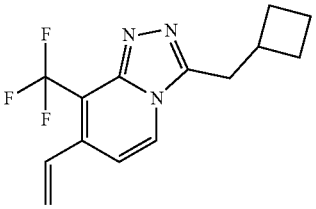<br>Intermediate 15 | Intermediate 11 | Extraction with DCM, purification by flash column chromatography (silica; MeOH in DCM 4/96). |
| 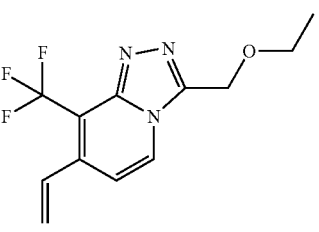<br>Intermediate 16 | Intermediate 12 | Purification by flash column chromatography (silica; EtOAc in DCM 0/100 to 10/90). |
| 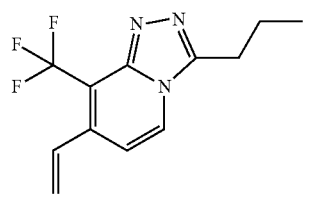<br>Intermediate 27 | Intermediate 26 | Reaction mixture performed at 150° C. in microwave. Purification by flash column chromatography (silica; EtOAc in DCM 0/100 to 10/90). |

Description 8

(a) Intermediate 17

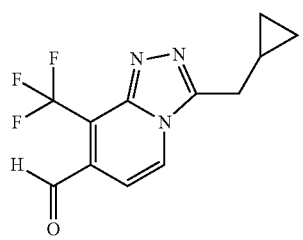 [SMILES: O=Cc1ccn2c(CC3CC3)nnc2c1C(F)(F)F]

Osmium tetraoxide (2.5% in t-BuOH, 10.103 mL, 0.781 mmol) and then, sodium periodate 12.53 g, 58.58 mmol) in water (48.5 mL) were added to a suspension of Intermediate 13 (6.08 g, 20.02 mmol) in dioxane (192 mL). The mixture was stirred at room temperature for 2 h.

The mixture was treated with water and EtOAc and it was filtered off through a pad of diatomaceous earth. The filtrate was extracted with EtOAc. The organic layer was separated, dried ($Na_2SO_4$), filtered and the solvents evaporated in vacuo. The crude product was washed with $Et_2O$ and it was filtered and dried to yield intermediate 17 (4.25 g, 79%) as a brown solid.

(b) Intermediate 18

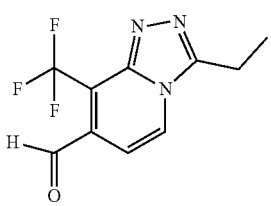 [SMILES: CCc1nnc2c(C(F)(F)F)c(C=O)ccn12]

A suspension of sodium periodate (5.04 g, 23.54 mmol) in distilled water (19 mL) was added to a stirred solution of osmium tetraoxide (2.5% in t-BuOH, 4.06 mL, 0.31 mmol) and intermediate 14 (2.08 g, 7.85 mmol) in dioxane (75 mL). The mixture was stirred at room temperature for 150 min, and then the mixture was treated with sat $NaHCO_3$ and brine, and extracted with DCM. The organic layer was separated, dried ($Na_2SO_4$), filtered and concentrated in vacuo. The product was triturated with $Et_2O$ and filtered in vacuo, and finally put in desiccator at 50° C. for 18 h, to yield intermediate 18 (1.6 g, 80%) as a brown solid.

The following intermediates were synthesized following a synthetic sequence analogous to that reported in Description

| Intermediate | Starting material | Conditions |
|---|---|---|
| 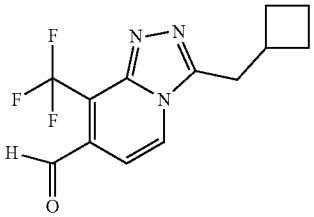<br>Intermediate 19 | Intermediate 15 | Procedure as in (a). |
| 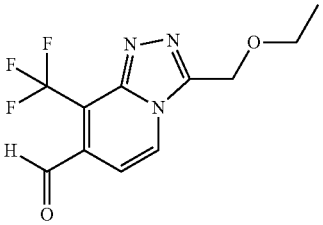<br>Intermediate 20 | Intermediate 16 | Procedure as in (a). |
| 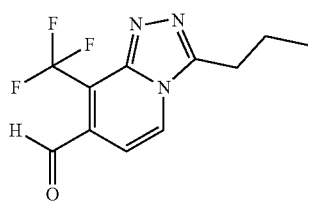<br>Intermediate 28 | Intermediate 27 | Procedure as in (a), order of addition: osmium tetroxide was added to a stirred solution of intermediate 27 in 1,4-dioxane, then a suspension of sodium periodate in water was added and the reaction mixture was stirred for 2 h at RT. No filtration through a pad of diatomaceous earth. |

Description 9

(a) Intermediates 21a, 21b and 21c

Intermediate 21a

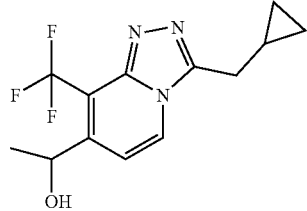

Intermediate 21b

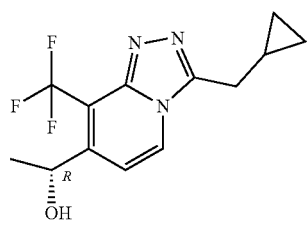

Intermediate 21c

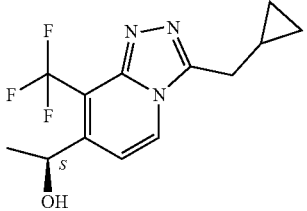

Methylmagnesium bromide (1.4 M in THF, 12.40 mL, 17.37 mmol) was added dropwise to a stirred suspension of intermediate 17 (4.25 g, 15.79 mmol) in THF (281.07 mL) at −20° C. under $N_2$ atmosphere. The mixture was stirred at −20° C. for 45 minutes. The crude was treated with a sat. sol. of $NH_4Cl$ and extracted with EtOAc. The organic layer was separated, dried ($Na_2SO_4$), filtered and concentrated in vacuo. The residue was purified by flash column chromatography (silica; MeOH in DCM 0/100 to 4/96). The desired fractions were collected and concentrated in vacuo to yield intermediate 21a (racemic mixture) (2.96 g, 66%). Intermediate 21a (1.82 g) was purified by chiral SFC: [Stationary phase: CHIRALPAK AD-H (5 μm 250×20 mm), Mobile phase: 80% $CO_2$, 20% EtOH] yielding 21b (R-enantiomer) (0.453 g, 10%) as a pale grey solid and intermediate 21c (S-enantiomer) (0.439 g, 10%).

(b) Intermediate 22

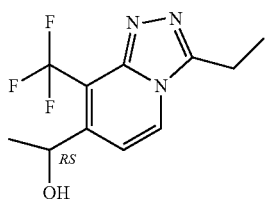 [SMILES: CCc1nnc2c(C(F)(F)F)c(C(C)O)ccn12]

Methylmagnesium bromide (1.4 M in THF, 3.97 mL, 5.56 mmol) was added dropwise to a stirred suspension of intermediate 18 (1.23 g, 5.06 mmol) in THF (90 mL) at −20° C. under $N_2$ atmosphere. The mixture was stirred at −20° C. for 45 minutes. The crude was treated with a sat. sol. of $NH_4Cl$ and extracted with EtOAc. The organic layer was separated, dried ($Na_2SO_4$), filtered and concentrated in vacuo. The residue was purified by flash column chromatography (silica; MeOH in DCM 0/100 to 4/96). The desired fractions were collected and concentrated in vacuo. The residue thus obtained was triturated with $Et_2O$ to yield intermediate 22 (620 mg, 35%) as a pale yellow solid. The following intermediates were synthesized following a synthetic sequence analogous to that reported in Description 9.

| Intermediate | Starting material | Conditions |
|---|---|---|
| Intermediate 23 | Intermediate 19 | Procedure (b). |
| Intermediate 24a | Intermediate 20 | Procedure (b). |
| Intermediate 29 | Intermediate 28 | Procedure (b). |

Intermediate 24a was further separated into Intermediate 24b and Intermediate 24c:

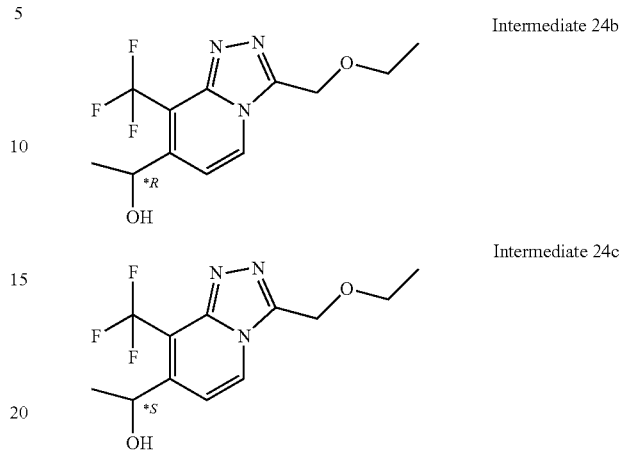

Chiral SFC conditions: Stationary phase Chiralpak AD-H 5 μm 250*30 mm; Mobile phase: 80% $CO_2$, 15% EtOH Preparation of the Final Compounds of Formula (I-B)

Example 1

(a) Synthesis of Compounds 4-b, 6-b and 5-b

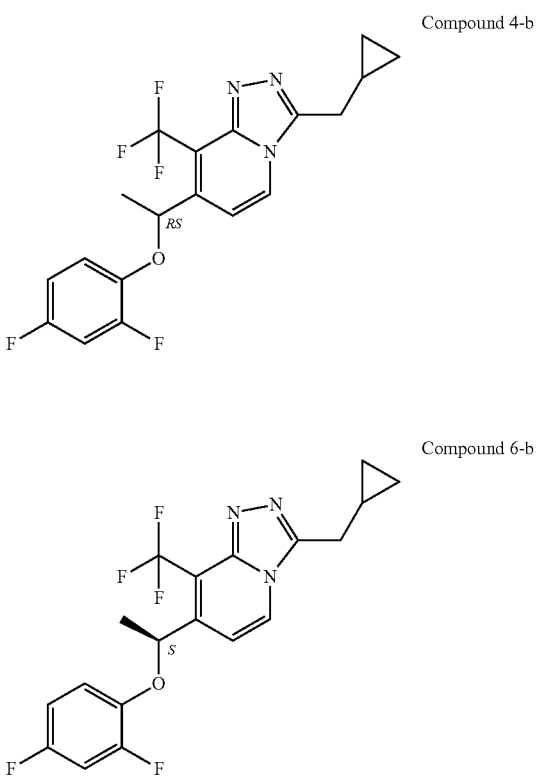

-continued

Compound 5-b

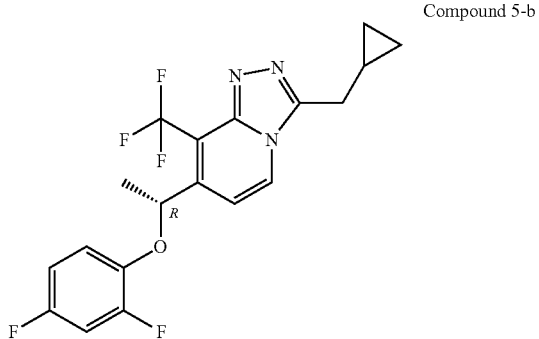

DIAD (2.07 mL, 10.52 mmol) was added dropwise to a stirred solution of intermediate 21a (2 g, 7.01 mmol), 2,4-difluorophenol (1.00 mL, 10.52 mmol) and triphenylphosphine (2.76 g, 10.52 mmol) in THF (74.18 mL) at 0° C. and under nitrogen atmosphere. The mixture was stirred at 100° C. for 10 minutes under microwave irradiation. The mixture was diluted with EtOAc and washed with a sat. sol. of $NaHCO_3$. The organic layer was separated, dried ($Na_2SO_4$), filtered and concentrated in vacuo. The residue was purified by flash column chromatography (silica; MeOH in DCM 0/100 to 97/3). The desired fractions were collected and concentrated in vacuo. The residue was triturated with DIPE to give compound 4-b (1.46 g, 52%) as a white solid, which was purified by chiral SFC [Stationary phase: Chiralpak AD (5 m 250*30 mm, Mobile phase: 85% $CO_2$, 15% iPrOH)], yielding compound 6-b (0.659 g, 24%) and compound 5-b (0.693 g, 25%).

(b) Alternative Synthesis of Compound 6-b

Co. No. 6-b

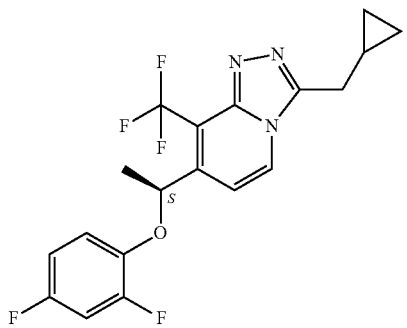

DIAD (31.06 μL, 0.16 mmol) was added dropwise to a stirred solution of intermediate 21b (30 mg, 0.11 mmol), 2,4-difluorophenol (15.07 μL, 0.16 mmol) and triphenylphosphine (41.38 mg, 0.16 mmol) in THF (1.11 mL) at 0° C. and under nitrogen atmosphere. The mixture was stirred at 100° C. for 10 minutes under microwave irradiation. The mixture was diluted with EtOAc and washed with a sat. sol. of $NaHCO_3$. The organic layer was separated, dried ($Na_2SO_4$), filtered and concentrated in vacuo. The residue was purified by flash column chromatography (silica; MeOH in DCM 0/100 to 97/3). The desired fractions were collected and concentrated in vacuo. The residue was triturated with DIPE to give compound 6-b (40 mg, 96%) as a white solid.

(c) Synthesis of Compound 6-b Hydrochloride Salt (.HCl)

DIAD (207.06 μL, 1.05 mmol) was added dropwise to a stirred solution of intermediate 21b (200 mg, 0.70 mmol), 2,4-difluorophenol (100.45 μL, 1.05 mmol) and triphenylphosphine (275.84 mg, 1.0516 mmol) in THF (4 mL) at 0° C. and under nitrogen atmosphere. The mixture was stirred at 100° C. for 15 minutes under microwave irradiation. The mixture was diluted with EtOAc and washed with a sat. sol. of $NaHCO_3$. The organic layer was separated, dried ($Na_2SO_4$), filtered and concentrated in vacuo. The residue was purified by RP HPLC (Stationary phase: C18 XBridge 30×100 mm 5 μm, Mobile phase: Gradient from 60% 0.1% $NH_4CO_3H/NH_4OH$ pH 9 solution in Water, 40% $CH_3CN$ to 43% 0.1% $NH_4CO_3H/NH_4OH$ pH 9 solution in Water, 57% $CH_3CN$), yielding a white solid residue that was dissolved in $Et_2O$ (8 mL) and 1,4-dioxane (0.5 mL). To the solution thus obtained HCl (4M in dioxane, 200 μL) was added dropwise. The white solid precipitate was filtered, washed with $Et_2O$, dried ($Na_2SO_4$) and evaporated under vacuum. The white residue thus obtained was triturated with $Et_2O$ to give compound 6-b .HCl (110 mg, 36%) as a white solid.

The following compounds were synthesized following a synthetic sequence analogous to that reported in Example 1(b), starting from intermediate 21b.

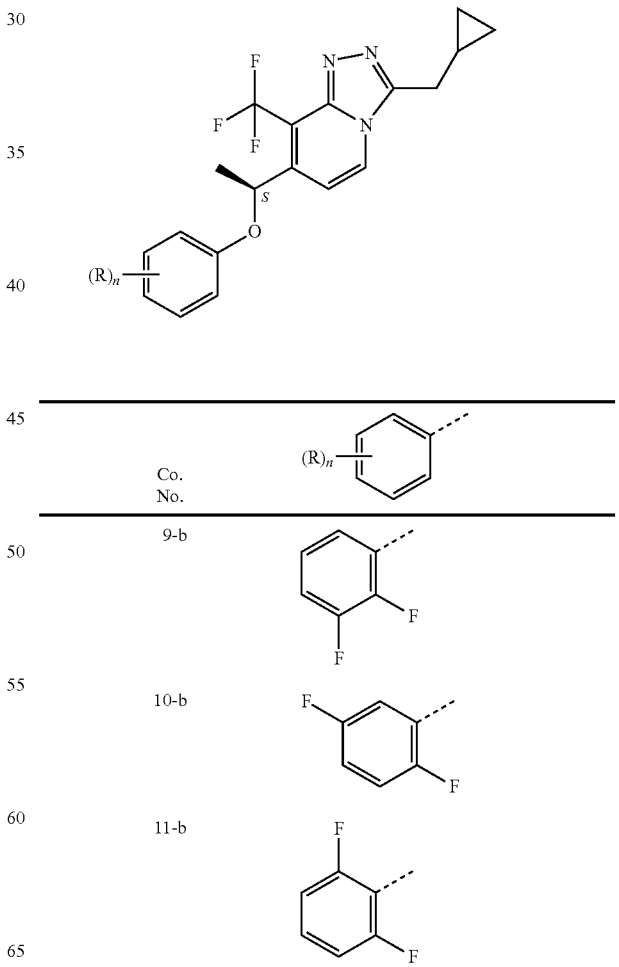

| Co. No. | 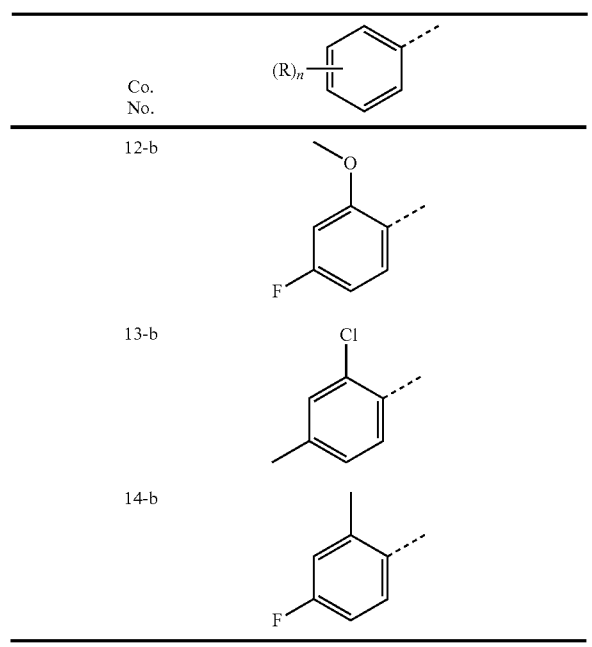 |
|---|---|
| 12-b | |
| 13-b | |
| 14-b | |

Example 2

Synthesis of Compound 7-b

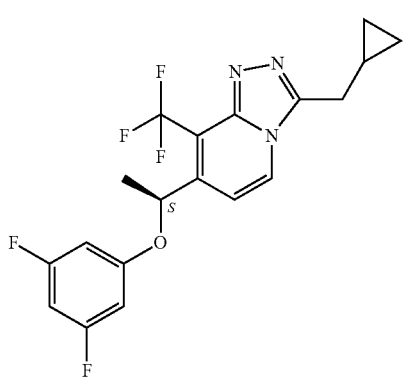

Co. No. 7-b

Procedure (a): DIAD (31.06 μL, 0.158 mmol) was added dropwise to a stirred solution of intermediate 21b (30 mg, 0.105 mmol), 3,5-difluorophenol (20.52 mg, 0.158 mmol) and triphenylphosphine (41.38 mg, 0.158 mmol) in THF (1.113 mL) at 0° C. and under nitrogen atmosphere. The mixture was stirred at 100° C. for 10 minutes under microwave irradiation. The mixture was diluted with EtOAc and washed with a sat. sol. of NaHCO$_3$. The organic layer was separated, dried (Na$_2$SO$_4$), filtered and concentrated in vacuo. The residue was purified by flash column chromatography (silica; MeOH in DCM 0/100 to 96/4). The desired fractions were collected and concentrated in vacuo. The residue was triturated with DIPE to give compound 7-b (21 mg, 50%) as a white solid.

Procedure (b): Alternatively, compound 7 was also synthesized following a synthetic sequence analogous to that reported in Example 1(b), starting from intermediate 21b.

Example 3

Synthesis of Compound 8-b

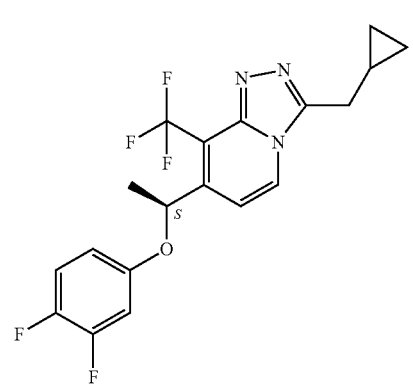

Co. No. 8-b

Procedure (a): DIAD (31.06 μL, 0.158 mmol) was added dropwise to a stirred solution of intermediate 21b (30 mg, 0.105 mmol), 3,4-difluorophenol (20.52 mg, 0.158 mmol) and triphenylphosphine (41.38 mg, 0.158 mmol) in THF (1.11 mL) at 0° C. and under nitrogen atmosphere. The mixture was stirred at 100° C. for 10 minutes under microwave irradiation. The mixture was diluted with EtOAc and washed with a sat. sol. of NaHCO$_3$. The organic layer was separated, dried (Na$_2$SO$_4$), filtered and concentrated in vacuo. The residue was purified by flash column chromatography (silica; MeOH in DCM 0/100 to 96/4). The desired fractions were collected and concentrated in vacuo. The residue was triturated with DIPE to give compound 8-b (10.6 mg, 25%) as a white solid.

Procedure (b): Alternatively, compound 8-b was also synthesized following a synthetic sequence analogous to that reported in Example 1(b), starting from intermediate 21b.

Example 4

Synthesis of Compound 15-b

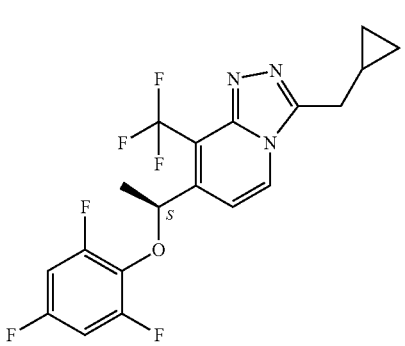

Co. No. 15-b

Procedure (a): DIAD (155.3 μL, 0.789 mmol) was added dropwise to a stirred solution of intermediate 21b (150 mg, 0.526 mmol), 2,4,6-trifluorophenol (116.8 mg, 0.789 mol) and triphenylphosphine (206.88 mg, 0.789 mmol) in THF (5.56 mL) at 0° C. and under nitrogen atmosphere. The mixture was stirred at 100° C. for 10 minutes under microwave. The mixture was diluted with DCM and washed with a sat. sol. of NaHCO$_3$. The organic layer was separated, dried (Na$_2$SO$_4$), filtered and concentrated in vacuo, then purified by flash column chromatography (silica; MeOH/NH$_3$ 7 N in DCM 0/100 to 90/10). The desired fractions were collected and concentrated in vacuo. The was purified by RP HPLC (Stationary phase: C18 XBridge 30×100 mm 5 m, Mobile phase: Gradient from 54% 0.1% NH$_4$CO$_3$H/NH$_4$OH pH 9 solution in Water, 46% CH$_3$CN to 64% 0.1% NH$_4$CO$_3$H/NH$_4$OH pH 9 solution in Water, 36% CH$_3$CN) yielding a colourless oil that was crystallized upon standing (2 days). The solid was triturated with heptane to give compound 15-b (129.8 mg, 59%) as a white solid. Procedure (b): Alternatively, compound 15-b was also synthesized following a synthetic sequence analogous to that reported in Example 1(b), starting from intermediate 21b.

Example 5

Synthesis of Compounds 1-b, 2-b and 3-b 1.69 mmol), 4-fluorophenol (227.77 mg, 2.03 mmol) and triphenylphosphine (666.14 mg, 2.54 mmol) in THF (17.91 mL) as described in Example 1(a) yielded a residue that was purified by flash column chromatography (silica; EtOAc in DCM 0/100 to 90/10). The desired fractions were collected and concentrated in vacuo. The resulting residue was triturated with DIPE to yield compound 1-b (320 mg, 50%) as a white solid, which was purified by chiral SFC [Stationary phase: Chiralpak AD (5 μm 250*30 mm, Mobile phase: 77% CO$_2$, 23% MeOH)], yielding compound 2-b (131 mg, 20%) and compound 3-b (129 mg, 20%) as white solids.

Example 6

Synthesis of Compounds 24-b, 26-b, and 27-b

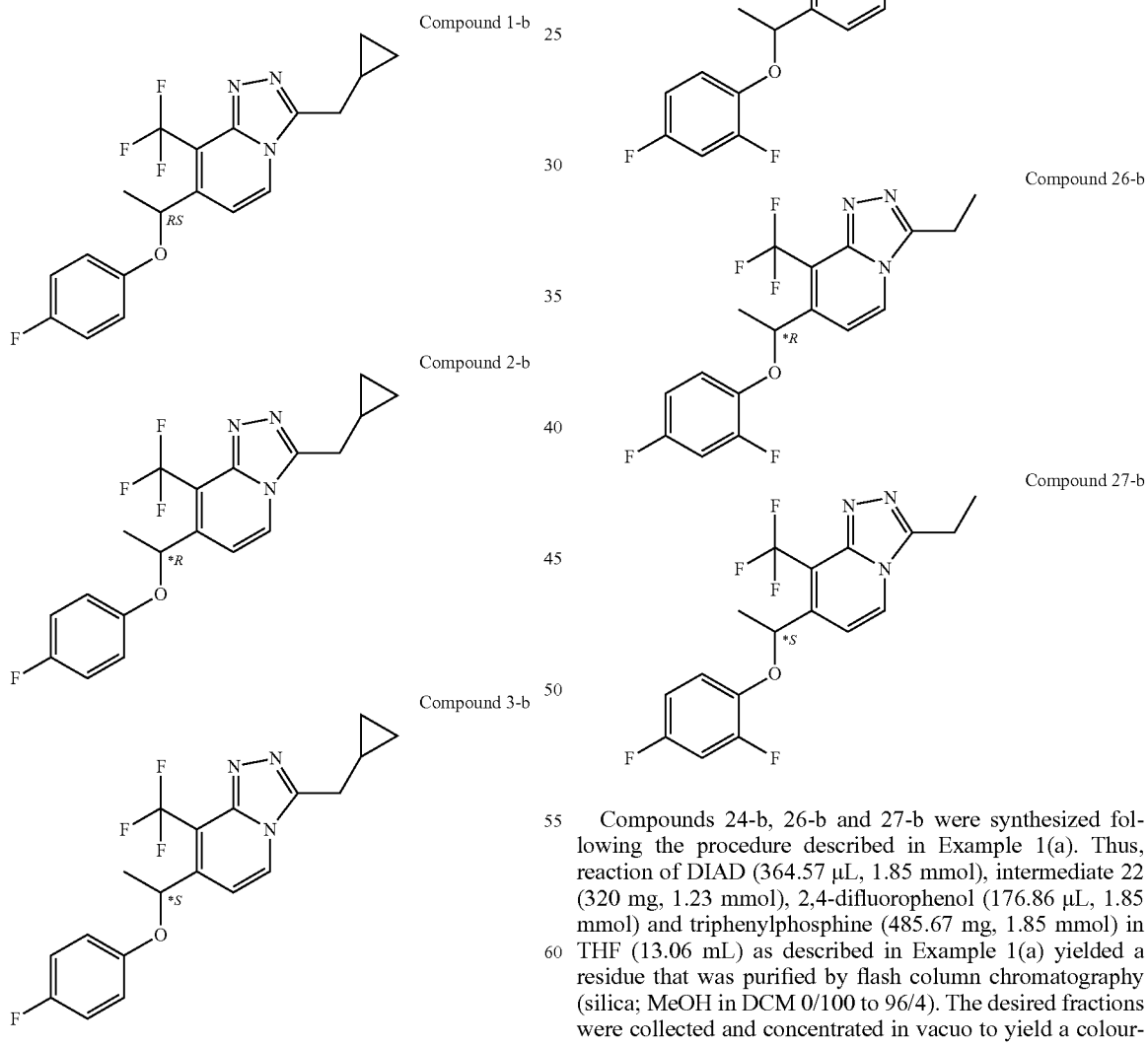

Compounds 24-b, 26-b and 27-b were synthesized following the procedure described in Example 1(a). Thus, reaction of DIAD (364.57 μL, 1.85 mmol), intermediate 22 (320 mg, 1.23 mmol), 2,4-difluorophenol (176.86 μL, 1.85 mmol) and triphenylphosphine (485.67 mg, 1.85 mmol) in THF (13.06 mL) as described in Example 1(a) yielded a residue that was purified by flash column chromatography (silica; MeOH in DCM 0/100 to 96/4). The desired fractions were collected and concentrated in vacuo to yield a colourless oil that crystallized with DIPE to give compound 24 as a white solid, which was purified by RP HPLC (Stationary phase: C18 XBridge 30×100 mm 5 m; mobile phase: Gradient from 54% 0.1% NH$_4$CO$_3$H/NH$_4$OH pH 9 solution in Compounds 1-b, 2-b and 3-b were synthesized following the procedure described in Example 1(a). Thus, reaction of DIAD (500.05 μL, 2.54 mmol), intermediate 21a (483 mg, Water, 46% CH₃CN to 64% 0.1% NH₄CO₃H/NH₄OH pH 9 solution in Water, 36% CH₃CN) yielding a colourless oil that was crystallized upon trituration with heptane to give 240 mg (52%) of compound 24-b as a white solid, which was then purified by chiral SFC (Stationary phase: CHIRALPAK AD-H 5 µm 250×20 mm; mobile phase: 85% CO₂, 15% iPOH (0.3% iPrNH₂)), yielding compound 26-b (103 mg, 22%) and compound 27-b (107 mg, 23%).

The following compounds were obtained following a synthetic sequence similar to that reported in Example 1(a).

Compound 25-b

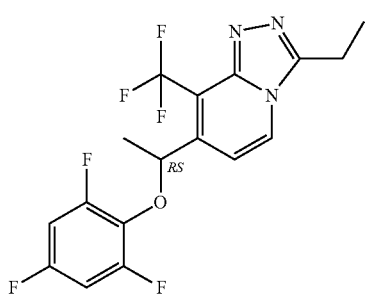

Compound 28-b

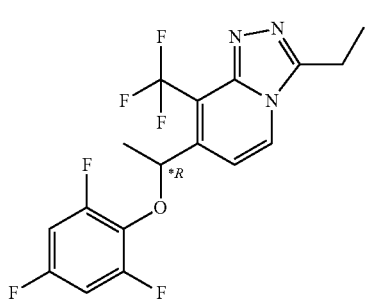

Compound 29-b

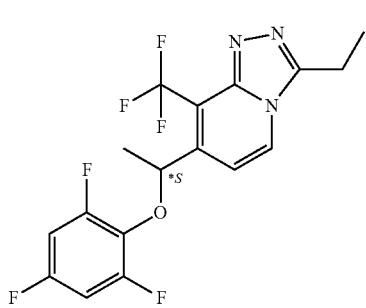

Starting material: Intermediate 22
Chiral SFC conditions: Stationary phase: Chiralpak AD-H 5µm 250 x 20 mm); Mobile phase: 85% CO₂, 15% mixture of EtOH/iPrOH 50/50 v/v (+0.3% iPrNH₂)

Compound 16-b

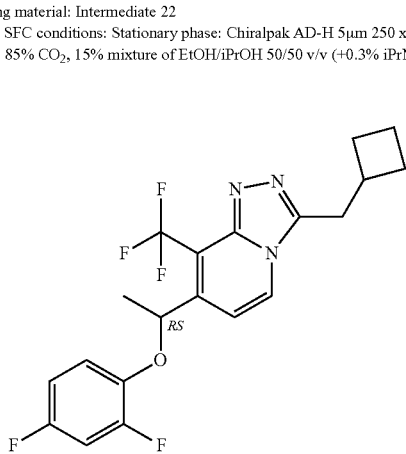

Compound 17-b

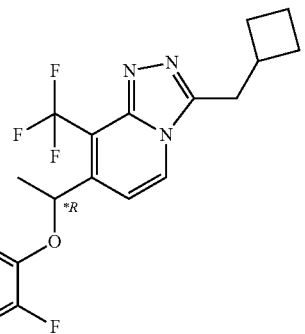

Compound 18-b

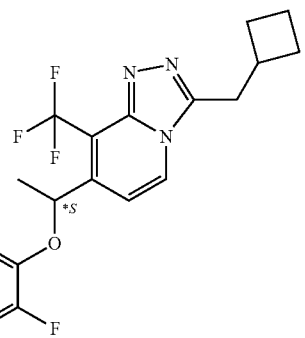

Starting material: Intermediate 23
Chiral SFC conditions: Stationary phase: Chiralpak AD-H (5 µm 250*30 mm); Mobile phase: 80% CO₂, 20% mixture MeOH/iPrOH 50/50 v/v (+0.3% iPrNH₂)

The following compounds were synthesized following a synthetic sequence as reported in Example 1(b), starting from the indicated intermediates.

Compound 20-b

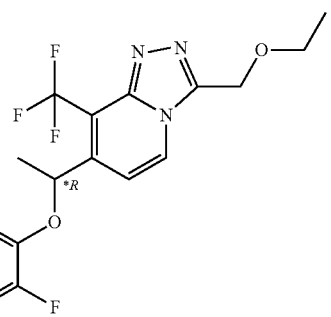

obtained from intermediate 24c

-continued

Compound 21-b obtained from intermediate 24b

Compound 19-b obtained from intermediate 24a

Compound 22-b obtained from intermediate 24c

Compound 23-b obtained from intermediate 24c

-continued

Compound 30-b obtained from intermediate 29

Compound 31-b

Compound 32-b

Starting material: Intermediate 30
Chiral SFC conditions: Stationary phase: Chiralpak AD-H 5μm 250 x 20 mm);
Mobile phase: 85% CO$_2$, 15% iPrOH.

Table A below lists additional compounds of Formula (I-B) which were prepared by analogy to the above examples (Exp. no.).

TABLE A

Example compounds according to Formula (I-B).

| Co. no. | Exp no. | R$^1$ | Ar | Stereo-chem. |
|---|---|---|---|---|
| 1-b | E5# | | | RS |

TABLE A-continued

Example compounds according to Formula (I-B).

| Co. no. | Exp no. | R¹ | Ar | Stereo-chem. |
|---|---|---|---|---|
| 2-b | E5# | cyclopropyl | 4-F-phenyl | *R |
| 3-b | E5# | cyclopropyl | 4-F-phenyl | *S |
| 4-b | E1# | cyclopropyl | 2,3-diF-phenyl | RS |
| 5-b | E1# | cyclopropyl | 3,4-diF-phenyl | R |
| 6-b | E1(a) and (b)# | cyclopropyl | 3,4-diF-phenyl | S |
| 6-b·HCl | E1(c)# | | | |
| 7-b | E2# | cyclopropyl | 3,5-diF-phenyl | S |
| 8-b | E3# | cyclopropyl | 3,4-diF-phenyl | S |
| 9-b | E1(b) | cyclopropyl | 2,3-diF-phenyl | S |
| 10-b | E1(b) | cyclopropyl | 2,5-diF-phenyl | S |
| 11-b | E1(b) | cyclopropyl | 2,6-diF-phenyl | S |
| 12-b | E1(b) | cyclopropyl | 5-F-2-OMe-phenyl | S |
| 13-b | E1(b) | cyclopropyl | 2-Cl-5-Me-phenyl | S |
| 14-b | E1(b) | cyclopropyl | 5-F-2-Me-phenyl | S |
| 15-b | E4# | cyclopropyl | 2,4,6-triF-phenyl | S |
| 16-b | E1(a) | cyclobutyl | 2,4-diF-phenyl | RS |
| 17-b | E1(a) | cyclobutyl | 2,4-diF-phenyl | *R |
| 18-b | E1(a) | cyclobutyl | 2,4-diF-phenyl | *S |
| 19-b | E1(b) | ethoxymethyl | 2,4-diF-phenyl | RS |
| 20-b | E1(b) | ethoxymethyl | 2,4-diF-phenyl | *R |
| 21-b | E1(b) | ethoxymethyl | 2,4-diF-phenyl | *S |

TABLE A-continued

Example compounds according to Formula (I-B).

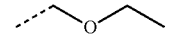

| Co. no. | Exp no. | R¹ | Ar | Stereo-chem. |
|---|---|---|---|---|
| 22-b | E1(b) | 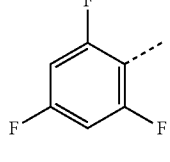 | 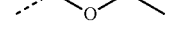 | *R |
| 23-b | E1(b) | 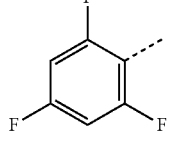 |  | *S |
| 24-b | E6[#] | 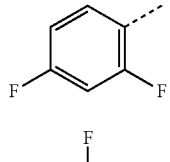 |  | RS |
| 25-b | E1(a) | 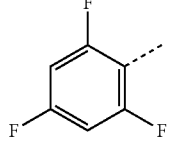 |  | RS |
| 26-b | E6[#] | 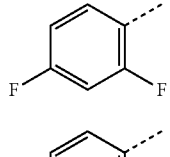 |  | *R |
| 27-b | E6[#] | 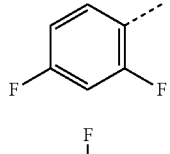 |  | *S |
| 28-b | E1(a) | 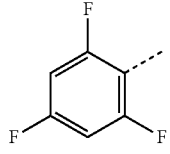 |  | *R |
| 29-b | E1(a) | 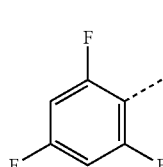 |  | *S |
| 30-b | E1(b) | 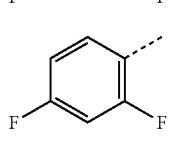 | 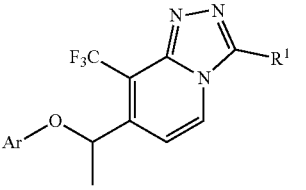 | RS |
| 31-b | E1(b) |  | 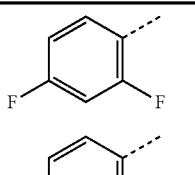 | *R |
| 32-b | E1(b) |  | 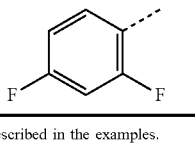 | *S |

[#]indicates that the experimental procedure is described in the examples.

Analytical Part

Optical Rotations

Optical rotations were measured on a Perkin-Elmer 341 polarimeter with a sodium lamp and reported as follows: [α]° (λ, c g/100 ml, solvent, T° C.). $[α]^T=(100α)/(l×c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

LCMS

For (LC)MS-characterization of the compounds of the present invention, the following methods were used.

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE B

LCMS Method codes (Flow expressed in mL/min; column temperature (T) in ° C.; Run time in minutes).

| Instrument | Column | Mobile phase | Gradient | Flow Col T | Run time | LCMS Method |
|---|---|---|---|---|---|---|
| Waters: Acquity ® UPLC ®-DAD and SQD | Agilent: Eclipse Plus C18 RRHD (1.8 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 — 50 | 5 | 1 |
| Waters: Acquity ® UPLC ®-DAD and SQD | Waters: CSH™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 — 50 | 5 | 2 |
| Waters: Acquity UPLC ®-DAD and Quatro Micro™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 — 40 | 6.2 | 3 |
| Waters: Acquity ® UPLC ®-DAD and SQD | Waters: CSH™ C18 (1.7 μm, 2.1 × 50 mm) | A: 95% $CH_3COONH_4$ 6.5 mM + 5% $CH_3CN$, B: $CH_3CN$ | From 95% A to 5% A in 7.8 min, held for 1.2 min | 1 — 50 | 9 | 4 |

Melting Points

Values are peak values, and are obtained with experimental uncertainties that are commonly associated with this analytical method.

Mettler FP 81HT/FP90 Apparatus

For a number of compounds, melting points were determined in open capillary tubes on a FP 81HT/FP90 apparatus (Mettler-Toledo). Melting points were measured with a temperature gradient of 1, 3, 5 or 10° C./minute. Maximum temperature was 300° C. The melting point was read from a digital display.

TABLE C

Physico-chemical data for some compounds, retention time ($R_t$) in min, [M + H]$^+$ peak (protonated molecule), LCMS method and mp (melting point in ° C.). (n.d. =not determined).

| Co. no. | Mp (° C.) | $R_t$ (min) | [MH$^+$] | LCMS method | Optical Rotation |
|---|---|---|---|---|---|
| 1-b | 156.3 | 2.32 | 380 | 1 | |
| 2-b | 176.9 | 2.93 | 380 | 3 | −58.5° (589 nm, c 0.53 w/v %, DMF, 20° C.) |
| 3-b | 177.3 | 2.93 | 380 | 3 | +59.4° (589 nm, c 0.52 w/v %, DMF, 20° C.) |
| 4-b | 121.7 | 2.41 | 398 | 1 | |
| 5-b | 142 | 2.99 | 398.3 | 3 | +95.7° (589 nm, c 0.69 w/v %, DMF, 20° C.) |
| 6-b | 142.4 | 2.99 | 398.2 | 3 | −95.4° (589 nm, c 0.7 w/v %, DMF, 20° C.) |
| 7-b | 170.08 | 2.37 | 398 | 2 | −55.7° (589 nm, c 0.96 w/v %, DMF, 20° C.) |
| 8-b | n.d. | 2.32 | 398 | 2 | n.d. |
| 9-b | n.d. | 2.32 | 398 | 2 | n.d. |
| 10-b | n.d. | 2.25 | 398 | 2 | n.d. |
| 11-b | n.d. | 2.28 | 398 | 2 | n.d. |
| 12-b | n.d. | 2.16 | 410 | 2 | n.d. |
| 13-b | 144.1 | 2.68 | 410 | 2 | n.d. |
| 14-b | 161.7 | 2.51 | 394 | 2 | n.d. |
| 15-b | 80.3 | 2.37 | 416 | 2 | −167.0° (589 nm, c 0.55 w/v %, DMF, 20° C.) |
| 16-b | n.d. | 2.50 | 412 | 2 | n.d. |
| 17-b | n.d. | 3.12 | 412 | 3 | n.d. |
| 18-b | n.d. | 3.12 | 412 | 3 | n.d. |
| 19-b | n.d. | 2.39 | 402 | 2 | n.d. |
| 20-b | n.d. | 2.3 | 402 | 2 | n.d. |
| 21-b | n.d. | 3.36 | 402 | | n.d. |
| 22-b | n.d. | 2.35 | 420 | 2 | n.d. |
| 23-b | n.d. | 2.35 | 420 | 2 | n.d. |
| 24-b | 135.7 | 2.05 | 372 | 2 | n.d. |
| 25-b | 138.3 | 2.13 | 390 | 2 | n.d. |
| 26-b | n.d. | 2.80 | 372 | 3 | −83.9° (589 nm, c 0.52 w/v %, DMF, 25° C.) |
| 27-b | n.d. | 2.80 | 372 | 3 | +92.1° (589 nm, c 0.55 w/v %, DMF, 25° C.) |
| 28-b | n.d. | 2.85 | 390 | 3 | −129.2° (589 nm, c 0.5 w/v %, DMF, 25° C.) |
| 29-b | n.d. | 2.85 | 390 | 3 | +137.3° (589 nm, c 0.51 w/v %, DMF, 25° C.) |
| 30-b | 130.6 | 2.29 | 386 | 2 | n.d. |
| 31-b | 127.85 | 2.29 | 386 | 2 | −67.5° (589 nm, c 0.83 w/v %, DMF, 20° C.) |
| 32-b | 127.69 | 2.29 | 386 | 2 | +89.5° (589 nm, c 0.83 w/v %, DMF, 20° C.) |

SFC-MS

General Procedure

The SFC measurement was performed using Analytical system from Berger instrument comprising a FCM-1200 dual pump fluid control module for delivering carbon dioxide ($CO2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 µa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1:

In addition to the general procedure: The analytical chiral separation in SFC-MS was carried out on a CHIRALPAK AD DAICEL column (10 µm, 4.6×250 mm) at 35° C. with a flow rate of 3.0 ml/min. The mobile phase is 85% $CO_2$, 15% iPrOH (+0.3% $iPrNH_2$) hold 7 min in isocratic mode.

Method 2:

In addition to the general procedure: The analytical chiral separation in SFC-MS was carried out on a CHIRALPAK AD DAICEL column (10 µm, 4.6×250 mm) at 35° C. with a flow rate of 3.0 ml/min. The mobile phase is 75% CO2, 15% iPrOH (+0.3% $iPrNH_2$) hold 7 min in isocratic mode.

Method 3:

In addition to the general procedure: The analytical chiral separation in SFC-MS was carried out on a CHIRALPAK AD DAICEL column (10 µm, 4.6×250 mm) at 35° C. with a flow rate of 3.0 ml/min. The mobile phase is 80% CO2, 10% Methanol+10% iPrOH (+0.3% $iPrNH_2$) hold 7 min in isocratic mode.

TABLE D

Analytical SFC data-$R_t$ means retention time (in minutes), [M + H]⁺ means the protonated mass of the compound, method refers to the method used for SFC/MS analysis of enantiomerically pure compounds. The measurement was compared against the mixture.

| Co. Nr. | $R_t$ | [M + H]⁺ | UV Area % | Method | Isomer Elution Order* |
|---|---|---|---|---|---|
| 6-b | 4.28 | 398 | 100 | 1 | A |
| 5-b | 5.98 | 398 | 100 | 1 | B |
| 2-b | 2.13 | 380 | 100 | 2 | A |
| 3-b | 2.97 | 380 | 100 | 2 | B |
| 17-b | 2.46 | 412 | 100 | 3 | A |
| 18-b | 3.12 | 412 | 100 | 3 | B |
| 31-b | 2.93 | 386 | 100 | 1 | A |
| 32-b | 3.81 | 386 | 100 | 1 | B |

*A means the first isomer that elutes. B means the second isomer that elutes.

Nuclear Magnetic Resonance (NMR)

For a number of compounds, ¹H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Co. No. 6-b: ¹H NMR (400 MHz, $CDCl_3$) δ ppm 0.30-0.38 (m, 2H), 0.59-0.68 (m, 2H), 1.14-1.22 (m, 1H), 1.72 (d, J=6.5 Hz, 3H), 3.02-3.14 (m, 2H), 5.84 (q, J=6.3 Hz, 1H), 6.67-6.73 (m, 1H), 6.80-6.89 (m, 2H), 7.30 (d, J=7.4 Hz, 1H), 8.11 (d, J=7.4 Hz, 1H)

Co. No. 7-b: ¹H NMR (400 MHz, $CDCl_3$) δ ppm 0.30-0.39 (m, 2H), 0.59-0.68 (m, 2H), 1.11-1.23 (m, 1H), 1.70 (d, J=6.5 Hz, 3H), 3.01-3.14 (m, 2H), 5.83 (q, J=6.2 Hz, 1H), 6.35-6.45 (m, 3H), 7.13 (d, J=7.2 Hz, 1H), 8.08 (d, J=7.4 Hz, 1H)

Co. No. 8-b: ¹H NMR (400 MHz, $CDCl_3$) δ ppm 0.30-0.38 (m, 2H), 0.58-0.68 (m, 2H), 1.11-1.22 (m, 1H), 1.69 (d, J=6.2 Hz, 3H), 3.01-3.13 (m, 2H), 5.79 (q, J=6.2 Hz, 1H), 6.53 (dtd, J=9.2, 3.1, 3.1, 1.7 Hz, 1H), 6.72 (ddd, J=11.6, 6.5, 3.1 Hz, 1H), 6.95-7.04 (m, 1H), 7.15 (d, J=7.4 Hz, 1H), 8.07 (d, J=7.4 Hz, 1H)

Co. No. 15-b: ¹H NMR (500 MHz, $CDCl_3$) δ ppm 0.30-0.41 (m, 2H), 0.59-0.71 (m, 2H), 1.16-1.25 (m, 1H), 1.70 (d, J=6.4 Hz, 3H), 3.05-3.16 (m, 2H), 5.80 (q, J=6.4 Hz, 1H), 6.62-6.70 (m, 2H), 7.45 (d, J=7.5 Hz, 1H), 8.16 (d, J=7.2 Hz, 1H)

Co. No. 13-b: ¹H NMR (500 MHz, $CDCl_3$) δ ppm 0.27-0.39 (m, 2H), 0.58-0.67 (m, 2H), 1.12-1.21 (m, 1H), 1.73 (d, J=6.4 Hz, 3H), 2.22 (s, 3H), 3.06 (qd, J=15.4, 6.6 Hz, 2H), 5.92 (q, J=6.4 Hz, 1H), 6.71 (d, J=8.4 Hz, 1H), 6.89 (dd, J=8.4, 1.4 Hz, 1H), 7.18 (d, J=1.7 Hz, 1H), 7.32 (d, J=7.2 Hz, 1H), 8.07 (d, J=7.2 Hz, 1H)

Co. No. 14-b: ¹H NMR (500 MHz, $CDCl_3$) δ ppm 0.28-0.39 (m, 2H), 0.57-0.69 (m, 2H), 1.12-1.21 (m, 1H), 1.70 (d, J=6.6 Hz, 3H), 2.31 (s, 3H), 3.01-3.12 (m, 2H), 5.79 (q, J=6.6 Hz, 1H), 6.55 (dd, J=9.0, 4.3 Hz, 1H), 6.69 (td, J=8.5, 3.0 Hz, 1H), 6.87 (dd, J=9.0, 2.9 Hz, 1H), 7.17 (d, J=7.5 Hz, 1H), 8.06 (d, J=7.2 Hz, 1H)

Co. No. 20-b: ¹H NMR (500 MHz, $CDCl_3$) δ ppm 1.22 (t, J=7.1 Hz, 3H), 1.72 (d, J=6.4 Hz, 3H), 3.58 (q, J=7.1 Hz, 2H), 5.03-5.10 (m, 2H), 5.84 (q, J=6.5 Hz, 1H), 6.67-6.74 (m, 1H), 6.81-6.88 (m, 2H), 7.34 (d, J=7.2 Hz, 1H), 8.40 (d, J=7.5 Hz, 1H)

Co. No. 22-b: ¹H NMR (500 MHz, $CDCl_3$) δ ppm 1.23 (t, J=6.9 Hz, 3H), 1.70 (d, J=6.4 Hz, 3H), 3.58 (q, J=7.0 Hz, 2H), 5.05-5.12 (m, 2H), 5.81 (q, J=6.6 Hz, 1H), 6.62-6.70 (m, 2H), 7.48 (d, J=7.5 Hz, 1H), 8.45 (d, J=7.2 Hz, 1H)

Co. No. 31-b: ¹H NMR (400 MHz, $CDCl_3$) δ ppm 1.07 (t, J=7.40 Hz, 3H) 1.72 (d, J=6.24 Hz, 3H) 1.92 (sxt, J=7.63 Hz, 2H) 2.98-3.14 (m, 2H) 5.84 (q, J=6.47 Hz, 1H) 6.65-6.74 (m, 1H) 6.78-6.89 (m, 2H) 7.29 (d, J=7.40 Hz, 1H) 8.02 (d, J=7.40 Hz, 1H).

In Vitro Testing of Compounds of Formula (I-B)

The compounds of Formula (I-B) provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I-B) are present. Compounds of Formula (I-B) are expected to have their effect substantially at mGluR2 by virtue of their ability to enhance the function of the receptor. The effects of positive allosteric modulators tested at mGluR2 using the [³⁵S]GTPγS binding assay method described below and which is suitable for the identification of such compounds, and more particularly the compounds according to Formula (I-B), are shown in Table E.

[³⁵S]GTPγS Binding Assay

The [³⁵S]GTPγS binding assay is a functional membrane-based assay used to study G-protein coupled receptor (GPCR) function whereby incorporation of a non-hydrolysable form of GTP, [³⁵S]GTPγS (guanosine 5'-triphosphate, labelled with gamma-emitting ³⁵S), is measured. The G-protein α subunit catalyzes the exchange of guanosine 5'-diphosphate (GDP) by guanosine triphosphate (GTP) and on activation of the GPCR by an agonist, [³⁵S]GTPγS, becomes incorporated and cannot be cleaved to continue the exchange cycle (Harper (1998) Current Protocols in Pharmacology 2.6.1-10, John Wiley & Sons, Inc.). The amount of radioactive [³⁵S]GTPγS incorporation is a direct measure of the activity of the G-protein and hence the activity of the agonist can be determined. mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the positive allosteric modulation (PAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with a vortex and pipetting up and down. The suspension was centrifuged at 16,000 RPM (Sorvall RC-5C plus rotor SS-34) for 10 minutes and the supernatant discarded. The pellet was homogenized in 5 mM Tris-HCl, pH 7.4 using an ultra-turrax homogenizer and centrifuged again (18,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 μM GDP. Human mGlu2 receptor-containing membranes were thawed on ice and diluted in assay buffer supplemented with 14 μg/ml saponin. Membranes were pre-incubated with compound alone or together with a predefined (∼EC$_{20}$) concentration of glutamate (PAM assay) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 μg of membrane protein in 10 mM HEPES acid, 10 mM HEPES salt, pH 7.4, 100 mM NaCl, 3 mM MgCl$_2$, 10 μM GDP and 2 μg/ml saponin. Total reaction volume was 200 μl. Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried, and 40 μl of liquid scintillation cocktail (Microscint-O) was added to each well. Membrane-bound radioactivity was counted in a Microplate Scintillation and Luminescence Counter from Perkin Elmer.

Data Analysis

The concentration-response curves of representative compounds of the present invention-obtained in the presence of EC$_{20}$ of mGluR2 agonist glutamate to determine positive allosteric modulation (PAM)—were generated using the Lexis software interface (developed at J&J). Data were calculated as % of the control glutamate response, defined as the maximal response that is generated upon addition of glutamate alone. Sigmoid concentration-response curves plotting these percentages versus the log concentration of the test compound were analyzed using non-linear regression analysis. The concentration producing half-maximal effect is then calculated as EC$_{50}$. The pEC$_{50}$ values below were calculated as the −log EC$_{50}$, when the EC$_{50}$ is expressed in M. E$_{max}$ is defined as relative maximal effect (i.e. maximal % effect relative to the control glutamate response).

Table E below shows the pharmacological data obtained for compounds of Formula (I-B) and current pharmacological data obtained for compounds of Formulae (I) and (I-A).

TABLE E

Pharmacological data for compounds according to the invention.

| Co. No. | GTPγS- hmGluR2 PAM pEC$_{50}$ | GTPγS - hmGluR2 PAM E$_{max}$ |
|---|---|---|
| 1-b | 6.59 | 296 |
| 2-b | 6.84 | 228 |
| 3-b | 5.79 | 187 |
| 6-b | 7.39 | 256 |
| 5-b | 6.06 | 141 |
| 4-b | 7.04 | 329 |
| 7-b | 7.31 | 292 |
| 8-b | 7.04 | 244 |
| 9-b | 7.3 | 260 |
| 10-b | 7.47 | 218 |
| 11-b | 8.25 | 239 |
| 12-b | 6.99 | 178 |
| 16-b | 7.54 | 284 |
| 13-b | 7.75 | 280 |
| 14-b | 7.53 | 281 |
| 15-b | 8.16 | 293 |
| 19-b | 6.71 | 297 |
| 25-b | 6.9 | 233 |
| 24-b | 6.42 | 193 |
| 17-b | 7.73 | 317 |
| 18-b | 6.24 | 213 |
| 22-b | 7.61 | 325 |
| 23-b | 5.94 | 167 |
| 21-b | 6.32 | 102 |
| 20-b | 7.07 | 332 |
| 26-b | 6.78 | 214 |
| 27-b | n.c. | 51 |
| 30-b | 6.9 | 227 |
| 28-b | 7.19 | 234 |
| 29-b | 5.85 | 77 |
| 31-b | 7.05 | 251 |
| 32-b | 5.71 | 116 |
| 1 | 7.11 | 258 |
| 1a | 6.95 | 286 |
| 2 | 7.82 | 290 |
| 2a | 7.61 | 484 |
| 3 | 7.55 | 212 |
| 4 | 6.88 | 260 |
| 5 | 6.26 | 231 |
| 6 | 7.79 | 263 |
| 6a | 7.68 | 261 |
| 7 | 8.45 | 263 |
| 8 | 6.73 | 360 |
| 9 | 6.9 | 462 |
| 10 | 7.21 | 357 |
| 11 | 6.94 | 310 |
| 12 | 8.36 | 261 |
| 13 | 6.9 | 278 |
| 1-a | 6.78 | 314 |
| 2-a | 6.84 | 340 |
| 3-a | 6.88 | 231 |
| 4-a | 6.6 | 269 |
| 5-a | n.t. | |
| 6-a | 6.34 | 255 |
| 7-a | 6.64 | 291 |
| 8-a | 6.04 | 157 |
| 9-a | 6.59 | 222 |
| 10-a | 6.88 | 290 |
| 11-a | 7.11 | 249 |
| 12-a | 7.03 | 242 |
| 13-a | 6.67 | 212 |
| 14-a | 6.92 | 259 |
| 15-a | 7 | 253 |

TABLE E-continued

Pharmacological data for compounds according to the invention.

| Co. No. | GTPγS-hmGluR2 PAM pEC$_{50}$ | GTPγS-hmGluR2 PAM E$_{max}$ |
|---|---|---|
| 16-a | 7.12 | 223 |
| 17-a | 6.54 | 261 |
| 18-a | n.t. | |
| 19-a | 6.71 | 240 |
| 20-a | 6.91 | 243 |
| 21-a | 6.25 | 207 |
| 22-a | 6.05 | 259 |
| 23-a | 6.58 | 203 |
| 24-a | 6.91 | 258 |
| 25-a | 7.07 | 261 |
| 26-a | 6.5 | 248 |
| 27-a | 6.48 | 284 |
| 28-a | 6.96 | 297 |
| 29-a | 6.97 | 317 |
| 30-a | n.t. | |
| 31-a | n.t. | |
| 32-a | 6.66 | 347 |
| 33-a | 6.58 | 362 | n.c. means that the pEC$_{50}$ could not be calculated
n.t. means not tested pEC$_{50}$ values were not calculated in cases where the concentration-response curve did not reach a plateau level.

All compounds were tested in presence of mGluR2 agonist glutamate at a predetermined EC$_{20}$ concentration, to determine positive allosteric modulation. pEC$_{50}$ values were calculated from a concentration-response experiment of at least 8 concentrations.

B) Anticonvulsant Studies with mGluR2 Compounds (Orthosteric Agonist and Compounds of Formulae (I)/(I-A)/(I-B)

General

Preparation of Test Compounds and Solutions

Test compounds were administered using an optimal fluid volume to body fluid ratio. Test compounds were administered to mice in a volume of 0.01 mL/g of body weight (White H. S., et al., General Principles: Experimental selection, quantification, and evaluation of antiepileptic drugs, in Antiepileptic Drugs, Fourth Edition, R. H. Levy, R. H. Mattson, and B. S. Meldrum, Editors. 1995, Raven Press, Ltd.: New York, pp. 99-110). For subcutaneous (s.c.) administration, the test compounds were administered into a loose fold of skin along the back of the animal except compound 6-b, which was administered orally (p.o.). For each of the tests performed on the test compounds (except on compound 6-b), final compound concentrations were administered as aqueous solution in 20% Hp-1-CD. For compound 6-b, a 40% Hp-β-CD stock solution was first prepared and utilized for formulating compound 6-b at the desired concentrations for testing via the oral route; final compound concentrations were administered as suspensions in 20% Hp-1-CD. A 20% Hp-β-CD solution was used for the vehicle groups.

For LY-404039, final compound concentrations were administered as a saline solution s.c.

For compound CAS 1092453-15-0, final compound concentrations were administered in 10% Hp-β-CD (+NaCl) vehicle following dissolution.

Final levetiracetam concentrations were administered in a 0.5% methylcellulose (MC) aqueous solution administered by intraperitoneal (i.p.) injection.

Critical Reagents a) Vehicle Solutions
0.5% Methylcellulose (MC)
40% Hydroxypropyl-β-cyclodextrin (Hp-β-CD) stock solution b) Miscellaneous Solutions Tetracaine (0.5% solution w/v) was added dropwise from a plastic dropper bottle onto the eyes of all animals that would subsequently receive electrical stimulation via corneal electrodes.

Animals and Animal Husbandry

Adult male CF No 1 albino mice (26-35 g) were obtained from Charles River, Portage, Mich. The animals were maintained on an adequate diet (Prolab RMH 3000) and allowed free access to food and water, except during the short time they were removed from their cage for testing. Animals newly received in the laboratory were allowed sufficient time to correct for possible food and water restriction incurred during transit before being employed in testing. All mice were housed in plastic cages in specially constructed rooms with controlled humidity, exchange of air and controlled lighting (12 hours on—12 hours off). The animals were housed, fed, and handled in a manner consistent with the recommendations in the National Council Publication, "Guide for the Care and Use of Laboratory Animals".

Minimal Motor Impairment (MMI)

Acute MMI was assessed by a combination of direct observations of the animal for overt symptoms of the animal's neurological or muscular function. In mice, the rotarod procedure was used to disclose minimal muscular or neurological impairment. When a mouse is placed on a rod that rotates at a speed of 6 rpm, the animal can maintain its equilibrium for long periods of time. The animal was considered toxic if it fell off this rotating rod three times during a 1 min period.

Determination of Median Effective and Toxic Doses (ED$_{50}$ and TD$_{50}$)

In the determination of an ED$_{50}$ or TD$_{50}$ for each test compound, the first dose administered is usually the same dose as that used in a successful TPE determination.

If the initial dose employed was effective or toxic in more than 50% of animals, the next dose would be one-half that of the initial dose; if the initial dose was effective or toxic in less than 50% of animals, the following dose would be twice that of the initial dose. Third and fourth doses were selected to produce an evenly spaced dose response line. There should be a minimum of 4 points either including or lying between 0 and 100%.

TPE Determination

Groups of generally four animals each were administered test compounds and each group was tested at one of five time points: 0.25, 0.5, 1, 2, or 4 h post-treatment (White et al. 1995). TPE was determined using the 6 Hz (32 mA) assay. The time (0.25, 0.5, 1, 2, or 4 h post-treatment) at which maximal protection was observed was considered the Time of Peak Effect (TPE).

At the TPE determined for this study, or determined previously, compounds were tested in the 6 Hz assay (32 and/or 44 mA), across several doses and comprising doses that elicited little or no protection to full protection.

An ED$_{50}$ and 95% confidence interval (C.I.) were calculated using Probit analysis on a computer program provided in the laboratory (Finney "Probit Analysis" 34d Ed 1971, London: Cambridge University Press).

Serum Collection for pK/pD Analysis

In various tests, animals were sacrificed following testing, and trunk blood and/or brain tissue (whole brains) was collected for quantification of drug levels. Immediately after testing, animals were decapitated and trunk blood was collected into a BD Vacutainer® tube containing K2EDTA and chilled on ice until centrifugation. Following centrifugation (13000-18000 rpm, 5-7 min), the plasma was removed and transferred to a labeled microcentrifuge tube and stored at −80° C. For brain tissue collection, brains were removed immediately following decapitation and flash frozen. The frozen sample was placed in a labeled centrifuge tube and stored at −80° C.

6 Hz Psychomotor Seizure Test in Mice

The 6 Hz seizure test is used as a model of pharmacoresistant limbic seizures. The 6 Hz seizure displays a resistance to phenytoin, carbamazepine, lamotrigine, and topiramate (Barton et al. "Pharmacological characterization of the 6 Hz psychomotor seizure model of partial epilepsy" Epilepsy Research 2001, Vol. 47, pp. 217-222).

Method for 6 Hz Psychomotor Seizure Test

Focal seizures were induced in mice via corneal stimulation (6 Hz, 0.2 msec rectangular pulse, 3 sec duration; Barton et al. 2001). Mice were tested at either 32 mA or 44 mA. Prior to stimulation, drops of 0.5% tetracaine were applied to each eye. The seizures that arise from corneal stimulation in this assay are characterized by a minimal clonic phase followed by stereotyped automatistic behaviors including stun, forelimb clonus, twitching of the vibrissae, and Straub-tail. Animals not displaying these behaviors were considered protected.

Example 1—Studies with Compounds 1 and 2

1.1. Combination Study with Co. No. 1, Co. No. 2 and Levetiracetam

First, each compound was tested individually at a dose that displayed minimal activity in the 6 Hz 44 mA test at each compound's TPE. When the mGluR2 PAM compounds and levetiracetam were administered in combination (same dose and time-point as individual tests) nearly complete protection was observed in the 6 Hz 44 mA test (Table 2). In addition to recording the efficacy and toxicity data for these compounds alone or in combination, both plasma and brain samples were collected from each of the groups for pharmacokinetic/pharmacokinetic analysis. No pharmacokinetic interaction was observed based on compound levels in the plasma and brain samples (data not shown). In summary, compounds 1 and 2 displayed positive pharmacodynamic interaction with levetiracetam in the 6 Hz model that does not appear to be due to pharmacokinetic interaction, and without increasing motor impairment (Tables 2, 2a, 2b). The effect of 1 dose of Compound 2 was also tested on the dose-response of LEV. As shown in Table 3, there was a ~200-fold shift in the $ED_{50}$ of LEV compared to when LEV was tested alone. LEV seemed to increase the potency of Co No. 2 slightly (Table 3).

1.2. Isobolographic Analysis of Interactions Between Co. No. 1 and Levetiracetam in the 6 Hz Seizure Model Isobolographic studies were conducted for the combined administration of Co. No. 1 with LEV in the 6 Hz (44 mA) assay. Studies were conducted according to previously described methods (Madsen et al. 2011). Initial $ED_{50}$ values were determined for both Co. No. 1 and LEV and used to calculate theoretical $ED_{50}$ (±standard error of the mean, SEM) values for three fixed dose ratio combinations (LEV: Co. No. 1): 1:3, 1:1, and 3:1. Doses used were proportional to calculated $ED_{50}$ values. For example, the dose ratio used for the 1:1 paradigm was based on $0.5 \times ED_{50}$ for LEV and $0.5 \times ED_{50}$ for Co. No. 1. Similarly, the 1:3 paradigm used $0.25 \times ED_{50}$ for LEV and $0.75 \times ED_{50}$ for Co. No. 1. The 3:1 dose ratio used $0.75 \times ED_{50}$ LEV and $0.25 \times ED_{50}$ for Co. No. 1. Experimental treatment doses (see Table 4) were based on theoretical values and adjusted according to observed effects. Experimentally determined $ED_{50}$ (±SEM) values for each fixed dose-ratio combination were compared to the theoretical values (t-test) for statistical purposes. The dose ratio was determined to be supra-additive (synergistic) if the experimentally-determined $ED_{50}$ value was significantly lower than the theoretical $ED_{50}$. Subsequently, the experimental combined doses were determined for the same paradigms in the 6 Hz seizure test (Table 4 below). The isobolographic study with compound 1 and levetiracetam in the 6 Hz model demonstrates a significant synergistic pharmacodynamic interaction at all dose ratios evaluated and corresponds closely with compound 1 plasma levels. Furthermore, no motor impairment was observed at any of the dose ratios evaluated suggesting that the synergistic pharmacodynamics interaction does not produce increased motor toxicity.

1.3. Mouse Corneal Kindling Model and Studies with Compound 1

Mice were kindled electrically with 3 second, 3 mA, 60 Hz stimulus, twice daily using corneal electrodes until a criterion of 5 consecutive Stage 5 seizures as defined by Racine (Racine "Modification of seizure activity by electrical stimulation" II. motor seizure" Electroenceph Clin Neurophysiol 1972, 32, pp. 281-294). After the mice reached a stable kindled state, the test compound or vehicle was administered and, at the previously determined TPE, each animal was given the electrical stimulus indicated above. Following stimulation, the animals were observed for the presence or absence of the seizure activity scored on the Racine scale (0-5) with 5 representing the highest stage rearing and falling. One dose of LEV and two doses of Co. No. 1 were tested individually and in combination against corneal kindled seizures. Combination of compound 1 with levetiracetam in this model suggests a positive pharmacodynamics interaction (Table 5 below).

A summary of the data for the compounds tested alone is presented in Table 1 and additional results of studies performed according to example 1 are listed in Tables 2-5 below.

TABLE 1

Summary of the acute anticonvulsant data in the 6 Hz model at 32 mA and 44 mA for the mGluR2 PAM compounds 1, 2, 11, 2-a, 25-a, 6-b and LY-404039 following s.c. administration (except compound 6-b, which was tested p.o.). TPE means time of peak effect, CI means confidence interval, s.c. means subcutaneous, p.o. means orally, nt. means not tested. TPE was determined in 32 mA 6 Hz test. Effects are generally observed at doses that do not produce impairment in rotarod test. For compounds 11 and 2-a the individual values of repeat experiments are provided. For compound 25a, both 0.25 and 1 h time points were used for 6 Hz (44 mA) studies.

| Co. No. | TPE (h) | $ED_{50}$ (95% CI) mg/kg, s.c. 32 mA | $ED_{50}$ (95% CI) mg/kg, s.c. 44 mA | Seizure score (dose) Corneal kindling |
|---|---|---|---|---|
| 11 | 0.5 | 4.77 (3.54-6.76) 9.41 (1.53-15.1) | 31.5 (15.1-47.3) | 2.8 (100 mg/kg) |

TABLE 1-continued

Summary of the acute anticonvulsant data in the 6 Hz model at 32 mA and 44 mA for the mGluR2 PAM compounds 1, 2, 11, 2-a, 25-a, 6-b and LY-404039 following s.c. administration (except compound 6-b, which was tested p.o.). TPE means time of peak effect, CI means confidence interval, s.c. means subcutaneous, p.o. means orally, nt. means not tested. TPE was determined in 32 mA 6 Hz test. Effects are generally observed at doses that do not produce impairment in rotarod test. For compounds 11 and 2-a the individual values of repeat experiments are provided. For compound 25a, both 0.25 and 1 h time points were used for 6 Hz (44 mA) studies.

| Co. No. | TPE (h) | ED$_{50}$ (95% CI) mg/kg, s.c. 32 mA | ED$_{50}$ (95% CI) mg/kg, s.c. 44 mA | Seizure score (dose) Corneal kindling |
|---|---|---|---|---|
| 2 | 0.25 | 3.83 (1.62-6.71) | 5.89 (3.89-8.45) | 3.4 (40 mg/kg) |
| 1 | 0.5 | 2.8 (1.3-4.3) | 10.2 (3.1-12.4) | 3.7 (20 mg/kg) |
| 25-a | 1 | 7.7 (2.3-18.4) | 1 hr TPE: 25.9 (15.5-33.7) 0.25 hr TPE: 29.1 (21.6-39.6) | n.t. |
| 2-a | 0.5 | 44.7 (23.4-80.5) 20.8 (10.0-31.7) 12.2 (8.4-17.4) | 50% protection at 100 mg/kg 21 (17.9-27.4) | 4.4 (100 mg/kg) |
| 6-b | 0.5 | 7.2 (4.2-11.8) | 16.1 (13.0-20.1) | n.t. |
| LY-404039 | 0.5 | 10.2 (3.62-12.4) | n.t. | 3.1 (100 mg/kg) |

TABLE 1a

Summary of the 6 Hz 32 mA TPE determination for Co. No. 1

| Dose (mg/kg, s.c.) | Time (h) | 6 Hz 32 mA | Motor impairment |
|---|---|---|---|
| 10 | 4 | 0/4 | 0/0 |
|  | 2 | 0/4 | 0/0 |
|  | 1 | 3/4 | 0/0 |
|  | 0.5 | 4/4 | 0/0 |
|  | 0.25 | 4/4 | 0/0 |
| 5 | 0.5 | 8/12 | 0/0 |
|  | 0.25 | 8/12 | 0/0 |
| 2.5 | 0.5 | 5/8 | 0/0 |
|  | 0.25 | 1/8 | 0/0 |

(number of mice protected in 6 Hz or toxic on rotarod/number/tested)

TABLE 1b

Dose-response studies for Co. No. 1. The TPE for Co. No. 1 was previously determined to be 0.5 h (results shown above in table 1a). Several doses of Co. No. 1 were administered at this TPE and tested in the 6 Hz assay, using both 32 and 44 mA stimulus intensities.

| Test | Dose (mg/kg, s.c.) | #protected/#tested | #rotarod motor impairment/#tested |
|---|---|---|---|
| 6 Hz 32 mA | 20 | 8/8 | 1/8 |
|  | 10 | 7/8 | 0/8 |
|  | 5 | 8/12 | 0/12 |
|  | 2.5 | 7/16 | 0/16 |
|  | 0.5 | 1/8 | 0/8 |
| ED$_{50}$ (95% CI): 2.8 mg/kg (1.3 to 4.3) | | | |
| 6 Hz 44 mA | 20 | 8/8 | 1/8 |
|  | 15 | 7/8 | 0/8 |
|  | 10 | 4/8 | 0/8 |
|  | 2.5 | 0/8 | 0/8 |
| ED$_{50}$ (95% CI): 10.2 mg/kg (3.1 to 12.4) | | | |

TABLE 2

Summary of interaction of Co. No. 1 and Co. No. 2 with Levetiracetam (LEV) in the mouse 6 Hz, 44 mA seizure model. Results are listed as number of mice exhibiting full protection/total number of mice tested in each dosing group (at the specified test compound or combination dosage levels).

|  | Dose | Time (h) | #protected/#tested | #mortortox/#tested |
|---|---|---|---|---|
| LEV | 10 mg/kg i.p. | 1 | 1/6 | 0/6 |
| Co. No. 2 + LEV | 3 mg/kg s.c. | 0.25 | 5/6 | 0/6 |
| Co. No. 2 | 3 mg/kg s.c. | 0.25 | 1/6 | 0/6 |
| LEV | 10 mg/kg i.p. | 1 | 1/8 | 0/8 |
| Co. No. 1 + LEV | 2.5 mg/kg s.c. | 0.5 | 6/8 | 0/8 |
| Co. No. 1 | 2.5 mg/kg s.c. | 0.5 | 0/8 | 0/8 |

TABLE 2a

Plasma and brain levels Co. No. 1. in combination study with Levetiracetam (LEV). BQL means below quantifiable limit.

| Co. No. 1 | LEV | Plasma (ng/ml) | Co. No. 1 | Plasma (ng/ml) | 6 Hz Protection |
|---|---|---|---|---|---|
| 6 Hz 44 mA | 10 mg/kg | 9350 | 2.5 mg/kg | BQL | Yes |
|  |  | 8580 |  | 244 | No |
|  |  | 10900 |  | 314 | Yes |
|  |  | 10300 |  | 382 | Yes |
|  |  | 9780 |  | 416 | Yes |
|  |  | 9780 |  | 377 | Yes |
|  |  | 13700 |  | 2260* | No |
|  |  | 10100 |  | 607 | Yes |
| Mean Plasma Level |  | 10311 |  | 657.1 (390) | 6/8 |
| Mean Plasma Levels (non-combination) | 1/8 | 8254 | 0/8 | 438 |  |

Mean plasma level shown in parenthesis ( ) is calculated with a statistical outlier* removed

TABLE 2b

Plasma and brain levels Co. No. 2 in combination study with Levetiracetam (LEV). AQL means above quantifiable limit.

| Co. No. 2 | LEV | Plasma (ng/ml) | Brain (ng/ml) | Co. No. 2 | Plasma (ng/ml) | Brain (ng/ml) | 6 Hz Protection |
|---|---|---|---|---|---|---|---|
| 6 Hz 44 mA | 10 mg/kg | 6450 | 6290 | 3 mg/kg | 1830 | 1540 | Yes |
| | | 8200 | 7990 | | 386 | 1020 | Yes |
| | | 3540 | 4760 | | 4700 | 1310 | Yes |
| | | 3850 | NA | | 467 | NA | No |
| | | 7150 | 6380 | | AQL (>500) | 1120 | Yes |
| | | 3890 | 3960 | | 2080 | 1140 | Yes |
| Mean Plasma/ Brain Levels | | 5513 | 5876 | | 1893 | 1226 | 5/6 |
| Mean Plasma/ Brain Levels (non-combination) | 1/6 | 8750 | 5773 | 1/6 | 1295 | 1113 | |

NA-sample not available for analysis

TABLE 3

Figure 1:
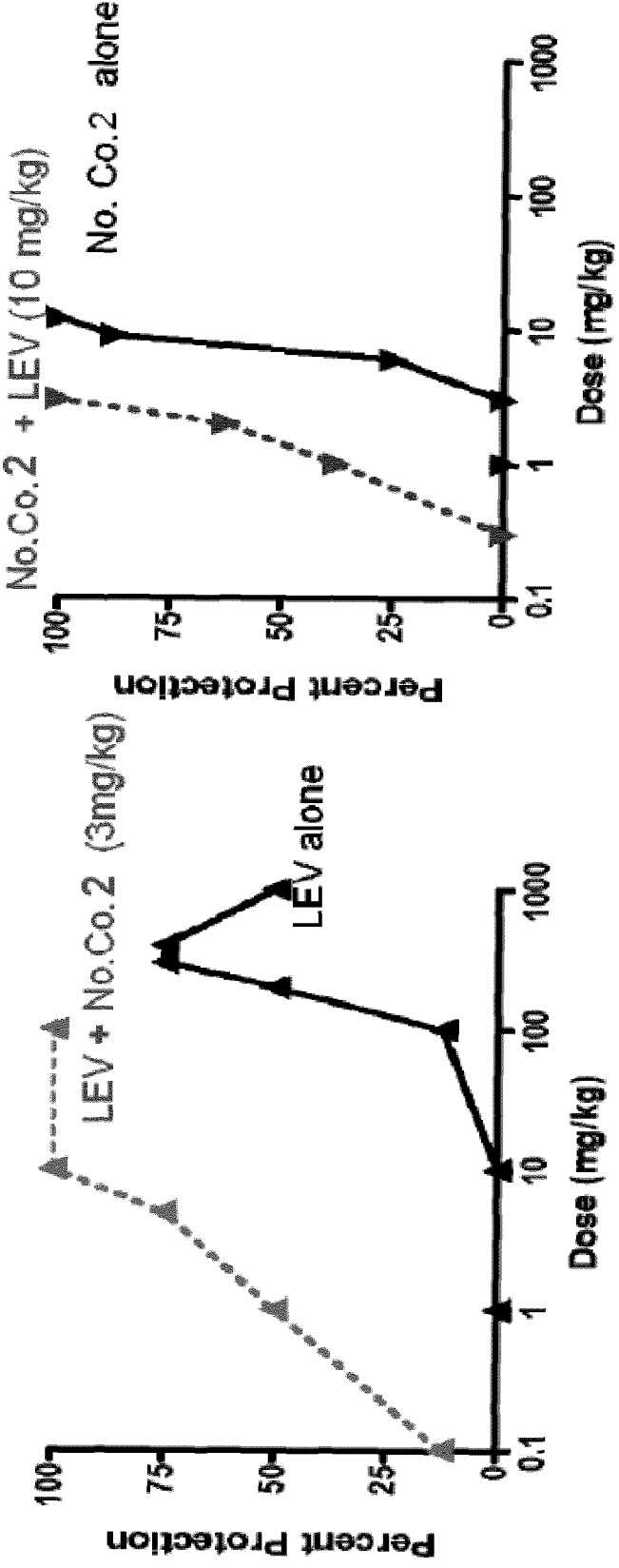
FIG. 1: Dose response for the 6 Hz 44 mA $ED_{50}$ determination for the Co. No. 2 and LEV alone and in combination.

6 Hz seizure (44 mA) model $ED_{50}$ determinations for No. Co. 2 and levetiracetam (LEV) alone and in combination. LEV at a dose of 10 mg/kg increased the potency of the No. Co. 2 (~5-fold shift in $ED_{50}$). Co. No. 2 at a dose of 3 mg/kg increased both the efficacy (to 100% protection) and potency of LEV (~200-fold shift in $ED_{50}$). FIG. 1 shows the dose-response for the 6 Hz 44 mA $ED_{50}$ determinations for the Co. No. 2 and LEV alone and in combination.

| Treatment | $ED_{50}$ (95% CI) mg/kg | Maximum Effect (% Protection) |
|---|---|---|
| Co. No. 2 alone | 6.97 (5.44-8.30) | 100% |
| Co. No. 2 + LEV (10 mg/kg) | 1.35 (0.8-1.9) | 100% |
| LEV alone | ~200 | 75% |
| LEV + Co. No. 2 (3 mg/kg) | 1.0 (0.23-2.24) | 100% |

TABLE 4

Results of Co. No. 1 and Levetiracetam in Isobolographic Study.

| Group | LEV (mg/kg i.p.) | f | Co. No. 1 (mg/kg s.c.) | f | combined dose (mg/kg) | Rotarod #motortox/ # tested | 6 Hz (44 mA) #protected/ #tested |
|---|---|---|---|---|---|---|---|
| 1:1 paradigm | 181 | 0.5 | 5.1 | 0.5 | 93.1 | 0/8 | 8/8 |
| | 90.5 | | 2.6 | | 46.6 | 0/8 | 6/8 |
| | 45.3 | | 1.3 | | 23.3 | 0/8 | 3/8 |
| | 22.6 | | 0.6 | | 11.6 | 0/8 | 3/8 |
| | $ED_{50}$ (95% CI; mg/kg): 22.2 (8.4-35.7) | | | | | | |
| 1:3 paradigm | 45.3 | .25 | 3.8 | .75 | 14.2 | 0/8 | 8/8 |
| | 22.6 | | 1.9 | | 7.1 | 0/8 | 4/8 |
| | 11.3 | | 1.0 | | 3.6 | 0/8 | 2/8 |
| | $ED_{50}$ (95% CI; mg/kg): 5.9 (3.5-8.7) | | | | | | |
| 31 paradigm | 271.5 | .75 | 2.6 | .25 | 204.3 | 0/8 | 8/8 |
| | 135.8 | | 1.3 | | 102.2 | 0/8 | 3/8 |
| | 67.9 | | 0.6 | | 51.1 | 0/8 | 3/8 |
| | 33.9 | | 0.3 | | 25.5 | 0/8 | 0/8 |
| | $ED_{50}$ (95% CI; mg/kg): 86.3 (56.8-131.4) | | | | | | |

Figure 2:
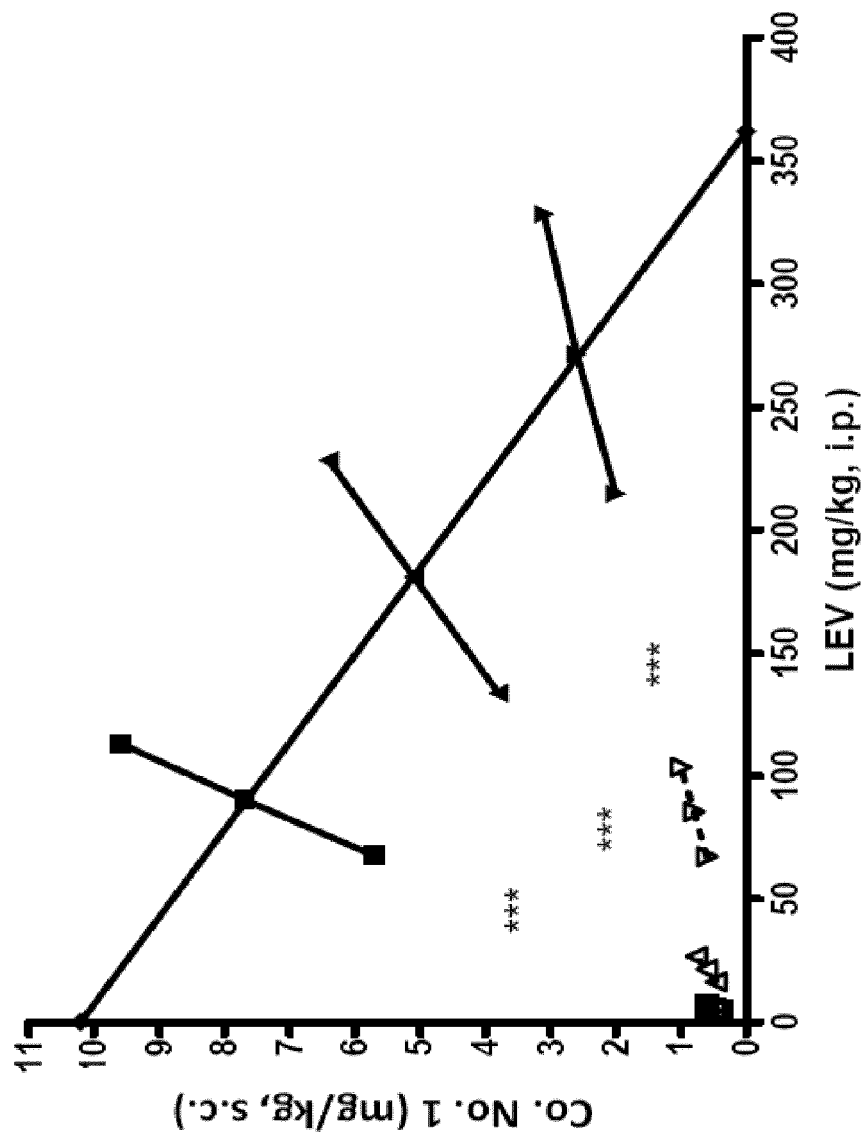
FIG. 2: Isobolographic analysis for the combination of Co. No. 1 with levetiracetam (LEV) in the 6 Hz (44 mA) assay. Initial $ED_{50}$ values (shown below) were determined for both Co. No. 1 and LEV (data points on x- and y-axes; filled diamonds). The theoretical line of additivity connects the calculated $ED_{50}$ values for the two compounds (solid black line). Theoretical $ED_{50}$ (+SEM) for three fixed dose ratio combinations (LEV: Co. No. 1) are plotted: 1:3—filled squares/solid black line, 1:1—filled upward triangles/solid black line, and 3:1—filled downward triangles/solid black line. Experimental treatment doses were initially derived from theoretical values and adjusted according to observed effects. Experimentally-determined $ED_{50}$ (+SEM) values for each fixed dose-ratio combination are also shown: 1:3'—open squares/dotted line, 1:1'—open upward triangles/dotted line, and 3:1'—open downward triangles/dotted line. Comparisons between theoretical and experimentally-determined $ED_{50}$ values were compared using a t-test (\*\*\*P<0.001). N=8 per group.

The isobolographic analysis (FIG. 2) demonstrates that the combination of Co. No. 1 and levetiracetam results in a significantly positive synergistic effect.

TABLE 5

Results of Co. No. 1 and Levetiracetam combination study in the corneal kindling model in mice.

| Compound(s) | # protected/ # tested | % Protected | Mean Seizure Score |
|---|---|---|---|
| Vehicle (20% HPBCD@30', s.c.; 0.5% MC@60', i.p.) | 0/10 | 0% | 4.7 |
| LEV 3 mg/kg | 5/13 | 38% | 3.3 |
| Co. No. 1 30 mg/kg | 3/12 | 25% | 4.0 |
| LEV 3 mg/kg & Co. No. 1 30 mg/kg | 10/10 | 100% | 0.6 |
| Co. No. 1 20 mg/kg | 5/16 | 31% | 3.7 |
| LEV 3 mg/kg & Co. No. 1 20 mg/kg | 7/10 | 70% | 1.9 |

Racine Seizure Score  0 to 5
0 = no seizure activity
5 = maximal seizure activity Example 2—Studies with Compounds 25-a and 2-a 2.1. Combination Study with Co. No. 25-a and Levetiracetam Independent dose-response studies were performed in the 6 Hz 44 mA test for both compounds to determine $ED_{50}$ values at the TPE of 1 h i.p. for levetiracetam and 1 h s.c. for Co. No. 25-a. The $ED_{50}$ value for Co. No. 25-a was 25.9 mg/kg and for levetiracetam the value was estimated to be approximately 345 mg/kg. The dose-response for levetiracetam was repeated with co-administration of 10 mg/kg Co. No. 25-a (a dose of Co. No. 25-a that alone did not protect in the 6 Hz 44 mA model). The co-administration of 10 mg/kg Co. No. 25-a produced an $ED_{50}$ in the levetiracetam dose-response of 4.9 mg/kg (~70-fold lower compared with levetiracetam alone) and importantly yielded full protection in the 6 Hz 44 mA seizure model. These results are suggestive of a positive pharmacodynamic interaction in the 6 Hz seizure model between Co. No. 25-a and levetiracetam.

TABLE 6

Time-to-Peak Effect Determination for Co. No. 25-a in the 6 Hz (32 mA) Assay. Two doses were used in this study, 10 and 20 mg/kg, across several time points (0.25-4 h). The compound showed the greatest degree of protection in the 6 Hz assay between 0.25 and 1 h, which was more evident at 20 mg/kg. Plasma levels of the compound generally corresponded to behavioural seizure protection. A TPE of 0.25 h was used for 6 Hz (32 mA) studies whereas both the 0.25 and 1 h time points were used for 6 Hz (44 mA) studies.

| Dose (mg/kg, s.c.) | Time (h) | #protected/ # tested | # rotarod motor impairment/ # tested | Co. No. 25-a mean plasma levels (ng/mL) |
|---|---|---|---|---|
| 10 | 0.25 | 2/4 | 0/4 | 10,983 (2,477) |
|  | 0.5 | 1/4 | 0/4 | 3,330 |
|  | 1 | 1/4 | 1/4 | 700 |
|  | 2 | 0/4 | 0/4 | 256 |
|  | 4 | 0/4 | 0/4 | 40 |
| 20 | 0.25 | 4/4 | 0/4 | 4,095 |
|  | 0.5 | 3/4 | 1/4 | 2,800 |
|  | 1 | 4/4 | 1/4 | 1,765 |
|  | 2 | 1/4 | 0/4 | 618 |
|  | 4 | 1/4 | 1/4 | 28 | s.c. means subcutaneous
Mean plasma level shown in parenthesis ( ) is calculated with a statistical outlier removed.

TABLE 7

Dose-Response Studies for Co. No. 25-a in the 6 Hz Assay (32 mA$^a$ and 44 mA$^b$)

| Test | Dose (mg/kg, s.c.) | # protected/ # tested | # rotarod motor impairment/ # tested | Co. No. 25-a mean plasma levels (ng/mL) |
|---|---|---|---|---|
| 6 Hz 32 mA | 20 | 8/8 | 0/8 | 5,570 |
|  | 15 | 3/8 | 0/8 | 1,201 |
|  | 10 | 4/8 | 0/8 | 6,113 |
|  | 5 | 4/8 | 0/8 | 2,558 |
|  | 1 | 1/8 | 0/8 | 466 |
|  | $ED_{50}$ (95% CI): 7.7 mg/kg (2.3 to 18.4) | | | |
| 6 Hz 44 mA | 40 | 7/8 | 0/8 | 6,263 |
|  | 30 | 3/8 | 0/8 | 7,220 |
|  | 20 | 2/8 | 0/8 | 3,368 |
|  | 10 | 0/8 | 0/8 | 4,345 (1,526) |
|  | 5 | 0/8 | 1/8 | 1,428 |
|  | $ED_{50}$ (95% CI): 29.1 mg/kg (21.6 to 39.6) | | | |

CI means confidence interval
$^a$The time-to-peak effect in the 6 Hz 32 mA assay for Co. No. 25-a was determined to be 0.25 h (see Table 1).
$^b$The time-to-peak effect in the 6 Hz 44 mA assay for Co. No. 25-a was similar for 0.25 h and 1 h; results for 1 h confirmed the $ED_{50}$ (95% CI) 25.9 (15.5-33.7) (see Table 1 and 6).
Mean plasma level shown in parenthesis ( ) is calculated with a statistical outlier removed.

TABLE 8

Combination Studies for Co. No. 25-a with Levetiracetam (LEV) in the 6 Hz (44 mA) Assay.

| Drug | Dose (mg/kg, s.c.) | # protected/ # tested | # rotarod motor impairment/# tested |
|---|---|---|---|
| LEV | 200 | 2/8 | 0/8 |
|  | 400 | 4/9 | 0/9 |
|  | 800 | 10/12 | 0/12 |
| $ED_{50}$ (95% CI): 345.4 mg/kg (211.0 to 485.3) | | | |
| LEV + Co. No. 25-a 10 mg/kg | 200 | 8/8 | 1/8 |
|  | 100 | 7/8 | 2/8 |
|  | 50 | 5/8 | 1/8 |
|  | 10 | 4/8 | 0/8 |
|  | 1 | 4/8 | 1/8 |
| $ED_{50}$ (95% CI): 4.9 (0.0-14.2) | | | |

Co. No. 25-a (s.c.) 10 mg/kg tested in combination with LEV (i.p.)-Co. No. 25-a 10 mg/kg, not active when administered alone.

2.2. Combination Study with Co. No. 2-a and Levetiracetam

Dose-response studies were performed in the 6 Hz 32 mA and 44 mA tests (table 9 below) and in the combination test with levetiracetam (effect of Co. No. 2-a on the dose-response of LEV in tables 10a and effect of LEV on the dose-response of Co. No. 2-a in table 10b below) in the same manner as described for the studies with Co. No. 25-a and levetiracetam above.

TABLE 9

Dose-Response Studies for Co. No. 2-a in the 6 Hz Assay (32 mA and 44 mA; 0.5 h TPE). A time-to-peak effect of 0.5 h was determined in the 32 mA 6 Hz test (s.c.) and used for 6 Hz (32 mA and 44 mA) studies.

| Test | Dose (mg/kg, s.c.) | # protected/ # tested | # rotarod motor impairment/# tested |
|---|---|---|---|
| 6 Hz 32 mA | 40 | 8/8 | 2/8 |
|  | 20 | 6/8 | 3/8 |
|  | 10 | 4/8 | 0/8 |
|  | 5 | 0/8 | 0/8 |
|  | 2.5 | 0/8 | 1/8 |
| $ED_{50}$ (95% CI): 12.2 mg/kg (8.4 to 17.4) | | | |
| 6 Hz 44 mA | 40 | 8/8 | 4/8 |
|  | 20 | 3/8 | 0/8 |
|  |  | 3/8 | 0/8 |
|  | 15 | 2/8 | 1/8 |
|  | 10 | 0/8 | 1/8 |
|  |  | 0/8 | 0/8 |
| ED50 (95% CI): 21.0 mg/kg (17.9 to 27.4) | | | |
| $TD_{50}$: >40 mg/kg$^a$ | | | |

$^a$40 mg/kg-6 out of 16 total (32 mA and 44 mA combined) with impairment.
Dose selected for combination studies with LEV in 6 Hz (44 mA): Co. No. 2-a 10 mg/kg.

TABLE 10a

Combination Studies for Co. No. 2-a with Levetiracetam (LEV) in the 6Hz (44 mA) Assay. Combination of 10 mg/kg Co. No. 2-a with varying doses of levetiracetam.

| Drug | Dose (mg/kg) | # protected/ # tested | # rotarod motor impairment/# tested |
|---|---|---|---|
| LEV | 200 | 2/8 | 0/8 |
|  | 400 | 4/9 | 0/9 |
|  | 800 | 10/12 | 0/12 |
| LEV $ED_{50}$ (95% CI): 345.4 mg/kg (211.0 to 485.3) | | | |

TABLE 10a-continued

Combination Studies for Co. No. 2-a with Levetiracetam (LEV) in the 6Hz (44 mA) Assay. Combination of 10 mg/kg Co. No. 2-a with varying doses of levetiracetam.

| Drug | Dose (mg/kg) | # protected/ # tested | # rotarod motor impairment/# tested |
|---|---|---|---|
| LEV + Co. No. 2-a 10 mg/kg[a] | 200 | 6/8 | 1/8 |
| | 100 | 6/8 | 0/8 |
| | 50 | 6/8 | 0/8 |
| | 25 | 8/8 | 0/8 |
| | 12.5 | 5/8 | 0/8 |
| | 6.25 | 4/8 | 0/8 |
| | 3.125 | 3/8 | 1/8 |
| | 1.5625 | 0/8 | 0/8 |
| LEV $ED_{50}$ (95% CI): 9.6 mg/kg (1.7-21.9) | | | |

[a]Co. No. 2-a (s.c.) 10 mg/kg tested in combination with LEV (i.p.); Co. No. 2-a 10 mg/kg, not active when administered alone.
Additional LEV (low-dose) control groups were tested at 25 and 6.25 mg/kg (1/8 and 0/6 protected, respectively).
Vehicle-treated mice (0.5% methylcellulose i.p. (1 h)/20% HPBCD s.c. (0.5 h)) showed no protection (0/8 protected).

TABLE 10b

Combination Studies for Co. No. 2-a with Levetiracetam (LEV) in the 6 Hz (44 mA) Assay. Combination of 350 mg/kg levetiracetam with varying doses of Co. No. 2-a.

| Drug | Dose (mg/kg) | # protected/ # tested | # rotarod motor impairment/ # tested |
|---|---|---|---|
| LEV (alone)[a] | 350 | 3/8 | 0/8 |
| LEV 350 mg/kg + Co. No. 2-a[b] | 20 | 8/8 | 2/8 |
| | 10 | 7/8 | 1/8 |
| | 5 | 7/8 | 1/8 |
| | 2.5 | 5/8 | 0/8 |
| | 1.25 | 4/8 | 0/8 |
| previous Co. No. 2-a $ED_{50}$ (95% CI): 21.0 mg/kg (17.9 to 27.4) | | | |
| LEV combination Co. No. 2-a $ED_{50}$ (95% CI): 1.5 mg/kg (0.1-2.7) ~14-fold shift in potency | | | |

[a]LEV $ED_{50}$ (presented separately) previously determined in 6 Hz (44 mA): 345 mg/kg.
[b]Co. No. 2-a (s.c.) 10 mg/kg tested in combination with LEV (i.p.); Co. No. 2-a 10 mg/kg, not active when administered alone.
Additional LEV (low-dose) control groups were tested at 25 and 6.25 mg/kg (1/8 and 0/6 protected, respectively).
Vehicle-treated mice (0.5% methylcellulose i.p. (1 h)/20% HPBCD s.c. (0.5 h) showed no protection (0/8 protected).

At a dose of 10 mg/kg s.c., Co. No. 2-a increases the potency of LEV, leading to an approximate 35-fold shift in the $ED_{50}$. This suggests a positive pharmacodynamic relationship (Table 10a). At a dose of 350 mg/kg i.p., LEV increases the potency of Co. No. 2-a, leading to an approximate 14-fold shift in the $ED_{50}$. This suggests a positive pharmacodynamics relationship (Table 10b).

Example 3—Studies with Compound 6-b 3.1. Combination Study with Co. No. 6-b and Levetiracetam Independent dose-response studies were performed in the 6 Hz 44 mA test for both compounds to determine $ED_{50}$ values at the TPE of 1 h i.p. for levetiracetam and 0.5 h p.o. for Co. No. 6-b. The $ED_{50}$ value for Co. No. 6-b was 16.1 mg/kg and for levetiracetam the value was estimated to be approximately 345 mg/kg. The dose-response for levetiracetam was repeated with co-administration of 10 mg/kg Co. No. 6-b (a dose of Co. No. 6-b that alone did not protect in the 6 Hz 44 mA model). The co-administration of 10 mg/kg Co. No. 6-b produced an $ED_{50}$ in the levetiracetam dose-response of 2.4 mg/kg (~100-fold lower compared with levetiracetam alone) and importantly yielded full protection in the 6 Hz 44 mA seizure model. These results are suggestive of a positive pharmacodynamic interaction in the 6 Hz seizure model between Co. No. 6-b and levetiracetam.

The results of the studies performed with compound 6-b are listed in Tables 11-13 below.

TABLE 11

Time-to-Peak Effect Determination for Co. No. 6-b (p.o.) in the 6 HZ (32 mA) Assay.

| Dose (mg/kg, p.o.) | Time (h) | protected #/ # tested | # rotarod motor impairment/ # tested |
|---|---|---|---|
| 10 | 0.25 | 1/4 | 0/4 |
| | 0.5 | 3/4 | 0/4 |
| | 1 | 0/4 | 0/4 |
| | 2 | 1/4 | 0/4 |
| | 4 | 0/4 | 0/4 |
| 20 | 0.25 | 4/4 | 0/4 |
| | 0.5 | 3/4 | 0/4 |
| | 1 | 4/4 | 0/4 |
| | 2 | 0/4 | 0/4 |
| | 4 | 1/4 | 0/4 |

TPE determined to be 0.5 h.

TABLE 12

Dose-Response Study for Co. No. 6-b in the 6 Hz Assay (32 mA and 44 mA; 0.5 h TPE).

| Test | Dose (mg/kg, p.o.) | # protected/ # tested | # rotarod motor impairment/ # tested |
|---|---|---|---|
| 6 Hz 32 mA | 20 | 7/8 | 0/8 |
| | 10 | 6/8 | 0/8 |
| | 5 | 2/8 | 0/8 |
| | 2.5 | 1/8 | 0/8 |
| $ED_{50}$ (95% CI): 7.2 mg/kg (4.2 to 11.8) | | | |
| 6 Hz 44 mA | 40 | 8/8 | 0/8 |
| | 20 | 6/8 | 0/8 |
| | 15 | 4/8 | 0/8 |
| | 10 | 0/8 | 0/8 |
| $ED_{50}$ (95% CI): 16.1 mg/kg (13.0 to 20.1) | | | |

TABLE 13

Combination Studies for Co. No. 6-b with LEV in the 6 Hz Assay (44 mA).

| Drug | Dose (mg/kg) | # protected/ # tested | # rotarod motor impairment/# tested |
|---|---|---|---|
| LEV | 200 | 2/8 | 0/8 |
| | 400 | 4/9 | 0/9 |
| | 800 | 10/12 | 0/12 |
| $ED_{50}$ (95% CI): 345.4 mg/kg (211.0 to 485.3) | | | |
| LEV + Co. No. 6-b 10 mg/kg | 200 | 8/8 | 0/8 |
| | 100 | 8/8 | 0/8 |
| | 50 | 5/8 | 0/8 |
| | 10 | 5/8 | 0/8 |
| | 1 | 5/8 | 0/8 |
| $ED_{50}$ (95% CI): 2.4 (0.0-6.4) | | | |

Co. No. 6-b (p.o.) 10 mg/kg tested in combination with LEV (i.p.)
Co. No. 6-b 10 mg/kg, not active when administered alone Example 4—Studies with Compound LY404039

3.1. Combination Study with LY404039 and Levetiracetam

LY-404039 was tested alone and in combination with levetiracetam according to the procedures already described hereinabove. The results of the studies performed with LY-404039 are listed in tables 14-15.

TABLE 14

Dose-Response Studies for LY404039 in the 6 Hz Assay (32 mA and 44 mA). A time-to-peak effect of 0.5 h was determined in the 32 mA 6 Hz test (s.c.) and used for 6 Hz (32 mA and 44 mA) studies.

| Test | Dose (mg/kg, s.c.) | # protected/ # tested | # rotarod motor impairment/# tested |
|---|---|---|---|
| 6 Hz 32 mA | 40 | 8/8 | 1/8 |
| | 20 | 6/8 | 1/8 |
| | 10 | 5/8 | 0/8 |
| | 5 | 1/16 | 1/16 |
| | $ED_{50}$ (95% CI): 10.9 mg/kg (7.8 to 15.9) | | |
| 6 Hz 44 mA | 40 | 7/8 | 2/8 |
| | 20 | 7/8 | 1/8 |
| | 10 | 3/8 | 1/8 |
| | 5 | 0/16 | 0/16 |
| | $ED_{50}$ (95% CI): 14.1 mg/kg (10.0 to 20.6) | | |
| | $TD_{50}$: >40 mg/kg[a] | | |

[a]40 mg/kg-3 out of 16 total (32 mA and 44 mA combined) with impairment.

Note:
no activity observed following vehicle administration in 32 or 44 mA.

Dose selected for combination studies with LEV in 6 Hz (44 mA): LY404039 5 mg/kg.

TABLE 15

Combination Studies for LY404039 with Levetiracetam (LEV) in the 6 Hz (44 mA) Assay.

| Drug | Dose (mg/kg) | # protected/ # tested | # rotarod motor impairment/# tested |
|---|---|---|---|
| LEV[a] | 200 | 2/8 | 0/8 |
| | 400 | 4/9 | 0/9 |
| | 800 | 10/12 | 0/12 |
| | LEV $ED_{50}$ (95% CI): 345.4 mg/kg (211.0 to 485.3) | | |
| LEV + LY404039 5 mg/kg[b] | 200 | 8/8 | 0/8 |
| | 50 | 6/8 | 1/8 |
| | 20 | 6/8 | 2/8 |
| | 5 | 2/8 | 1/8 |
| | LEV $ED_{50}$ (95% CI): 12.8 mg/kg (2.5-25.2) | | |

[a]LEV alone shown previously, confirmation doses performed in combination with Co. No. 2-a (see previous table above).

[b]LY404039 (s.c.) 5 mg/kg tested in combination with LEV (i.p.); LY404039 5 mg/kg was not active when administered alone.

Additional LEV (low-dose) control groups were tested at 25 and 6.25 mg/kg (1/8 and 0/6 protected, respectively).

Vehicle-treated mice (10% sterile water-NaCl; s.c., 0.5 h TPE and 0.5% MC, i.p., 1 h TPE) showed no protection or rotarod impairment.

At a dose of 5 mg/kg LY404039 increases the potency of LEV, leading to an approximate 27-fold shift in the $ED_{50}$. This suggests a positive pharmacodynamic relationship.

Example 4—Studies with Compound CAS 1092453-15-0

4.1. Combination Study with 2,3-dihydro-7-methyl-5-[3-(1-piperazinylmethyl)-1,2,4-oxadiazol-5-yl]-2-[[4-(trifluoromethoxy)phenyl]methyl]-1H-isoindol-1-one [CAS 1092453-15-0] (Described in WO 2008150233, WO 2011084098) and Levetiracetam

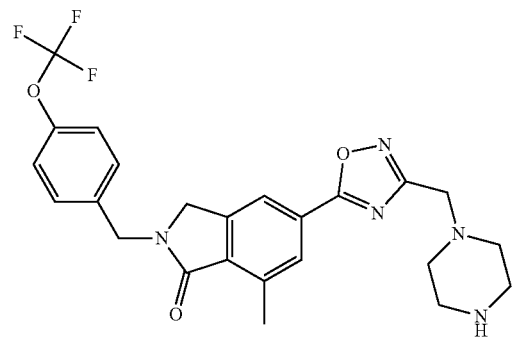 [SMILES: Cc1cc(-c2nc(CN3CCNCC3)no2)cc2c1C(=O)N(Cc1ccc(OC(F)(F)F)cc1)C2]

CAS 1092453-15-0 was tested alone and in combination with levetiracetam according to the procedures already described hereinabove. The results of example 5 are listed in tables 16-17.

TABLE 16

Dose-Response Studies for CAS 1092453-15-0 in the 6 Hz Assay (32 mA).

| Dose (mg/kg, s.c.) | Time (h) | # protected/ # tested | # rotarod motor impairment/# tested |
|---|---|---|---|
| 20 | 0.25 | 1/4 | 0/4 |
| | 0.5 | 0/4 | 0/4 |
| | 1 | 1/4 | 0/4 |
| | 2 | 0/4 | 0/4 |
| | 4 | 0/4 | 0/4 |
| 40 | 0.25 | 1/4 | 0/4 |
| | 0.5 | 1/4 | 0/4 |
| | 1 | 1/4 | 0/4 |
| | 2 | 0/4 | 0/4 |
| | 4 | 0/4 | 0/4 |
| 80 | 0.25 | 0/4 | 0/4 |
| | 0.5 | 0/4 | 0/4 |
| | 1 | 1/4 | 1/4 |

Low activity was observed at doses and time points tested. Greatest activity at 0.25-1 h in tested doses. Combination studies were performed using 20 mg/kg, s.c, 1 h TPE in the 6 Hz (44 mA) assay.

TABLE 17

Combination Studies for CAS 1092453-15-0 with Levetiracetam (LEV) in the 6 Hz (44 mA) Assay.

| Drug | LEV Dose (mg/kg) | # protected/ # tested | # rotarod motor impairment/# tested |
|---|---|---|---|
| LEV[a] | 200 | 2/8 | 0/8 |
| | 400 | 4/9 | 0/9 |
| | 800 | 10/12 | 0/12 |
| | LEV $ED_{50}$ (95% CI): 345.4 mg/kg (211.0 to 485.3) | | |
| [CAS 1092453-15-0] (20 mg/kg, alone) | | 0/8 | 0/8 |

TABLE 17-continued

Combination Studies for CAS 1092453-15-0 with Levetiracetam (LEV) in the 6 Hz (44 mA) Assay.

| Drug | LEV Dose (mg/kg) | # protected/ # tested | # rotarod motor impairment/# tested |
|---|---|---|---|
| LEV + [CAS 1092453-15-0] 20 mg/kg[b] | 400 | 4/8 | 0/8 |
| | 200 | 5/8 | 0/8 |
| | 50 | 3/8 | 0/8 |
| | 20 | 2/8 | 0/8 |
| | 5 | 1/8 | 1/8 |
| LEV ED$_{50}$ (95% CI): 238.9 mg/kg (41.6-above highest dose tested) | | | |

[a]Additional LEV (low-dose) control groups were tested at 25 and 6.25 mg/kg (1/8 and 0/6 protected, respectively).
[b][CAS 1092453-15-0] 20 mg/kg (s.c.; 1 h TPE) tested in combination with LEV (i.p.; 1 h TPE); [CAS 1092453-15-0] 20 mg/kg displayed low activity when administered alone (6 Hz, 32 mA), and it was not tested in 6 Hz (44 mA). This compound displayed an in vitro EC$_{50}$ = 562 nM (Emax = 197%) when tested in the GTPγS assay described hereinbefore and no occupancy was observed in ex vivo experiments in rats.
Note:
Vehicle-treated animals (10% HPβCD-NaCl, s.c., 1 h and 0.5% MC, i.p., 1 h) showed no protection or motor impairment, N = 8.

The current data set indicates that mGlu2 PAM or agonist molecules have anticonvulsant activity in the 6 Hz animal model. Tested mGlu2 PAMs with EC$_{50}$ potencies ≤150 nM (as determined in the [$^{35}$S]GTPγS assay), appropriate PK parameters and brain penetration, showed activity in both the 32 and 44 mA 6 Hz paradigm. Furthermore, all the tested molecules showed synergistic effects with LEV. In contrast, molecule CAS 1092453-15-0, which was only weakly active (EC$_{50}$ 562 nM) in vitro, did not show activity in either of the 6 Hz tests, and also did not display synergy with LEV.

Importantly, the data indicate that, under conditions of comparable PK characteristics and appropriate brain penetration, the most potent mGlu2 PAMs, based on in vitro EC$_{50}$ values, also appeared most potent in vivo, suggesting that in vitro and in vivo potency can be linked. Moreover, synergistic effects with LEV were consistently seen with mGlu2 PAM doses similar to the ED$_{50}$ obtained in the 32 mA model or at least 2-fold lower as the ED$_{50}$ determined in the 44 mA paradigm (i.e. a dose inactive in the 44 mA test when the molecules were tested alone).

Also for LY404039, the mGlu2/3 agonist, activity in both 6 Hz tests was seen and synergy was seen at a dose 3-fold lower than the ED$_{50}$ determined in the 44 mA model, which was inactive when tested alone.

Based on the available preclinical data in the 6 Hz 44 mA model, it seems that combining a potent SV2A ligand and a potent mGlu2 PAM, leads to a decrease in the median effective dose or ED$_{50}$ of the SV2A ligand, such as LEV, between 35 and 100-fold.

Thus, while not wishing to be bound by theory, it is suggested that positive allosteric modulator of metabotropic glutamatergic receptor subtype 2 (mGluR2 PAM) compounds, in particular mGluR2 PAM compounds having an EC$_{50}$ potency of ≤150 nM (as determined in the [$^{35}$S]GTPγS assay), wherein EC$_{50}$ is the concentration producing half-maximal effect in a concentration-response curve obtained in the presence of EC$_{20}$ of glutamate, and appropriate PK parameters and brain penetration, result in a synergistic combination with an SV2A ligand, in particular levetiracetam, at non-effective doses of one or both of compound (a) and compound (b) of the combination of the invention.

Thus, in a further embodiment, the positive allosteric modulator of metabotropic glutamatergic receptor subtype 2 (mGluR2 PAM) compound of the combination of the invention as defined herein is selected from an mGluR2 PAM compound having an EC$_{50}$ potency of 150 nM (as determined in the [$^{35}$S]GTPγS assay), wherein EC$_{50}$ is the concentration producing half-maximal effect in a concentration-response curve obtained in the presence of EC$_{20}$ of glutamate.

PROPHETIC EXAMPLES

A) Dominant-Submissive Relations (DSR) in Rat In Vivo Assay

The DSR assay is divided into two models: Reduction of Dominant Behavior Model (RDBM) of mania and Reduction of Submissive Behavior Model (RSBM) of depression. The RDBM, wherein the dominant animals are treated with test compound, is predictive of the ability of the test compound to treat mania. The RSBM, wherein the submissive animals are treated with test compound, is predictive of the ability of the test compound to treat depression.

Male Sprague Dawley rats (140 to 160 g) from Charles River Laboratories Wilmington, Mass. are used in this assay. Shipments of rats are received at two-week intervals. Each shipment will go through five-day quarantine, one-week acclimation period and one-week selection process, followed by five-weeks of drug or vehicle treatment to those pairs selected.

Rats will be housed four per cage. Access to food will be restricted to one hour per day after testing on Monday through Thursday. After testing on Friday, rats will have free access to food until being fasted again on Sunday. At no time will the rats be deprived of water. The food deprivation periods used will have little effect on weight gain as the average weight of rats will be about 300 g by the end of the study. At the conclusion of experiment rats will be sacrificed by decapitation, the trunk blood and brains will be collected for in vitro experiments and drug concentration measurements.

The basic testing apparatus consisted of two chambers connected with a tunnel only large enough to allow one rat to pass through at a time. On the floor, at the mid-point of the tunnel will be a container of sweetened milk. This basic apparatus will be replicated, so that a total of four pairs of rats can be video tracked simultaneously. The camera can distinguish rats marked by different colors. Thus, the rats' heads will be colored for the purpose of video tracking, red in one cage and yellow in the other cage. Only one animal at a time can have comfortable access to the feeder, but both animals can drink milk during the five-minute daily session. During the five-minute daily sessions, time spent in the feeder zone by each rat will be recorded by the video tracking software and saved into a text file.

The test will begin with a random assignment of rats into pairs. Each member of a pair will be placed in an opposite chamber of the testing apparatus. The time spent in the feeder zone by each animal will be recorded. During the first week (five days) of testing the animals habituate to the new environment. Dominance will be assigned to the animal with the highest score during the second week of testing if three criteria are achieved. First, there must be a significant difference (two-tailed t-test, P<0.05) between the average daily drinking scores of both animals. Second, the dominant animal score must be at least 25% greater than the submissive animal's score. Finally, there must be no "reversals" during the pair selection week where the putative submissive rat out-scored its dominant partner on isolated occasions. Ideally there will be minimal reversals during the acclimation week as well. Only animal pairs that achieve these criteria will be continued in the study.

Significant differences between time spent on the feeder by dominant and submissive rats will be determined by ANOVA using GraphPad Prism software (GraphPad Software, Inc. San Diego, Calif.) followed by a two-tailed t-test (P<0.05). Comparisons will be made between treatment groups using normalized dominance level values in paired animals. The dominance level is a value that measures social relation between paired subjects. Dominance level (DL)=FTD-FTS where FTD is the feeder time of dominant rats and FTS is the feeder time of submissive rats. The normalization will be conducted according to the formula:

Dominance Level (week $n$ in %)=(Dominance Level (week $n$))/(Dominance Level (week 2))

The statistical significance of the difference in dominance level between the control group (pairs of rats where both dominant and submissive animals will be treated with vehicle) and the treatment group (submissive rats will be treated with drug and dominant rats with vehicle) will be determined by ANOVA, followed by a t-test. The activity onset time value at 50% of response (AOT-50) and the minimum and maximum response to drug will be calculated based on the reduction of the dominance level value using non-linear regression analysis (GraphPad Software, Inc., San Diego, Calif.). The normalized DL values will be used for this calculation, where DL values for treatment weeks will be normalized as a percent of the second week (pre-treatment) value of that pair according the above formula. In these settings the minimum of the response (DL) determines drug positive activity, corresponding to efficacy, since DL values will be reduced if the response to a drug is positive. In the case of the negative response to a drug (worsening of symptoms) DL values will be increased. If the drug does not have such activity the maximum of the response will not exceed 100%. Any maximal DL value significantly higher than control value (about 100%) indicates drug negative activity.

Levetiracetam and mGluR2 PAM/agonist compound (e.g. compounds 2, 2-a, 25-a, 6-b or LY-404039) will be evaluated in the rat RDBM according to the procedure described in more detail below.

Groups of dominant rats will be treated p.o. QD with levetiracetam 10 mg/kg and mGluR2 PAM/agonist compound at various concentrations from approximately 0.05 mg/kg (n≥3), at 0.5 mg/kg (n≥3), at 2.5 mg/kg (n≥3), at 5.0 mg/kg (n≥3) and at 50.0 mg/kg (n≥3). A vehicle control group of dominant rats will be treated with 0.5% methyl-cellulose (n≥3) and a second control group of dominant rats will be treated i.p. QD with sodium valproate at 30 mg/kg (n≥6 from 2 studies of n≥3 each).

All treatments will be administered approximately 1 hour prior to testing. All treatments will be started on Saturday after the second testing week (selection week). The levetiracetam and mGluR2 PAM/agonist compound will be administered orally (p.o.).

When dominant animals are treated with levetiracetam 10 mg/kg and mGluR2 PAM/agonist compound the difference between dominant and submissive rats will be lost after the first or second week of treatment depending on the dosage. Similarly, when dominant animals are treated with sodium valproate, the difference between dominant and submissive rats will also be lost after first week of treatment. The permissiveness of the dominant rats treated with levetiracetam and mGluR2 PAM/agonist compound or sodium valproate may be observed to increase. Thus the treated dominant rats will permit their submissive partners to increase their time on the feeder.

To compare different drug and dose effects the data will be normalized to the initial control week values. The strongest effect of levetiracetam and mGluR2 PAM/agonist compound combination will be observed where there is a significant difference in dominance level (DL) values between vehicle and combination treated rats starting in the second week and continuing through the treatment duration of 5 weeks. In comparison, animals (30 mg/kg) that will be treated with sodium valproate will consistently show a decreased dominance level after the second week of treatment with the effect increasing in the following weeks.

To estimate activity onset time (AOT), daily average values for feeder time of dominant and submissive animal pairs will be plotted and significant differences between these two groups will be calculated using the two-tail t-test.

To compare activity onset time (AOT) between different treatments the activity onset time will be estimated from the non-linear regression fit. The non-linear regression model will fit for each drug, combination and dose normalized daily DL values.

Effects of levetiracetam and mGluR2 PAM/agonist compound in the RDBM are expected to be dose dependent.

In this assay, the combination of levetiracetam and mGlu2 PAM/agonist compounds is expected to reduce dominant behavior indicating that the combination is active as an anti-manic.

B) Oral Tablets

As a specific embodiment of an oral composition, 100 mg of a mGluR2 PAM/agonist compound is formulated with sufficiently finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method for the treatment of epilepsy comprising administering to a patient in need thereof a therapeutically effective amount of:
   (a) a synaptic vesicle protein 2A ("SV2A") ligand selected from the group consisting of levetiracetam and brivaracetam; and
   (b)

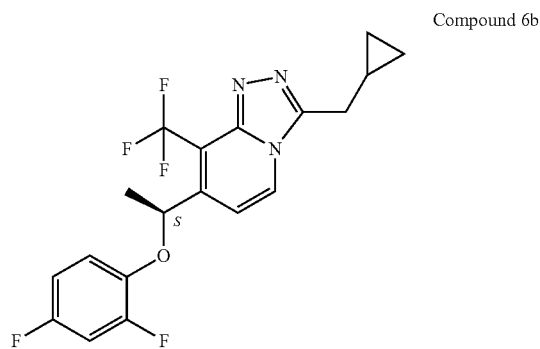

Compound 6b or a pharmaceutically acceptable salt thereof.

2. The method of claim 1 wherein the SV2A ligand is levetiracetam.

3. The method of claim 1 wherein the SV2A ligand is brivaracetam.

4. The method of claim 1 wherein the SV2A ligand and Compound 6b or a pharmaceutically acceptable salt thereof are administered simultaneously.

5. The method of claim 1 wherein the SV2A ligand and Compound 6b or a pharmaceutically acceptable salt thereof are administered separately.

6. The method of claim 1 wherein the SV2A ligand and Compound 6b or a pharmaceutically acceptable salt thereof are administered sequentially.

7. The method of claim 1 wherein the epilepsy is partial onset seizures or focal onset seizures.

8. The method of claim 1 wherein the epilepsy is myoclonic seizures.

9. The method of claim 1 wherein the epilepsy is primary generalized tonic-clonic seizures.

10. The method of claim 1 wherein the epilepsy is treatment resistant epilepsy.

11. The method of claim 1, comprising administering to the patient a therapeutically effective amount of (a) the SV2A ligand; and
(b) Compound 6b.

12. The method of claim 11 wherein the SV2A ligand is levetiracetam.

13. The method of claim 11 wherein the SV2A ligand is brivaracetam.

14. The method of claim 11 wherein the SV2A ligand and Compound *6b* or a pharmaceutically acceptable salt thereof are administered simultaneously.

15. The method of claim 11 wherein the SV2A ligand and Compound *6b* or a pharmaceutically acceptable salt thereof are administered separately.

16. The method of claim 11 wherein the SV2A ligand and Compound *6b* or a pharmaceutically acceptable salt thereof are administered sequentially.

17. The method of claim 11 wherein the epilepsy is partial onset seizures or focal onset seizures.

18. The method of claim 11 wherein the epilepsy is myoclonic seizures.

19. The method of claim 11 wherein the epilepsy is primary generalized tonic-clonic seizures.

20. The method of claim 11 wherein the epilepsy is treatment resistant epilepsy.

* * * * *